US012441816B2

(12) United States Patent
Liu et al.

(10) Patent No.: US 12,441,816 B2
(45) Date of Patent: Oct. 14, 2025

(54) HETERODIMERIC Fc FOR MAKING FUSION PROTEINS AND BISPECIFIC ANTIBODIES

(71) Applicant: QILU PUGET SOUND BIOTHERAPEUTICS CORPORATION, Bothel, WA (US)

(72) Inventors: Zhi Liu, Shoreline, WA (US); Victor Hermand, Lynnwood, WA (US); Hua Liu, Shoreline, WA (US); Wei Yan, Sammamish, WA (US)

(73) Assignee: QILU PUGET SOUND BIOTHERAPEUTICS CORPORATION, Bothell, WA (US)

( * ) Notice: Subject to any disclaimer, the term of this patent is extended or adjusted under 35 U.S.C. 154(b) by 137 days.

(21) Appl. No.: 17/933,954

(22) Filed: Sep. 21, 2022

(65) Prior Publication Data

US 2023/0116446 A1 Apr. 13, 2023

Related U.S. Application Data

(60) Provisional application No. 63/246,573, filed on Sep. 21, 2021.

(51) Int. Cl.

*C07K 16/46* (2006.01)
*C07K 16/28* (2006.01)
*C12N 15/86* (2006.01)

(52) U.S. Cl.

CPC ........ *C07K 16/462* (2013.01); *C07K 16/2887* (2013.01); *C07K 16/2896* (2013.01); *C12N 15/86* (2013.01); *C07K 2317/24* (2013.01); *C07K 2317/31* (2013.01); *C07K 2317/53* (2013.01); *C07K 2317/565* (2013.01); *C07K 2319/00* (2013.01)

(58) Field of Classification Search

CPC .............. C07K 16/462; C07K 16/2887; C07K 16/2896; C07K 2317/24; C07K 2317/31; C07K 2317/53; C07K 2317/565; C07K 2319/00; C07K 2317/526; C07K 2317/92; C07K 16/244; C07K 16/28; C07K 16/2803; C07K 16/2866; C07K 2317/60; C07K 16/468; C07K 2317/52; C07K 2317/55; C07K 2317/56; C07K 2317/73; C07K 16/32; C12N 15/86; A61P 35/00

See application file for complete search history.

(56) References Cited

U.S. PATENT DOCUMENTS

| | | | | |
|---|---|---|---|---|
| 7,033,590 | B1 | 4/2006 | Scheiflinger et al. | |
| 7,112,324 | B1 | 9/2006 | Dorken et al. | |
| 7,235,641 | B2 | 6/2007 | Kufer | |
| 10,752,929 | B2 * | 8/2020 | De Kruif | C07K 16/468 |
| 2003/0133939 | A1 | 7/2003 | Ledbetter et al. | |
| 2005/0136049 | A1 | 6/2005 | Ledbetter et al. | |
| 2006/0135430 | A1 | 6/2006 | Chan et al. | |
| 2006/0246004 | A1 | 11/2006 | Adams et al. | |
| 2007/0059306 | A1 | 3/2007 | Grossmaire et al. | |
| 2008/0279850 | A1 | 11/2008 | Brady et al. | |
| 2009/0010921 | A1 | 1/2009 | Umana et al. | |
| 2010/0189722 | A1 * | 7/2010 | Heider | C07K 16/28 435/69.6 |
| 2012/0219549 | A1 | 8/2012 | Fertig et al. | |
| 2012/0276119 | A1 | 11/2012 | Decker et al. | |
| 2014/0348745 | A1 | 11/2014 | Larsen et al. | |
| 2020/0095310 | A1 | 3/2020 | Regula et al. | |
| 2021/0214436 | A1 | 7/2021 | Chang et al. | |
| 2021/0246228 | A1 | 8/2021 | Schlothauer et al. | |
| 2021/0277150 | A1 | 9/2021 | Von Kreudenstein | |
| 2022/0411492 | A1 * | 12/2022 | Yang | C07K 16/28 |

FOREIGN PATENT DOCUMENTS

| | | | |
|---|---|---|---|
| CA | 3165045 | A1 | 7/2021 |
| CN | 101815725 | A | 8/2010 |
| CN | 102159243 | A | 8/2011 |

(Continued)

OTHER PUBLICATIONS

Merchant, A. Margaret, et al. "An efficient route to human bispecific lgG." Nature biotechnology 16.7 (1998): 677-681. (Year: 1998).*

Ha, Ji-Hee, Jung-Eun Kim, and Yong-Sung Kim. "Immunoglobulin Fc heterodimer platform technology: from design to applications in therapeutic antibodies and proteins." Frontiers in Immunology 7 (2016): 394. (Year: 2016).*

Moore, Gregory L., et al. "A robust heterodimeric Fc platform engineered for efficient development of bispecific antibodies of multiple formats." Methods 154 (2019): 38-50. (Year: 2019).*

Li, Yifeng, et al. "A roadmap for lgG-like bispecific antibody purification." Approaches to the purification, analysis and characterization of antibody-based therapeutics. Elsevier, 2020. 167-179. (Year: 2020).*

Muda et al. "Therapeutic assessment of SEED: a new engineered antibody platform designed to generate monoand pispecific antibodies," Protein Engineering, Design & Selection, May 31, 2011 (May 31, 2011), vol. 24, No. 5, pp. 447-454. entire document.

(Continued)

*Primary Examiner* — Julie Wu
*Assistant Examiner* — Bryan William Heck
(74) *Attorney, Agent, or Firm* — Procopio, Cory, Hargreaves & Savitch LLP

(57) ABSTRACT

Provide herein are variant-Fc-region fusion proteins, variant-Fc-region-antibodies and/or heterodimeric-variant-Fc-region-bispecific-antibodies optionally produced by a host cell line, nucleic acids encoding the variant-Fc-region fusion proteins, variant-Fc-region-antibodies and/or heterodimeric-variant-Fc-region-bispecific-antibodies, host cells containing such nucleic acids, and methods of treatment using the variant-Fc-region fusion proteins, variant-Fc-region-antibodies and/or heterodimeric-variant-Fc-region-bispecific-antibodies, or nucleic acids encoding the variant-Fc-region fusion proteins, variant-Fc-region-antibodies and/or heterodimeric-variant-Fc-region-bispecific-antibodies described herein. Also described are methods of producing the variant-Fc-region fusion proteins, variant-Fc-region-antibodies and/or heterodimeric-variant-Fc-region-bispecific-antibodies in host cells.

46 Claims, 22 Drawing Sheets

Specification includes a Sequence Listing.

(56) References Cited

FOREIGN PATENT DOCUMENTS

| | | | | | |
|---|---|---|---|---|---|
| CN | 1852976 | B | | 5/2012 | |
| CN | 103360494 | A | | 10/2013 | |
| CN | 101827611 | B | | 1/2014 | |
| CN | 103501815 | A | | 1/2014 | |
| CN | 1902231 | B | | 5/2015 | |
| CN | 112062855 | A | * | 12/2020 | ......... A61K 47/6801 |
| EP | 2586798 | A2 | | 1/2013 | |
| EP | 2562187 | A1 | | 2/2013 | |
| EP | 3489262 | A1 | * | 5/2019 | ......... C07K 16/1018 |
| WO | 2009126944 | A1 | | 10/2009 | |
| WO | 2013033008 | A2 | | 3/2013 | |
| WO | 2014081954 | A1 | | 5/2014 | |
| WO | WO-2017205014 | A1 | * | 11/2017 | ........... A61K 9/0019 |
| WO | WO-2020180811 | A1 | * | 9/2020 | .............. A61P 35/00 |
| WO | 2021026387 | A9 | | 2/2021 | |

OTHER PUBLICATIONS

International Search Report and Written Opinion for PCT/US2022/076758 dated Jan. 23, 2023, 13 pages.

Krah et al., "Generation of human bispecific common lightchain antibodies by combining animalimmunization and yeast display", Protein Engineering, Design & Selection, vol. 30, No. 4—pp. 291-301; Jan. 6, 2017.

Labrijn et al., "Bispecific antibodies: a mechanistic review of the pipeline", Nature Reviews, Drug Discovery, Jun. 7, 2019.

Gunasekaran et al., "Enhancing Antibody Fc Heterodimer Formation throughElectrostatic Steering Effects", The Journal of Biological Chemistry, vol. 285, No. 25, pp. 19637-19646, Jun. 18, 2010.

Suurs et al., "A review of bispecific antibodies and antibody constructs in oncology and clinical challenges", Pharmacology & Therapeutics, Apr. 24, 2019.

Ridgway et al., Knobs-into-holes engineering of antibody CH3 Domains for heavy chain heterodimerization, Protein Engineering, vol. 9, pp. 617-621, 1996.

Liu et al., A Novel Antibody Engineering Strategy for MakingMonovalent Bispecific Heterodimeric IgG Antibodies byElectrostatic Steering Mechanism, Journal of Biological Chemistry, vol. 290, No. 12, Mar. 20, 2015.

Davis et al., SEEDbodies: fusion proteins based on strand-exchange engineered domain (SEED) CH3 heterodimers in an Fc analogue platform for asymmetric binders or immunofusions and bispecific antibodies, Protein Engineering Design & Selection, vol. 23, No. 4, pp. 195-202, 2010.

Kai et al., Switching constant domainsenhances agonist activitiesof antibodies to athrombopoietin receptor, Nature Biotechnology, vol. 26, No. 2, Feb. 2008.

Alduaij et al., "The future of anti-CD20 monoclonal antibodies: are we making progress?", School of Cancer and Enabling Sciences, vol. 117, No. 11, Mar. 17, 2011.

Cragg, "CD20 antibodies: doing the time warp", Bloodjournal.org, Sep. 2, 2015.

Vugmeyster et al., "Depletion of B Cells by a Humanized Anti-CD20Antibody PRO70769 inMacaca Fascicularis", J Immunother vol. 28, No. 3, May/Jun. 2005.

Niederfellner et al., "Epitope characterization and crystal structure of GA101 provide insights into themolecular basis for type I/II distinction of CD20 antibodies", Lymphoid Neoplasia, vol. 118, Jan. 12, 2015.

Beers et al., "Type II (tositumomab) anti-CD20 monoclonal antibody out performs type I(rituximab-like) reagents in B-cell depletion regardless of complement activation", Blood, vol. 112, No. 10, Nov. 15, 2008.

Illdge et al., "Obinutuzumab in hematologic malignancies: Lessons learned to date", Cancer Treatment Reviews 41 (2015) 784-792.

Teelin et al., "The Biological Activity of Human CD20 Monoclonal Antibodies is Linked to Unique Epitopes on CD20", The Journal of Immunology, Sep. 1, 2015.

Quinta's-Cardama, "Investigational Immunotherapeutics for B-Cell Malignancies", Journal Ofclinicaloncology, vol. 28, No. 5, Feb. 10, 2010.

Letters to the Editor, "Action of novel CD37 antibodies on chronic lymphocytic leukemia cells", Leukemia (2012) 26, 546-549; doi:10.1038/leu.2011.233; published online Sep. 2, 2011.

Zhao et al., "Targeting CD37-positive lymphoid malignancies with a novel engineered small modular Immunopharmaceutical", Blood Journal, Oct. 31, 2015.

Heider et al., "A novel Fc-engineered monoclonal antibody to CD37 with enhanced ADCC and high proapoptotic activity for treatment of B-cell malignancies", The American Society of Hermatology, 2011.

Deckert et al., "A novel anti-CD37 antibody-drug conjugate with multiple anti-tumor mechanisms for the treatment of B-cell malignancies", Blood Journal, The American Society of Hermatology, 2013.

Berberichl "Cross-linking CD40 on B cells preferentially induces stress-activated protein kinases rather than mitogen-activated protein kinases" The EMBO Journal vol. 15 No. 1 pp. 92-101, 1996.

Robak, GA-101, a third-generation, humanized and glyco-engineered anti-CD20 mAb for the treatment of B-cell ymphoid malignanices, Thomson Reuters, 2009.

Klein et al., "Epitope interactions of monoclonal antibodies targeting CD20 and their relationship to functional properties", mAbs 5:1, 22-33; Jan./Feb. 2013; Landes Bioscience.

Vaughan et al., "Activatory and Inhibitory FcReceptors AugmentRituximab-mediated Internalization of CD20 Independent ofSignaling via the Cytoplasmic Domain", The Journal of Biological Chemistry vol. 290, No. 9, pp. 5424-5437, Feb. 27, 2015.

Small et al., Analysis of innate and acquired resistance to anti-CD20 antibodies in, malignant and nonmalignant B cells, Peer J., Nov. 21, 2012.

Mossner, "Increasing the efficacy of CD20 antibody therapy through the engineering of anew type II anti-CD20 antibody with enhanced direct and immune effectorcell-mediated B-cell cytotoxicity" Blood Journal, Jun. 3, 2010.

Camilla De Nardis et al: "A new approach for generating bispecific antibodies based on a common light chain format and the stable architecture of human immunoglobulin G 1", Journal of Biological Chemistry, vol. 292, No. 35, Sep. 1, 2017 (Sep. 1, 2017), pp. 14706-14717, XP055403663, US || SSN: 0021-9258, DOI: 1074/jbc.M117.793497.

Partial Search Report for European Application No. Application No. 22873817.5, dated Sep. 7, 2025, 41 pages.

* cited by examiner

A

B

| | aCLDN18.2 | Bispecific | Isotype control |
|---|---|---|---|
| EC50 (nM) | 4.52 | 16.92 | N.A. |

| | aCLDN18.2 | aSIRPα | aCLDN18.2 + aSIRPα | Bispecific | Isotype control |
|---|---|---|---|---|---|
| EC50 (nM) | N.A. | N.A. | 0.223 | 0.172 | N.A. |

| | IL15 and IL15Ra Sushi domain | Hetero-Fc alone | IL-15 |
|---|---|---|---|
| EC50 (nM) | 0.06583 | N.A. | 0.02094 |

HETERODIMERIC Fc FOR MAKING FUSION PROTEINS AND BISPECIFIC ANTIBODIES

RELATED APPLICATIONS

This application claims priority to U.S. Provisional Application No. 63/246,573, filed on Sep. 21, 2021, the contents of the aforementioned application is incorporated herein by reference in its entirety.

FIELD

The compositions and methods described herein are in the field of recombinant antibodies and methods for their production.

BACKGROUND

Recombinant monoclonal antibodies have emerged as a very successful class of biological drugs for the treatment of a variety of different diseases during the past two decades. They have been used both with and without the co-administration of small molecule-based drugs. Due to the biological complexity of some diseases, bispecific antibodies that target more than one antigen or epitope can be more effective than single antibodies in treating certain conditions. See, e.g., Lindzen et al., (2010), Proc. Natl. Acad. Sci. 107 (28): 12550-12563; Nagorsen and Baeuerle (2011), Exp. Cell Res. 317 (9): 1255-60.

Fc-fusion proteins are molecules in which the Fc fragments are fused to proteins of interests, such as extracellular domains of receptors, soluble cytokines, ligands, enzymes, engineered domains, or peptides. Fc-fusion proteins inherit some antibody-like properties such as relatively good physicochemical characteristics for easy expression, purification, formulation, storage and transportation, long serum half-life, effector functions, which increases the possibilities for clinic use. Standard Fc is a homodimer. In some cases, fusion of a single partner, or fusion of different partners with different geometry, is preferred. For example, when the fusion partner is an agonist which can lead to the activation of certain biological system in body, over-activation due to more than one fusion molecule could bring undesirable high side effects. Heterodimeric Fc, in which each Fc chain can fuse to single partner at either N- or C-terminus, easily solves this problem.

Bispecific antibodies can target two different proteins expressed either on the same cells or on different cells, bispecific antibodies can target two different epitopes on the same antigen as well. Bispecific antibodies can unlock new mechanisms of actions such as linking together two different types of cells (e.g. immune cell and cancerous cell) or blocking two non-redundant pathways with a single drug. Three bispecific antibodies have been approved by FDA so far, the latest approval was for Janssen's Rybrevant (Amivantamab-vmjw), the first treatment for adult patients with non-small cell lung cancer, approved on May 21st of this year. The others are Amgen's Blincyto (blinatumomab) for patients with ALL (acute lymphoblastic leukemia) and Roche's Hemlibra (emicizumab-kxwh) for patients with hemophilia. Hundreds of bispecific antibodies are at different stages of clinical development.

More than fifty different formats of bispecific antibodies have been developed, many of them are using asymmetrical Fc technology. The knob-into-hole technology from Genentech (Protein Eng. 1996; 9 (7): 617-21), charge-pairs technology from Amgen (J Biol Chem. 2010; 285 (25): 19637-46), SEED technology from EMD Serono (Protein Eng. Des. Sel. 2010; 23:195-202) are well-known for making bispecific antibodies. However, when applying the above technologies, unwanted homodimeric antibody can be produced if the expression of two HCs is not balanced, creating some level of product impurity. So far, no good strategy except ours has been described for precise control of the cognate HC/LC pairings when making bispecific antibody from two different HCs and two different LCs.

Accordingly, additional processes for producing novel heterodimeric Fc fusion protein and related bispecific antibodies for treating cancers and inflammatory diseases are needed.

SUMMARY

Provided herein is a variant-Fc-region comprising a set of amino acid substitutions compared to native human IgG, selected from: a first variant-Fc-region comprising S364D, K370D, N390D, and S400D; a second Fc region comprising S364K, and S400K. In additional embodiments, the variant-Fc-region can further comprise Y349C and K392G in the first variant-Fc-region, and S354C and N390P in the second variant-Fc-region. In other embodiments, the variant-Fc-region is a variant-Fc-region-fusion protein further comprising a partner-ligand recombinantly fused thereto at either the N-terminus or C-terminus. In particular embodiments, the partner-ligand is selected from the group consisting of: extracellular domains of receptors, soluble full-length or domain of cytokines, ligands, enzymes, antibody domains, peptides, anti-CD3 scFv, IL-2, IL-12, IL-15, IL21, or mutein cytokines. In yet other embodiments, the variant-Fc-region or variant-Fc-region fusion protein is derived from a native human IgG is an isotype selected from the group consisting of: IgG, IgD, IgM, IgA, or IgE class; or following subclass IgG1, IgG2, IgG3, or IgG4.

Also provided herein is a substantially pure heterodimeric-variant-Fc-region fusion protein composition, wherein said composition comprises the first and second variant-Fc-region set forth hereinabove. In another embodiment, the substantially pure heterodimeric-variant-Fc-region fusion protein composition is substantially free of homodimeric proteins. In other embodiments, the amount of homodimeric proteins in said composition is less than 5, 4, 3, 2, 1, 0.5, 0.4, 0.3, 0.2, 0.1%.

In yet another embodiment, the substantially pure heterodimeric-variant-Fc-region protein composition further comprises:

a. only one of the first and second variant-Fc-regions comprises a partner-ligand attached thereto at either the N-terminus or C-terminus;

b. both the first and second variant-Fc-regions comprise the same partner-ligands attached thereto at either the N-terminus or C-terminus; or c. both the first and second variant-Fc-regions comprise different partner-ligands attached thereto at either the N-terminus or C-terminus. In other embodiments, the substantially pure heterodimeric-variant-Fc-region protein is selected from a heterodimeric variant-Fc-region monospecific antibody; or a heterodimeric variant-Fc-region bispecific antibody.

Also provided herein is a substantially pure heterodimeric-variant-Fc-region antibody composition, wherein said composition comprises:

a heterodimeric-variant-Fc-region antibody comprising a first variant Fc-region having 4 variant negative charge residues at specified residues on the CH3 region; and comprising a second variant Fc-region having 2 variant and 2 native positive charge residues at the corresponding-specified residues on the CH3 region as in the first Fc-region, wherein an amount of homodimeric antibodies in said composition is less than 5, 4, 3, 2, 1, 0.5, 0.4, 0.3, 0.2, 0.1%. In other embodiments of the heterodimeric-variant-Fc-region antibody composition, the first Fc-region has 4 variant negative charge residues corresponding to S364D, K370D, N390D, and S400D. In another embodiment, the second Fc-region has 2 variants and 2 native positive charge residues corresponding to S364K, 370K, 392K, and S400K. In yet other embodiments, the heterodimeric-variant-Fc-region antibody composition further comprises a variant cysteine residue in the CH3 region of the first and second Fc-regions. In yet another embodiment of the heterodimeric-variant-Fc-region antibody composition, the variant cysteine residue in the CH3 region of the first Fc-region corresponds to Y349C. In yet another embodiment, the variant cysteine residue in the CH3 region of the second Fc-region corresponds to S354C.

Also provided herein is a heterodimeric variant-Fc-region-bispecific antibody comprising the variant-Fc region and/or variant-Fc-regions-fusion protein set forth herein, wherein the heterodimeric variant-bispecific antibody further comprises:

a. a first and second Heavy Chain (HC) region, wherein the first and second HC regions differ from each other; and b. a first and second Light Chain (LC) region, wherein the first and second LC regions differ from each other. In one embodiment, the first HC region comprises substitutions corresponding to K147D, F170C, V173C in its CH1 domain and C220G in upper hinge region of the HC region; the first LC region comprises substitutions corresponding to S131K, Q160C, S162C and C214S in its CK domain; and the first HC and first LC form a cognate pair, whereas no substitution is introduced in the second HC and the second LC. In another embodiment, no substitution is introduced in the first HC and the first LC, whereas the second HC region comprises substitutions corresponding to K147D, F170C, V173C in its CH1 domain and C220G in upper hinge region of the HC region; the second LC region comprises substitutions corresponding to S131K, Q160C, S162C and C214S in its CK domain. In yet other embodiments, the heterodimeric bispecific antibody is selected from a. anti-hCD20×hCD37 comprising an anti-hCD20 VL CDR1, VL CDR2, VL CDR3 set forth in SEQ ID NO:36, or a complete anti-hCD20 VL sequence set forth in SEQ ID NO:36; an anti-hCD20 VH CDR1, VH CDR2, and VH CDR3 set forth in SEQ ID NO:30, or a complete anti-hCD20 VH sequence set forth in SEQ ID NO:30; an anti-hCD37 VL CDR1, VL CDR2, VL CDR3 set forth in SEQ ID NO:50, or a complete anti-hCD37 VL sequence set forth in SEQ ID NO:50; and an anti-hCD37 VH CDR1, VH CDR2, and VH CDR3 set forth in SEQ ID NO:42, or a complete anti-hCD37 VH sequence set forth in SEQ ID NO:42; and b. anti-hSIRPα×hCLDN18.2 comprising an anti-hSIRPa VL CDR1, VL CDR2, VL CDR3 set forth in SEQ ID NO:74, or a complete anti-hSIRPa VL sequence set forth in SEQ ID NO: 74; an anti-hSIRPa VH CDR1, VH CDR2, and VH CDR3 set forth in SEQ ID NO:70, or a complete anti-hSIRPa VH sequence set forth in SEQ ID NO:70; an anti-hCLDN18.2 VL CDR1, VL CDR2, VL CDR3 set forth in SEQ ID NO:64, or a complete anti-hCLDN18.2 VL sequence set forth in SEQ ID NO:64; and an anti-hCLDN18.2 VH CDR1, VH CDR2, and VH CDR3 set forth in SEQ ID NO:58, or a complete anti-hCLDN18.2 VH sequence set forth in SEQ ID NO:58. In a particular embodiment, the heterodimeric bispecific antibody corresponds to an anti-CD20×CD37, selected from the group consisting of:

a. the first HC region corresponding to anti-hCD37 Ab1.A1.2 HC (SEQ ID NO:42) (DCCG-CKKPKK); the first LC region corresponding to anti-hCD37 Ab1.A1.1 LC (SEQ ID NO:50) (KCCS); the second HC region corresponding to anti-hCD20 Ab1.2.5 HC (SEQ ID NO:30) (CDDDGD); and the second LC region corresponding to anti-hCD20 Ab1.2 (SEQ ID NO:36); and b. the first HC region corresponding to anti-hCD37 Ab1.A1.3 HC (SEQ ID NO:44) (DCCG-CDDDGD); the first LC region corresponding to anti-hCD37 Ab1.A1.1LC (SEQ ID NO:50) (KCCS); the second HC region corresponding to anti-hCD20 Ab1.2.6 HC (SEQ ID NO:32) (CKKPKK); and the second LC region corresponding to anti-hCD20 Ab1.2 (SEQ ID NO:36).

In yet another embodiment, the heterodimeric bispecific antibody corresponds to an anti-hSIRPα×hCLDN18.2, selected from the group consisting of:

a. the first HC region corresponding to anti-hCLDN18.2 HC1 (SEQ ID NO:58) (DCCG-CDDDGD); the first LC region corresponding to anti-hCLDN18.2 LC1 (SEQ ID NO:64) (KCCS); the second HC region corresponding to anti-hSIRPα HC2 (SEQ ID NO:70) (CKKPKK); and the second LC region corresponding to anti-hSIRPα LC2 (SEQ ID NO:74).

Also provided herein is a humanized anti-hCLDN18.2 monoclonal antibody wherein said antibody comprises a variable heavy chain (VH) amino acid sequence corresponding to SEQ ID NO: 52; and a variable light chain (VL) amino acid sequence corresponding to SEQ ID NO:60. In a particular embodiment, the humanized anti-hCLDN18.2 monoclonal antibody further comprises a heavy chain (HC) amino acid sequence selected from SEQ ID NO:54, SEQ ID NO:56 or SEQ ID NO: 58; and a light chain (LC) amino acid sequence selected from SEQ ID NO:62 or SEQ ID NO: 64.

Also provided herein are methods of making the invention variant-Fc-regions, variant-Fc-region fusion proteins or heterodimeric-variant-Fc-region antibodies (e.g., heterodimeric variant-Fc-region bispecific antibodies) set forth herein, comprising the steps of:

(a) culturing the host cell line expressing the mixture of antibodies in a culture medium, and (b) recovering the variant-Fc-region fusion proteins or heterodimeric-variant-Fc-region antibodies from the cell mass or the culture medium. In a particular embodiment, the host cell line is a mammalian cell line. In another embodiment, the host cell line is a CHO cell line. In other embodiments, the method further comprises a step of purifying the variant-Fc-region fusion proteins or heterodimeric-variant-Fc-region antibodies from other components present in the cell mass or the culture medium.

Also provided herein, is a host cell line that produces the variant-Fc-region, variant-Fc-region fusion protein or heterodimeric-variant-Fc-region antibody provided herein. In one embodiment, the host cell line is a mammalian cell line. In another embodiment, the host cell line is a CHO cell line.

Also provided herein are nucleic acid(s) encoding the variant-Fc-region, variant-Fc-region fusion protein or heterodimeric-variant-Fc-region antibody set forth herein. In particular embodiments, one or more vector(s) are provided containing the nucleic acid(s). In particular embodiments, the vector(s) is a mammalian expression vector. In another embodiment, the vector(s) is a viral vector. In particular embodiments, the vector(s) is an adenovirus, an adeno-associated virus (AAV), a retrovirus, a vaccinia virus, a modified vaccinia virus Ankara (MVA), a herpes virus, a lentivirus, or a poxvirus vector. Also provided herein is host cell line containing the nucleic acid(s) and/or the vector(s) set forth herein.

Also provided herein is a method of treating a disease comprising administering to a patient having the disease the variant-Fc-region fusion proteins or heterodimeric-variant-Fc-region antibodies (e.g., heterodimeric variant-Fc-region bispecific antibodies) set forth herein, wherein the disease is a cancer, a metabolic disease, an infectious disease, or an autoimmune or inflammatory disease. In one embodiment, the disease is a cancer. Also provided is a method of treating a disease or cancer (e.g., breast cancer) comprising administering to a patient having the disease a variant-Fc-region fusion protein or heterodimeric-variant-Fc-region antibody (e.g., heterodimeric variant-Fc-region bispecific antibodies) set forth herein. In certain embodiments, the variant-Fc-region fusion protein composition or heterodimeric-variant-Fc-region antibody composition is substantially free of homodimeric proteins having homodimeric variant Fc-regions; and wherein the amount of homodimeric proteins in said composition is less than 5, 4, 3, 2, 1, 0.5, 0.4, 0.3, 0.2, 0.1%. Also provided is a method of treating a patient having a tumor comprising injecting into the tumor a variant-Fc-region fusion protein or heterodimeric-variant-Fc-region antibody set forth herein. Also provided is a method of treating a cancer patient comprising administering to the patient the nucleic acid(s) and/or the vector(s) set forth herein. In a particular embodiment, the patient has a tumor and the nucleic acid(s) and/or vector(s) is (are) administered directly to the tumor. In another embodiment, the nucleic acid(s) and/or the vector(s) are injected into the tumor.

TABLE 1

Figure 1:
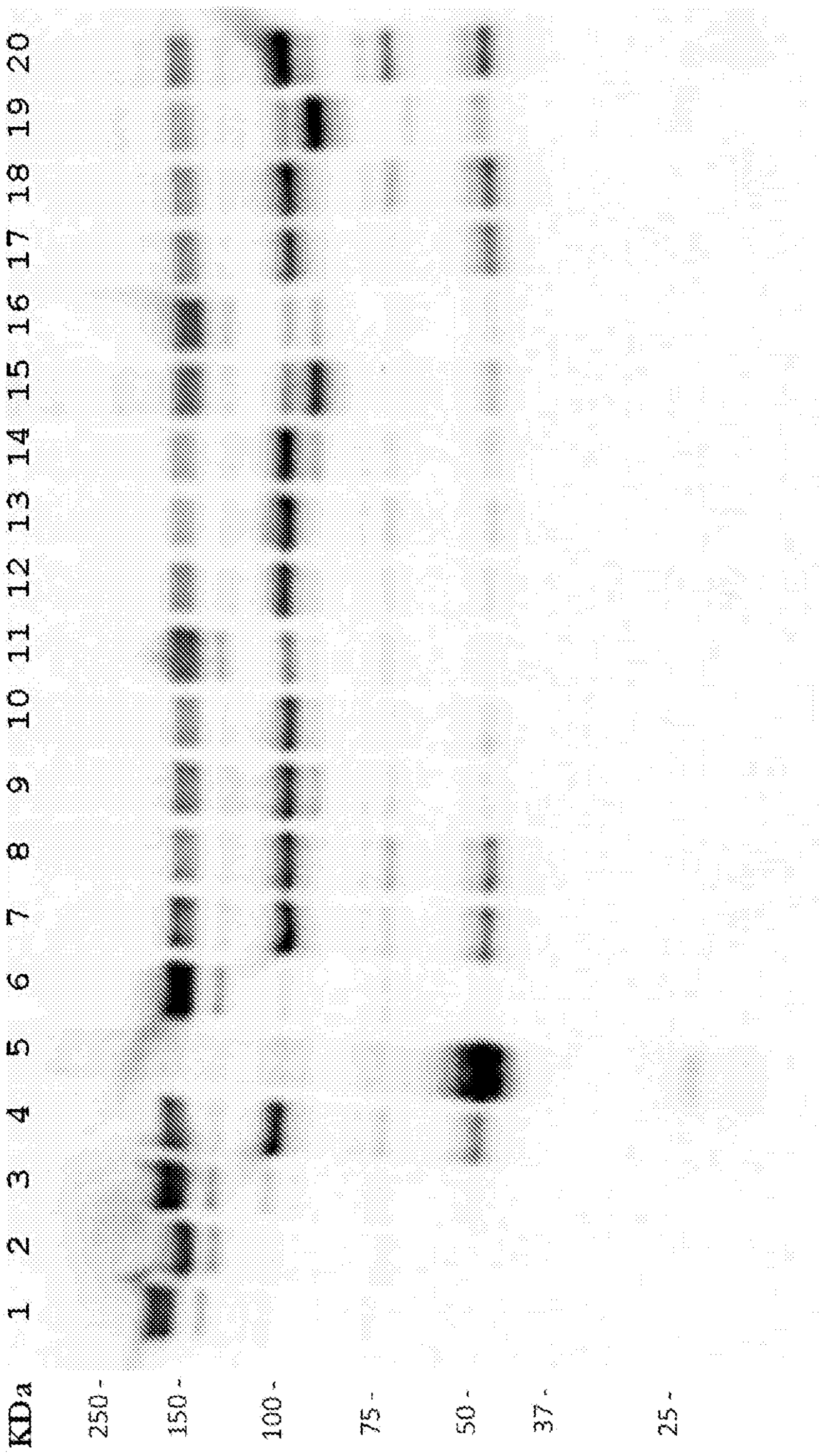
FIG. 1: Co-expression by transient transfections to assess the heterodimeric variant-Fc-region formation. Lane 1 contains cell supernatants from control transfections containing anti-HER2 antibody 4D5-8 IgG1 (comprising the amino acid sequences SEQ ID NOs. 4 and 8), lane 2 containing anti-HER2 antibody 2C4 IgG1 (which contains the amino acid sequences of SEQ ID NOs. 12 and 16). As indicated, all other samples are in groups of three and contain cell supernatants from transfections containing the DNAs encoding combinations of anti-HER2 4D5-8 LC, anti-HER2 4D5-8 HC variant-Fc-regions, and dummy Fc variants, as explained in Example 2. These antibodies are either unaltered (designated "WT") or altered in various positions in different lanes as indicated in the tables below. Positions of molecular weight standards are indicated at left.

Alterations in antibody chains in samples shown in FIG. 1

| | Anti-HER2 4D5-8 human IgG1 | | Dummy Fc |
|---|---|---|---|
| Lane | LC | HC | Fc |
| 3 | WT | WT | |
| 4 | WT | WT | WT |
| 5 | | | WT |
| 6 | WT | N390K, **K392K**, S400K | |
| 7 | WT | N390K, **K392K**, S400K | WT |
| 8 | WT | N390K, **K392K**, S400K | N390D, K392D, S400D |
| 9 | WT | N390K, **K392K**, S400K | Y349C, N390D, K392D, S400D |
| 10 | WT | N390K, **K392K**, S400K | S354C, N390D, K392D, S400D |
| 11 | WT | Y349C, N390K, **K392K**, S400K | |
| 12 | WT | Y349C, N390K, **K392K**, S400K | WT |
| 13 | WT | Y349C, N390K, **K392K**, S400K | N390D, K392D, S400D |
| 14 | WT | Y349C, N390K, **K392K**, S400K | Y349C, N390D, K392D, S400D |
| 15 | WT | Y349C, N390K, **K392K**, S400K | S354C, N390D, K392D, S400D |
| 16 | WT | S354C, N390K, **K392K**, S400K | |
| 17 | WT | S354C, N390K, **K392K**, S400K | WT |
| 18 | WT | S354C, N390K, **K392K**, S400K | N390D, K392D, S400D |
| 19 | WT | S354C, N390K, **K392K**, S400K | Y349C, N390D, K392D, S400D |
| 20 | WT | S354C, N390K, **K392K**, S400K | S354C, N390D, K392D, S400D |

*Blank boxes indicate the absence of the chain listed in the heading above the box. Bolded residues are WT with no mutation, but listed for reference.

Figure 2A:
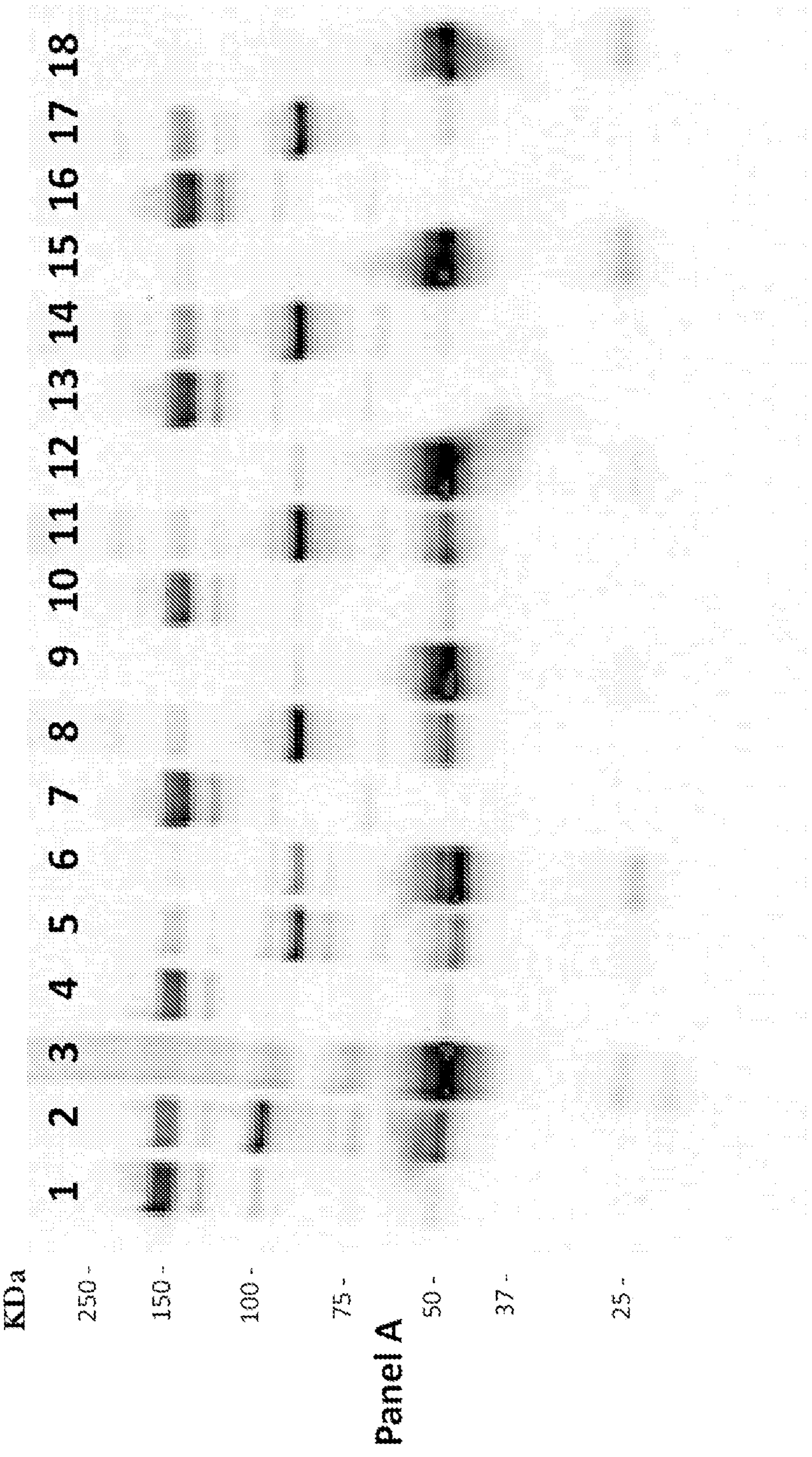
Figure 2B:
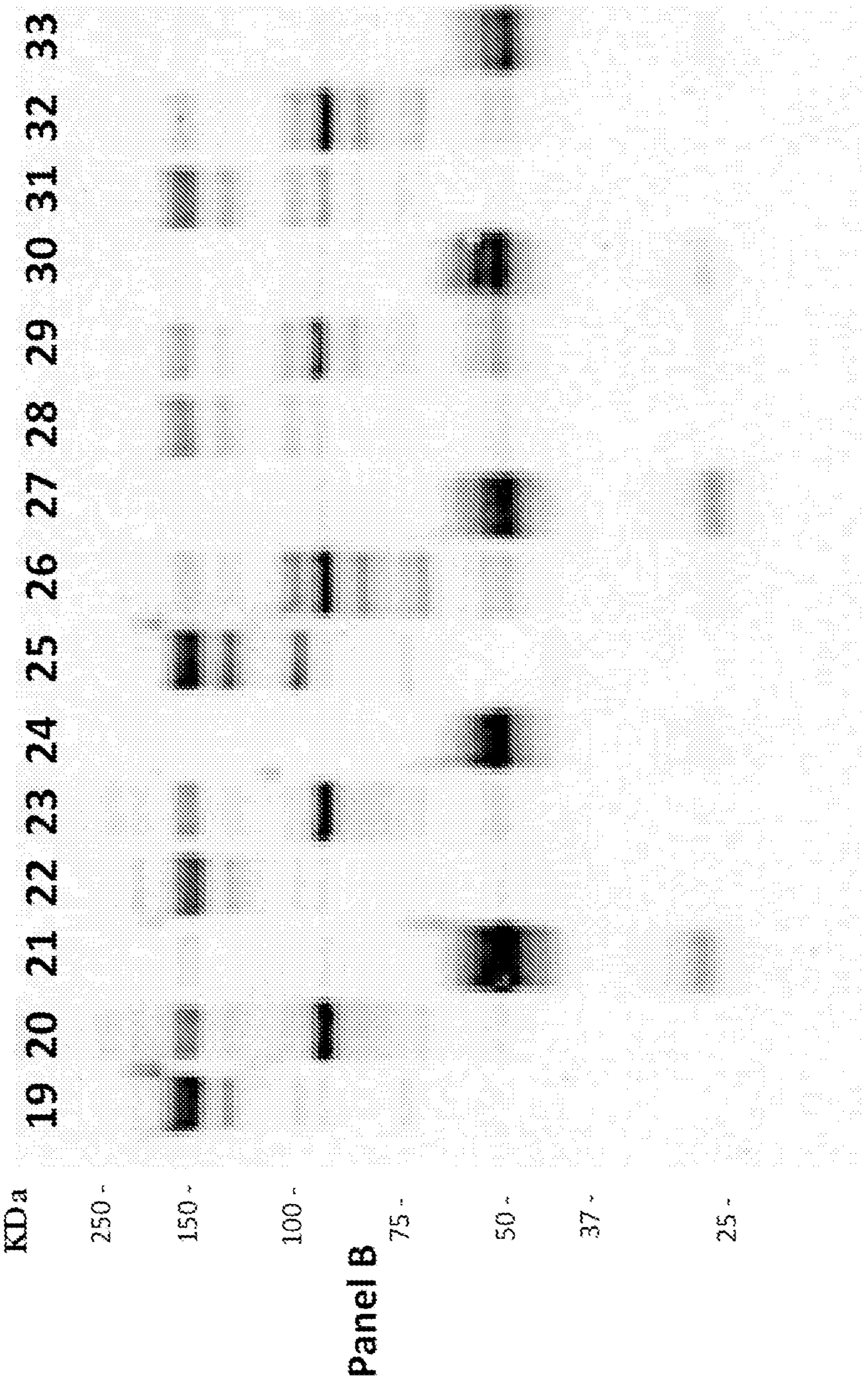

FIG. 2A-2B: Co-expression by transient transfections to assess the heterodimeric variant-Fc-region formation. Experiments are described in Example 2. As indicated, all samples are in groups of three and contain cell supernatants from transfections containing the DNAs encoding combinations of anti-HER2 4D5-8 LC, anti-HER2 4D5-8 HC variants, and dummy Fc variants. These antibodies are either unaltered (designated "WT") or altered in various positions in different lanes as indicated in the tables below. Positions of molecular weight standards are indicated at left.

TABLE 2

Alterations in antibody chains in samples shown in Panel A of FIG. 2

| | Anti-HER2 4D5-8 human IgG1 | | Dummy Fc |
|---|---|---|---|
| Lane | LC | HC | Fc |
| 1 | WT | WT | |
| 2 | WT | WT | WT |
| 3 | | | WT |
| 4 | WT | S354C, N390K, **K392K**, S400K | |
| 5 | WT | S354C, N390K, **K392K**, S400K | Y349C, N390D, K392D, S400D |
| 6 | | | Y349C, N390D, K392D, S400D |
| 7 | WT | S354C, N390K, **K392K**, S400K | |
| 8 | WT | S354C, N390K, **K392K**, S400K | Y349C, N390D, K392A, S400D |
| 9 | | | Y349C, N390D, K392A, S400D |
| 10 | WT | S354C, N390K, **K392K**, S400K | |

TABLE 2-continued

| Alterations in antibody chains in samples shown in Panel A of FIG. 2 | | | |
|---|---|---|---|
| | Anti-HER2 4D5-8 human IgG1 | | Dummy Fc |
| Lane | LC | HC | Fc |
| 11 | WT | S354C, N390K, **K392K**, S400K | Y349C, N390D, K392I, S400D |
| 12 | | | Y349C, N390D, K392I, S400D |
| 13 | WT | S354C, N390A, **K392K**, S400K | |
| 14 | WT | S354C, N390A, **K392K**, S400K | Y349C, N390D, K392D, S400D |
| 15 | | | Y349C, N390D, K392D, S400D |
| 16 | WT | S354C, N390N, **K392K**, S400K | |
| 17 | WT | S354C, N390N, **K392K**, S400K | Y349C, N390D, K392D, S400D |
| 18 | | | Y349C, N390D, K392D, S400D |

*Blank boxes indicate the absence of the chain listed in the heading above the box. Bolded residues are WT with no mutation, but listed for reference.

TABLE 3

| Alterations in antibody chains in samples shown in Panel B of FIG. 2 | | | |
|---|---|---|---|
| | Anti-HER2 4D5-8 human IgG1 | | Dummy Fc |
| Lane | LC | HC | Fc |
| 19 | WT | S354C, N390I, **K392K**, S400K | |
| 20 | WT | S354C, N390I, **K392K**, S400K | Y349C, N390D, K392D, S400D |
| 21 | | | Y349C, N390D, K392D, S400D |
| 22 | WT | S354C, N390P, **K392K**, S400K | |
| 23 | WT | S354C, N390P, **K392K**, S400K | Y349C, N390D, K392G, S400D |
| 24 | | | Y349C, N390D, K392G, S400D |
| 25 | WT | S354C, N390S, **K392K**, S400K | |
| 26 | WT | S354C, N390S, **K392K**, S400K | Y349C, N390D, K392F, S400D |
| 27 | | | Y349C, N390D, K392F, S400D |
| 28 | WT | S354C, N390V, **K392K**, S400K | |
| 29 | WT | S354C, N390V, **K392K**, S400K | Y349C, N390D, K392Q, S400D |
| 30 | | | Y349C, N390D, K392Q, S400D |
| 31 | WT | S354C, N390S, **K392K**, S400K | |
| 32 | WT | S354C, N390S, **K392K**, S400K | Y349C, N390D, K392G, S400D |
| 33 | | | Y349C, N390D, K392G, S400D |

*Blank boxes indicate the absence of the chain listed in the heading above the box. Bolded residues are WT with no mutation, but listed for reference.

Figure 3:
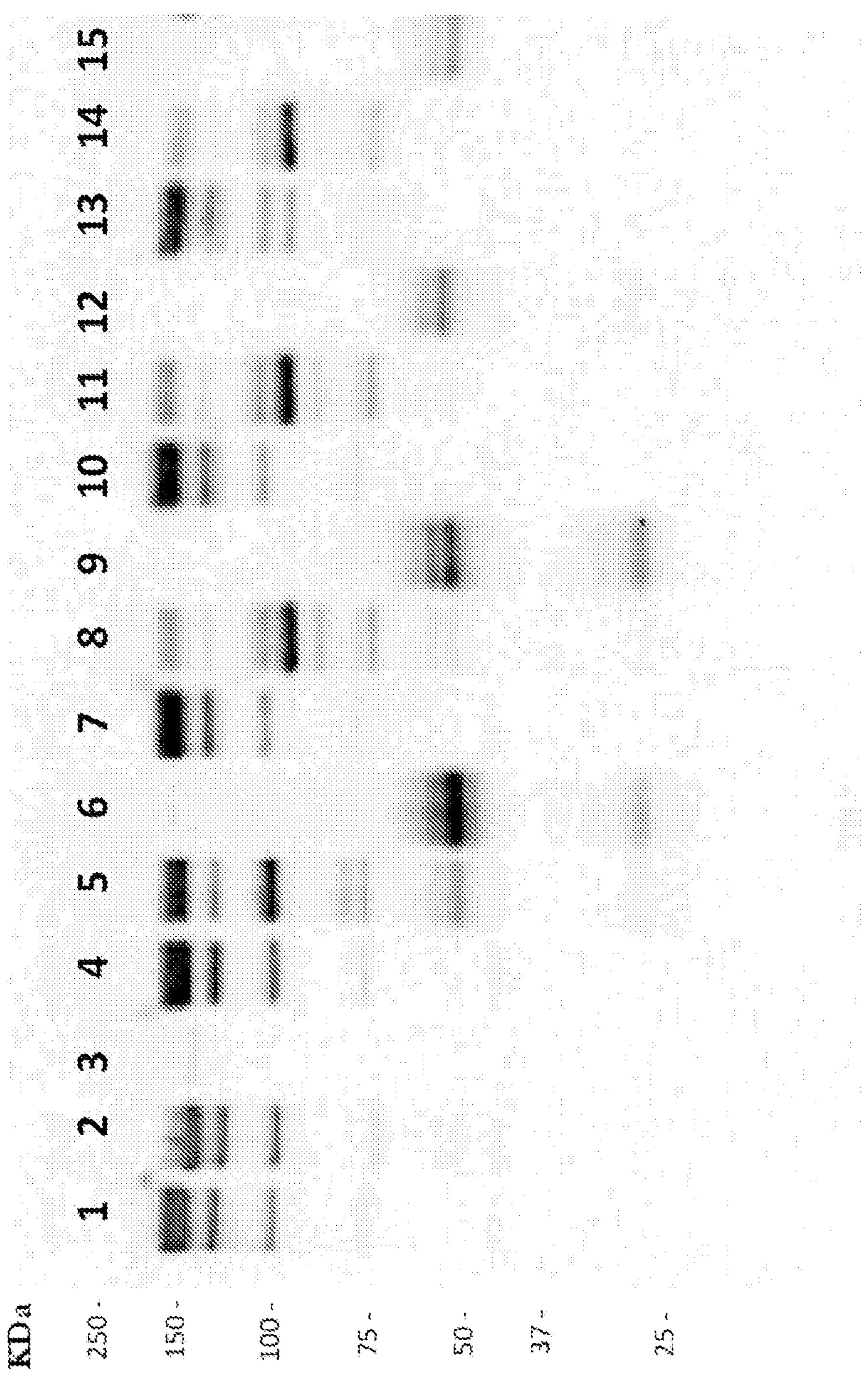

FIG. 3: Co-expression by transient transfections to assess the heterodimeric variant-Fc-region formation. Experiments are described in Example 2. Lane 1 contains cell supernatants from control transfections containing anti-HER2 antibody 4D5-8 IgG1 (comprising the amino acid sequences SEQ ID NOs. 4 and 8), lane 2 containing anti-HER2 antibody 2C4 IgG1 (which contains the amino acid sequences of SEQ ID NOs: 12 and 16), lane 3 containing no plasmid DNA to serve as a mock transfection control. As indicated, all other samples are in groups of three and contain cell supernatants from transfections containing the DNAs encoding combinations of anti-HER2 4D5-8 LC, anti-HER2 4D5-8 HC variants, and dummy Fc variants, as explained in Example 2. These antibodies are either unaltered (designated "WT") or altered in various positions in different lanes as indicated in the tables below. Positions of molecular weight standards are indicated at left.

TABLE 4

| Alterations in antibody chains in samples shown in FIG. 3 | | | |
|---|---|---|---|
| | Anti-HER2 4D5-8 human IgG1 | | Dummy Fc |
| Lane | LC | HC | Fc |
| 4 | WT | WT | |
| 5 | WT | WT | WT |
| 6 | | | WT |
| 7 | WT | S354C, Q362K, **K370K**, N390K, **K392K**, S400K | |
| 8 | WT | S354C, Q362K, **K370K**, N390K, **K392K**, S400K | Y349C, Q362D, K370D, N390D, K392I, S400D |
| 9 | | | Y349C, Q362D, K370D, N390D, K392I, S400D |
| 10 | WT | S354C, Q362K, **K370K**, **N390N**, **K392K**, S400K | |
| 11 | WT | S354C, Q362K, **K370K**, **N390N**, **K392K**, S400K | Y349C, Q362D, K370D, N390D, K392D, S400D |
| 12 | | | Y349C, Q362D, K370D, N390D, K392D, S400D |
| 13 | WT | S354C, Q362K, **K370K**, N390P, **K392K**, S400K | |
| 14 | WT | S354C, Q362K, **K370K**, N390P, **K392K**, S400K | Y349C, Q362D, K370D, N390D, K392G, S400D |
| 15 | | | Y349C, Q362D, K370D, N390D, K392G, S400D |

*Blank boxes indicate the absence of the chain listed in the heading above the box. Bolded residues are WT with no mutation, but listed for reference.

Figure 4:
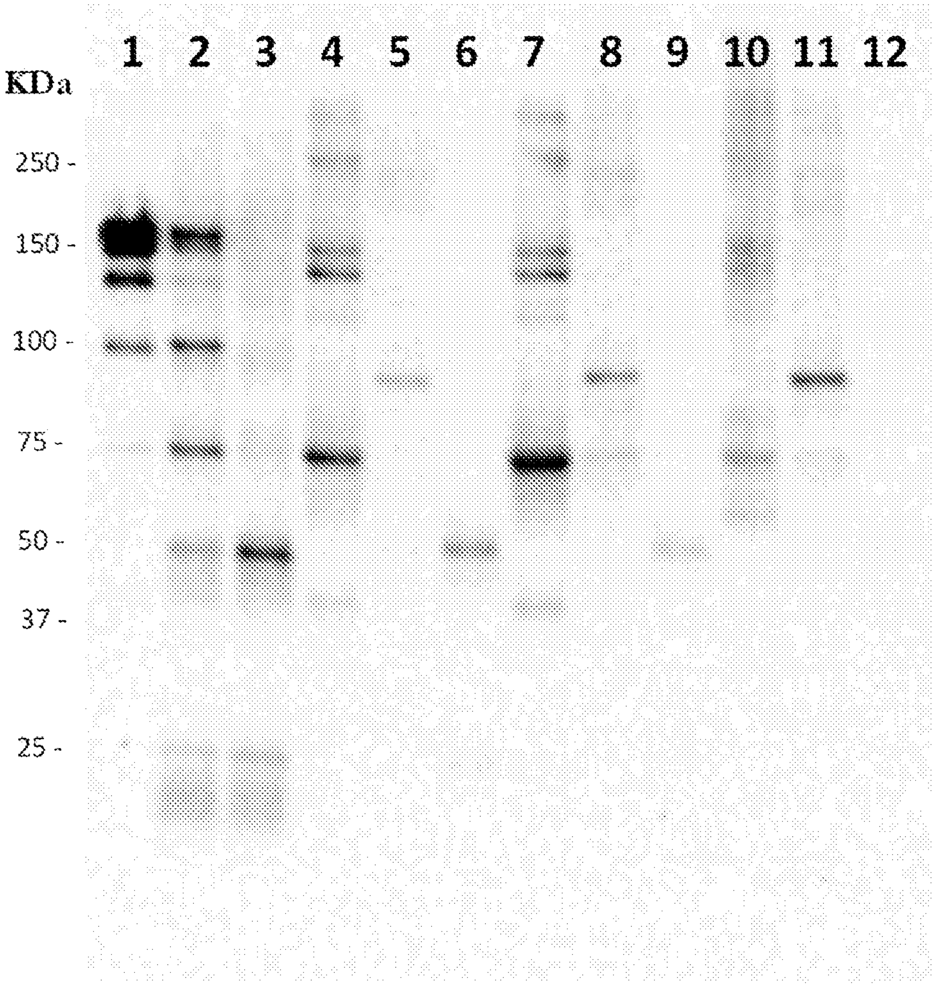

FIG. 4: Co-expression by transient transfections to assess the heterodimeric variant-Fc-region formation. Experiments are described in Example 2. As indicated, all samples are in groups of three and contain cell supernatants from transfections containing the DNAs encoding combinations of anti-HER2 4D5-8 LC, anti-HER2 4D5-8 HC variants, and dummy Fc variants, as explained in Example 2. These antibodies are either unaltered (designated "WT") or altered in various positions in different lanes as indicated in the tables below. Positions of molecular weight standards are indicated at left.

TABLE 5

| Alterations in antibody chains in samples shown in FIG. 4 | | | |
|---|---|---|---|
| | Anti-HER2 4D5-8 human IgG1 | | Dummy Fc |
| Lane | LC | HC | Fc |
| 1 | WT | WT | |
| 2 | WT | WT | WT |
| 3 | | | WT |
| 4 | WT | S354C, S364K, **K370K**, N390K, **K392K**, S400K | |
| 5 | WT | S354C, S364K, **K370K**, N390K, **K392K**, S400K | Y349C, S364D, K370D, N390D, K392I, S400D |
| 6 | | | Y349C, S364D, K370D, N390D, K392I, S400D |
| 7 | WT | S354C, S364K, **K370K**, **N390N**, **K392K**, S400K | |
| 8 | WT | S354C, S364K, **K370K**, **N390N**, **K392K**, S400K | Y349C, S364D, K370D, N390D, K392D, S400D |
| 9 | | | Y349C, S364D, K370D, N390D, K392D, S400D |
| 10 | WT | S354C, S364K, **K370K**, N390P, **K392K**, S400K | |
| 11 | WT | S354C, S364K, **K370K**, N390P, **K392K**, S400K | Y349C, S364D, K370D, N390D, K392G, S400D |
| 12 | | | Y349C, S364D, K370D, N390D, K392G, S400D |

*Blank boxes indicate the absence of the chain listed in the heading above the box. Bolded residues are WT with no mutation, but listed for reference.

Figure 5:
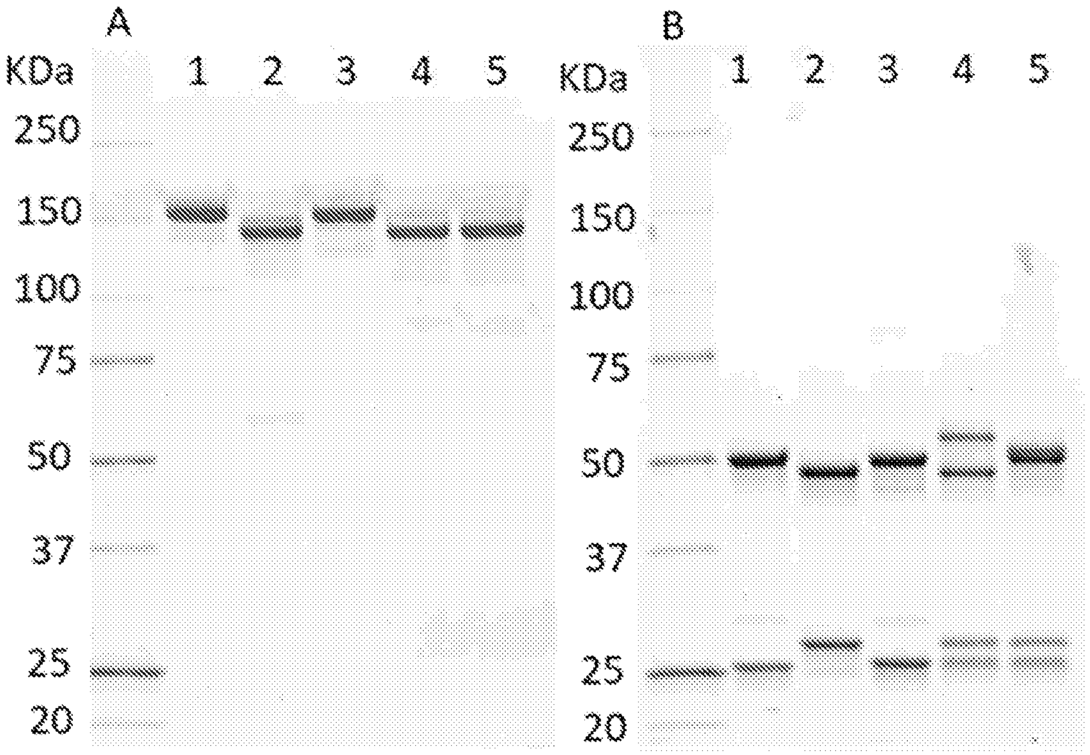

FIG. 5: SDS-PAGE analysis of non-reduced (panel A) and reduced (panel B) samples of purified antibodies. This experiment is described in Example 3. Leftmost lane contains molecular weight standards. Each lane contains 2 μg of non-reduced or reduced samples of the antibody. Lane 1 contains anti-HER2 4D5-8 IgG1 (comprising the amino acid sequences SEQ ID NOs: 4 and 8). Lane 2 contains anti-hCD20 Ab1.2 IgG (comprising the amino acid sequences SEQ ID NOs. 28 and 36). Lane 3 contains anti-hCD37 Ab1.A1 (comprising the amino acid sequences SEQ ID NOs. 40 and 48). Lane 4 contains bispecific anti-hCD20 (Ab1.2.5)×CD37 (Ab1.A1.2), the anti-hCD20 Ab1.2.5 comprises the amino acid sequences SEQ ID NOs. 30 and 36, and anti-hCD37 Ab1.A1.2 comprises the amino acid sequences SEQ ID NOs 42 and 50. Lane 5 contains bispecific anti-hCD20 (Ab1.2.6)×CD37 (Ab1.A1.3), the anti-hCD20 Ab1.2.6 comprises the amino acid sequences SEQ ID NOs. 32 and 36, and anti-hCD37 Ab1.A1.3 comprises the amino acid sequences SEQ ID NOs 44 and 50. Positions of molecular weight standards are indicated at left.

Figure 6:
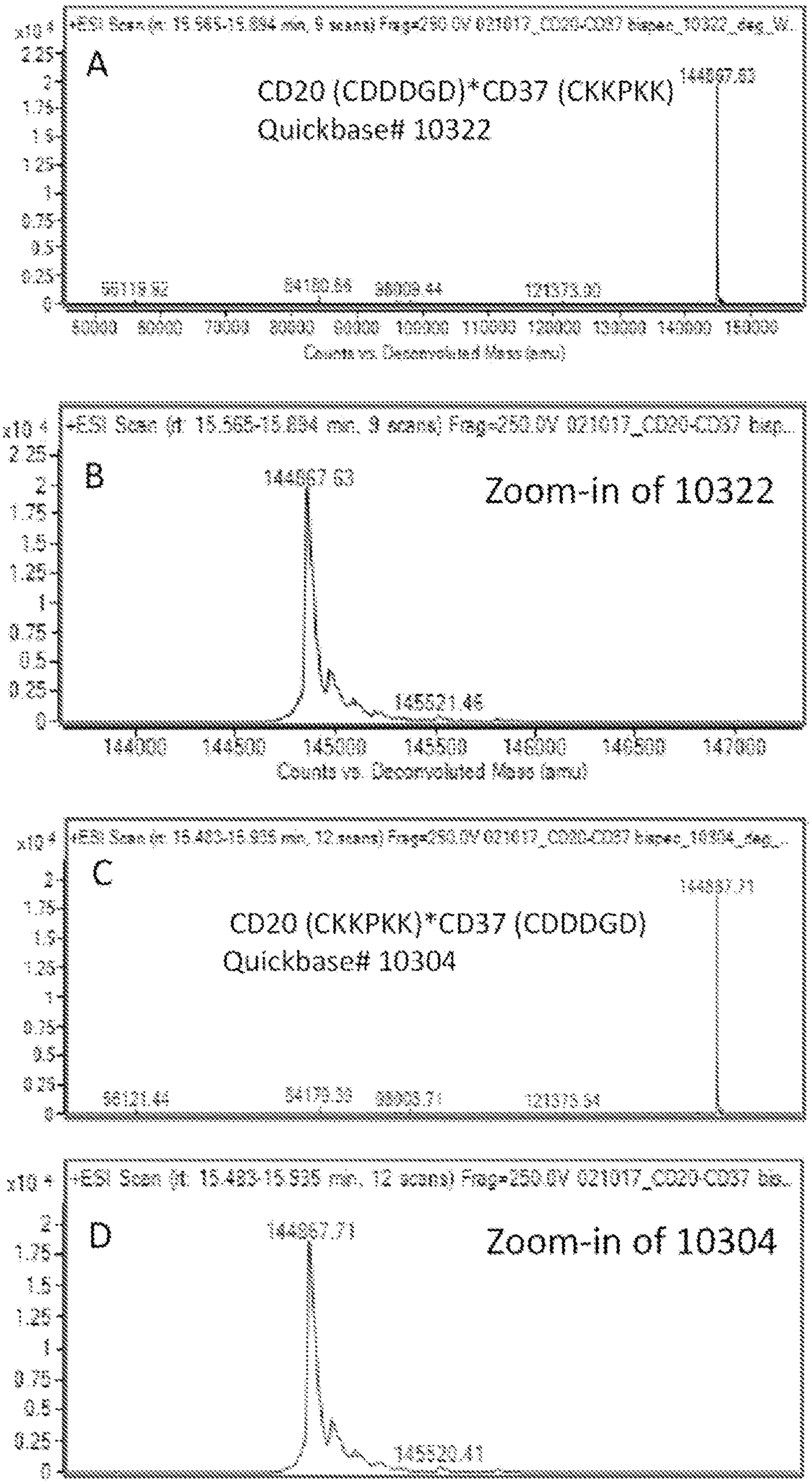

FIG. 6: Mass spectrometry analysis of intact anti-hCD20×CD37 bispecific antibody after deglycosylation by PNGase F. These experiments are described in Example 4. As indicated, the x axes show deconvoluted mass, and the y axes show counts, which are reflective of the quantity of protein at a given mass. Panel A, this panel shows analysis of the anti-hCD20 (Ab1.2.5)×CD37 (Ab1.A1.2) bispecific antibody, the anti-hCD20 Ab1.2.5 comprises the amino acid sequences SEQ ID NOs. 30 and 36, and anti-hCD37 Ab1.A1.2 comprises the amino acid sequences SEQ ID NOs 42 and 50. Panel B, zoom-in of panel A at around the mass of 150,000 daltons. Panel C, this panel shows analysis of the anti-hCD20 (Ab1.2.6)×CD37 (Ab1.A1.3) bispecific antibody, the anti-hCD20 Ab1.2.6 comprises the amino acid sequences SEQ ID NOs. 32 and 36, and anti-hCD37 Ab1.A1.3 comprises the amino acid sequences SEQ ID NOs 44 and 50. Panel D. zoom-in of panel C at around the mass of 150,000 daltons. The experimental mass of each peak is shown above the peak.

Figure 7:
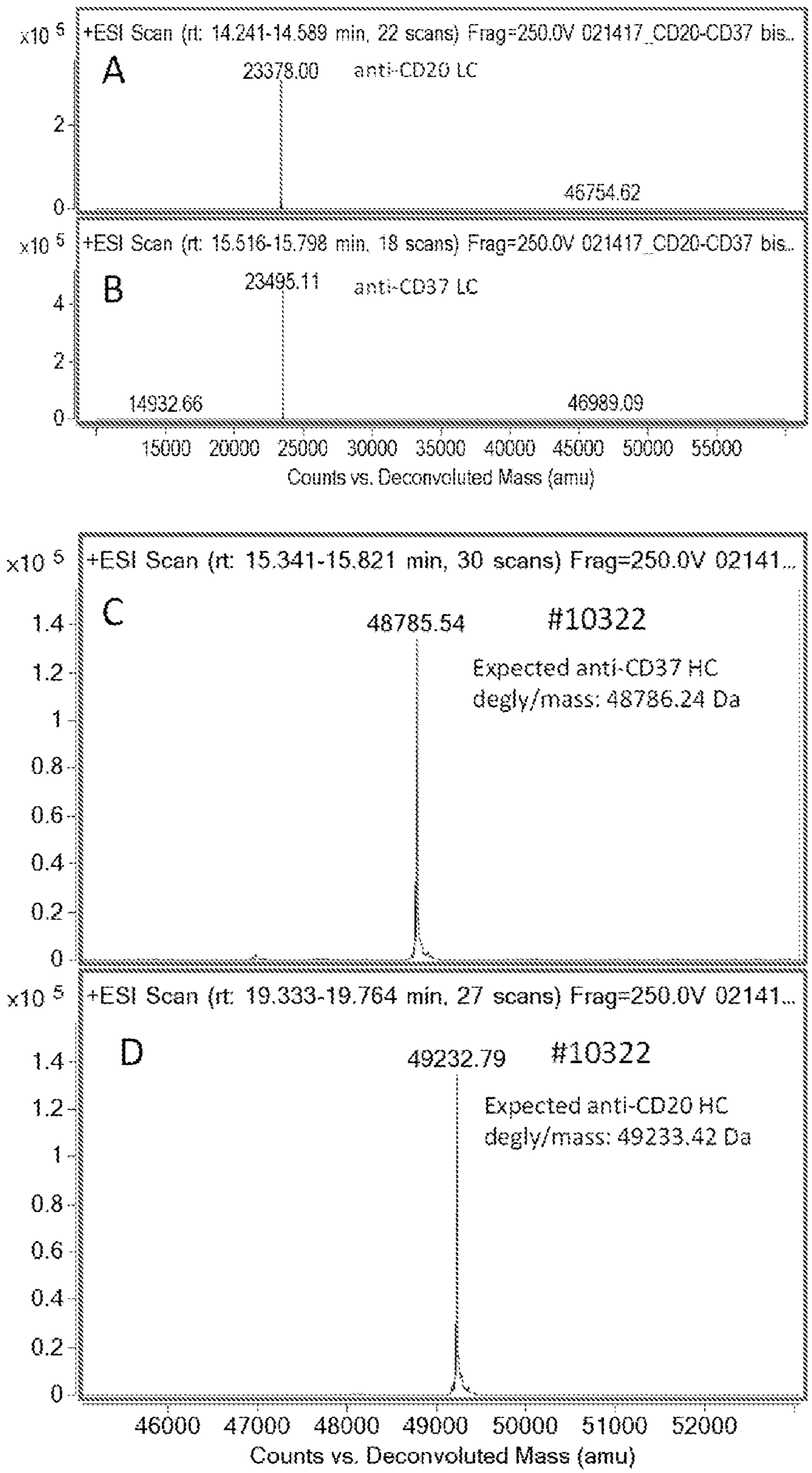

FIG. 7: Mass spectrometry analysis of reduced anti-hCD20 (Ab1.2.5)×CD37 (Ab1.A1.2) bispecific antibody after the treatment by PNGase F and 100 mM DTT. These experiments are described in Example 4. As indicated, the x axes show deconvoluted mass, and the y axes show counts, which are reflective of the quantity of protein at a given mass. Panel A, this panel shows analysis of the first LC of the anti-hCD20 (Ab1.2.5) in the context of anti-hCD20 (Ab1.2.5)×CD37 (Ab1.A1.2) bispecific antibody, corresponding to SEQ ID NO. 36. The theoretical mass is 23378.22 daltons. Panel B, this panel shows analysis of the second LC of anti-hCD37 (Ab1.A1.2) in the context of anti-hCD20 (Ab1.2.5)×CD37 (Ab1.A1.2) bispecific antibody, corresponding to SEQ ID NO. 50. The theoretical mass is 23495.15 daltons. Panel C, this panel shows analysis of the second HC of anti-hCD37 (Ab1.A1.2) in the context of anti-hCD20 (Ab1.2.5)×CD37 (Ab1.A1.2) bispecific antibody, corresponding to SEQ ID NO. 42. The theoretical mass is 48,786.24 daltons. Panel D, this panel shows analysis of the first HC of anti-hCD20 (Ab1.2.5) in the context of anti-hCD20 (Ab1.2.5)×CD37 (Ab1.A1.2) bispecific antibody, corresponding to SEQ ID NO. 30. The theoretical mass is 49,233.42 daltons.

Figure 8:
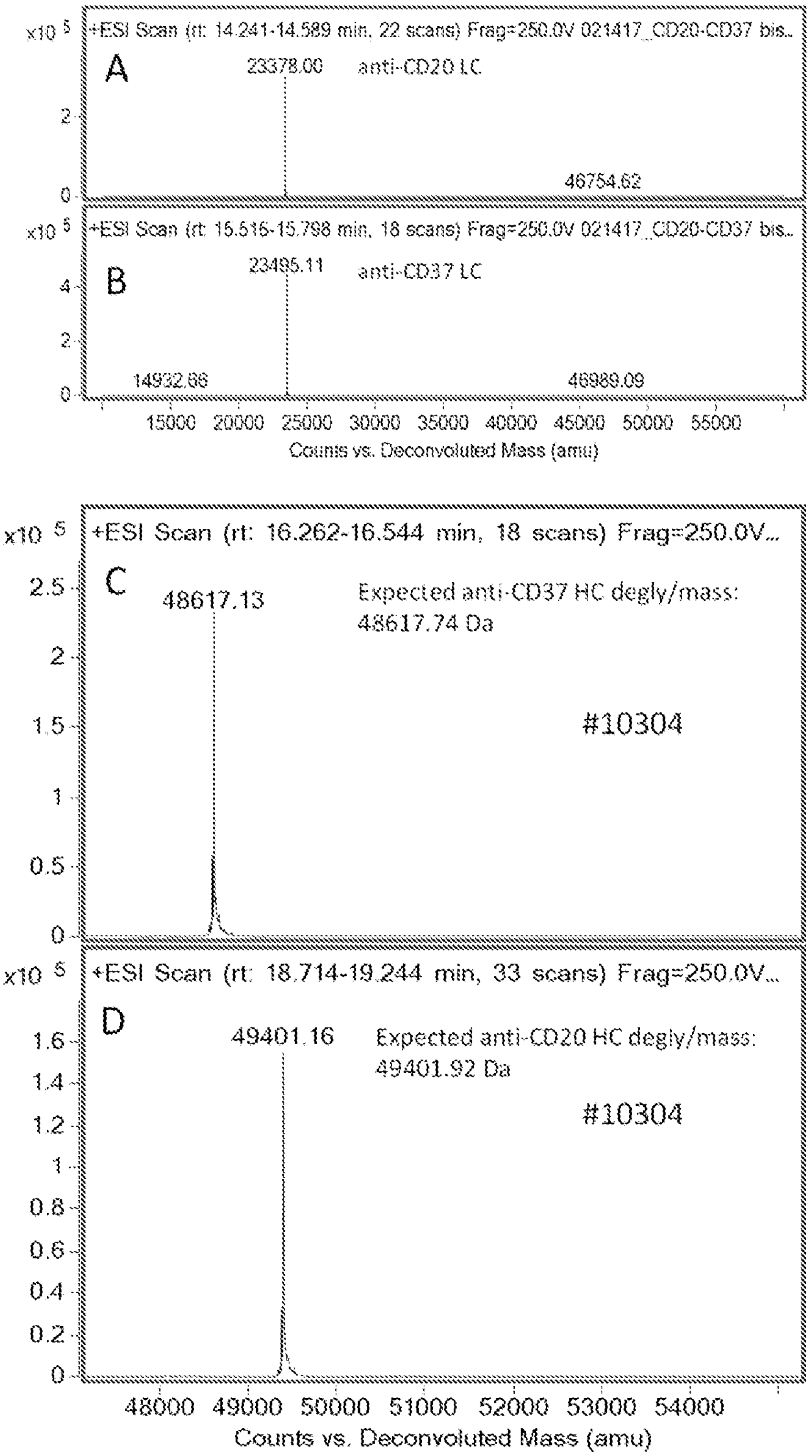

FIG. 8: Mass spectrometry analysis of reduced anti-hCD20 (Ab1.2.6)×CD37 (Ab1.A1.3) bispecific antibody after the treatment by PNGase F and 100 mM DTT. These experiments are described in Example 4. As indicated, the x axes show deconvoluted mass, and the y axes show counts, which are reflective of the quantity of protein at a given mass. Panel A, this panel shows analysis of the first LC of the anti-hCD20 (Ab1.2.6) in the context of anti-hCD20 (Ab1.2.6)×CD37 (Ab1.A1.3) bispecific antibody, corresponding to SEQ ID NO. 36. The theoretical mass is 23378.22 daltons. Panel B, this panel shows analysis of the second LC of anti-hCD37 (Ab1.A1.3) in the context of anti-hCD20 (Ab1.2.6)×CD37 (Ab1.A1.3) bispecific antibody, corresponding to SEQ ID NO. 50. The theoretical mass is 23495.15 daltons. Panel C, this panel shows analysis of the second HC of anti-hCD37 (Ab1.A1.3) in the context of anti-hCD20 (Ab1.2.6)×CD37 (Ab1.A1.3) bispecific antibody, corresponding to SEQ ID NO. 44. The theoretical mass is 48,617.74 daltons. Panel D, this panel shows analysis of the first HC of anti-hCD20 (Ab1.2.6) in the context of anti-hCD20 (Ab1.2.6)×CD37 (Ab1.A1.3) bispecific antibody, corresponding to SEQ ID NO. 32. The theoretical mass is 49,401.92 daltons.

Figure 9:
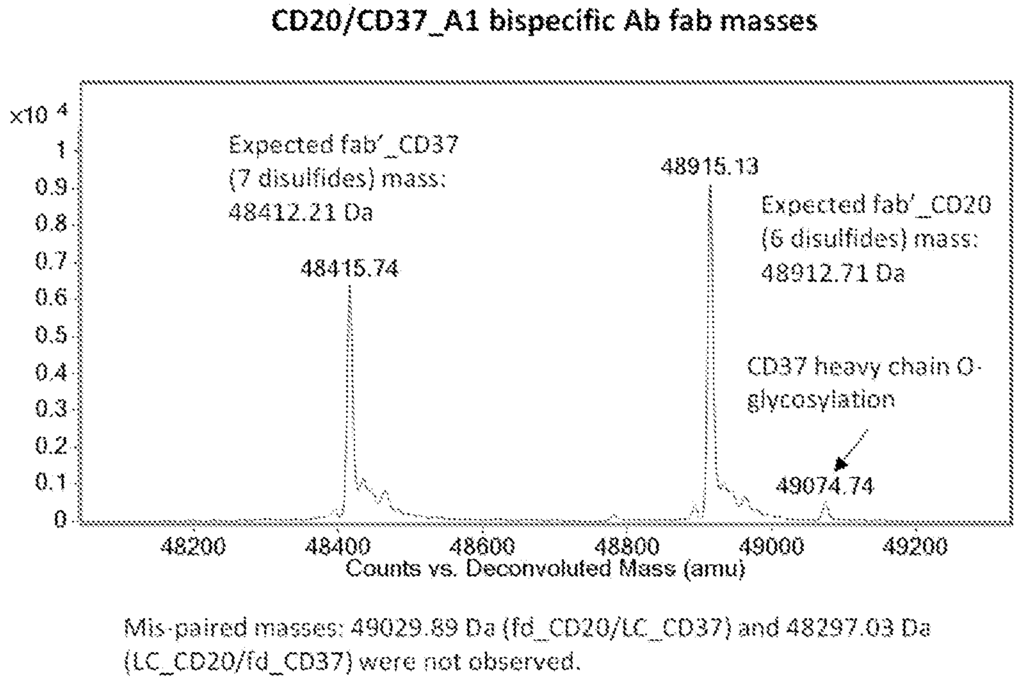

FIG. 9: Mass spectrometry analysis of Fab fragments from the anti-hCD20 (Ab1.2.5)×CD37 (Ab1.A1.2) bispecific antibody. The experiment is described in Example 4. The Fab fragments were generated by IdeS Protease digestion and followed by 2-MEA/EDTA treatment. As indicated, the x axis shows deconvoluted mass, and the y axis shows counts, which are reflective of the quantity of protein at a given mass. The expected masses of the two Fab fragments containing cognate HC/LC pairs are indicated, as are the actual masses of the fragments detected above each peak. The small peak at far right with 49074.74 daltons indicates the Fab fragment of anti-hCD37 in which the O-glycosylation was modified in the HC of anti-hCD37 antibody. The mass spectrometry analysis of Fab fragments from the other anti-hCD20 (Ab1.2.6)×CD37 (Ab1.A1.3) bispecific antibody was carried out in the same way, and the same results were obtained (not shown) because these two bispecific antibodies contain the same Fab fragments but differ in the variant-Fc-regions.

Figure 10:
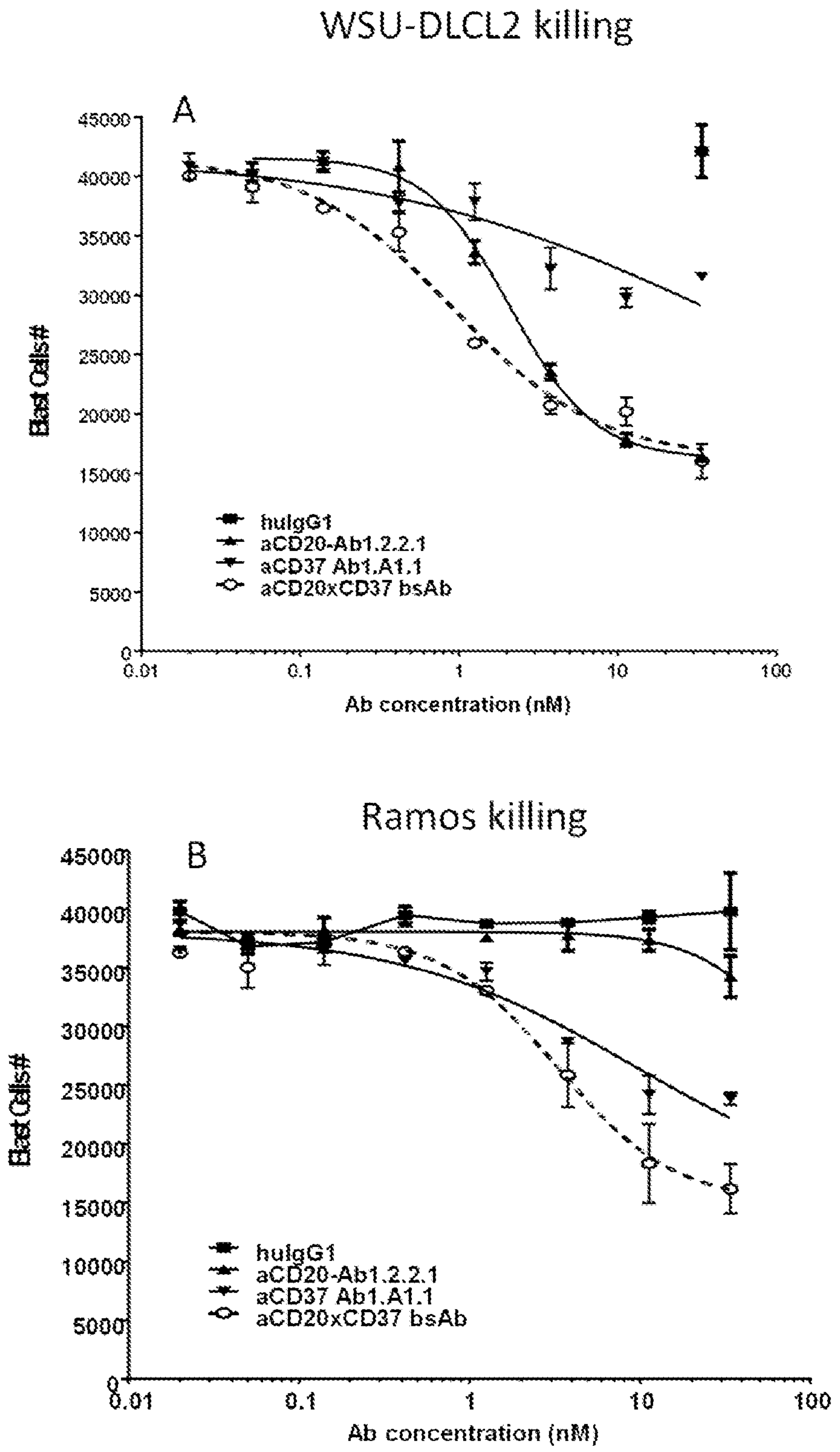

FIG. 10: Direct cell killing of anti-hCD20 and anti-hCD37 antibodies on WSU-DLCL2 cells (A) and Ramos cells (B). This experiment is described in Example 5. The antibodies used as samples in the experiment are indicated as follows: huIgG1, a control IgG1/κ isotype control antibody. aCD20 Ab1.2.2.1, an anti-hCD20 IgG4/1 hybrid antibody that contains the $C_H1$ and upper hinge regions from human IgG4, hinge and CH2 and CH3 regions from human IgG1. Substitutions of S239D and S298A for ADCC enhancement, and D399R and K409E for MabPair formation were introduced in its HC. The amino acid sequences for LC and HC are listed as SEQ ID NOs 36 and 76, respectively. aCD37 Ab1.A1.1, an anti-hCD37 IgG1 antibody that contains DCCG and K409R substitutions in HC; KCCS substitutions in LC. The amino acid sequences for LC and HC are listed as SEQ ID NOs 50 and 78, respectively. aCD20×C37 bsAb, the heterodimeric variant-Fc-region anti-hCD20 (Ab1.2.5)×CD37 (Ab1.A1.2) bispecific antibody, the amino acid sequences are listed as SEQ ID NOs 30 and 36 for anti-hCD20 (Ab1.2.5), SEQ ID NOs 42 and 50 for anti-hCD37 (Ab1.A1.2) antibody. The vertical Y axis indicates the number of blast cells. The horizontal X axis indicates the concentration of the antibody in the sample in nanomoles/liter (nM).

Figure 11:
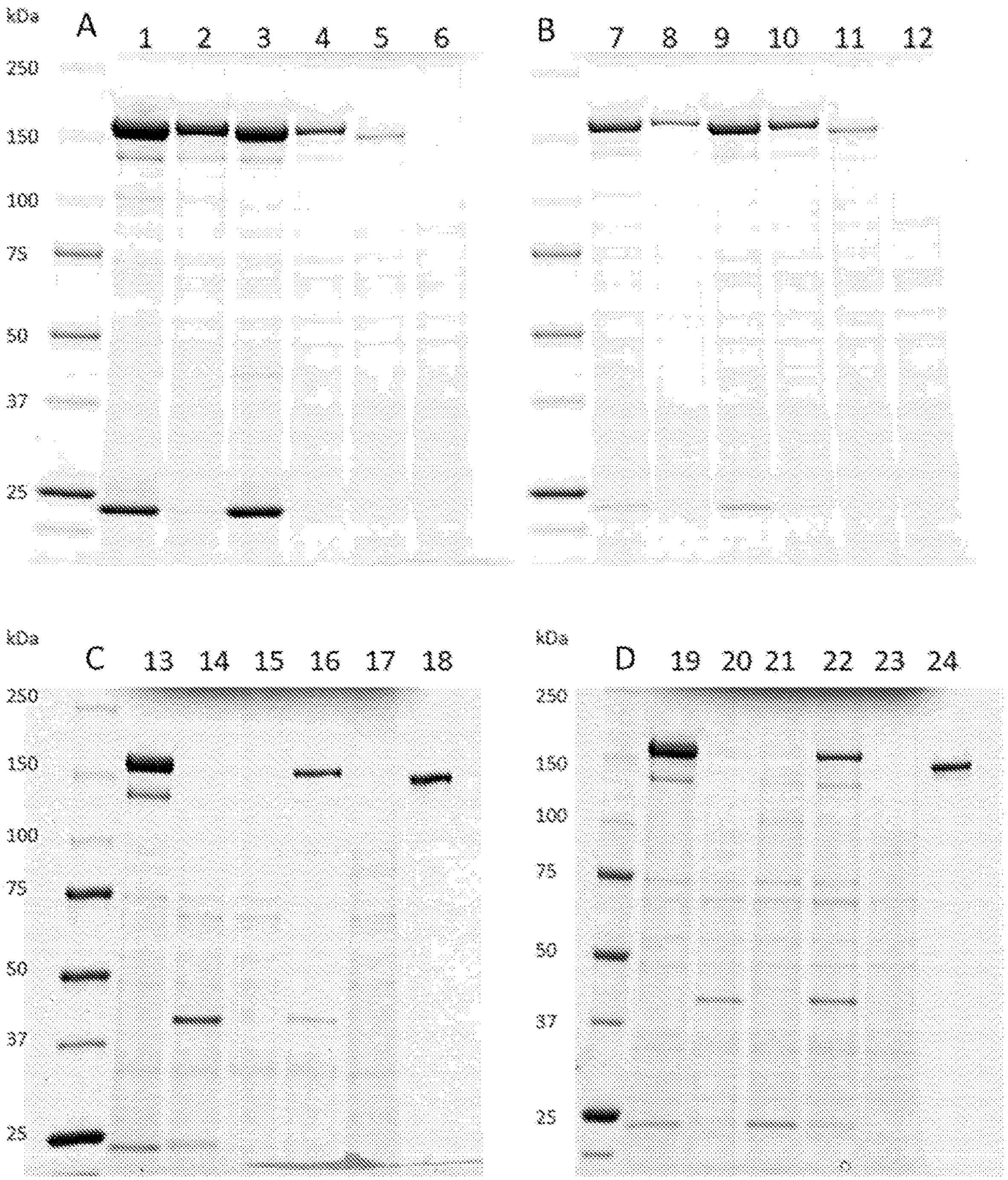

FIG. 11: Co-expression by transient transfections to assess the HC/LC pairings of anti-hSIRPα and anti-hCLDN18.2 before (panels A and B) and after (panels C and D) antibody engineering. Experiments are described in Example 6. Panels A and B are supernatant from duplicated transfected Expi293 cells in SDS-PAGE gel. Lanes 1 and 7 contain cell supernatants from transfections containing anti-hCLDN18.2 antibody 59F9E1 IgG1 WT (SEQ ID NOs 54 and 62); lanes 4 and 10 contain cell supernatants from transfections containing anti-hSIRPα antibody #24 IgG WT (SEQ ID NOs 68 and 74); lanes 2 and 8 contain cell supernatants from transfections containing the HC of anti-hCLDN18.2 antibody 59F9E1 IgG1 (SEQ ID NO 54) and LC of anti-hSIRPα antibody #24 (SEQ ID NO:74); lanes 3 and 9 contain cell supernatants from transfections containing the HC of anti-hSIRPα antibody #24 (SEQ ID NO:68) and LC of anti-hCLDN18.2 antibody 59F9E1 IgG1 (SEQ ID NO:62); lanes 5 and 11 contain cell supernatants from transfections containing the HC (SEQ ID NO:80) and LC (SEQ ID NO:82) of anti-DNP IgG1 antibody which served as a positive control for the 24 deep well transfection; lanes 6 and 12 contain cell supernatants from mock transfections in which no plasmid DNA was used. Panels C and D are supernatant from duplicated transfected Expi293 cells in SDS-PAGE gel. Lanes 13 and 19 contain cell supernatants from transfections containing the cognate HC1 with DCCG and LC1 with KCCS of engineered anti-hCLDN18.2 antibody 59F9E1 IgG1 (comprising the amino acid sequences SEQ ID NOs. 56 and 64); lanes 14 and 20 contain cell supernatants from transfections containing the mis-paired HC1 with DCCG from anti-hCLDN18.2 (SEQ ID NO:56) and LC2 from anti-hSIRPα (SEQ ID NO:74); lanes 15 and 21 contain cell supernatants from transfections containing mis-paired HC2 from anti-hSIRPα (SEQ ID NO:70) and LC1 with KCCS from anti-hCLDN18.2 (SEQ ID NO: 64); lanes 16 and 22 contain cell supernatants from transfections containing cognate HC2 (SEQ ID NO:70) and LC2 (SEQ ID NO:74) from anti-hSIRPα IgG; lanes 17 and 23 contain cell supernatants from mock transfections in which no plasmid DNA was used; lanes 18 and 24 contain protein A purified irrelevant anti-DNP IgG1 antibody (SEQ ID NOs: 80 and 82) for size reference.

Figure 12:
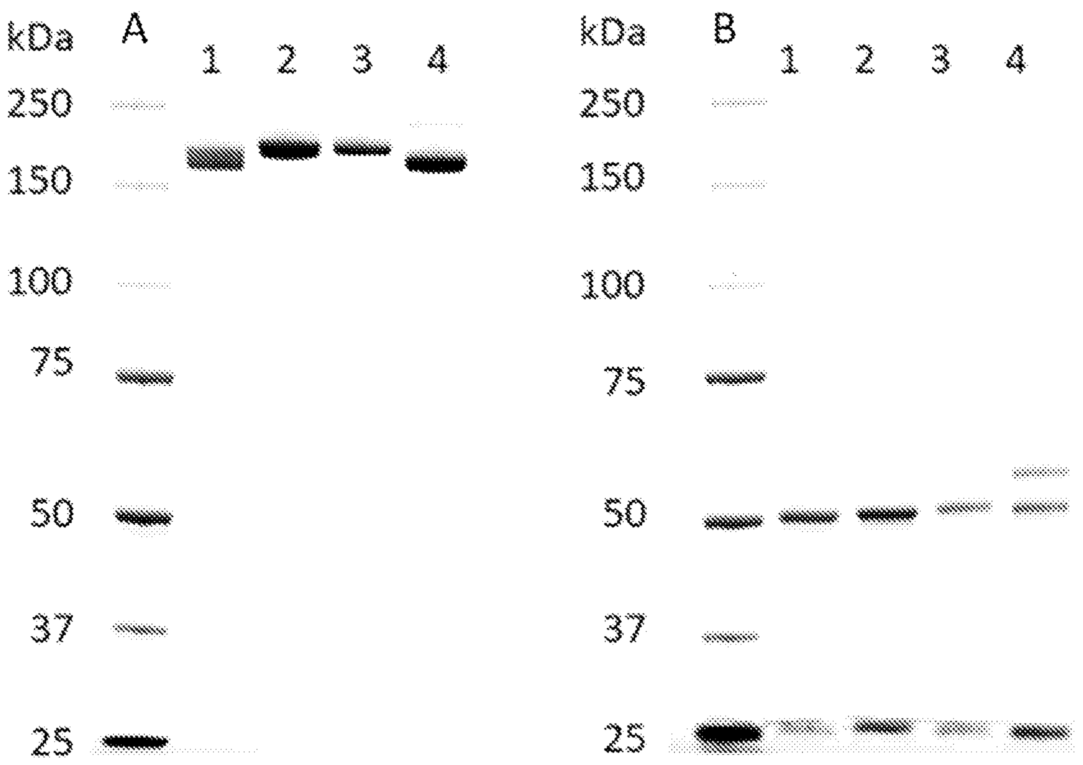

FIG. 12: SDS-PAGE analysis of non-reduced (A) and reduced (B) anti-hSIRPα and anti-hCLDN18.2 antibodies. This experiment is described in Example 6. Leftmost lane contains molecular weight standards. Each lane contains 2 μg of non-reduced or reduced samples of the antibody. Lane 1 contains anti-HER2 4D5-8 IgG1 antibody which is encoded by SEQ ID NOs 4 and 8. Lane 2 contains anti-hSIRPα IgG antibody which is encoded by SEQ ID NOs 68 and 74. Lane 3 contains anti-hCLDN18.2 clone 59F9E1 IgG1 which is encoded by SEQ ID NOs 54 and 62. Lane 4 contains the heterodimeric variant-Fc-region anti-hSIRPα× CLDN18.2 bispecific antibody which is encoded by SEQ ID NOs 70 and 74 for anti-hSIRPα, SEQ ID NOs 58 and 64 for anti-hCLDN18.2 antibody. Positions of molecular weight standards are indicated at left.

Figure 13:
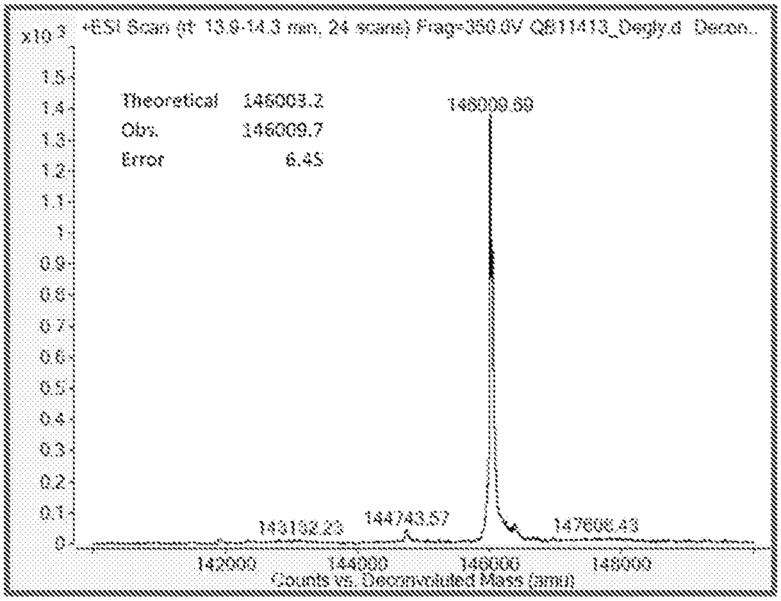
Figure 13:
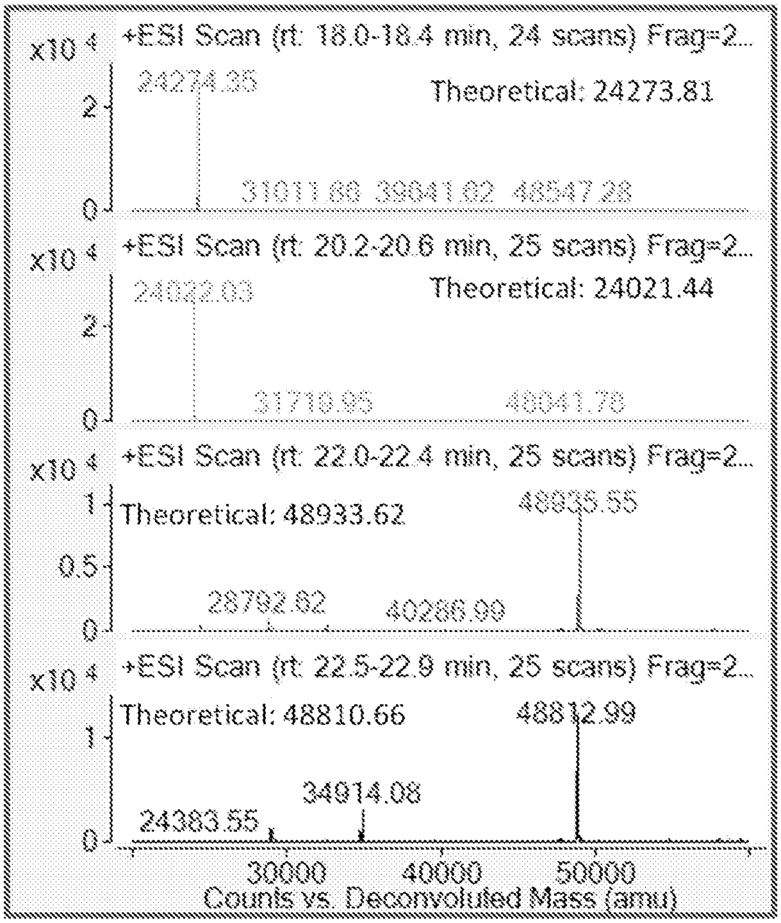

FIG. 13: Mass spectrometry analysis of the non-reduced (A) and reduced (B) anti-hSIRPα×anti-hCLDN18.2 bispecific antibody. These experiments are described in Example 7. As indicated, the x-axes show deconvoluted mass, and the y-axes show counts, which are reflective of the quantity of protein at a given mass. Panel A shows the analysis of the bispecific antibody after deglycosylation by PNGase F under non-reducing conditions, the anti-hSIRPα part is encoded by SEQ ID NOs 70 and 74, the anti-hCLDN 18.2 part is encoded by SEQ ID NOs 58 and 64. The theoretical (164003.2 Da) and observed (146009.7 Da) masses are indicated as well as the error (6.45 Da). Panel B shows the analysis of reduced anti-hSIRPα×anti-hCLDN18.2 bispecific antibody after the treatment by PNGase F and 100 mM DTT to obtain the reduced mass of individual chains. The top electropherogram reveals the main peak with a mass of 24274.35 Da which closely matches the theoretical mass of anti-hCLDN18.2 LC, SEQ ID NO:64 (24273.81 Da). The second electropherogram has a peak at 24022.03 Da which closely matches the theoretical mass of anti-hSIRPα LC, SEQ ID NO:74 (24021.44 Da). The third electropherogram shows a peak at 48935.55 Da and corresponds to anti-hCLDN18.2 HC, SEQ ID NO:58 (48935.55 Da). The fourth electropherogram has a peak at 48812.99 which matches the anti-hSIRPα HC, SEQ ID NO:70 (48810.66 Da).

Figure 14:
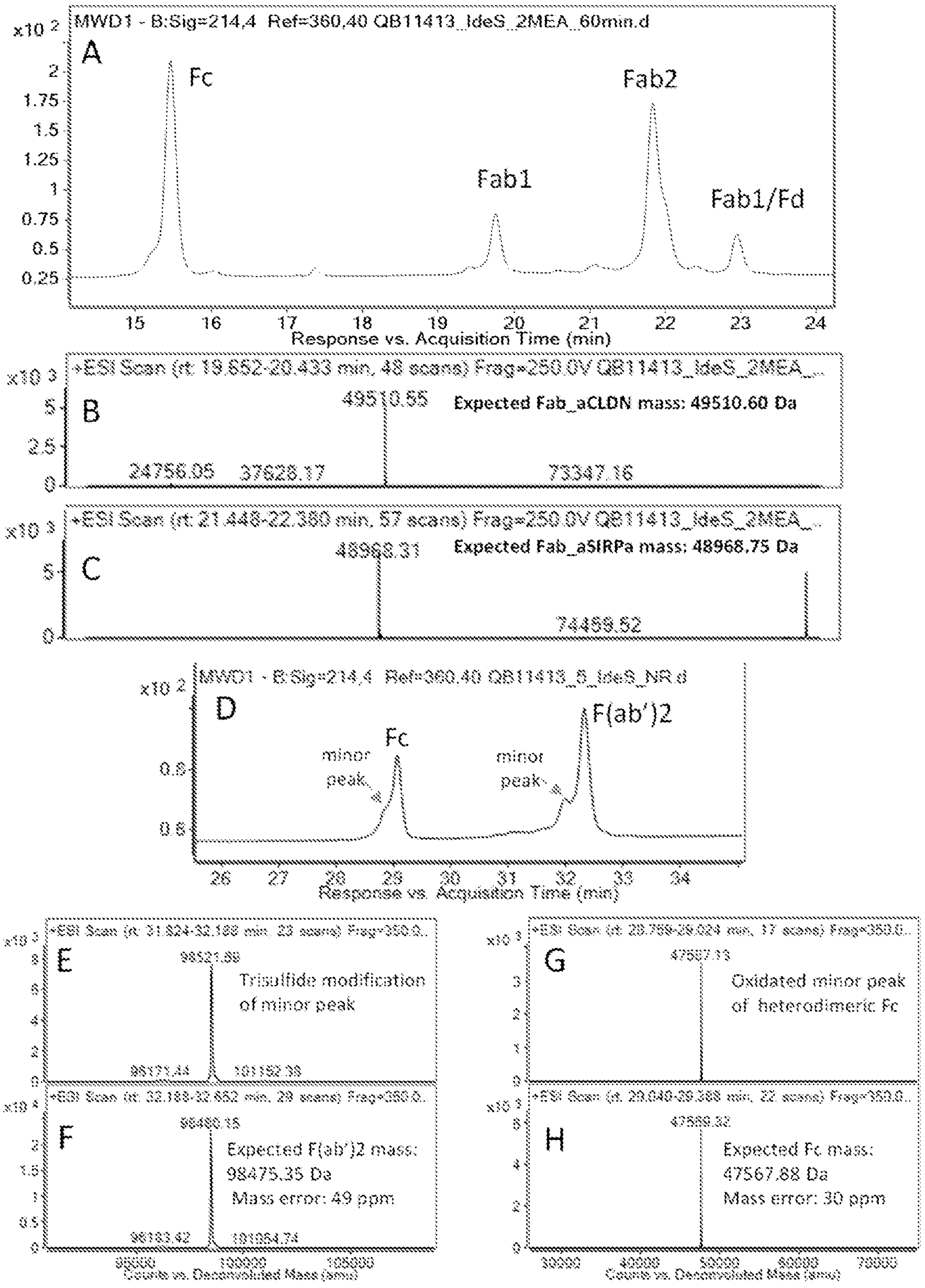

FIG. 14: Mass spectrometry analysis of Fab and F(ab')2 fragments from the anti-hSIRPα×anti-hCLDN18.2 bispecific antibody. The experiment is described in Example 7. As indicated, the x-axis shows deconvoluted mass, and the y axis shows counts, which are reflective of the quantity of protein at a given mass. Panels A to C: the Fab fragments were generated by IdeS Protease digestion and followed by 2-MEA/EDTA treatment. Panel A shows the U.V. traces with the 4 annotated peaks. The peak on the far right matches the incompletely digested Fab of anti-hSIRPα which is attached to the Fd of aCLDN18.2. Panel B shows the mass peak with 49,510.55 Da containing the Fab fragment of anti-hCLDN18.2 with expected mass of 49,510.60 Da. Panel C shows the mass peak with 48,968.31 Da containing the Fab fragment of anti-hSIRPα with expected mass of 48,968.75 Da. Panels D to H show the analysis of F(ab')2 and Fc fragments from an anti-hSIRPα×anti-hCLDN18.2 bispecific. Samples were deglycosylated by PNGase F and digested by IdeS Protease to generate the F(ab')2 and Fc Fragments. Panel D indicates the UV traces of Fc and F(ab')2 fragments. Panels E and F are deconvoluted masses of the F(ab')2 peaks while Panels G and H are deconvoluted masses of the Fc peaks. Panel F indicates the mass of the main peak of the expected F(ab')2 fragment while panel H indicates the mass of the main peak of the heterodimeric Fc fragment. Panels E and G are the minor peaks that are compatible with post-translational modifications of the F(ab')2 and Fc, respectively. Both panels E and G do not match potential mismatched fragments. As indicated, the x-axis shows time or deconvoluted mass, and the y axis shows counts, which are reflective of the quantity of protein at a given mass.

Figure 15:
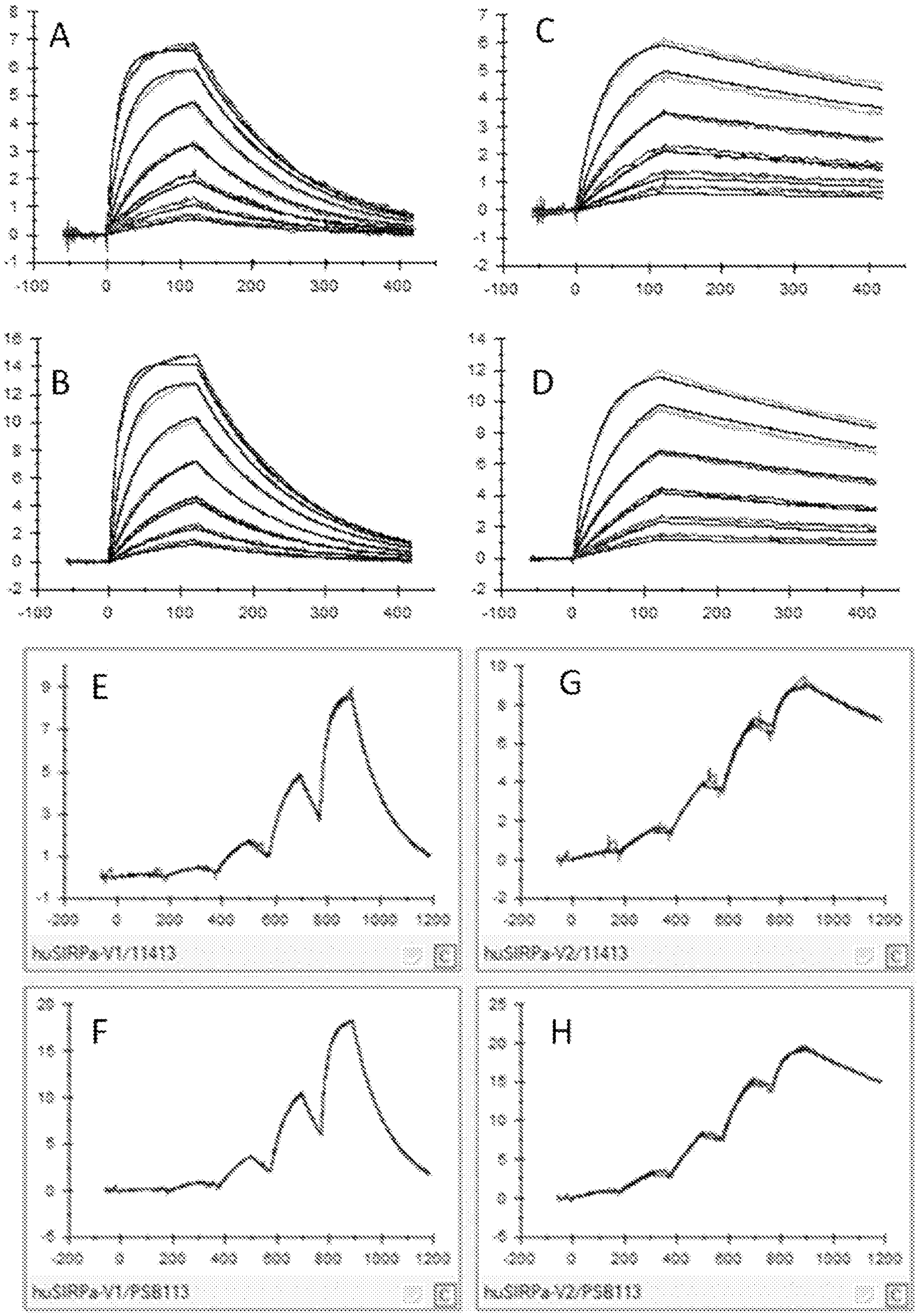

FIG. 15: Kinetic analysis of anti-hSIRPα×anti-hCLDN18.2 bispecific antibody binding to human SIRPα v1 and v2 alleles by Biacore measurement. The experiment is described in Example 8. Antibodies were captured to the CM5 chip surface on which goat anti-human polyclonal antibody (Fc specific) was immobilized. Monomeric huSIRPa-v1 and huSIRPa-v2 were used as analytes and were injected for a 2-minute association period followed by a 5-minute dissociation period. Each concentration was run in duplicates. For human SIRPα v1 the incremental concentrations used are 3.13, 6.25, 12.5, 25, 50, 100, or 200 nM; For human SIRPα v2 the incremental concentrations used are 0.78, 1.56, 3.13, 6.25, 12.5, or 25 nM. At the end of each analyte injection, the chip was either regenerated with 10 mM glycine-HCl, pH 1.5 (Panels A-D) for multi-cycle kinetics or not regenerated (Panels E-H) for single-cycle kinetics. Data were evaluated using the Biacore T200 Evaluation Software, version 3.2. Data was double referenced then fit with a 1:1 binding model. Panels A and E indicate the binding of anti-hSIRPα×anti-hCLDN18.2 bispecific antibody to hSIRPα v1, panels B and F indicate the binding of anti-hSIRPα #24 IgG antibody to hSIRPα v1, panels C and G indicate the binding of anti-hSIRPα×anti- hCLDN18.2 bispecific antibody to human SIRPα v2, panels D and H indicate the binding of anti-hSIRPα #24 IgG antibody to human SIRPα v2. The x-axis represents the time (seconds), the y-axis represents the RU (Response Units).

Figure 16:
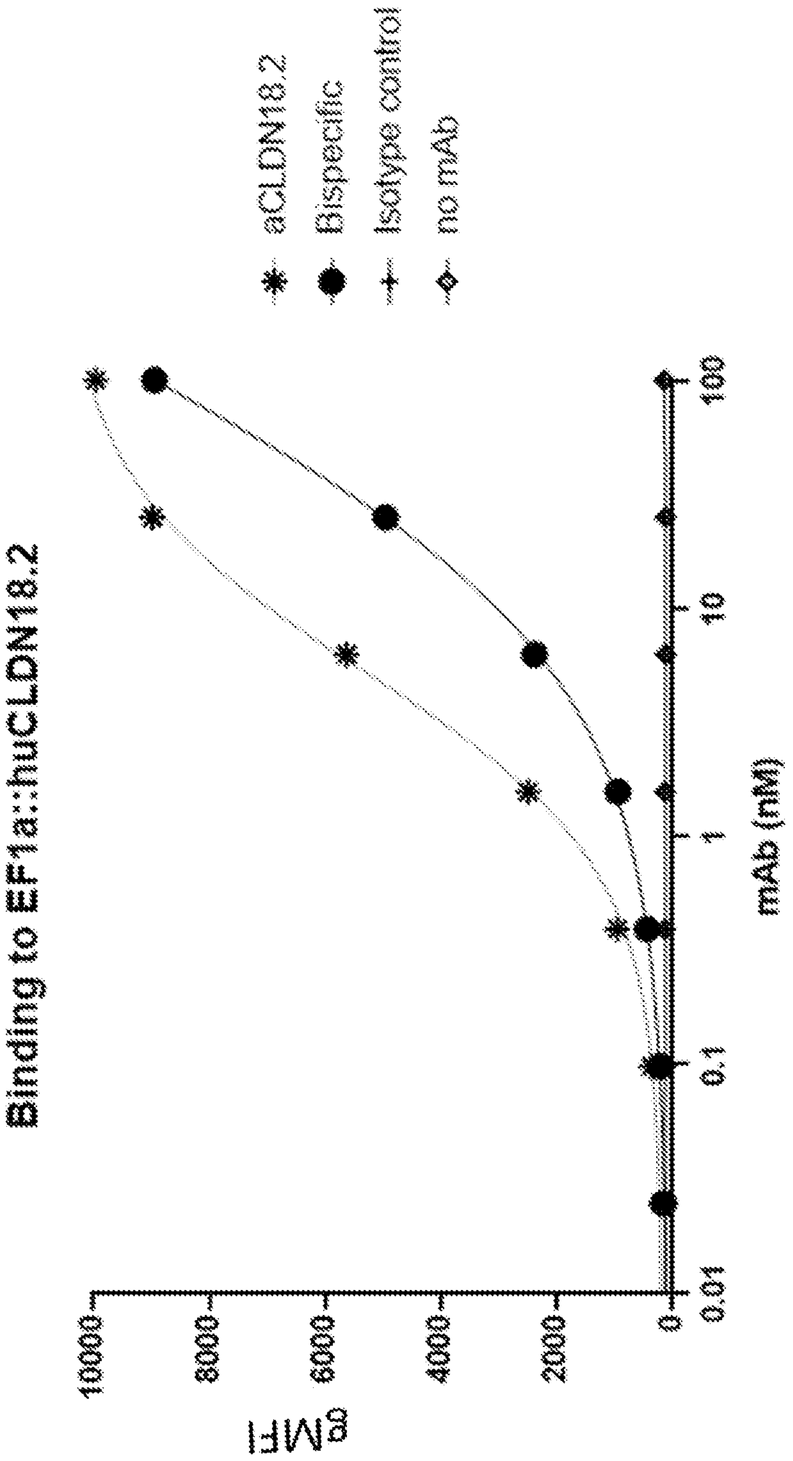

FIG. 16: Binding of anti-hSIRPα×anti-hCLDN18.2 bispecific antibody to human claudin 18.2 protein expressed on Expi293 cell surfaces after stable transfection. The experiments are described in Example 9. A plasmid DNA containing the human CLDN18.2 cDNA under the control of the human EF1a promoter was used for transfection of Expi293 cells, and stable pools were obtained under G418 selection. Cells were incubated with an anti-CLDN18.2 antibody (aCLDN18.2), anti-hSIRPα×anti-hCLDN18.2 bispecific antibody (Bispecific), an IgG1 isotype control (Isotype control), or buffer only (no mAb). Binding was detected using a secondary antibody specific to the human Fc and conjugated with the fluorophore APC, samples were run on an LSRII flow cytometer. X axis represents the antibody concentration (nM) and Y axis represents the binding intensity as gMFI (geometric mean fluorescence intensity).

Figure 17:
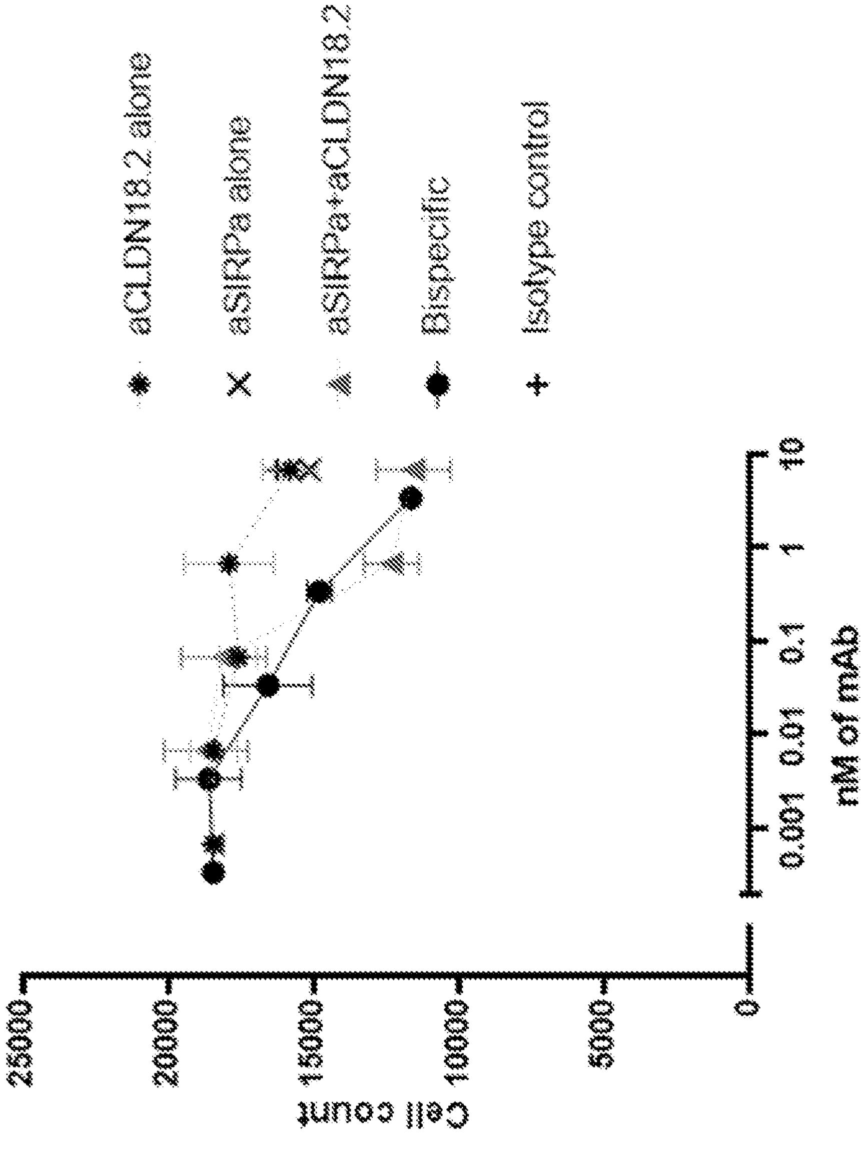

FIG. 17: Antibody dependent cell phagocytosis (ADCP) killing of PaTu 8898s cells induced by antibodies and macrophages. The experiment is described in Example 10. PaTu 8898s cells were incubated with anti-hSIRPα antibody (aSIRPα alone) or IgG1 isotype control (Isotype control) at the highest concentration (10 μg/ml), or the anti-hCLDN18.2 antibody (aCLDN18.2 alone), the combination of anti-hCLDN18.2 antibody and anti-hSIRPα antibody (aSIRPa+aCLDN18.2), or the anti-hSIRPα×anti-hCLDN18.2 bispecific antibody (Bispecific) with 1:3 series dose titrations. X axis represents the antibody concentration (nM), Y axis represents the counts of PaTu 8898s cells left in each well after 48 hours of incubation. EC50 (nM) numbers of fitted curves are shown at the bottom.

Figure 18:
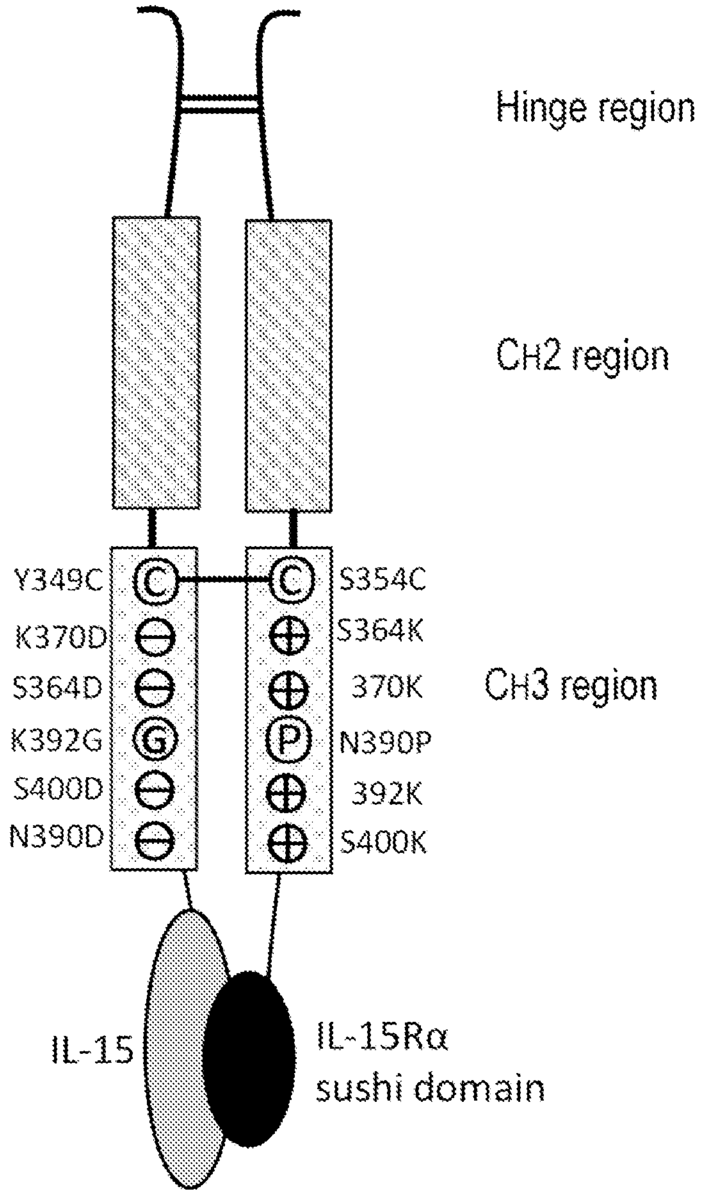

FIG. 18: Schematic representation of the Fc-IL15×Fc-IL15Ra sushi domain construct. The DNA encoding the human IL15 is fused to the C-terminus of a IgG1 Fc fragment which contains 6 substitutions (Y349C, K370D, S364D, K392G, S400D, N390D). The DNA encoding the human IL15Ra sushi domain is fused to the C-terminus of a IgG1 Fc fragment which contains 4 substitutions (S354C, S364K, N390P, S400K), two other native basic residues (370K and 392K) are involved in the interaction networks. With the combination effect of electrostatic steering and formation of disulfide bond between Y349C and S354C, the two different chains come together to form heterodimeric Fc fusion molecules, whereas the production of homodimeric Fc molecules are prevented.

Figure 19:
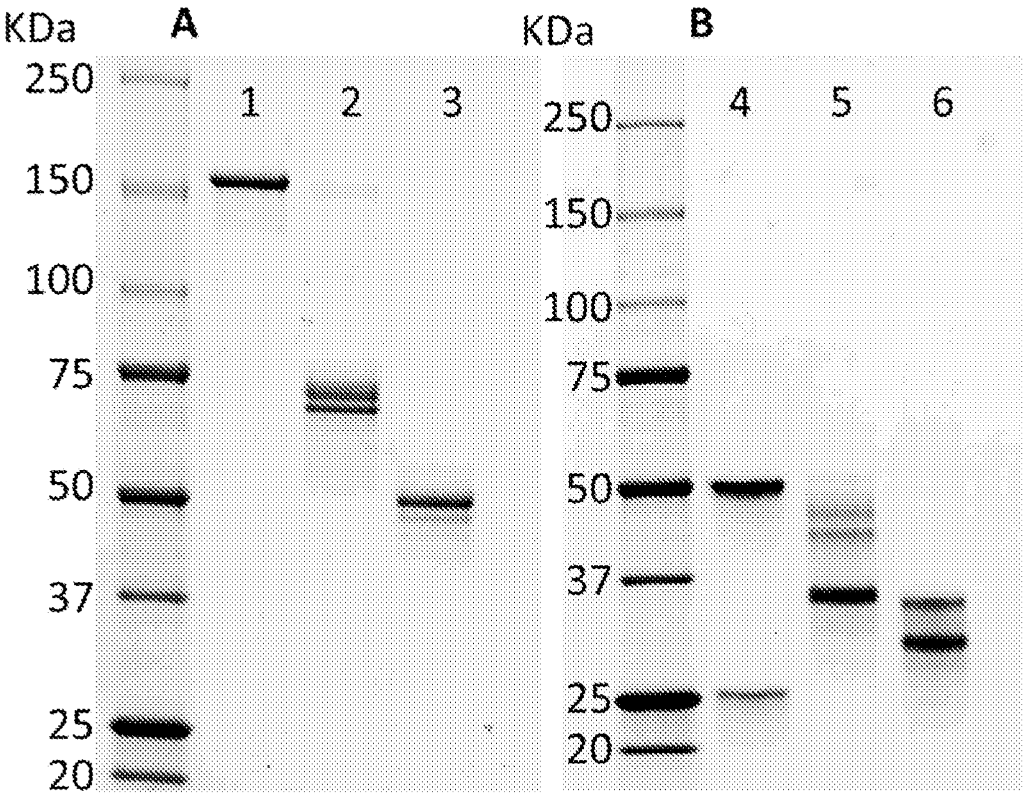

FIG. 19: SDS-PAGE analysis of non-reduced (panel A) and reduced (panel B) samples of purified antibody and Fc fusion protein. This experiment is described in Example 12. The leftmost lane contains molecular weight standards. Each lane contains 2 μg of sample. On panel A, Lane 1 contains anti-HER2 4D5-8 IgG1 (comprising the amino acid sequences SEQ ID NOs: 4 and 8). Lane 2 contains Hetero-Fc construct with Fc-IL15×Fc-IL15Rα sushi domain (comprising the amino acid sequences SEQ ID NOs. 108 and 110). Lane 3 contains the control dummy Fc heterodimer (comprising the amino acid sequences SEQ ID NOs. 112 and 114). On panel B, Lanes 4, 5, and 6 contain the same samples as in lanes 1, 2 and 3 respectively with the addition of 100 mM dithiothreitol (DTT) to reduce the disulfide bonds.

Figure 20:
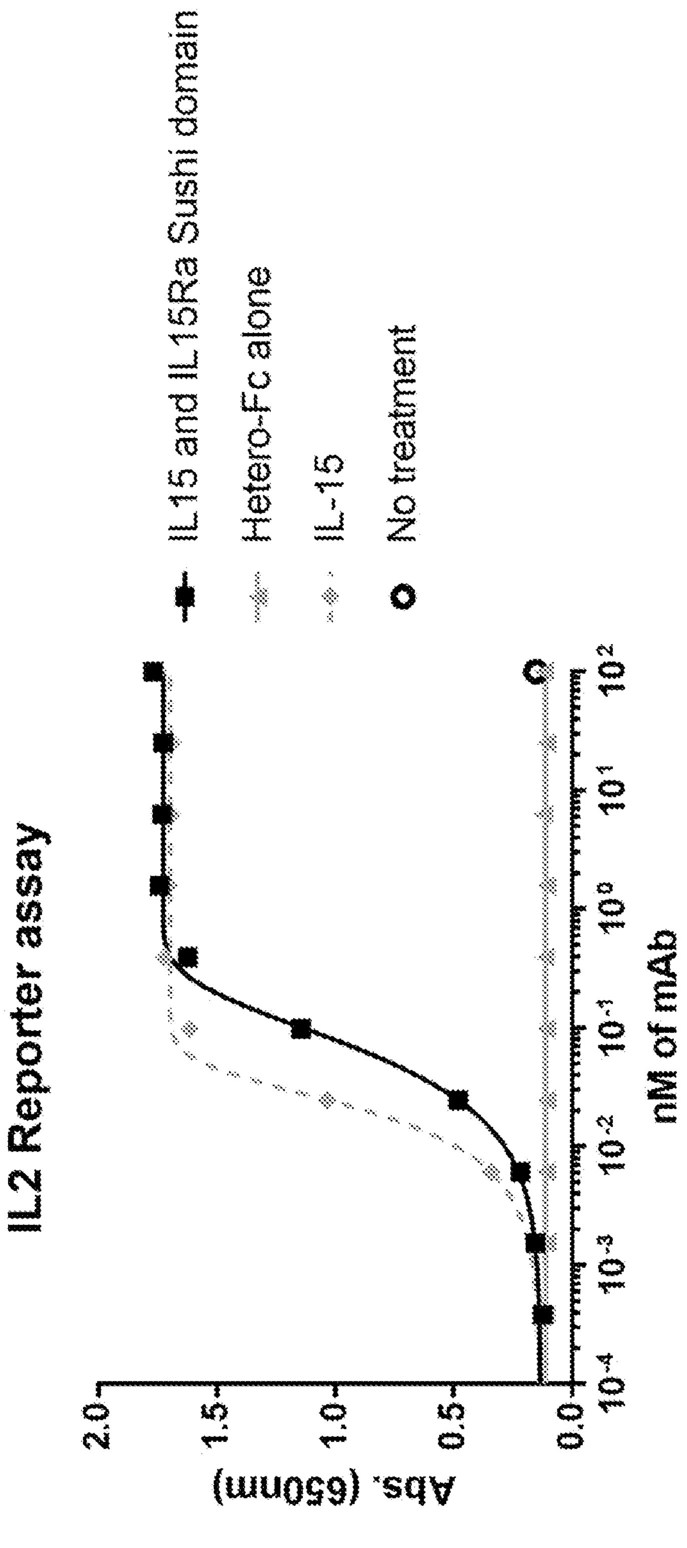

FIG. 20: IL2 reporter assay using a InvivoGen (Catalog #hkb-IL2) kit. IL2 and IL15 share two common receptor subunits (CD122 and CD132), the IL2 reporter assay was used to validate the IL15 and Fc fusion protein. Recombinant IL-15 (Peprotech Cat #200-15), the Hetero-Fc protein of Fc-IL15×Fc-IL15Ra sushi domain and the dummy Hetero-Fc protein without any cytokine were incubated with the reporter cells following the manufacturer's recommendations, see Example 13. Each construct was tested at 1:4 series dilutions at 100 nM, 25 nM, 6.25 nM, 1.56 nM, 390 pM, 98 pM, 24 pM, 6.1 pM, 1.52 pM, 0.38 pM, 0.1 pM and 0.024 pM. The next day, the supernatants were collected and the cells absorbance at 650 nm was measured on a plate reader 1 hour after the addition of the QUANTI-Blue™ Solution (InvivoGen cat. no. rep-qbs). Results were analyzed using GraphPad prism and EC50 values were determined using a fitted response curve.

Figure 21:
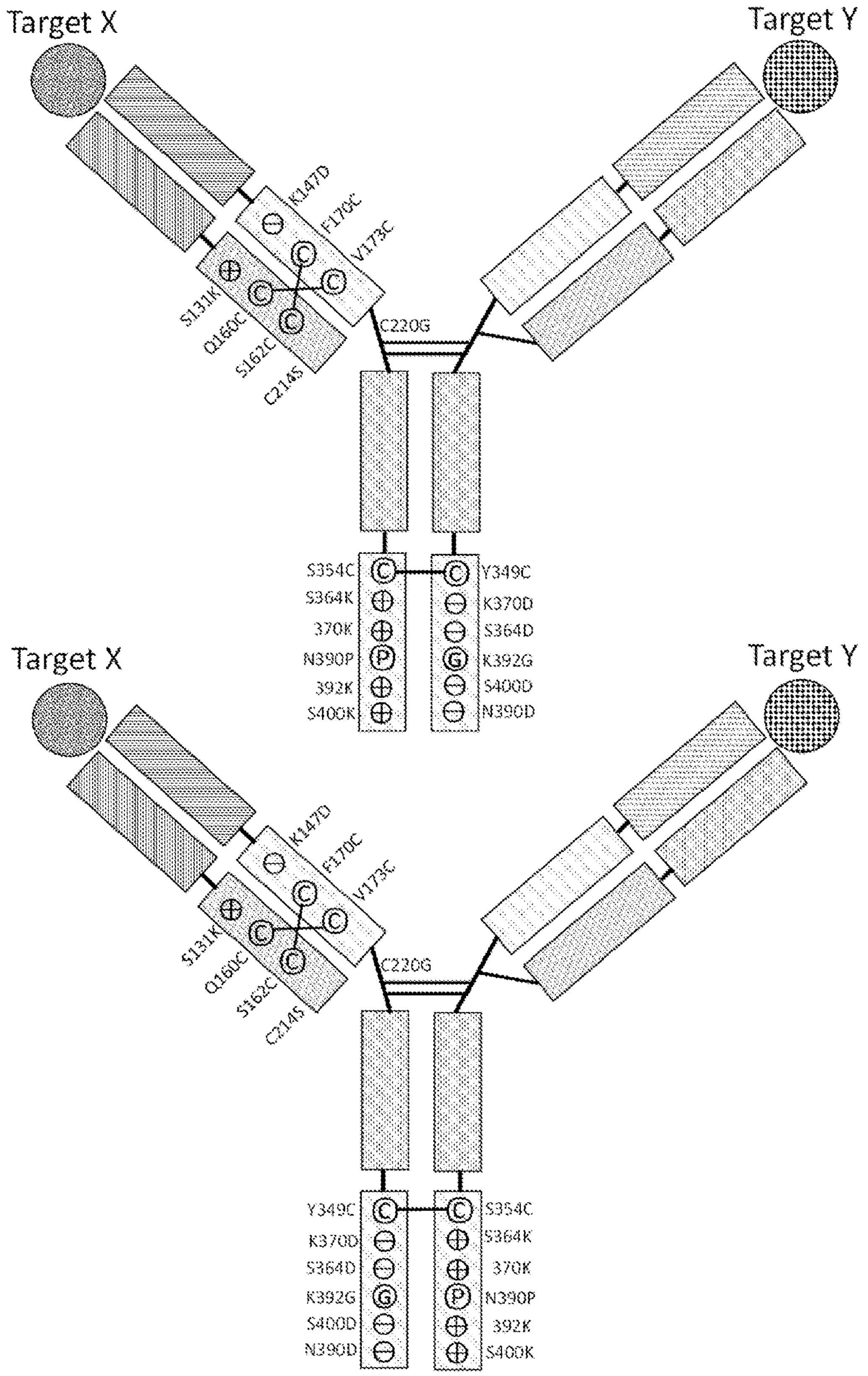

FIG. 21: Depiction for heterodimeric bispecific antibody. Panel A, the LC of anti-target-X has 4 substitutions S131K, Q160C, S162C, and C214S in Cκ region, whereas the HC of anti-target-X has 3 substitutions K147D, F170C, V173C in CH1 region; 1 substitution C220G in upper hinge region; and 4 substitutions S354C, S364K, N390P, S400K in CH3 region. The LC of anti-target-Y is kept as wild type (WT) whereas the HC of anti-target-Y has 5 substitutions Y349C, K370D, S364D, K392G, S400D, N390D in CH3 region. The substitutions C214S in Cκ region and C220G in upper hinge region together abolish the naturally occurring disulfide bond pre-existing in IgG1 antibody. The substitutions Q160C in Cκ region and V173C in CH1 region are spatially close to form a new disulfide bond; similarly, the substitutions S162C in Cκ region and F170C in CH1 region are also spatially close to form a new disulfide bond. The two new disulfide bonds help stabilize the Fab arm of anti-target-X antibody. The introduced charge pair S131K in Cκ and K147D in CH1 can be accommodated in the Fab arm of anti-target-X antibody, whereas the S131K is repulsive to the naturally occurring 147K in the CH1 region of the HC of the anti-target-Y antibody, to increase the stringency of cognate LC-HC pairings. In the CH3 regions, the Cys residue from S354C substitution of anti-target-X antibody forms a new disulfide bond with the Cys residue from Y349C substitution of anti-target-Y antibody. Positive charge residues S364K, native 370K, native 392K, and S400K of anti-target-X antibody form salt bridges with K370D, S364D, S400D, an N390D of anti-target-Y antibody, respectively. The substitution N390P in CH3 region of anti-target-X antibody and the substitution K392G in CH3 region of anti-target-Y antibody offer flexibility for folding after all these substitutions are introduced. Panel B shows the same idea for making heterodimeric bispecific antibody as panel A, with the swapped substitutions in CH3 regions.

Brief Description of the Sequences

| SEQID NO | DESCRIPTION |
|---|---|
| SEQ ID NO: 1 | Nucleotide sequence encoding the VL domain of the anti-HER2 humAb4D5-8 |
| SEQ ID NO: 2 | Amino acid sequence of the VL domain of the anti-HER2 humAb4D5-8 |
| SEQ ID NO: 3 | Nucleotide sequence encoding the LC of the anti-HER2 humAb4D5-8 |
| SEQ ID NO: 4 | Amino acid sequence of the LC of the anti-HER2 humAb4D5-8 |
| SEQ ID NO: 5 | Nucleotide sequence encoding the VH domain of the anti-HER2 humAb4D5-8 |
| SEQ ID NO: 6 | Amino acid sequence of the VH domain of the anti-HER2 humAb4D5-8 |
| SEQ ID NO: 7 | Nucleotide sequence encoding the HC of the anti-HER2 humAb4D5-8 IgG1 |
| SEQ ID NO: 8 | Amino acid sequence of the HC of the anti-HER2 humAb4D5-8 IgG1 |
| SEQ ID NO: 9 | Nucleotide sequence encoding the VL domain of the anti-HER2 humAb2C4 |

-continued

Brief Description of the Sequences

| SEQID NO | DESCRIPTION |
|---|---|
| SEQ ID NO: 10 | Amino acid sequence of the VL domain of the anti-HER2 humAb2C4 |
| SEQ ID NO: 11 | Nucleotide sequence encoding the LC of the anti-HER2 humAb2C4 |
| SEQ ID NO: 12 | Amino acid sequence of the LC of the anti-HER2 humAb2C4 |
| SEQ ID NO: 13 | Nucleotide sequence encoding the VH domain of the anti-HER2 humAb2C4 |
| SEQ ID NO: 14 | Amino acid sequence of the VH domain of the anti-HER2 humAb2C4 |
| SEQ ID NO: 15 | Nucleotide sequence encoding the HC of the anti-HER2 humAb2C4 IgG1 |
| SEQ ID NO: 16 | Amino acid sequence of the HC of the anti-HER2 humAb2C4 IgG1 |
| SEQ ID NO: 17 | Nucleotide sequence encoding the HC of the anti-HER2 humAb4D5-8 (CDDDGD) |
| SEQ ID NO: 18 | Amino acid sequence of the HC of the anti-HER2 humAb4D5-8 (CDDDGD) |
| SEQ ID NO: 19 | Nucleotide sequence encoding the HC of the anti-HER2 humAb4D5-8 (CKKPKK) |
| SEQ ID NO: 20 | Amino acid sequence of the HC of the anti-HER2 humAb4D5-8 (CKKPKK) |
| SEQ ID NO: 21 | Nucleotide sequence encoding the Dummy Fc (C220G and CDDDGD) |
| SEQ ID NO: 22 | Amino acid sequence of the Dummy Fc (C220G and CDDDGD) |
| SEQ ID NO: 23 | Nucleotide sequence encoding the Dummy Fc (C220G and CKKPKK) |
| SEQ ID NO: 24 | Amino acid sequence of the Dummy Fc (C220G and CKKPKK) |
| SEQ ID NO: 25 | Nucleotide sequence encoding the VH of the humanized anti-hCD20 Ab1.2 and Ab1.2.5 and Ab1.2.6 |
| SEQ ID NO: 26 | Amino acid sequence of the VH of the humanized anti-hCD20 IgG Ab1.2 and Ab1.2.5 and Ab1.2.6 |
| SEQ ID NO: 27 | Nucleotide sequence encoding the HC of the humanized anti-hCD20 IgG Ab1.2 (WT) |
| SEQ ID NO: 28 | Amino acid sequence of the HC of anti-hCD20 IgG Ab1.2 (WT) |
| SEQ ID NO: 29 | Nucleotide sequence encoding the HC of the humanized anti-hCD20 IgG Ab1.2.5 (CDDDGD) |
| SEQ ID NO: 30 | Amino acid sequence of the HC of anti-hCD20 IgG Ab1.2.5 (CDDDGD) |
| SEQ ID NO: 31 | Nucleotide sequence encoding the HC of the humanized anti-hCD20 IgG Ab1.2.6 (CKKPKK) |
| SEQ ID NO: 32 | Amino acid sequence of the HC of the humanized anti-hCD20 IgG Ab1.2.6 (CKKPKK) |
| SEQ ID NO: 33 | Nucleotide sequence encoding the VL of the humanized anti-hCD20 antibodies Ab1.2 and Ab1.2.5 and Ab1.2.6 |
| SEQ ID NO: 34 | Amino acid sequence of the VL of the humanized anti-hCD20 antibodies Ab1.2 and Ab1.2.5 and Ab1.2.6 |
| SEQ ID NO: 35 | Nucleotide sequence encoding the LC of the humanized anti-hCD20 antibodies Ab1.2 Ab1.2.2.1, Ab1.2.5, and Ab1.2.6 |
| SEQ ID NO: 36 | Amino acid sequence of the LC of the humanized anti-hCD20 antibodies Ab1.2 Ab1.2.2.1, Ab1.2.5 and Ab1.2.6 |
| SEQ ID NO: 37 | Nucleotide sequence encoding the VH of the humanized anti-hCD37 Ab1.A1, Ab1.A1.1, Ab1.A1.2 and Ab1.A1.3 |
| SEQ ID NO: 38 | Amino acid sequence of the VH of the humanized anti-hCD37 Ab1.A1, Ab1.A1.1, Ab1.A1.2 and Ab1.A1.3 |
| SEQ ID NO: 39 | Nucleotide sequence encoding the HC of the humanized anti-hCD37Ab1.A1 IgG1 (WT) |
| SEQ ID NO: 40 | Amino acid sequence of the HC of the humanized anti-hCD37 Ab1.A1 IgG1 (WT) |
| SEQ ID NO: 41 | Nucleotide sequence encoding the HC of the humanized anti-hCD37 Ab1.A1.2 IgG1 (DCCG + CKKPKK) |
| SEQ ID NO: 42 | Amino acid sequence of the HC of the humanized anti-hCD37 Ab1.A1.2 IgG1 (DCCG + CKKPKK) |
| SEQ ID NO: 43 | Nucleotide sequence encoding the HC of the humanized anti-hCD37 Ab1.A1.3 IgG1 (DCCG + CDDDGD) |
| SEQ ID NO: 44 | Amino acid sequence of the HC of the humanized anti-hCD37 Ab1.A1.3 IgG1 (DCCG + CDDDGD) |
| SEQ ID NO: 45 | Nucleotide sequence encoding the VL of the humanized anti-hCD37 Ab1.A1 and Ab1, A1.2 and Ab1, A1.3 |
| SEQ ID NO: 46 | Amino acid sequence of the VL of the humanized anti-hCD37 Ab1, A1 and Ab1, A1.2 and Ab1, A1.3 |
| SEQ ID NO: 47 | Nucleotide sequence encoding the LC of the humanized anti-hCD37Ab1.A1 (WT) |
| SEQ ID NO: 48 | Amino acid sequence of the LC of the humanized anti-hCD37 Ab1.A1 (WT) |
| SEQ ID NO: 49 | Nucleotide sequence encoding the LC of the humanized anti-hCD37 Ab1, A1.2 and Ab1, A1.3 (KCCS) |
| SEQ ID NO: 50 | Amino acid sequence of the LC of the humanized anti-hCD37 Ab1, A1.2 and Ab1, A1.3 (KCCS) |
| SEQ ID NO: 51 | Nucleotide sequence encoding the VH of the humanized anti-hCLDN18.2 clone 59F9E1 |
| SEQ ID NO: 52 | Amino acid sequence of the VH of the humanized anti-hCLDN18.2 clone 59F9E1 |
| SEQ ID NO: 53 | Nucleotide sequence encoding the HC of the humanized anti-hCLDN18.2 clone 59F9E1 IgG1 (WT) |
| SEQ ID NO: 54 | Amino acid sequence of the HC of the humanized anti-hCLDN18.2 clone 59F9E1 IgG1 (WT) |
| SEQ ID NO: 55 | Nucleotide sequence encoding the HC of the humanized anti-hCLDN18.2 clone 59F9E1 IgG1 (DCCG) |
| SEQ ID NO: 56 | Amino acid sequence of the HC of the humanized anti-hCLDN18.2 clone 59F9E1 IgG1 (DCCG) |
| SEQ ID NO: 57 | Nucleotide sequence encoding the HC of the humanized anti-hCLDN18.2 clone 59F9E1 IgG1 (DCCG + CDDDGD) |
| SEQ ID NO: 58 | Amino acid sequence of the HC of the humanized anti-hCLDN18.2 clone 59F9E1 IgG1 (DCCG + CDDDGD) |
| SEQ ID NO: 59 | Nucleotide sequence encoding the VL of the humanized anti-hCLDN18.2 clone 59F9E1 |
| SEQ ID NO: 60 | Amino acid sequence of the VL of the humanized anti-hCLDN18.2 clone 59F9E1 |
| SEQ ID NO: 61 | Nucleotide sequence encoding the LC of the humanized anti-hCLDN18.2 clone 59F9E1 (WT) |
| SEQ ID NO: 62 | Amino acid sequence of the LC of the humanized anti-hCLDN18.2 clone 59F9E1 (WT) |
| SEQ ID NO: 63 | Nucleotide sequence encoding the LC of the humanized anti-hCLDN18.2 clone 59F9E1 (KCCS) |
| SEQ ID NO: 64 | Amino acid sequence of the LC of the humanized anti-hCLDN18.2 clone 59F9E1 (KCCS) |
| SEQ ID NO: 65 | Nucleotide sequence encoding the VH of the humanized anti-hSIRPα clone #24 IgG |
| SEQ ID NO: 66 | Amino acid sequence of the VH of the humanized anti-hSIRPα clone #24 IgG |
| SEQ ID NO: 67 | Nucleotide sequence encoding the HC of the humanized anti-hSIRPα clone #24 IgG (WT) |
| SEQ ID NO: 68 | Amino acid sequence of the HC of the humanized anti-hSIRPα clone #24 IgG (WT) |
| SEQ ID NO: 69 | Nucleotide sequence encoding the HC of the humanized anti-hSIRPα clone #24 IgG (CKKPKK) |
| SEQ ID NO: 70 | Amino acid sequence of the HC of the humanized anti-hSIRPα clone #24 IgG (CKKPKK) |
| SEQ ID NO: 71 | Nucleotide sequence encoding the VL of the humanized anti-hSIRPα clone #24 |
| SEQ ID NO: 72 | Amino acid sequence of the VL of the humanized anti-hSIRPα clone #24 |
| SEQ ID NO: 73 | Nucleotide sequence encoding the LC of the humanized anti-hSIRPα clone #24 (WT) |
| SEQ ID NO: 74 | Amino acid sequence of the LC of the humanized anti-hSIRPα clone #24 (WT) |
| SEQ ID NO: 75 | Nucleotide sequence encoding the HC of the humanized anti-hCD20 Ab1.2.2.1 |
| SEQ ID NO: 76 | Amino acid sequence of the HC of the humanized anti-hCD20 Ab1.2.2.1 |
| SEQ ID NO: 77 | Nucleotide sequence encoding the HC of the humanized anti-hCD37 Ab1.A1.1 |
| SEQ ID NO: 78 | Amino acid sequence of the HC of the humanized anti-hCD37 Ab1.A1.1 |
| SEQ ID NO: 79 | Nucleotide sequence encoding the HC of the anti-DNP IgG1 antibody |
| SEQ ID NO: 80 | Amino acid sequence of the HC of the anti-DNP IgG1 antibody |
| SEQ ID NO: 81 | Nucleotide sequence encoding the LC of the anti-DNP IgG1antibody |
| SEQ ID NO: 82 | Amino acid sequence of the LC of the anti-DNP IgG1 antibody |
| SEQ ID NO: 83 | Amino acid sequence of VL CDR1 of the humanized anti-hCLDN18.2 clone 59F9E1 |

-continued

| Brief Description of the Sequences | |
|---|---|
| SEQID NO | DESCRIPTION |
| SEQ ID NO: 84 | Amino acid sequence of VL CDR2 of the humanized anti-hCLDN18.2 clone 59F9E1 |
| SEQ ID NO: 85 | Amino acid sequence of VL CDR3 of the humanized anti-hCLDN18.2 clone 59F9E1 |
| SEQ ID NO: 86 | Amino acid sequence of VH CDR1 of the humanized anti-hCLDN18.2 clone 59F9E1 |
| SEQ ID NO: 87 | Amino acid sequence of VH CDR2 of the humanized anti-hCLDN18.2 clone 59F9E1 |
| SEQ ID NO: 88 | Amino acid sequence of VH CDR3 of the humanized anti-hCLDN18.2 clone 59F9E1 |
| SEQ ID NO: 89 | Consensus amino acid sequence for human VH domains |
| SEQ ID NO: 90 | Consensus amino acid sequence for CH1 domains |
| SEQ ID NO: 91 | Amino acid sequence of a human IgG1 CH1 domain |
| SEQ ID NO: 92 | Amino acid sequence of a human IgG2 CH1 domain |
| SEQ ID NO: 93 | Amino acid sequence of a human IgG3 CH1 domain |
| SEQ ID NO: 94 | Amino acid sequence of a human IgG4 CH1 domain |
| SEQ ID NO: 95 | Amino acid sequence of a human IgG1 Fc fragment |
| SEQ ID NO: 96 | Amino acid sequence of a human IgG2 Fc fragment |
| SEQ ID NO: 97 | Amino acid sequence of a human IgG3 Fc fragment |
| SEQ ID NO: 98 | Amino acid sequence of a human IgG4 Fc fragment |
| SEQ ID NO: 99 | Consensus amino acid sequence of a human VL domain |
| SEQ ID NO: 100 | Consensus amino acid sequence of a CLλ domain |
| SEQ ID NO: 101 | Consensus amino acid sequence of a CLκ domain |
| SEQ ID NO: 102 | Amino acid sequence of a human CL domain (IMGT accession no. J00241) |
| SEQ ID NO: 103 | Amino acid sequence of a human CLκ domain (IMGT accession no. M11736) |
| SEQ ID NO: 104 | Amino acid sequence of a human CLκ domain (IMGT accession no. M11737) |
| SEQ ID NO: 105 | Amino acid sequence of a human CLκ domain (IMGT accession no. AF0017732) |
| SEQ ID NO: 106 | Amino acid sequence of a human CLκ domain (IMGT accession no. AF11387) |
| SEQ ID NO: 107 | Nucleotide sequence encoding IL15 fused to the C-terminal end of an Fc chain (CDDDGD) |
| SEQ ID NO: 108 | Amino acid sequence encoding IL15 fused to the C-terminal end of an Fc chain (CDDDGD) |
| SEQ ID NO: 109 | Nucleotide sequence encoding IL15Ra Sushi domain fused to the C-terminal end of an Fc chain (CKKPKK) |
| SEQ ID NO: 110 | Amino acid sequence encoding IL15Ra Sushi domain fused to the C-terminal end of an Fc chain (CKKPKK) |
| SEQ ID NO: 111 | Nucleotide sequence encoding an Fc chain (CDDDGD) |
| SEQ ID NO: 112 | Amino acid sequence encoding an Fc chain (CDDDGD) |
| SEQ ID NO: 113 | Nucleotide sequence encoding an Fc chain (CKKPKK) |
| SEQ ID NO: 114 | Amino acid sequence encoding an Fc chain (CKKPKK) |

REFERENCE TO SEQUENCE LISTING

This application includes a sequence listing appended hereto. An electronic version of the Sequence Listing is filed herewith, the contents of which are incorporated by reference in their entirety. The electronic file was created on Sep. 21, 2022 and is 195,699 bytes and is titled 126861-0007UT01_Sequence_listing.xml

DETAILED DESCRIPTION

Provided herein are variant-Fc-region fusion proteins, variant-Fc-region-antibodies and heterodimeric-variant-Fc-region-bispecific-antibodies comprising a set of amino acid substitutions compared to native human IgG. In a particular embodiment, the set of amino acid substitutions can be selected from: a first variant-Fc-region comprising S364D, K370D, N390D, and S400D; a second Fc region comprising S364K, and S400K. In additional embodiments, the variant-Fc-region can further comprise Y349C and K392G in the first variant-Fc-region, and S354C and N390P in the second variant-Fc-region. In other embodiments, the variant-Fc-region is a variant-Fc-region-fusion protein further comprising a partner-ligand recombinantly fused thereto at either the N-terminus or C-terminus. In particular embodiments, the partner-ligand is selected from the group consisting of: extracellular domains of receptors, soluble full-length or domain of cytokines, ligands, enzymes, antibody domains, peptides, anti-CD3 scFv, IL-2, IL-12, IL-15, IL21, or mutein cytokines. In yet other embodiments, the variant-Fc-region or variant-Fc-region fusion protein is derived from a native human IgG is an isotype selected from the group consisting of: IgG, IgD, IgM, IgA, or IgE class; or following subclass IgG1, IgG2, IgG3, or IgG4.

In another embodiment of the invention, provided herein are variant-Fc-regions comprising a combination of 4 charge pairs and 1 cysteine pair in CH3 region of the Fc region that strongly favors the production of heterodimeric Fc, with little to no production, of homodimers. The 4 negative charge residues (Asp, D) in one HC or the 4 positive charge residues (Lys, K) in other HC are too repulsive to form homodimers of the same HCs. Accordingly, only the 2 different HCs having opposite charge polarity can come together to form heterodimers, then are locked by a new disulfide bond and secreted from mammalian cells.

In accordance with the present invention, it has been found that heterodimeric variant-Fc-region bispecific antibody with natural antibody configuration and without any linker(s) is a favorable format since this configuration retains all antibody properties and reduces the immunogenicity from linker(s) or the junction of antibody-linker(s). For example, under standard conditions in one cell, 10 different antibodies can be produced if 2 different HCs and 2 different LCs are randomly paired; whereas in accordance with the present invention, a single heterodimeric bispecific antibody is produced from a particular cell. The cognate HC-LC pairing is required for making bispecific heterodimeric antibody from the same cells. Although it may be possible to identify a common LC that can pair with both HCs, it is not always easy to identify such LC, since this usually results in decreased binding affinity for at least one of the antibody moieties.

In particular embodiments of the present invention heterodimeric antibodies, a combination of cysteine pairs and/or a charge pair in CH1/Ck, as set forth in WO 2017/205014A1, which is incorporated herein by reference in its entirety for all purposes, has been applied to make invention of two individual antibodies (referred as MabPair) from a single cell. In these embodiments, two different HCs and two different LCs automatically assemble into two individual antibodies, substantially without detectable heterodimeric antibody and without mis-paired HC-LC species.

The invention methods provided herein can be applied to any pair of Fc regions; or any pair of antibodies known in the art to advantageously make and use invention heterodimer variant-Fc-region bispecific antibodies.

In two particular embodiments, invention heterodimer bispecific antibodies, corresponding to anti-hCD20×hCD37 and anti-hSIRPα×hCLDN18.2, are provided herein, wherein each of these are characterized by their robust production and high homogeneity. Because the substitutions have been introduced in CH1/Ck constant regions, not in VH/VL regions, each Fab arm of antibody retains the binding and activity of parental antibodies. In particular embodiments, the anti-hCD20× hCD37 bispecific antibody can be used for treating B-NHL and CLL; whereas the anti-hSIRPα× hCLDN18.2 bispecific antibody can be used for treating gastric and pancreatic cancers. In other embodiments, the invention Fc fusion proteins, heterodimeric Fc fusion proteins, and heterodimeric IgG-like bispecific antibodies provided herein are contemplated herein to treat a variety of diseases in humans.

Fc-Region Engineering:

For one embodiment, after multiple rounds of Fc engineering, substitutions were introduced: at Y349C, S364D, K370D, N390D, K392G and S400D in the CH3 region of one Fc; and at S354C, S364K, N390P and S400K in the CH3 region of the other Fc, in which 2 naturally occurring Lys residues (370K and 392K) are involved in the interaction network. As a result of introducing all these negative charge residues (Asp, D) in the same Fc chain, strong repulsion occurs due to the same polarity, which advantageously prevents the formation of homodimer Fc having S364D/K370D/N390D/S400D. Similarly, as a result of introducing all these positive charge residues (Lys, K) in the other Fc chain, a similar strong repulsion occurs due to the same polarity, which advantageously disfavors the formation of homodimer Fc having S634K/370K/392K/S400K. In certain embodiments, the substitutions K392G in one Fc chain and N390P in the other Fc chain advantageously provides flexibility of respective Fc chain to interact with each other. In accordance with the present inventions, when 2 different HCs having opposite polarities come close, they are allowed to form heterodimers by salt bridges. In addition, in other embodiments, substitutions Y349C in one Fc chain and S354C in the other Fc chain form a new covalent disulfide bond to lock and stabilize the heterodimers.

In addition to the Fc region engineered substitutions described above and herein, in certain embodiments of the invention heterodimeric bispecific antibodies provide herein, substitutions including S131K, Q160C, S162C and C214S in the Ck domain (also referred to herein as "KCCS"); and K147D, F170C, V173C and C220G in the CH1 domain and upper hinge region of HC (also referred to herein as "DCCG"), are introduced in a first antibody (of the bispecific antibody), while the Fab region of the second antibody of the bispecific antibody is kept as wild type. This particular set of substitutions have previously been used to make MabPair products and are well-known in the art, as set forth WO2017/205014, which is incorporated herein by reference in its entirety for all purposes. These well-known strategies from MabPair technology are used herein to ensure the cognate HC-LC pairings.

In accordance with particular embodiments of the present invention, two heterodimeric bispecific antibodies have been made and tested: an anti-hCD20×hCD37 as well as an anti-hCLDN18.2×hSIRPα antibody. The anti-hCD20× hCD37 heterodimeric bispecific antibody engages two different targets on B cells simultaneously to kill tumor cells while ADCC function from Fc region of bispecific antibody can engage NK cells to further kill tumor cells. The anti-CLDN18.2×SIRPα heterodimeric bispecific antibody bridges Claudin 18.2 on cancer cells and SIRPα on macrophages, so the macrophages can phagocyte and kill tumor cells by blocking CD47/SIRPα axis and by ADCP effector function of Fc region of bispecific antibody. A diagram of a particular embodiment of suitable residue substitutions for making these particular heterodimeric bispecific antibodies is shown FIG. 21. Different shadings indicate different domains of HCs and LCs. Overall, it has been found that the invention heterodimeric bispecific antibody retains the standard IgG configuration by having 2 different HCs and 2 different LCs. No artificial linker is used. No excessive aggregation is found. Most substitutions are buried or partially exposed. Fully HCs are assembled to form heterodimers together with cognate HC-LC pairings.

Definitions

As used herein, the phrase "Fc-region," refers to most or all of a hinge domain, plus a CH2 and a CH3 domain from an HC. For example, amino acid sequences of exemplary human IgG Fc-regions are shown in Table 9.

As used herein, the phrase "variant-Fc-region" refers to a native Fc-region that undergoes at least one substitution, insertion, or deletion of a single amino acid therein, which can optionally include a substitution of a charged amino acid or a cysteine for the naturally occurring amino acid. As set forth herein, the invention variant-Fc-regions can be recombinantly combined with any moiety, such as a pharmaceutically-active-moiety to form a fusion protein; or the invention variant-Fc-regions can be used to form heterodimeric variant-Fc-region antibodies and/or heterodimeric variant-Fc-region bispecific antibodies. In certain embodiments, the invention Fc-regions are prepared such that upon heterodimerization, only one of the Fc regions has a moiety attached thereto. This embodiment advantageously permits finer control over which pharmaceutically-active-moieties are administered and the quantity and/or dose of the desired moiety that is administered.

As used herein, the phrase "variant-Fc-region fusion protein" refers to a chimeric protein resulting from protein synthesis, including as a result of expression of a recombinant nucleic acid construct encoding an invention variant-Fc-region chimerically recombined with any desired protein moiety, either at the N- or C-terminus of the variant-Fc-region. In certain embodiments, the protein moiety of the fusion protein is a partner-ligand that is able to bind to a desired target, such as for use in therapeutic or diagnostic methods.

As used herein, the phrase "partner-ligand," or grammatical variations thereof, refers to any molecule or moiety that can bind to a desired target molecule. In particular embodiments, he partner-ligan is recombinantly fused to an invention variant-Fc-region.

As used herein, the phrase "heterodimeric variant-Fc-region antibody" refers to antibodies made in a host cell line into which DNAs encoding two different IgG antibodies has been introduced, where the major species of antibodies is a variant-Fc-region bispecific antibody comprising a cognate HC/LC pair from each of the two IgG antibodies. In particular embodiments, the invention heterodimeric variant-Fc-region antibodies (e.g., a heterodimeric variant-Fc-region bispecific antibody) are substantially free of any homodimeric variant-Fc-region antibodies. In particular embodiments, exemplary substantially pure heterodimeric variant-Fc-region bispecific antibodies contains an amount of homodimeric variant-Fc-region antibodies in said composition is less than 5, 4, 3, 2, 1, 0.5, 0.4, 0.3, 0.2, 0.1%.

An "alteration that favors heterodimers," as meant herein, is a substitution, insertion, or deletion of a single amino acid within a CH3 domain amino acid sequence in an antibody, optionally a human, humanized, or primate CH3 domain amino acid sequence, where the substitution, insertion, or deletion favors the formation of heterodimers in the context of invention variant-Fc-regions, variant-Fc-region-fusion proteins, and/or heterodimeric variant-Fc-region bispecific antibodies. Invention variant-Fc-regions, variant-Fc-region-fusion proteins, and/or heterodimeric variant-Fc-region bispecific antibodies can comprise more than one alteration that favors heterodimers, and multiple alterations that favor heterodimers can occur at multiple sites in one or more invention variant-Fc-regions, variant-Fc-region-fusion proteins, and/or heterodimeric variant-Fc-region bispecific antibodies. A single alteration that favors heterodimer formation need not be completely effective in forming heterodimers, or effective by itself, to be considered an "alteration that favors heterodimers," as long as it is partially effective and/or effective when paired with one or more other alterations. Included among the alterations can be the substitution of a charged residue for the residue present in the wild type sequence. Whether one or more alteration(s) has (have) an effect on HC/HC heterodimer formation can be determined by the methods described in Examples 1 and 2. Data from such experiments is shown in FIGS. 1-6. Alterations that favor heterodimers occur at "domain interface residues." Domain interface residues are discussed in US Patent 8,592,562 in Table 1 and accompanying text, which are incorporated herein by reference. Such domain interface residues are said to be "contacting" residues or are said to "contact" each other if they are predicted to be physically close, i.e., at most 12 angstroms (Å) between the alpha carbons (Cα, i.e., the carbon between the amino and the carboxyl moiety of the amino acid) of the two amino acids or at most 5.5 Å between a side chain heavy atom (any atom other than hydrogen) of one amino acid and any heavy atom of the other amino acid according to known structure models. Such structures are available online, for example, through the Protein Data Bank (available at www.rcsb.org/pdb/home/home.do) or through the INTERNATIONAL IMMUNOGENETICS INFORMATION SYSTEM® (IMGT; available at www.imgt.org). In Table 6 below, examples of contacting residues at the CH3/CH3 interface in a human IgG antibody are listed.

TABLE 6

Contacting residues at a human IgG CH3/CH3 interface

| Contacting residue in first CH3* | Residues in second CH3* having a heavy atom within 4.5 angstroms of a side chain heavy atom of the contacting amino acid in first CH3 |
|---|---|
| Q347 | K360 |
| Y349 | S354, D356, E357, K360 |
| T350 | S354, R355 |
| L351 | L351, P352, P353, S354, T366 |
| S354 | Y349, T350, L351 |
| R355 | T350 |
| D356 | Y349, K439 |
| E357 | Y349, K370 |
| K360 | Q347, Y349 |
| S364 | L368, K370 |
| T366 | L351, Y407 |
| L368 | S364, K409 |
| K370 | E357, S364 |
| N390 | S400 |
| K392 | L398, D399, S400, F405 |
| T394 | T394, V397, F405, Y407 |
| P395 | V397 |
| V397 | T393, T394, P395 |
| D399 | K392, K409 |
| S400 | N390, K392 |
| F405 | K392, T394, K409 |
| Y407 | T366, T394, Y407, S408, K409 |
| K409 | L368, D399, F405, Y407 |
| K439 | D356 |

*Numbering is according to Edelman et al. (1969), Proc. Natl. Acad. Sci. USA 63: 78-85, which is incorporated herein in its entirety Examples of alterations that favor heterodimers include, e.g., S364D, K370D, N390D, and S400D in a primate and/or humanized IgG heavy chain, optionally in the context of heterodimeric variant-Fc-region-bispecific antibodies that includes another IgG antibody comprising, in one embodiment, S364K, and S400K.

An "amino acid," an "amino acid residue," a "residue," or a "position," within a HC or LC amino acid sequence refers to an amino acid at a position numbered as shown in Tables 6-12. Thus, for example, it is possible for two different HC amino acid sequences to have the same or different amino acids at a particular position in the two HC amino acid sequences. Further, an "HC position," an "HC residue," an "LC position," or an "LC residue" refers to an amino acid at a position in any HC or LC amino acid sequence numbered as shown in Tables 7-13.

An "antibody," as meant herein, is a protein that contains at least one heavy chain variable (VH) domain or light chain variable (VL) domain. An antibody often contains both VH and VL domains. VH and VL domains are described in full detail in, e.g., Kabat et al., SEQUENCES OF PROTEINS OF IMMUNOLOGICAL INTEREST, FIFTH EDITION, U.S. Department of Health and Human Services, Public Health Service, National Institutes of Health, NIH Publication No. 91-3242, 1991, pp. xvi-xix and pp. 103-533, which are incorporated by reference herein. "Antibody" includes molecules having different formats such as single chain Fv antibodies (scFv, which contain VH and VL regions joined by a linker), Fab, F(ab) 2, Fab', scFv: Fc antibodies (as described in Carayannopoulos and Capra, Ch. 9 in FUNDAMENTAL IMMUNOLOGY, 3.sup.rd ed., Paul, ed., Raven Press, New York, 1993, pp. 284-286, which is incorporated herein by reference), bispecific antibodies and monovalent antibodies in any of a variety of formats, and full-length and IgG antibodies as defined below, among other possible formats for an antibody.

A "bispecific antibody," as meant herein, binds to two different epitopes, which can reside on one target molecule or on two separate target molecules. A bispecific antibody can be a full-length antibody, IgG antibody, or an antibody having a different format. A bispecific antibody can be made in a host cell line (as defined above) into which DNA encoding two different IgG antibodies, i.e., two different heavy chains and two different light chains, has been introduced. A bispecific antibody can also be made in a cell population into which DNA(s) encoding two different IgG antibodies has (have) been introduced, where a clonal host cell line is not purified from the cells into which the DNA(s) was (were) introduced. An example of this kind of situation could involve transiently transfecting DNA(s) encoding two different IgG antibodies into, e.g., 293 or ExpiCHO cells, and subsequently obtaining the bispecific antibodies produced by the cells from the cell supernatant of the transfected cells.

A "bivalent antibody," as meant herein, can simultaneously bind to two epitopes, which can be identical or different and can reside on one target molecule or on two separate target molecules.

A "charge pair," of amino acids, as meant herein, is a pair of oppositely charged amino acids at "contacting" amino acid residues as defined herein. Such charged amino acids can be on the same polypeptide chain or on different polypeptide chains.

A "charged" amino acid, as meant herein, is an acidic or basic amino acid that can have a charge at near-physiologic pH. These include the acidic amino acids glutamic acid (E) and aspartic acid (D), which are negatively charged at physiologic pH, and the basic amino acids arginine (R) and lysine (K), which are positively charged at physiologic pH. The weakly basic amino acid histidine, which can be partially charged at near-physiologic pH, is not within the definition of "charged" amino acid herein. To avoid confusion, a positive charge is considered to be "opposite" to a negative charge, as meant herein. Thus, for example, amino acid residues E and R are opposite in charge.

A "cognate" HC in the context of antibodies (e.g., a heterodimeric variant-Fc-region bispecific antibody), as meant herein, is the HC that a particular LC is known to pair with to form a binding site for a particular antigen. For example, if a known full-length Antibody X binds to Antigen X, the Antibody X HC is the cognate HC of the Antibody X LC, and vice versa, in the context of a heterodimeric variant-Fc-region bispecific antibody that comprises Antibody X, among other antibodies. Further, if the bispecific antibody also comprises an Antibody Y, the antibody Y HC is "non-cognate" with respect to the Antibody X LC and vice versa.

A "complementarity determining region" (CDR) is a hypervariable region within a VH or VL domain. Each VH and VL domain contains three CDRs called CDR1, CDR2, and CDR3. The CDRs form loops on the surface of the antibody and are primarily responsible for determining the binding specificity of an antibody. The CDRs are interspersed between four more conserved framework regions (called FR1, FR2, FR3, and FR4) as follows: FR1-CDR1-FR2-CDR2-FR3-CDR3-FR4. Positions of CDRs in a VH and a VL are indicated in Tables 7 and 11, respectively. Kabat et al. position the VH CDRS as follows: CDR1 is at positions 31-35 (with possible insertions numbered 35A and 35B); CDR2 is at positions 50-65 (with possible insertions numbered 52A-52C); and CDR3 is at positions 95-102 (with possible insertions numbered 100A-100K). Kabat et al., supra, at xvii. Kabat et al. position the VL CDRs as follows: CDR1 is at positions 24-34 (with possible insertions numbered 27A-27F); CDR2 is at positions 50-56; and CDR3 is at positions 89-97 (with possible insertions numbered 95A-95F).

A "cysteine substitution," as meant herein, refers to an amino acid substitution in a protein where a cysteine is substituted for any other amino acid.

Amino acid alterations within two or more related sequences "differ," as meant herein, (1) if they occur at different sites within two amino acid sequences that are the same or within two amino acid sequences that belong to the same class (e.g., VH domains) and can be aligned to a common numbering system via conserved amino acids, and/or (2) if the alteration is different, e.g., a different amino acid is substituted at the same site within two amino acid sequences that are otherwise the same or that belong to the same class or different numbers of amino acids and/or different amino acids are inserted into or deleted from two amino acid sequences that are otherwise the same or that belong to the same class. Of course, amino acid alterations in two or more unrelated sequences also "differ" from each other. Two or more antibodies are "different," as meant herein, if the amino acid sequences of all the polypeptide chains included in the antibody are not "the same," as meant herein.

Two or more amino acid sequences are "different," as meant herein, if they could not be encoded by the same DNA sequence. Thus, amino acid sequences that differ only because of post-translational modifications are not "different" as meant herein.

A "full-length antibody," as meant herein, comprises (1) two heavy chains of any isotype each comprising at least a VH domain, a first heavy chain constant (CH1) domain, a hinge domain, a second heavy chain constant (CH2) domain, and a third heavy chain constant (CH3) domain, and (2) two light chains, which can be either kappa (κ) or lambda (λ) chains, each comprising a VL and a light chain constant (CL) domain. These domains are described in detail Kabat et al., supra, pp. xv-xix and 647-699, which pages are incorporated herein by reference. The numbering system of Kabat et al., supra, is used for the VH and VL domains (see Tables 7 and 11 below), and the EU system (Edelman et al. (1969), Proc. Natl. Acad. Sci. USA 63:78-85, which is incorporated herein in its entirety) is used for the CL, CH1, hinge, CH2, and CH3 domains. See Tables 8-10, 12, and 13.

A "heavy chain (HC)," as meant herein, comprises at least VH, CH1, hinge, CH2, and CH3 domains. An HC including all of these domains could also be referred to as a "full-length HC." Some isotypes such as IgA or IgM can contain additional sequences, such as the IgM CH4 domain. The numbering system of Kabat et al., supra, is used for the VH domain (see Table 7 below), and the EU system (Edelman et al. (1969), Proc. Natl. Acad. Sci. USA 63:78-85, which is incorporated herein in its entirety) is used for the CH1, hinge, CH2, and CH3 domains. Tables 7 to 10 below provide a more specific picture of HC amino acid sequences.

TABLE 7

Consensus sequence of human VHs

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| | | | **L** | | | | **G** | | | | | | **P** | |

| 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| | S | V | L | S | **C** | | G | | | | | | | |
| | T | L | V | T | | | | | | | | | | |

TABLE 7-continued

Consensus sequence of human VHs

| ***31*** | ***32*** | ***33*** | ***34*** | ***35*** | ***35A*** | ***35B*** | 36 | 37 | 38 | 39 | 40 | 41 | 42 | 43 |
|---|---|---|---|---|---|---|---|---|---|---|---|---|---|---|
| | | | | | | | W | | R | Q | | | G | K |
| | | | | | | | | | | | | | | **Q** |

| **44** | 45 | 46 | 47 | 48 | 49 | ***50*** | ***51*** | ***52*** | ***52A*** | ***52B*** | ***52C*** | ***53*** | ***54*** | ***55*** |
|---|---|---|---|---|---|---|---|---|---|---|---|---|---|---|
| G | **L** | | **W** | | | | | | | | | | | |

| ***56*** | ***57*** | ***58*** | ***59*** | ***60*** | ***61*** | ***62*** | ***63*** | ***64*** | ***65*** | 66 | 67 | 68 | 69 | 70 |
|---|---|---|---|---|---|---|---|---|---|---|---|---|---|---|
| | | | | | | | | | | ***R*** | | | | |

| 71 | 72 | 73 | 74 | 75 | 76 | 77 | 78 | 79 | 80 | 81 | 82 | 82A | 82B | 82C |
|---|---|---|---|---|---|---|---|---|---|---|---|---|---|---|
| | | | S | | | | | | L | | | | | |

| 83 | 84 | 85 | 86 | 87 | 88 | 89 | 90 | 91 | 92 | 93 | 94 | ***95*** | ***96*** | ***97*** |
|---|---|---|---|---|---|---|---|---|---|---|---|---|---|---|
| | | | D | | | | **Y** | | **C** | | | | | |

| ***98*** | ***99*** | ***100*** | ***100A*** | ***100B*** | ***100C*** | ***100D*** | ***100E*** | ***100F*** | ***100G*** | ***100H*** | ***100I*** | ***100J*** |
|---|---|---|---|---|---|---|---|---|---|---|---|---|

| ***100K*** | ***101*** | ***102*** | 103 | 104 | **105** | 106 | 107 | 108 | 109 | 110 | 111 | 112 | 113 | |
|---|---|---|---|---|---|---|---|---|---|---|---|---|---|---|
| | | | **W** | | **Q** | **G** | | | **V** | | **V** | **S** | | (SEQ ID NO: 89) |

Table 7 shows conserved amino acids based on the human VH amino acid sequences (I-III) in Kabat et al. (supra). Numbering is according to Kabat et al., supra. Site numbers within the CDRs are written in bold italics. Position numbers with letters after them, e.g., 100A, may or may not be filled by an amino acid due to the varying lengths of CDRs. A single boldface amino acid at a particular position indicates an "invariant" amino acid in all three classes of human VH domains as described by Kabat et al. (supra). At sites of interest where the amino acid at a given position is most commonly one amino acid or either of two amino acids, those amino acids are indicated in plain text. Site numbers in underlined boldface indicate positions that are described as being altered herein. Positions where no amino acid is designated did not meet the criteria stated above.

Table 7 shows that there are numerous conserved amino acids that would allow alignment of any VH sequence with the conserved amino acids spaced as shown above by eye. Alternatively, a novel sequence could be aligned with a known VH sequence using alignment software, for example, alignment software available on the International ImMunoGeneTics (IMGT) Information system® (for example, IMGT/DomainGapAlign, which is available at www.imgt.org or CLUSTAL Omega (Sievers et al., (2011), Molecular Systems Biology 7 (1): 539).

Table 8 below shows a consensus amino acid sequence of CH1 domains.

TABLE 8

CH1 consensus

| 118 | 119 | 120 | 121 | 122 | 123 | 124 | 125 | 126 | 127 | 128 | 129 | 130 | **131** | 132 |
|---|---|---|---|---|---|---|---|---|---|---|---|---|---|---|
| | | | | | **P** | | | | **P** | | | | L | |

| **133** | 134 | 134 | 136 | 137 | 138 | 139 | 140 | 141 | 142 | 143 | 144 | 145 | 146 | **147** |
|---|---|---|---|---|---|---|---|---|---|---|---|---|---|---|
| R/K | | | | | | | | | | | **C** | **L** | | K |

| 148 | 149 | 150 | 151 | 152 | 153 | 154 | 155 | 156 | 157 | 158 | 159 | 160 | 161 | 162 |
|---|---|---|---|---|---|---|---|---|---|---|---|---|---|---|
| | | | **P** | | | | | | | **W** | | | | |

| 163 | 164 | 165 | 166 | 167 | **168** | 169 | **170** | 171 | 172 | **173** | 174 | 175 | **176** | 177 |
|---|---|---|---|---|---|---|---|---|---|---|---|---|---|---|
| | | | | | H | | F | | | V | | | A | |

| 178 | 179 | 180 | **181** | 182 | **183** | 184 | 185 | 186 | 187 | 188 | 189 | 190 | 191 | 192 |
|---|---|---|---|---|---|---|---|---|---|---|---|---|---|---|
| | | | T | | S | **S** | | | | | | | | |

| 193 | 194 | 195 | 196 | 197 | 198 | 199 | 200 | 201 | 202 | 203 | 204 | 205 | 206 | 207 |
|---|---|---|---|---|---|---|---|---|---|---|---|---|---|---|
| | | | | | | | C | | | | | | | |

| 208 | 209 | 210 | 211 | 212 | 213 | 214 | 215 | |
|---|---|---|---|---|---|---|---|---|
| | | | | | | | | (SEQ ID NO: 90) |

TABLE 8: The numbering is the numbering according to Edelman et al. (supra).

The single amino acids shown in boldface below the numbers are "invariant" residues according to Kabat et al. (supra) from alignments of CH1 domains from a variety of species.

Sites selected for alteration herein (131, 133, 147, 168, 170, 173, 176, 181, and 183) are shown in underlined boldface.

At these sites, the most common one or two amino acids in the 63 primate CH1 sequences reported in Kabat et al. (supra) are shown in plain text.

Positions where no amino acid is designated were not "invariant" and were not selected for alteration.

Table 9 below shows an alignment human CH1 domains of the IgG1, IgG2, IgG3 and IgG4 isotypes. This alignment highlights the very strong conservation of sequence among these closely-related CH1 domains.

TABLE 9

Alignment of human IgG1, IgG2, IgG3, and IgG4 CH1 domains

```
   118 120       130          140           150         160           170         177
     * *           *            *             *           *             *           *
IgG1 ASTKGPSVFPLAPSSKSTSGGTAALGCLVKDYFPEPVTVSWNSGALTSGVHTFPAVLQSS

IgG2 ASTKGPSVFPLAPCSRSTSESTAALGCLVKDYFPEPVTVSWNSGALTSGVHTFPAVLQSS

IgG3 ASTKGPSVFPLAPCSRSTSGGTAALGCLVKDYFPEPVTVSWNSGALTSGVHTFPAVLQSS

IgG4 ASTKGPSVFPLAPCSRSTSESTAALGCLVKDYFPEPVTVSWNSGALTSGVHTFPAVLQSS

   178 180         190        200        210  215
     * *             *          *          *    *
IgG1 GLYSLSSVVTVPSSSLGTQTYICNVNHKPSNTKVDKKV (SEQ ID NO: 91)

IgG2 GLYSLSSVVTVPSSNFGTQTYTCNVDHKPSNTKVDKTV (SEQ ID NO: 92)

IgG3 GLYSLSSVVTVPSSSLGTQTYTCNVNHKPSNTKVDKRV (SEQ ID NO: 93)

IgG4 GLYSLSSVVTVPSSSLGTKTYTCNVDHKPSNTKVDKRV (SEQ ID NO: 94)
```

Table 9: The amino acid sequences of representative CH1 domains of human IgG1, IgG2, IgG3 and IgG4 antibodies were obtained from IMGT web page, accession numbers J00228, J00230, X03604, and K01316, respectively, and aligned with CLUSTALW software.
Residues are numbered according to the EU system of Edelman et al., supra.
"Invariant" residues according to Kabat et al., supra are shown in boldface.
These residues are highly conserved, but not completely invariant.
Residues that are underlined and in boldface italics are sites at which substitutions have been made and tested as reported in the Examples of WO 2017/205014A1.

Table 9: The amino acid sequences of representative CH1 domains of human IgG1, IgG2, IgG3 and IgG4 antibodies were obtained from IMGT web page, accession numbers J00228, J00230, X03604, and K01316, respectively, and aligned with CLUSTALW software. Residues are numbered according to the EU system of Edelman et al., supra. "Invariant" residues according to Kabat et al., supra are shown in boldface. These residues are highly conserved, but not completely invariant. Residues that are underlined and in boldface italics are sites at which substitutions have been made and tested as reported in the Examples of WO 2017/205014A1.

Table 10 below shows an alignment of human IgG Fc regions of the four human IgG subclasses, IgG1, IgG2, IgG3, and IgG4. This alignment shows the differences between these subclasses, as well as the high sequence conservation.

TABLE 10

Amino acid sequences of human IgG Fc regions

```
IgG1 -----------------------------------------------

IgG2 -----------------------------------------------

IgG3 ELKTPLGDTTHTCPRCPEPKSCDTPPPCPRCPEPKSCDTPPPCPRCP

IgG4 -----------------------------------------------

     216       226       236       246       256       266
     *         *         *         *         *         *
IgG1 EPKSCDKTHTCPPCPAPELLGGPSVFLFPPKPKDTLMISRTPEVTCVVVDVSHEDPEVKF

IgG2 ERKCCVE---CPPCPAPPVA-GPSVFLFPPKPKDTLMISRTPEVTCVVVDVSHEDPEVQF

IgG3 EPKSCDTPPPCPRCPAPELLGGPSVFLFPPKPKDTLMISRTPEVTCVVVDVSHEDPEVQF

IgG4 ESKYG---PPCPSCPAPEFLGGPSVFLFPPKPKDTLMISRTPEVTCVVVDVSQEDPEVQF

     276       286       296       306       316       326
     *         *         *         *         *         *
IgG1 NWYVDGVEVHNAKTKPREEQYNSTYRVVSVLTVLHQDWLNGKEYKCKVSNKALPAPIEKT

IgG2 NWYVDGMEVHNAKTKPREEQFNSTFRVVSVLTVVHQDWLNGKEYKCKVSNKGLPAPIEKT

IgG3 KWYVDGVEVHNAKTKPREEQYNSTFRVVSVLTVLHQDWLNGKEYKCKVSNKALPAPIEKT

IgG4 NWYVDGVEVHNAKTKPREEQFNSTYRVVSVLTVLHQDWLNGKEYKCKVSNKGLPSSIEKT
```

TABLE 10-continued

Amino acid sequences of human IgG Fc regions

| | | |
|---|---|---|
| | 336 346 356 366 376 386 | |
| IgG1 | ISKAKGQPREPQVYTLPPSREEMTKNQVSLTCLVKGFYPSDIAVEWESNGQPENNYKTTP | |
| IgG2 | ISKTKGQPREPQVYTLPPSREEMTKNQVSLTCLVKGFYPSDIAVEWESNGQPENNYKTTP | |
| IgG3 | ISKTKGQPREPQVYTLPPSREEMTKNQVSLTCLVKGFYPSDIAVEWESSGQPENNYNTTP | |
| IgG4 | ISKAKGQPREPQVYTLPPSQEEMTKNQVSLTCLVKGFYPSDIAVEWESNGQPENNYKTTP | |
| | 396 406 416 426 436 446 | |
| IgG1 | PVLDSDGSFFLYSKLTVDKSRWQQGNVFSCSVMHEALHNHYTQKSLSLSPGK | (SEQ ID NO: 95) |
| IgG2 | PMLDSDGSFFLYSKLTVDKSRWQQGNVFSCSVMHEALHNHYTQKSLSLSPGK | (SEQ ID NO: 96) |
| IgG3 | PMLDSDGSFFLYSKLTVDKSRWQQGNIFSCSVMHEALHNRFTQKSLSLSPGK | (SEQ ID NO: 97) |
| IgG4 | PVLDSDGSFFLYSRLTVDKSRWQEGNVFSCSVMHEALHNHYTQKSLSLSLGK | (SEQ ID NO: 98) |

A "host cell line" into which DNA(s) encoding one or more proteins has been introduced refers to a cell line derived from a single cell following the introduction of the DNA, e.g., by transfection. Methods for isolating such clonal cell lines following the introduction of DNA are well known in the art and include limiting dilution, among other possible methods that can include visually determining the existence of only one cell in a particular sample. See, e.g., Wewetzer (1995), J. Immunol. Methods 179 (1): 71-76, Underwood and Bean (1988), J. Immunol. Meth. 107 (1): 119-128.

"Human," nucleotide or amino acid sequences or nucleic acids or proteins include those that occur naturally in a human. Many human nucleotide and amino acid sequences are reported in, e.g., Kabat et al., supra, which illustrates the use of the word "human" in the art. A "human" amino acid sequence or protein, as meant herein, can contain one or more insertions, deletions, or substitutions relative to a naturally-occurring sequence, with the proviso that a "human" amino acid sequence or protein does not contain more than 10 insertions, deletions, and/or substitutions of a single amino acid per every 100 amino acids. Similarly, a human nucleic acid (e.g., DNA) or nucleotide sequence does not contain more than 30 insertions, deletions, and/or substitutions of a single nucleotide per every 300 nucleotides. In the particular case of a VH or VL sequence, the CDRs are expected to be extremely variable, and, for the purpose of determining whether a particular VH or VL amino acid sequence (or the nucleotide sequence encoding it) is a "human" sequence, the CDRs (or the nucleotides encoding them) are not considered part of the sequence.

A "humanized" nucleotide sequence encoding an antibody or antibody domain or a "humanized" amino acid sequence of an antibody or antibody domain, as meant herein, is a sequence that originated in a non-human organism but was engineered to be as similar as possible to a human sequence as possible without sacrificing the desired properties of the antibody, e.g., binding to a certain antigen with a certain avidity, among many possible desired properties. The process of humanization generally involves changing all constant domains to be human constant domains. In the variable domains, the original CDRs can be used to replace the CDRs of a human antibody sequence that is as similar as possible to the original variable domain (a process often referred to as CDR grafting). However, one or more changes in the framework regions may also be required. Thus, the amino acid sequence of a humanized antibody may or may not fall within the definition of "human" immediately above. This process is described in, e.g., Zhang and Ho, Scientific Reports 6:33878; doi: 10.1038/srep33878 (2016) and Miethe et al. PLOS One; doi: 10.137/journal.pone.0161446 (2016), both of which are incorporated herein by reference.

An "IgG antibody," as meant herein, refers to a full-length antibody, as defined herein, of the IgG isotype, including human, humanized, and primate antibodies of the IgG1, IgG2, IgG2, and IgG4 isotype subclasses.

The term "isotype," as meant herein, refers to whether the heavy chain constant regions in an antibody, i.e., the CH1, hinge, CH2, and CH3 domains, are of the IgG, IgD, IgM, IgA, or IgE class or a subclass thereof, such as IgG1, IgG2, IgG3, or IgG4. Such isotypes are known in the art and are described and explained in detail in, e.g., Janeway et al., The Immune System in Health and Disease, 5th ed., sections 4-15 to 4-19, Garland Science, New York, 2001 (available at www.ncbi.nlm.nih.gov/books/NBK27106/).

A "light chain (LC)," as meant herein, comprises a VL domain and a light chain constant (CL) domain, which can be a kappa (CLK) or lambda (CLA) domain. These domains, including exemplary amino acid sequences thereof, are described in Kabat et al., supra, pages xiii-lix, 103-309, and 647-660, which are incorporated herein by reference. The numbering system used herein for the light chain is that described in Kabat et al., supra for the VL domain and that described in Edelman et al., supra for the CL domain, as illustrated in Tables 11-13 below.

TABLE 11

Consensus sequence of human VL domains

| | | | | | | | | | | | | | | | | | | | |
|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | | | | | |
| 16 | 17 | 18 | 19 | 20 | 21 | 22 | 23 | 24 | 25 | ***24*** | ***25*** | ***26*** | ***27*** | ***27A*** | ***27B*** | ***27C*** | ***27D*** | ***27E*** | ***27F*** |
| G | | | | | | | **C** | | | | | | | | | | | | |

| | | | | | | | | | | | | | | | | |
|---|---|---|---|---|---|---|---|---|---|---|---|---|---|---|---|---|
| ***28*** | ***29*** | ***30*** | ***31*** | ***32*** | ***33*** | ***34*** | 35 | 36 | 37 | 38 | 39 | 40 | 41 | 42 | **43** | 44 |
| | | | | | | **W** | | | | | | | | A | P | |

TABLE 11-continued

Consensus sequence of human VL domains

| | | | | | | | | | | | | | | | |
|---|---|---|---|---|---|---|---|---|---|---|---|---|---|---|---|
| | | | | | | | | | | | | | | **S** | |
| | | | | | | | | | | | | | | ***P*** | |

| 45 | 46 | 47 | 48 | 49 | ***50*** | ***51*** | ***52*** | ***53*** | ***54*** | ***55*** | ***56*** | 57 | 58 | 59 | 60 |
|---|---|---|---|---|---|---|---|---|---|---|---|---|---|---|---|
| | | | | | | | | | | | | | I/V | P | |

| 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|
| R | F | S | G | S | | | | | | | | L | | |

| 76 | 77 | 78 | 79 | 80 | 81 | 82 | 83 | 84 | 85 | 86 | 87 | 88 |
|---|---|---|---|---|---|---|---|---|---|---|---|---|
| | | | | | | | | A/G | | **Y** | Y/F | |

| ***91*** | ***92*** | ***93*** | ***94*** | ***95*** | ***95A*** | ***96*** | ***97*** | 98 | 99 | **100** | 101 | 102 | 103 | 104 |
|---|---|---|---|---|---|---|---|---|---|---|---|---|---|---|
| | | | | | | | **F** | **G** | Q/G | **G** | **T** | | | |

105 106 106A 107 108 109 (SEQ ID NO: 99)

TABLE 11: The numbering is according to Kabat et al. (supra).
Numbers in bold italics indicate the positions of the CDRs.
Position numbers with letters after them, e.g., 27A, may or may not be filled by an amino acid, due to the varying lengths of CDRs.
Invariant residues for all human light chains in Kabat et al. (supra) are shown as bold letters indicating the amino acid found at that position.
At selected sites, the one to three most common amino acids found at that site are indicated in plain text.
In addition, many other amino acids are invariant or highly conserved within some subgroups of kappa or lambda VL domains, which can aid in categorizing a particular amino acid sequence as a VL domain.
Sites selected for alteration herein, as reported in the Examples below, are indicated by boldface underlined type.
Positions where no amino acid is designated and/or the number is not shown in boldface underlined type do not meet the criteria stated above.

TABLE 12

Consensus sequence and numbering for CL domains

| | 108 | 109 | 110 | 111 | 112 | 113 | 114 | 115 | 116 | **117** | 118 | 119 | 120 | 121 | 122 | 123 |
|---|---|---|---|---|---|---|---|---|---|---|---|---|---|---|---|---|
| K | | | | | | **P** | | | | I | | **P** | **P** | | | |
| λ | | | | | | **P** | | | | L | | **P** | **P** | | | |

| | 124 | 125 | 126 | 127 | 128 | 129 | 130 | **131** | 132 | 133 | 134 | 135 | 136 | 137 | 138 | 139 |
|---|---|---|---|---|---|---|---|---|---|---|---|---|---|---|---|---|
| K | | | | | | | | S | | **V** | **C** | | | | | |
| λ | | | | | | | | A | | **V** | **C** | | | | | |

| | 140 | 141 | 142 | 143 | 144 | 145 | 146 | 147 | 148 | 149 | 150 | 151 | 152 | 153 | 154 | 155 |
|---|---|---|---|---|---|---|---|---|---|---|---|---|---|---|---|---|
| K | | **P** | | | | | **V** | | **W** | | | | | | | |
| λ | | **P** | | | | | **V** | | **W** | | | | | | | |

| | 156 | 157 | 158 | 159 | **160** | 161 | **162** | 163 | 164 | 165 | 166 | 167 | 168 | 169 | 170 | 171 |
|---|---|---|---|---|---|---|---|---|---|---|---|---|---|---|---|---|
| K | | | | | Q | | S | | T | | | | | | | |
| λ | | | | | E | | T | | P | | | | | | | |

| | 172 | 173 | **174** | 175 | **176** | 177 | 178 | 179 | 180 | 181 | 182 | 183 | 184 | 185 | 186 | 187 |
|---|---|---|---|---|---|---|---|---|---|---|---|---|---|---|---|---|
| K | | | S | | **S** | **S** | T | **L** | T | **L** | | | | | | |
| λ | | | A/M | | **S** | **S** | Y | **L** | S | **L** | | | | | | |

| | 188 | 189 | 190 | 191 | 192 | 193 | 194 | 195 | 196 | 197 | 198 | 199 | 200 | 201 | 202 | 203 |
|---|---|---|---|---|---|---|---|---|---|---|---|---|---|---|---|---|
| K | | | | | | | **C** | | | | **H** | | | | | |
| λ | | | | | | | **C** | | | | **H** | | | | | |

| | 204 | 205 | 206 | 207 | 208 | **209** | 210 | 211 | 212 | 213 | **214** | |
|---|---|---|---|---|---|---|---|---|---|---|---|---|
| K | | | | | | F | | | | | **C** | (SEQ ID NO:100) |
| λ | | | | | | V | | | | | **C** | (SEQ ID NO: 101) |

TABLE 12: The numbering is according to Edelman et al.
(supra), which is the same as the numbering of Kabat et al. (supra) for CL domains.
The amino acids shown in bold below the numbers are "invariant" residues according to Kabat et al. (supra) from alignments of both kappa and lambda CL domains from a variety of species.
As indicated at selected sites (131, 160, 162, 174, 176, and 178), amino acids conserved in the ten human kappa chains (top) and 28 human lambda chains (below) reported in Kabat et al. (supra) are shown in plain text.
In cases where either of two different amino acids are found at one of these sites, the more common amino acid is shown prior to the less common, e.g., A/M.
Bold underlined numbers indicate sites that were altered as reported in the Examples below.
In addition, many other amino acids are invariant or highly conserved within some subgroups of CLK or CLλ domains, which can aid in categorizing a particular amino acid sequence as a CL domain.
Positions where no amino acid is designated and/or the number is not shown in boldface underlined type do not meet the criteria stated above.

TABLE 13

Alignment of human kappa chain CL domains

```
        108          120          130          140          150          160          167
         *            *            *            *            *            *            *
J00241   RTVAAPSVFIFPPSDEQLKSGTASVVCLLNNFYPREAKVQWKVDNALQSGNSQESVTEQD
M11736   RTVAAPSVFIFPPSDEQLKSGTASVVCLLNNFYPREAKVQWKVDNALQSGNSQESVTEQD
M11737   RTVAAPSVFIFPPSDEQLKSGTASVVCLLNNFYPREAKVQRKVDNALQSGNSQESVTEQD
AF017732 RTVAAPSVFIFPPSDEQLKSGTASVVCLLNNFYPREAKVQWKVDNALQSGNSQESVTEQD
AF113887 RTVAAPSVFIFPPSDEQLKSGTASVVCLLNNFYPREAKVQWKVDNALQSGNSQESVTEQD

        168 170          180       190          200          210 214
         *   *            *         *            *            *   *
J00241   SKDSTYSLSLSSTLTLSKADYEKHKVYACEVTHQGLSSPVTKSFNRGEC (SEQ ID NO: 102)
M11736   SKDSTYSLSSLSSTLILSKADYEKHKVYAGEVTHQGLSSPVTKSFNRGEC (SEQ ID NO: 103)
M11737   SKDSTYSLSLSSTLTLSKADYEKHKVYACEVTHQGLSSPVTKSFNRGEC (SEQ ID NO: 104)
AF017732 SKDSTYSLSLSSTLTLSKADYEKHKLYACEVTHQGLSSPVTKSFNRGEC (SEQ ID NO: 105)
AF113887 SKDSTYSLSLSNTLTLSKADYEKHKVYACEVTHQGLSSPVTKSFNRGEC (SEQ ID NO: 106)
```

Table 13: The amino acid sequences of human CL domains in this table are from the International ImMunoGeneTics information system® (IMGT) web page (http://www.imgt.org).
The accession number of each sequence is shown to the left of the sequence, and the sequences were aligned with CLUSTALW software (available at http://www.genome.jp/tools/clustalw/).
Numbering is according to Edelman et al. supra.

The boldface residues are invariant residues according to Kabat et al., supra.

Invariant sites where substitutions were made and the resulting antibodies were tested are indicated by boldface and underlined amino acids.
The bolded, italicized, and underlined residues are other sites where substitutions were made and the resulting antibodies were tested as reported in WO 2017/205014.

An "LC-partner-directing alteration," as meant herein, is a substitution, insertion, or deletion of a single amino acid at the HC/LC interface within a VH or CH1 amino acid sequence, optionally a substitution of a charged amino acid or a cysteine for the naturally occurring amino acid, which causes an HC, optionally a human, humanized, and/or primate IgG HC, containing the altered VH and/or CH1 amino acid sequence to associate more strongly with an LC, optionally one containing an "HC-partner-directing alteration" at a contacting amino acid residue.

Similarly, an "HC-partner-directing alteration" is the substitution, insertion, or deletion of a single amino acid in the HC/LC interface within a VL or CL amino acid sequence, optionally a substitution of a charged amino acid or a cysteine for the naturally occurring amino acid, which causes an LC, optionally a human, humanized, and/or primate kappa or lambda LC, containing the altered VL or CL amino acid sequence to associate more strongly with an HC, optionally one containing an LC-partner-directing alteration at a contacting amino acid residue. In some embodiments, a contacting pair of HC- and LC-partner-directing, or invention heterodimeric HC- and HC-partner-directing, alterations can be substitutions of charged amino acids having opposite charges, which form a "charge pair," as defined above. In other embodiments, if a charged amino acid already exists at one or more of the contacting sites of the HC (e.g., Lys at positions 370K and 392K in certain Fc-regions utilized herein) or LC, then alteration of only one chain is required to create a charge pair favoring formation of a cognate HC/LC or invention heterodimeric variant-Fc-region pair. In other embodiments, cysteine residues can be introduced at contacting sites so that disulfide bridges between a cognate HC/LC pair can form. In further embodiments, HC- and LC-partner-directing alterations can be substitutions or pre-existing amino acids that create a knob and a hole (or a protuberance and a cavity) at contacting residues as described in U.S. Pat. No. 8,679,785, the relevant portions of which are incorporated herein by reference. The HC can be of the IgG, IgA, IgD, IgM, or IgE isotype, optionally IgG1, IgG2, IgG3, or IgG4. HC- and LC-partner-directing alterations occur at contacting amino acid positions that form part of the HC/LC interface. Interface residues in the CL and CH1 domains include those within 4.5 Å, as explained in U.S. Pat. No. 8,592,562, Tables 4 and 5 and accompanying text in columns 10 and 11, all of which is incorporated herein by reference. Contacting residues in the CH1 and CL domains are catalogued in Table 14 below.

TABLE 14

Contacting residues between CH1 and CL

| CH1 residue | CLκ residue | CLλ residue |
|---|---|---|
| 125 | 123 | 119 |
| 126 | 121, 123, 124 | 117, 119, 120 |
| 127 | 121 | 117, 119 |
| 128 | 118, 133 | 114, 129 |
| 129 | 118 | 114 |
| 130 | 118 | |
| 139 | 116 | |
| 140 | 116 | |
| 141 | 116, 118, 135 | 112, 114 |
| 142 | 118 | 114 |
| 143 | | 114 |
| 145 | 124, 131 | 127, 129, 173 |
| 147 | 124, 131 | 125, 127 |
| 148 | | 125 |
| 168 | 137, 138, 174 | 133, 163, 169 |
| 169 | 164 | |
| 170 | 135, 162, 164, 174, 176 | 131, 133, 169, 171 |
| 171 | 162, 164 | 158, 161, 171 |
| 172 | | 158 |
| 173 | 160, 162 | 156, 158, 173 |

TABLE 14-continued

| Contacting residues between CH1 and CL | | |
|---|---|---|
| CH1 residue | CLκ residue | CLλ residue |
| 174 | 160 | 156 |
| 175 | 160 | 156 |
| 176 | | 156 |
| 181 | | 173 |
| 182 | | 173 |
| 183 | 176 | 129, 131, 173 |
| 185 | 135 | 114, 131 |
| 187 | 137 | |
| 213 | 123 | 119 |
| 218 | 122 | |

In the case of contacting residues on the interface between the VH and VL domains, pairs of residues, one in the VH and one in the VL domain, suitable for alteration were selected using the follow criteria: (1) the residues are buried or partially buried, i.e., inaccessible in the tertiary structure of a full-length antibody, (2) the residues are spatially close, that is, where the Calls of the two amino acids are within about 12 Å, or where there is at most 5.5 Å between a side chain heavy atom (any atom other than hydrogen) of one amino acid and any heavy atom of the other amino acid according to known structure models, (3) the residues are highly conserved, although they need not be totally invariant, and (4) the residues are not within or interacting with the complementarity determining regions (CDRs). Examples of such contacting residues include, without limitation, the following: position 44 (VH) and position 100 (VL); position 39 (VH) and position 38 (VL); and position 105 (VH) and position 43 (VL). A change in the strength of HC/LC association due to HC- and/or LC-partner-directing alterations can be measured by determining the relative amounts of various antibody species in a host cell into which DNA encoding at least two different antibodies has been introduced. As explained in detail in Examples 3 and 6 examples of contacting pairs of LC- and HC-partner-directing alterations include, without limitation, the following: substitutions in a first HC region corresponding to K147D, F170C, V173C in its CH1 domain and C220G in upper hinge region of the HC region; and substitutions in its cognate first LC region corresponding to S131K, Q160C, S162C and C214S in its Cκ domain. As these examples illustrate "contacting" pairs of LC- and HC-partner directing alterations can include amino acids opposite in charge. Many other examples are disclosed in the Description and Examples in WO 2017/205014A1, which is incorporated herein by reference in its entirety for all purposes. Alternatively, LC- and HC-partner-directing alterations could be "protuberance in cavity" style alterations as described in U.S. Pat. No. 8,679,785. The portions of this patent describing these kinds of alterations, especially col. 12, line 12 to col. 14, line 5, are incorporated herein by reference. The term "partner-directing alteration" refers to HC- and/or LC-partner-directing alterations.

A "primate," nucleotide or amino acid sequence or nucleic acid or protein includes molecules and sequences that occur naturally in a primate. Primates include animals from a number of families including, without limitation, prosimians (including lemurs), new world monkeys, chimpanzees, humans, gorillas, orangutans, gibbons, and old world monkeys. Specific primate species include, without limitation, *Homo sapiens, Macaca mulata* (rhesus macaque), *Macaca fascicularis* (cynomolgus monkey), and *Pan troglodytes* (chimpanzee), among many others. Many primate nucleotide and amino acid sequences are known in the art, e.g., those reported in, e.g., Kabat et al., supra. Generally, "primate" amino acid sequence, as meant herein, can contain one or more insertions, deletions, or substitutions relative to a naturally-occurring primate sequence, with the proviso that a "primate" amino acid sequence does not contain more than 10 insertions, deletions, and/or substitutions of a single amino acid per every 100 amino acids. Similarly, a primate nucleotide sequence can contain insertions, deletions, or substitutions relative to a naturally-occurring primate sequence, but does not contain more than 30 insertions, deletions, and/or substitutions of a single nucleotide per every 300 nucleotides. In the particular case of a VH or VL sequence, the CDRs are expected to be extremely variable, and, for the purpose of determining whether a particular VH or VL amino acid sequence (or the nucleotide sequence encoding it) is a "primate" sequence, the CDRs (or the nucleotides encoding them) are not considered part of the sequence.

Two amino acid sequences are "the same," as meant herein, if the two sequences could be encoded by the same DNA sequence. That is, amino acid sequences that differ only as a result of post-translational modifications, e.g., elimination of a carboxyl-terminal lysine or cyclization of N-terminal glutamate or glutamine residues, are "the same" as meant herein.

A "target molecule," as meant herein, is a molecule to which an antibody specifically binds. In some embodiments, a target molecule is a "target protein," i.e., a protein to which an antibody specifically binds.

Bispecific Antibodies and Methods of Producing Them

Described herein are heterodimeric variant-Fc-region bispecific antibodies having different binding specificities that are produced in host cells into which DNA(s) encoding the antibodies has (have) been introduced. The invention bispecific antibodies can be human, humanized, and/or primate full-length IgG antibodies. Also described are methods for producing such heterodimeric variant-Fc-region bispecific antibodies. The HCs and/or LCs of one or more of the antibodies used to make the bispecific antibody can comprise LC- and/or HC-partner-directing alterations. In some embodiments, the HCs of one or more of the antibodies can comprise one or more alterations that disfavor homodimers.

The method for producing the heterodimeric variant-Fc-region bispecific antibodies can comprise introducing DNA encoding the heterodimeric variant-Fc-region bispecific antibodies described herein into host cells, culturing the host cells, and recovering the heterodimeric variant-Fc-region bispecific antibodies from the cell mass or culture medium. DNA encoding the different antibodies that form the desired bispecific antibody can be introduced into host cells at the same time or at different times. For example, DNA encoding a second antibody can be introduced into a host cell population that already produces a first antibody encoded by DNA that was previously introduced into the host cell population. Alternatively, DNA encoding both antibodies can be introduced into the host cells at the same time. Further, after introduction of DNAs encoding multiple antibodies into the host cells, a clonal "host cell line" (as defined above) that produces the desired heterodimeric variant-Fc bispecific antibodies can be isolated from the population of cells into which the DNAs were introduced. Alternatively, heterodimeric variant-Fc-region bispecific antibodies can be produced by a host cell population into which the DNAs were introduced. As explained in detail below, the alteration(s) in the antibodies can advantageously limit the number of homodimeric antibodies produced by the host cells.

Accordingly, a substantially pure heterodimeric variant-Fc-region bispecific antibody composition can be obtained from a host cell culture supernatant or the cell mass, can be further purified, and can be formulated as appropriate for use as a pharmaceutical.

More specifically, DNAs encoding two different antibodies, optionally full-length IgG antibodies, binding to different epitopes and/or targets can be introduced into a host cell. The encoded antibodies can each comprise two HCs with the same amino acid sequence and two LCs with the same amino acid sequence, and each of the encoded antibodies can have both HCs and LCs that differ in amino acid sequence from the HCs and LCs of the other encoded antibody or antibodies. In some embodiments, the antibodies can be two full-length antibodies, each comprising two heavy chains having the same amino acid sequence and two light chains having the same amino acid sequence. Optionally, the antibodies are primate and/or human and/or humanized IgG antibodies. In some embodiments, at least one pair of oppositely charged residues, i.e., charge pairs, or cysteine residues at contacting sites in a cognate HC/LC pair (where at least one of these charged residues or cysteines results from an alteration) can be found in the interface between the LC of each antibody and its cognate HC. In other embodiments, such charge pairs and/or pairs of contacting cysteine residues can be found in one or both of the antibodies in the mixture, but in some embodiments need not be present in both antibodies in the mixture. Alterations in the LC and HC that create such pairs are called HC-partner-directing alterations and LC-partner-directing alterations, respectively. Each antibody can comprise multiple contacting pairs of LC- and/or HC-partner-directing alterations or can comprise no pairs of LC- and/or HC-partner-directing alterations. In preferred embodiments, there are alterations in the CH3 domains that favor the formation of heterodimeric HC/HC pairs. Such alterations can be present in one or both of the antibodies and can be absent from one or both of the antibodies. The host cell population or host cell line can be cultured, and the heterodimeric variant-Fc-region bispecific antibodies can be recovered in the cell mass and/or the culture medium. The invention heterodimeric variant-Fc-region bispecific antibodies can be further purified, and the mixture can be formulated as is appropriate for its pharmaceutical use.

In embodiments where DNAs encoding only two full-length antibodies (Ab1 and Ab2) are introduced into the host cells and each antibody comprises one or more HC- and/or LC-partner-directing alteration(s) such that few if any non-cognate HC/LC pairs form, substantially pure heterodimeric variant-Fc-region bispecific antibodies can be produced by the host cells. When the HCs form heterodimeric HC/HC pairs, a desired heterodimeric variant-Fc-region bispecific antibody comprising one HC and one LC from each antibody is produced by the host cells.

Further purification of an antibody supernatant made by a host cell population or host cell line can involve a number of steps. In some embodiments, the bispecific antibody supernatant is applied to a Protein A or Protein G affinity column and subsequently eluted. Other column chromatography steps such as cation or anion exchange chromatography, including low pH cation exchange chromatography as described below, size exclusion chromatography, reverse phase chromatography, or hydrophobic interaction chromatography (HIC) could also be used. Further purification steps can include diafiltration, among many possibilities.

Further, a heterodimeric variant-Fc-region bispecific antibody or nucleic acids encoding such an antibody can be formulated for its intended use. For use as a therapeutic, the antibody composition could be formulated as a liquid for parenteral administration, optionally for injection. Other kinds of formulations, e.g., gels, pastes, creams, or solids, are also possible. Formulations can include ingredients that can, for example, maintain, modify, or preserve the antibodies or nucleic acids and/or control factors such as pH, osmolarity, viscosity, clarity, odor, color, sterility, and/or rate of release or absorption in vivo. As such, it could include any buffer and/or excipient ordinarily used in such formulations. Examples of such ingredients include buffers, anti-microbials, chelating agents, salts, amino acids, and sugars, among many possibilities. The pH of the formulated mixture could be within a range from about pH 5 to about pH 8.5 or from about pH 6 to about pH 8.

The binding specificity of the antibodies can be determined by any binding assay well-known in the art, or similar to that described herein.

A method to determine whether two antibodies compete for a particular binding site or epitope on an antigen generally includes the following steps. First, a biotinylated antigen is incubated in the presence of varying amounts of a competitor antibody (mAb2). These combinations are referred to as "samples." The samples, which may include mAb2/antigen complexes as well as unbound mAb2 and/or antigen, are then added to wells in a microtiter plate coated with another antibody that binds the antigen (mAb1). As a control, samples including biotinylated antigen incubated without mAb2 can be added some wells. The plate is then washed to remove unbound antigen. If mAb1 and mAb2 do not compete, mAb1 can bind to the mAb2/antigen complexes, as well as free antigen. In this case, signal intensity (which is proportional to the amount of bound antigen or mAb2/antigen complexes) will not be diminished by the presence of mAb2 in a sample. In some cases mAb1 and mAb2 may compete completely, meaning that mAb1 will bind to free antigen, but not to mAb2/antigen complexes. In some cases, competition may occur but be less complete. In such a case, binding of mAb1 to mAb2/antigen complexes may be decreased rather than completely absent. In either case, signal intensity will be decreased by the presence of mAb2/antigen complexes in a sample. The signal is detected by adding streptavidin coupled to horse radish peroxidase (HRP), washing the plate, and adding a substrate for HRP that can be detected by colorimetric measurements. The plate is washed, and the reaction is stopped to prevent saturation of the signal. The colorimetric signal is detected. As meant herein, if two antibodies compete (either completely or partially) for binding to an antigen by the test described here, they are said to bind to the same epitope on the antigen.

The HCs of the antibodies in the mixture can be of any isotype, such as IgG (including either IgG1, IgG2, IgG3, or IgG4), IgA, IgM, IgE, or IgD. When an IgG4 HC is used, the HC can comprise the alteration S228P, which prevents Fab arm exchange. Silva et al. (2015), J. Biol. Chem. 290 (9): 5462-5469. Sequences for such heavy chains are known in the art. See, e.g., Kabat et al., supra, at pages 661-723, which is incorporated herein by reference. The heavy chains can be from any species, e.g., a mammal, a human, a primate, a mouse, or a rat, or the heavy chains can be artificially produced, for example using phage display or using a humanization process.

Similarly, the two different light chains can be lambda (λ) or kappa (κ) chains, which can be from any species and, optionally, can be mammalian, for example, human or humanized, primate, murine, or rat antibodies. The light chain could also be produced artificially, for example using phage display or a humanization process. Numerous examples of amino acid sequences of λs and κs are known in the art, for example those reported in Kabat et al., supra, pages 647-660, which are incorporated herein by reference. Positions in these sequences are determined according to the Kabat (Kabat et el., supra) numbering system for VL domains and the Edelman (Edelman et al., supra) numbering system for CL domains, as shown in Tables 11-13 and discussed in the accompanying text.

Both heavy and light chains can contain one or more alterations as described herein. Each alteration of can be a substitution, insertion, or deletion of a single amino acid. In some embodiments, each alteration is the substitution of one amino acid with another. Optionally, the alteration is the substitution of a charged amino acid or a cysteine for the amino acid originally present at that site. In some embodiments, the substituted amino acid can be any amino acid. In some embodiments, an amino acid other than cysteine can be substituted for cysteine. The amino acid other than cysteine can be any amino acid, although it can be serine, glycine, or alanine in some embodiments. In some embodiments the choice of the amino acid used to replace that in the original amino acid sequence is limited. For example, in such embodiments the amino acid used to replace the original amino acid can be any amino acid except one or more of the following amino acids: alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine(S), threonine (T), tryptophan (W), tyrosine (Y), and valine (V). In other embodiments, an original amino acid can be replaced with any other amino acid from among the group of twenty recited immediately above. In other embodiments, an original amino acid can be replaced with either of two, three or four amino acids and/or any amino acid within a group of amino acids having similar properties, such as the "conservative" amino acid substitutions described below. For example, such groups include (1) arginine and lysine, (2) serine and threonine, (3) aspartate and glutamate, or (4) asparagine and glutamine, among others.

One of skills in the art is aware that the amino acids present in living things can be grouped according to their properties and that replacement of an original amino acid with an amino acid having similar properties is called a "conservative substitution." The alterations described herein can, in some embodiments, include conservative substitutions. As meant herein, conservative substitutions include replacement of (1) A with V, L, or I, (2) R with K, Q, or N, (3) N with Q, (4) D with E, (5) C with S or A, (6) Q with N, (7) E with D, (8), G with P or A, (9) H with N, Q, K, or R, (10) I with L, V, M, A, or F, (11) L with I, V, M, A, or F, (12) K with R, Q, or N, (13) M with L, F, or I, (14) F with L, V, I, A, or Y, (15) P with A, (16) S with T, A, or C, (17) T with S, (18) W with Y or F, (19) Y with W, F, T, or S, and (20) V with I, M, L, F, or A.

Amino acids and amino acid substitutions at particular sites in a sequence are denoted herein as follows. The original amino acid in a sequence is followed by the position number in the heavy or light chain amino acid sequence (using the numbering systems illustrated in Table 7-13), which is followed by the amino acid used as a replacement. For example, K409E in an HC means that the lysine originally present at position 409 in the HC is replaced by glutamic acid. If position 409 in the heavy chain can originally contain either of two different amino acids, e.g., K or R, and these can be replaced with either of two amino acids, e.g., D or E, that could be denoted as K/R409D/E. This designation means that the lysine or arginine originally present at position 409 can be replaced with either an aspartic acid or a glutamic acid. In some cases, the original amino acid is not defined. For example, 409D in an HC would mean amino acid at position 409 is an aspartic acid, and the identity of the original amino acid is not defined and can be any amino acid, including aspartic acid. Similarly, a designation of K409 means that the original amino acid at position 409 is a lysine (and there is no alteration).

Tables 7-13 illustrate the level of sequence consensus among HCs and LCs, in some cases among human or primate HCs and LCs. The amino acid sequences of the variable regions vary particularly in the complementarity determining regions (CDRs, which are shown by bold italic numbers in Tables 7 and 11). However, the framework regions that surround the CDRs are more conserved and contain highly conserved amino acids at a number of positions. Many of the universally conserved or almost universally conserved amino acids, for example positions 4, 36, 38, and 39 in VH and 98, 99, 101, 102 in VL, are also conserved in VH and VL regions from non-human species. In addition, many other sites in VHs and VLs are highly conserved within specific groups of variable domains, although not across all VHs and VLs. Constant domains in HCs and LCs show a higher degree of sequence conservation than variable domains and contain a number of highly conserved amino acids. See Tables 8-10 and 12-13. Using these highly conserved amino acids, one of skill in the art would be able to align most immunoglobulin domains with the sequences disclosed in Kabat et al., supra to assign a numbering of those VHs and VLs according to the system of Kabat et al., supra or Edelman et al., supra.

The heterodimeric variant-Fc-region bispecific antibodies described herein can comprise HC- and/or LC-partner-directing alterations. In one embodiment, HC-partner-directing alterations provided herein serve the function of ensuring that each invention variant-Fc-region pairs with its cognate HC to form a substantially pure heterodimeric molecule, such as heterodimeric variant-Fc-region fusion proteins and/or heterodimeric variant-Fc-region bispecific antibodies. In particular embodiments, these heterodimeric variant-Fc-region fusion proteins and/or heterodimeric variant-Fc-region bispecific antibodies are substantially free of the corresponding homodimeric variant-Fc-region fusion proteins and/or homodimeric variant-Fc-region bispecific antibodies as described herein.

In another embodiment, HC- and/or LC-partner-directing alterations serve the function of ensuring that each LC pairs with its cognate HC and vice versa. In the absence of such alterations, up to ten different species of antibodies could potentially form in a host cell transfected with DNA encoding only two different full-length antibodies that have different HCs and LCs. However, if only cognate HC/LC pairing occurs, these numbers would be drastically reduced. Furthermore, in accordance with the present invention, if only heterodimeric HC/HC pairing occurs between the invention variant-Fc-regions provided herein, the number of species is advantageously reduced to the desired single species that is substantially free of any homodimeric species, such as any homodimeric variant-Fc-region bispecific antibodies. Since many of the possible species in the absence of HC/LC partner-directing alterations would have non-cognate HC/LC pairings, some of the resulting antibodies might not bind to any epitope and might therefore lack a desired function.

HC- and HC-heterodimeric-partner-directing alterations can occur at contacting sites in the CH3/CH3 domains interface, which are listed in Table 6 above; whereas HC- and LC-partner-directing alterations can occur at contacting sites in the CH1 and CL domains, which are listed in Table 14 above, and/or at contacting sites in VH and VL domains, as explained herein. For example, in particular embodiments, antibodies used to produce the invention heterodimeric variant-Fc-region bispecific antibodies provided herein can comprise one or more LC- and/or HC-partner-directing alteration(s) in their HC and/or LC, such as for example, 1, 2, 3, 4, 5, 6, 7, 8, 9, 10, 11, 12, 13, 14, 15, 16, 17, 18, 19, or 20 such respective partner-directing alterations; and/or not more than 1, 2, 3, 4, 5, 6, 7, 8, 9, 10, 11, 12, 13, 14, 15, 16, 17, 18, 19, or 20 such respective partner-directing alterations. In some embodiments, at least one antibody used to produce the invention heterodimeric variant-Fc-region bispecific antibodies can lack such alterations.

In some embodiments, these alterations include a substitution of a charged amino acid at a site that did not originally have a charged amino acid or substitution of a charged amino acid at a site that originally contained an amino acid of opposite charge. In embodiments where DNA encoding two different full-length antibodies, where the HCs and the LCs of the two antibodies are different, is introduced into a host cell, the LC- and HC-partner-directing alterations can occur at the same sites in the two different LCs and HCs, resulting in a situation where (1) the two different HCs have oppositely charged amino acids at the same HC site, (2) the two different LCs have oppositely charged amino acids at the same LC site, (3) the two different HCs have oppositely charged amino acids at an HC site contacting the LC site, and (4) for each cognate LC/HC pairing, the charged amino acid at the LC site is opposite in charge to the amino acid at the contacting HC site. In such a situation, the heterodimeric interaction between cognate pairs of invention variant-Fc-regions of HCs/HCs or cognate LCs and HCs is strengthened by an interaction between oppositely-charged amino acids, and the interaction between non-cognate homodimeric variant-Fc-region HC/HC and/or LC/HC pairings is highly disfavored due to repulsion of amino acids having the same charges situated at contacting sites in non-cognate variant-Fc-region HC/HC and/or HC/LC pairs. See FIGS. 1-2 of US WO 2017/205014, which is incorporated herein by reference in its entirety for all purposes. In other embodiments, only one antibody comprises a charge pair that favors cognate HC/LC pairing. See FIG. 3 of WO 2017/205014. In such a case, one of the amino acids in the charge pair may result from a partner-directing alteration where a charged amino acid residue is substituted for an oppositely charged amino acid residue. In this case, some non-cognate invention variant-Fc-region HC/HC pairs and/or HC/LC pairs would be disfavored due to repulsive charge interactions. Examples of contacting charge pairs optionally resulting from HC- and/or LC-partner-directing alterations include, without limitation, the following: 44D/E (HC) and 100R/K (LC); 44R/K (HC) and 100D/E (LC); 105E/D (HC) and 43R/K (LC); 105R/K (HC) and 43E/D (LC); 133R/K (HC) and 117D/E (LC); 133D/E (HC) and 117R/K (LC); 137R/K (HC) and 114D/E (LC); 137D/E (HC) and 114R/K (LC); 137R/K (HC) and 116D/E (LC); 137D/E (HC) and 116R/K (LC); 147R/K (HC) and 124D/E (LC); 147D/E (HC) and 124R/K (LC); 147R/K (HC) and 129D/E (LC); 147D/E (HC) and 129R/K (LC); 147R/K (HC) and 131D/E (LC); 147D/E (HC) and 131R/K (LC); 147R/K (HC) and 178D/E (LC); 147D/E (HC) and 178R/K (LC); 147R/K (HC) and 180D/E (LC); 147D/E (HC) and 180R/K (LC); 168D/E (HC) and 164R/K (LC); 168R/K (HC) and 164D/E (LC); 168D/E (HC) and 167R/K (LC); 168R/K (HC) and 167D/E (LC); 168D/E (HC) and 174R/K (LC); 168R/K (HC) and 174D/E (LC); 170D/E (HC) and 162R/K (LC); 170R/K (HC) and 162D/E (LC); 173D/E (HC) and 160R/K (LC); 173R/K (HC) and 160D/E (LC); 173D/E (HC) and 162R/K (LC); 173R/K (HC) and 162D/E (LC); 175D/E (HC) and 160R/K (LC); 175R/K (HC) and 160D/E (LC); 175D/E (HC) and 180R/K (LC); 175R/K (HC) and 180D/E (LC); 176D/E (HC) and 160R/K (LC); 176R/K (HC) and 160D/E (LC); 181R/K (HC) and 178D/E (LC); 181D/E (HC) and 178R/K (LC); 183R/K (HC) and 176D/E (LC); 183D/E (HC) and 176R/K (LC); 190R/K (HC) and 116D/E (LC); 190D/E (HC) and 116R/K (LC); 190R/K (HC) and 137D/E (LC); 190D/E (HC) and 137R/K (LC).

In a particular embodiment (see FIG. 18A), a first invention variant-Fc-region/HC1 comprises the following HC- and LC-partner-directing alterations: K147D, F170C, V173C, C220G, S354C, S364K, 370K, N390P, 392K and S400K (also referred to herein as an "DCCG-CKKPKK HC"). Also in this particular embodiment, a second invention variant-Fc-region/HC2 comprises the following HC-partner-directing alterations: Y349C, S364D, K370D, N390D, K392G, and S400D (also referred to herein as an "CDDDGD HC") (see FIG. 18A). Also in this particular embodiment, the LC1, which is cognate to the first variant-Fc-region/HC1 above comprises: S131K, Q160C, S162C and C214S (also referred to herein as a "KCCS LC") (see FIG. 18A).

Also contemplated herein is another embodiment, comprising a first invention variant-Fc-region/HC1 comprising the following HC- and LC-partner-directing alterations: K147D, F170C, V173C, C220G, Y349C, S364D, K370D, N390D, K392G, and S400D (also referred to herein as an "DCCG-CDDDGD HC") (see FIG. 18B); a second invention variant-Fc-region/HC2 comprising the following HC-partner-directing alterations: S354C, S364K, 370K, N390P, 392K and S400K (also referred to herein as an "CKKPKK HC") (see FIG. 18B); and an LC1, which is cognate to the first variant-Fc-region/HC1 above, and comprises: S131K, Q160C, S162C and C214S (also referred to herein as a "KCCS LC") (see FIG. 18B).

Accordingly, also contemplated herein in another embodiment of the invention heterodimeric anti-CD20/anti-CD37 bispecific antibodies is the placement of the DCCG (e.g., the K147D, F170C, V173C and C220G alterations described herein) on either the CDDDGD or CKKPKK versions of the anti-hCD20 HC; and the KCCS (e.g., K147D, F170C, V173C and C220G alterations described herein) on the anti-hCD20 LC; then the anti-hCD37 would have an unmodified LC.

In yet another embodiment, also contemplated herein for the invention heterodimeric anti-hSIRPα×hCLDN18.2 bispecific antibodies is the placement of the DCCG (e.g., the K147D, F170C, V173C and C220G alterations described herein) on either the CDDDGD or CKKPKK versions of the anti-hSIRPα HC; and KCCS (e.g., K147D, F170C, V173C and C220G alterations described herein) on the anti-hSIRPα LC; then the anti-hCLDN18.2 would have an unmodified LC.

In yet another embodiment, also contemplated herein for the invention heterodimeric anti-hSIRPα×hCLDN18.2 bispecific antibody, wherein the first HC region corresponds to anti-hCLDN18.2 HC1 having the corresponding DCCG-CKKPKK alterations described herein; the first LC region corresponding to anti-hCLDN18.2 LC1 having the corresponding KCCS alterations described herein; and the second HC region corresponding to anti-hSIRPα HC2 having the corresponding CDDDGD alterations described herein; and the second LC region corresponding to an unmodified anti-hSIRPα LC2 (SEQ ID NO:74).

In, for example, embodiments where DNA encoding two full-length antibodies (a first antibody comprising HC1 and LC1 and a second antibody comprising HC2 and LC2) has been introduced into a host cell, one or both sites in a pair of contacting sites in an HC/HC pair and/or an HC/LC pair may already contain a charged amino acid. For example, in some cases LC1 may comprise a charged amino acid at a site that contacts a site in the cognate HC1 that does not comprise a charged amino acid, or vice versa. In other embodiments, HC1 corresponding to the first variant-Fc-region may comprise a charged amino acid at a site that contacts a site in the cognate HC2 corresponding to the second variant-Fc-region that does not comprise a charged amino acid, or vice versa. In a specific example, position 160 in a human CL domain can comprise a glutamic acid (E), whereas contacting sites 173, 174, and 175 in a human CH1 domain commonly comprise V, L, and Q, respectively. In this case, one of the contacting CH1 sites, e.g., 173, can be altered such that it is opposite in charge to that of the E at position 160 in the CL domain, i.e. position 173 can be substituted with an R or a K. The same site in HC2 can be altered to a charged amino acid opposite in charge to that at the site in HC1 (i.e., this site can be substituted with a D or an E), and the contacting site in LC2 can be altered to a charged amino acid opposite in charge to that in LC1 (i.e., position 160 in LC2 can be substituted with an R or a K).

Other scenarios where one or more of the contacting sites in a cognate variant-Fc-region-HC/-HC pair and/or an HC/LC pair already comprise one or more charged amino acid(s), for example at sites 370K and 392K as used herein for particular invention variant-Fc-regions, and the like (see, e.g., FIG. 18 and the like), could be treated similarly with the end goal of creating oppositely charged amino acids at contacting sites in cognate HC/LC pairs. In some embodiments, the same pair of contacting sites can be altered such that they comprise oppositely charged amino acids in both antibodies, with the proviso that the charges of the amino acids at the HC site is opposite in HC1 and HC2 and the charges at the LC site are also opposite in the LC1 and LC2.

Similarly, for example in embodiments where DNA encoding two full-length antibodies (a first antibody comprising HC1 and LC1 and a second antibody comprising HC2 and LC2) has been introduced into a host cell, if contacting sites in HC1 and LC1 comprise oppositely charged amino acids, the same sites in HC2 and LC2 can be replaced with amino acids opposite in charge to those found in HC1 and LC1, respectively.

In other embodiments where DNA encoding two different full-length antibodies is introduced into a host cell, the LC- and HC-partner-directing alterations can occur at different sites in the two different LCs and HCs, resulting in a situation where (1) one LC and its cognate HC each have oppositely-charged amino acids at contacting sites and (2) the other LC and its cognate HC each have oppositely-charged amino acids at contacting sites that differ from those used in the first LC/HC pair. In these embodiments, the HC- and LC-partner-directing alterations serve to strengthen the interaction between cognate HC/LC pairs.

As set forth in FIG. 18, it is also contemplated herein that only one of the two cognate HC/LC pairs possesses the respective LC- and HC-partner-directing alterations. In other words, one of the antibodies in the context of bispecific antibody as described herein may not comprise a partner-directing alteration. In such embodiments, the other antibody in the context of bispecific antibody comprises one or more partner-directing alterations.

In other embodiments, HC- and LC-partner-directing alterations can result in the creation of disulfide bridges due to cysteine substitutions at contacting sites in cognate HC/LC pairs. In, for example, embodiments where DNA encoding two different full-length antibodies is introduced into a host cell, such LC- and HC-partner-directing alterations can occur at different sites in the two different LCs and HCs, resulting in a situation where cognate LC/HC pairs have cysteine substitutions at contacting sites, whereas non-cognate LC/HC pairs do not have cysteine substitutions at contacting sites. See, e.g., FIGS. 1-3 of WO 2017/205014. Thus, the two different cognate HC/LC pairs will have disulfide bridges at different places at the HC/LC interface, whereas a non-cognate HC/LC pair would not have such a disulfide bridge because the substituted cysteine residues would not be close enough to form a bridge. Hence, in these embodiments, the HC- and LC-partner-directing alterations serve to strengthen the interaction between cognate HC/LC pairs. In other embodiments, only one of the two antibodies transfected, can comprise cysteines at contacting sites in a cognate HC/LC pair. Examples of pairs of cysteine substitutions at contacting residues include, for example, the following pairs of alterations: 126C (HC) and 121C (LC); 126C (HC) and 124C (LC); 127C (HC) and 121C (LC); 128C (HC) and 118C (LC); 133C (HC) and 117C (LC); 133C (HC) and 209C (LC); 134C (HC) and 116C (LC); 141C (HC) and 116C (LC); 168C (HC) and 174C (LC); 170C (HC) and 162C (LC); 170C (HC) and 176C (LC); 173C (HC) and 160C (LC); 173C (HC) and 162C (LC); and 183C (HC) and 176C (LC).

In some embodiments, one or more cysteine residues that normally form part of a disulfide bridge between an HC and an LC can be replaced with another amino acid in at least one of the heterodimeric variant-Fc-region bispecific antibodies as described herein. For example, in a human IgG1 antibody, the cysteines at position 220 in the HC and 214 in the LC form a disulfide bridge between the HC and LC. These amino acids can be replaced with other amino acids, for example serine, alanine, or glycine, thereby eliminating a naturally occurring HC/LC disulfide bridge. Similar alterations can be made in antibodies of other IgG isotypes, i.e., IgG2, IgG3, or IgG4, with similar or different patterns of disulfide bond formation, in which the cysteine residues that participate in HC/LC disulfide bond formation can be substituted with other amino acids. For example, in human IgG2 and IgG4 antibodies, the cysteines at positions 131 (HC) and 214 (LC) can be substituted with other amino acids. Such alterations can weaken non-cognate HC/LC pairing, as well as cognate HC/LC pairing, since non-cognate pairs will also be unable to form the usual interchain disulfide bridges. Cognate HC/LC pairing can be strengthened by, e.g., adding partner-directing alterations to the cognate HC/LC pair lacking it usual disulfide bridge(s). Such partner-directing alterations can include cysteine substitutions at contacting residues in the HC and/or the LC so as to create new disulfide bridges and/or substitutions that introduce charged amino acids at contacting residues in the HC and/or LC so as to create charge pairs. See FIG. 3 of WO2017/205014.

In some embodiments where DNA encoding two different full-length antibodies having different HCs and LCs has been introduced into a host cell, the HCs of at least one or both of the two antibodies can comprise one or more alteration(s) that favors the formation of HC/HC heterodimeric pairings. In the context of a pharmaceutical production process, this leads to the advantageous situation where a pharmaceutical product consisting essentially of a single heterodimeric variant-Fc-region-bispecific antibody can be produced in a single cell line using a single production process. Examples of alterations (including in some cases amino acids present in the original sequence) that favor the formation of heterodimers include, without limitation, those set forth herein.

In further embodiments, one or more alterations that affect the pharmacokinetic properties of bispecific antibody as described herein can be introduced. For example, the in vivo half life or the area under the curve (AUC) can be shortened by alterations such as M252A, M252L, M252S, M252R, R255K or H435R. Other alterations well-known in the art that affect pharmacokinetic properties of bispecific antibody can be introduced. Those of skill in the art will readily understand that the 2 Fab arms are physically linked, such that any alterations of the half-life of one Fab arm will impact the whole molecule.

Antibodies

Described herein are antibodies that comprise partner-directing alterations to the invention variant-Fc-regions (e.g, within CH3) described herein. Such antibodies can be any antibody known to those of skill in the art of any format, so long as the antibody comprises at least one invention variant-Fc-region set forth herein. In some embodiments, such antibodies can be full-length IgG antibodies that can be IgG1, IgG2, IgG3, or IgG4 antibodies, which can be mammalian antibodies, e.g., primate, human, and/or humanized antibodies. These include, for example, an antibody comprising, for example, a primate, human, and/or humanized invention variant-Fc-region domains in combination with CL and IgG1 and/or IgG4 CH1 domains that comprise one or more charge pairs (which can result from partner-directing alteration(s)) at one or more of the following pairs of sites set forth in Table 6; or in the following pairs of sites in the HC and LC, respectively: 131, 147, 160, 168, 170, 173, 174, 178, 181, 214, 220, 349, 364, 370, 390, 392, and 400 (see, e.g., FIG. 18). In further embodiments, described herein are an antibody comprising, for example, primate, human, and/or humanized invention variant-Fc-region domains in combination with CL and IgG1 CH1 domains, wherein the antibody comprises one or more pairs of cysteine residues at contacting sites in the CH1 and CL domains, wherein the CH1 and CL positions, respectively, of these cysteine residues can be at any one or more of the following pairs: 126 and 124; 128 and 118; 133 and 117; 134 and 116; 168 and 174; 170 and 162; 170 and 176; and 173 and 160. In still other embodiments, described herein are an antibody comprising, for example, primate, human, and/or humanized invention variant-Fc-region domains in combination with CL and IgG4 CH1 domains, wherein the antibody comprises one or more pairs of cysteine residues at contacting sites in the CH1 and CL domains, wherein the CH1 and CL positions, respectively, of these cysteine residues can be at any one or more of the following pairs of residues: 126 and 124; 127 and 121; 128 and 118; 168 and 174; 170 and 162; and 173 and 162.

In a further embodiment, described herein is an IgG2 antibody comprising an invention variant-Fc-region domain in combination with, optionally a human, primate, and/or humanized antibody, lacking the naturally occurring disulfide bridge linking the HC and LC and containing one or more substitutions in both the HC and the LC that can create one or more new disulfide bridge. For example, the cysteine at position 131 in a human, humanized, and/or primate IgG2 HC can be replaced with another amino acid, e.g., serine, alanine, or glycine, and the cysteine at position 214 in the cognate LC can be replaced with another amino acid, e.g., serine, alanine, or glycine. These substitutions would eliminate the naturally occurring disulfide bridge between an IgG2 HC and its cognate LC. A new disulfide bridge could be created by introducing a cysteine substitution at each residue of a pair of contacting residues, where one residue is in the IgG2 HC and other is in the LC. For example, the substitutions F170C in the HC and S162C in the LC are such a pair of cysteine substitutions at contacting residues, as are V173C in the HC and Q160C in the LC. Other cysteine substitutions at other pairs of contacting residues could also be used. This approach could avoid the formation of multiple IgG2 structural isomers due to disulfide bond shuffling, which has been observed in native human IgG2 antibodies. See, e.g., Lightle et al. (2010), Protein Science 19:753-762. Formation of multiple structural isomers can be disadvantageous when manufacturing an antibody for use as a therapeutic since a homogeneous preparation is generally preferred.

Any of the antibodies described above can be made using standard methods in the art. For example, an antibody can be made by (1) introducing one or more DNAs encoding the antibody, optionally in one or more appropriate vectors, into host cells, (2) culturing the host cells under conditions conducive to expression of the antibody, and (3) obtaining the antibody from the cell supernatant or host cell mass.

Fusion Proteins

Also provided in accordance with the present invention are variant-Fc-region-fusion proteins (as a binding molecule) comprising one or more variant-Fc-regions recombinantly fused to one or more partner-ligand on either or both of N- or C-terminus of a respective variant-Fc-region. The invention variant-Fc-region fusion proteins may be bispecific (with one binding site for a first target and a second binding site for a second target) or may be multivalent (with two binding sites for the same target).

Exemplary ligand-proteins (or fragments thereof) known in the art for recombinantly fusing to an invention variant-Fc-region, as a partner-ligand, can be selected from the group consisting of: T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349:164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (λshkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

In one embodiment an invention variant-Fc-region fusion protein combines the binding domain(s) of the ligand or receptor (e.g. the extracellular domain (ECD) of a receptor), as the partner-ligand, with at least one variant-Fc-region and a synthetic connecting peptide. In one embodiment, when preparing the fusion proteins of the present invention, nucleic acid encoding the binding domain of the respective ligand or receptor will be fused C-terminally to nucleic acid encoding a variant-Fc-region sequence. N-terminal fusions are also contemplated herein where the binding domain of the respective ligand or receptor is fused N-terminally to nucleic acid encoding a variant-Fc-region sequence.

In one embodiment, it is also contemplated to fuse the entire heavy chain constant region comprising an invention variant-Fc-region to the sequence of the ligand or receptor domain. In another embodiment for example, a sequence beginning in the hinge region just upstream of the papain cleavage site which defines IgG Fc chemically (e.g., residue 216, taking the first residue of heavy chain constant region to be 114), or analogous sites of other immunoglobulins is used in the invention variant-Fc-region fusion protein. In some embodiments, the precise site at which the fusion is made is not critical; particular sites are well known in the art may be selected in order to optimize the biological activity, secretion, or binding characteristics of the fusion protein. Methods for making fusion proteins are known in the art.

For bispecific fusion proteins, the fusion proteins are assembled as multimers, and particularly as heterodimers or heterotetramers. Generally, these assembled immunoglobulins will have known unit structures. For example, a basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Additional exemplary ligands contemplated for use herein in the invention variant-Fc-region fusion proteins include the following:

Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

Adhesion Proteins

Adhesion molecules are membrane-bound proteins that allow cells to interact with one another. Various adhesion proteins, including leukocyte homing receptors and cellular adhesion molecules, of receptor binding portions thereof, can be incorporated in a fusion protein of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

Growth Factors and Growth Factor Receptors

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or 6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and II (IGF-I and IGF-II; U.S. Pat. Nos. 6,403,764 and 6,506,874); Erythropoietin (EPO); stein-cell factor (SCF), thrombopoietin (c-Mpl ligand), and the Wnt polypeptides (U.S. Pat. No. 6,159,462). Exemplary growth factor receptors which may be used as targeting receptor domains of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as p75NTR or p75, which binds NGF, BDNF, and NT-3, and high affinity receptors that are members of the trk family of the receptor tyrosine kinases (e.g. trkA, trkB (EP 455,460), trkC (EP 522,530)).

Hormones

Exemplary growth hormones for use as targeting agents in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

Clotting Factors

Exemplary blood coagulation factors for use as targeting agents in the fusion proteins of the invention include the clotting factors (e.g., factors V, VII, VIII, X, IX, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

Target Molecules Bound by the Variant-Fc-region Fusion Proteins, Variant-Fc-region-Antibodies and/or Heterodimeric-Variant-Fc-region-Bispecific-Antibodies The different invention variant-Fc-region-containing fusion proteins and/or antibodies, such as heterodimeric-variant-Fc-region-bispecific antibodies described herein, bind to different epitopes and can bind to one or more target molecule. The target molecules, optionally proteins, for these invention variant-Fc-region containing molecules described herein can be chosen in light of knowledge of the role of various molecules in a disease state. In some embodiments, the disease is a human disease, and the target molecule(s) is (are) one or more human protein(s). Similarly, the variant-Fc-region fusion proteins, variant-Fc-region-antibodies and/or heterodimeric-variant-Fc-region-bispecific-antibodies described above can bind to one of these target molecules.

In one example, the target protein(s) for the variant-Fc-region fusion proteins, variant-Fc-region-antibodies and/or heterodimeric-variant-Fc-region-bispecific-antibodies s described herein can be one or more protein(s) that serve(s) as a checkpoint that inhibits or blocks the activity of the immune system. Since cancers and infections can be surveilled by the immune system and the immune system may regulate and even eliminate tumors and infections, preventing regulation or blockage of immune system activity could potentially limit growth of cancer cells or eliminate infections, in some embodiments, viral infections. Checkpoint-blocking antibodies, such as those directed against cytotoxic T-lymphocyte antigen 4 (CTLA4) and programmed death 1 receptor (PD1), have demonstrated promise in the treatment of an expanding list of malignancies. While both CTLA4 and PD1 function as negative regulators, each plays a non-redundant role in modulating immune responses. CTLA4 attenuates the early activation of naïve and memory T cells, and PD1 is primarily involved in modulating T cell activity in peripheral tissues via interaction with its ligands, PD-L1 and PD-L2. An invention variant-Fc-region fusion proteins, variant-Fc-region-antibodies and/or heterodimeric-variant-Fc-region-bispecific-antibodies described herein could also bind to any of these target proteins.

Accumulating clinical evidence points toward a promising role for checkpoint-blocking antibodies in a rapidly expanding spectrum of solid tumors, including non-small cell lung cancer, renal cell cancer, ovarian cancer, bladder cancer, head and neck cancer, and gastric cancer. While blocking either the CTLA4 or the PD1 pathway inhibits growth of multiple tumor types, the overall response rate is still low, underscoring the importance of improving upon present options. Combined checkpoint blockade, to date explored with anti-CTLA4 (ipilimumab) and anti-PD1 (nivolumab) pathway blocking agents, has shown better clinical efficacy than ipilimumab alone or nivolumab alone in patients with untreated melanoma. Larkin et al. (2015), New Engl. J. Med. 373:23-34. In melanoma patients with programmed cell death 1 ligand (PD-L1; also known as PDCD1LG1, PDCD1L1, β7H1, and CD274)-positive tumors, progression-free survival using treatment with nivolumab alone was essentially the same as that observed using treatment with nivolumab plus ipilimumab and was higher than that observed using treatment with ipilimumab alone. Larkin et al., supra. In patients with PD-L1-negative tumors, combination therapy resulted in longer progression-free survival than was observed with nivolumab or ipilimumab alone. Larkin et al, supra. These data provide a strong rationale for anti-cancer therapeutics that include the variant-Fc-region fusion proteins, variant-Fc-region-antibodies and/or heterodimeric-variant-Fc-region-bispecific-antibodies described herein that block two or more immune system checkpoint proteins. Similar studies using another anti-PD1 antibody, pembrolizumab, are currently ongoing.

In the context of making different immune checkpoint-blocking variant-Fc-region fusion proteins, variant-Fc-region-antibodies and/or heterodimeric-variant-Fc-region-bispecific-antibodies described herein, the isotype of the antibodies can be of importance because different isotypes can elicit different effector functions. Of the five immunoglobulin isotypes, immunoglobulin G (IgG) is most abundant in human serum. The four IgG subclasses, IgG1, IgG2, IgG3, and IgG4, differ in their constant regions, especially in their hinge and upper CH2 domains. These regions are involved in binding to IgG-Fc receptors (FcγR), which can initiate antibody-dependent cell-mediated cytotoxicity (ADCC) and/or phagocytosis (ADCP), and Clq, which can initiate complement dependent cytotoxicity (CDC). Hence, the different subclasses have different effector functions. IgG1 and IgG3 antibodies can elicit potent effector responses including ADCC, ADCP, and CDC, whereas IgG2 and IgG4 antibodies elicit much more subtle effector responses and only do so in certain cases. Antibody responses to soluble protein antigens and membrane proteins primarily induce production of IgG1 antibodies, accompanied by lower levels of other IgG subclasses, mostly IgG3 and IgG4. Ferrante et al. (1990), *Pediatr. Infect. Dis. J.* 9 (8 Suppl): S16-24.

For therapeutic antibodies, IgG1 has been the most popular choice by far. Antibodies designed for selective eradication of cancer cells typically require an isotype that can elicit potent complement activation and effector-mediated cell killing by ADCC. Although IgG1 and IgG3 both meet these criteria, IgG3 has not been used for therapeutic antibody development, probably because of a shorter half-life, susceptibility of the relatively long hinge region to proteolysis, and extensive allotypic polymorphism.

Antibody isotype can be an important consideration for anti-CTLA4 antibodies used to treat cancer. Preclinical data suggests that a checkpoint-blocking anti-CTLA4 antibody might deliver much of its therapeutic effect through depletion of T regulatory (Treg) cells within tumors, thus releasing CD8 T cell-mediated anti-tumor immunity. Simpson et al. (2013), J Exp Med. 210 (9): 1695-1710. Similar mechanisms may operate in human patients. Ipilimumab, a human IgG1 anti-CTLA4 antibody, was recently shown to lead to ADCC-mediated lysis of human Tregs ex vivo. Romano et al. (2015), Proc. Natl. Acad. Sci. 112 (19): 6140-6145. Further, in a small clinical study, melanoma patients responding to ipilimumab had significantly higher baseline frequencies of nonclassical monocytes and more activated tumor-associated macrophages expressing FcγRIII, which correlated with lower intratumoral Treg numbers after therapy, suggesting that Treg deletion occurs in these patients. Therefore, an IgG1 or IgG3 isotype may be favored for an anti-CTLA4 antibody used in the treatment of cancer since the antibody might have the greatest effect if it causes potent killing of the Treg cells within the tumor.

The IgG isotype of choice for anti-PD1 antibodies is typically IgG4 or a mutated IgG1 with minimal FcγR interactions. PD1 is expressed on the surface of activated T cells, B cells, and macrophages, and negatively regulates immune responses. Since PD1 is expressed on these effector cells, it may not be desirable to use an isotype that can elicit strong effector functions, i.e., IgG1 or IgG3, because this could result in killing activated T cells, which might otherwise kill cancer cells.

Hence, in making an anti-cancer therapeutic containing a mixture of an anti-CTLA4 and an anti-PD1 antibody, the inclusion of an invention heterodimeric-variant-Fc-region-bispecific anti-CTLA4 anti-PD1 antibody may be inappropriate because, as explained above, different effector functions are appropriate for each of the two binding domains. Moreover, the effects of bringing regulatory T cells and effector T cells into close physical proximity by means of an anti-PD1 and anti-CTLA4 bispecific antibody are unpredictable.

Moreover, other combinations of immune checkpoint proteins could serve as targets for the variant-Fc-region fusion proteins, variant-Fc-region-antibodies and/or heterodimeric-variant-Fc-region-bispecific-antibodies described herein. For example, the human epidermal growth factor receptor (HER) family of proteins, i.e., HER1, HER2, HER3, and HER4, plays an important role in cell survival and proliferation and has been implicated in oncogenesis. These proteins are capable of forming heterodimers and homodimers, which can activate signal transduction pathways that regulate many cellular processes, including growth, proliferation, and survival. Overexpression of HER2 is associated with aggressive disease and poor prognosis in human breast cancer patients. Treatment of such patients with anti-HER2 antibodies, such as HERCEPTIN® (the brand name for a humanized anti-HER2 antibody called trastuzumab), with or without lapatinib (a small molecule tyrosine kinase inhibitor), has improved survival. Trastuzumab binds domain IV of HER2 and inhibits HER2-mediated cell proliferation by activating antibody-dependent cellular cytotoxicity (ADCC), preventing formation of p95HER2 (a truncated and constitutively active form of HER2), blocking ligand-independent HER2 signaling, and inhibiting HER2-mediated angiogenesis.

A different humanized anti-HER2 antibody called pertuzumab binds to a different epitope (in domain II of HER2) than trastuzumab and inhibits HER2 dimerization with other HER family members such as HER3 and HER1, thus inhibiting the downstream signaling processes that are associated with tumor growth and progression. The combination of pertuzumab and trastuzumab has a strongly enhanced antitumor effect compared to either agent alone and induces tumor regression in xenograft models (Yamashita-Kashima (2011), *Clin. Cancer Res.* 17 (15): 5060-5070; Scheuer et al. (2009), *Cancer Res* 69:9330-9336), something that cannot be achieved by either monotherapy. The enhanced efficacy of the combination was also observed after tumor progression during anti-HER2 trastuzmab monotherapy. Binding of pertuzumab to tumors is not impaired by trastuzumab pretreatment. Furthermore, both trastuzumab and pertuzumab potently activate ADCC. The strongly enhanced antitumor activity is likely due to the differing and complementary mechanisms of action of trastuzumab and pertuzumab. Potentially, a bispecific antibody that could bind to both epitopes on one or more molecules of HER2 protein simultaneously might have different activity, possibly greater or lesser, than the two separate antibodies. In some cases, a bispecific antibody binding to two different epitopes on a single target protein might not be able to simultaneously bind to the two epitopes on a single target protein. Thus, there is reason to believe that treatment with two or more anti-HER2 antibodies that bind to different epitopes, optionally including an invention heterodimeric-variant-Fc-region-bispecific-antibody, can be more effective than treatment with a single antibody.

Hence, the methods described herein could be used to make an invention heterodimeric-variant-Fc-region-bispecific-antibody containing two or more different anti-HER2 antibodies. Such heterodimeric-variant-Fc-region-bispecific-antibodies could be used to treat a subset of breast cancer patients, i.e., those with cancers that overexpress HER2, and possibly other cancer patients with HER2-mediated cancers.

Further, the methods described herein could be used to make invention heterodimeric-variant-Fc-region-bispecific-antibodies that bind to other cancer antigens, i.e., proteins that are overexpressed on cancer cells. In most of these cases, IgG1 and/or IgG3 isotype(s) would be desirable because killing of the cancer cells is a therapeutic objective. For example, the heterodimeric-variant-Fc-region-bispecific-antibody could bind to different epitopes on a single cancer antigen. Alternatively, the heterodimeric-variant-Fc-region-bispecific-antibody could bind to different cancer antigens if the cancer cells express multiple different cancer antigens.

Examples of pairs of target molecules from which to select suitable anti-"target" antibodies for use in the invention heterodimeric-variant-Fc-region-bispecific-antibodies described herein include, without limitation, the following pairs of target proteins (shown as first target protein/second target protein), which can be human proteins: PD1/CTLA4, PD1/lymphocyte activation gene 3 (LAG3), PD1/glucocorticoid-induced tumor necrosis factor receptor-related gene (GITR; also known as AITR or TNFRSF18), PD1/vascular endothelial growth factor A (VEGF; also known as VEGFA), PD1/colony-stimulating factor 1 receptor (CSF1R; also known as FMS, c-FMS and CD115), PD1/OX40 (also known as TNFRSF4, ACT35, and CD134), PD1/T-cell immunoreceptor with immunoglobulin and ITIM domains (TIGIT), PDL1/CTLA4, PDL1/VEGF, PDL1/OX40, PDL1/CSF1R, PDL1/TIGIT, PDL1/T-cell immunoglobulin and mucin domains-containing protein 3 (TIM3, also known as HAVCR2), CTLA4/VEGF, CTLA4/41BB (also known as TNFRSF9, ILA, and CD137), membrane-spanning 4 domains, subfamily A, member 1 (CD20; also known as MS4A1 and B1)/leukocyte surface antigen CD37 (CD37), angiopoietin 2 (ANG2; also known as ANGPT2)/VEGF, tumor necrosis factor (TNF; also known as TNFA and cachetin)/interleukin 17a (IL17a; also known as CTLA8), CD38 antigen (CD38)/CD138 antigen (CD138; also known as SDC1 and SYND1), epidermal growth factor receptor (EGFR; also known as ERBB1, HER1, and SA7)/HER2, EGFR/HER3, MET protooncogene (MET; also known as HGFR)/VEGF, MET/EGFR, thymic stromal lymphopoietin (TSLP)/interleukin 33 (IL33; also known as C9ORF26, NFHEV, and IL1F11), interleukin 4 (IL4; also known as BSF1)/interleukin 13 (IL13), HER2/HER2, PD1/CD96, PD1/Protein-tyrosine phosphatase, nonreceptor type, substrate-1 (also known as SIRP-alpha-1, PTPNS1, SIRPA, SHPS1, MYD1, and MFR), and PD1/Chemokine, CC motif, receptor 8 (also known as CCR8, Chemokine, CC motif, receptor-like 2 (CMKBRL2), Chemokine receptor-like 1 (CKRL1), and CMKBR8). Single variant-Fc-region fusion proteins and variant-Fc-region monospecific antibodies could also bind to any of these target molecules.

In other embodiments directed to invention heterodimeric variant-Fc-region bispecific antibodies, those of skill in the art will readily understand than any combination of anti-"target" antibodies (e.g., monoclonal antibodies) known in the art against the target molecules set forth above can be used to make the invention heterodimeric bispecific antibodies, so long as the at least the respective CDRs and/or Variable Light Chain and Variable Heavy Chain regions of these known (e.g., "cognate HC/LC" as set forth in Example 2) antibodies are recombinantly combined with the invention variant-Fc-regions.

The examples of particular targets discussed above are exemplary. Variant-Fc-region-containing fusion proteins and/or antibodies, such as heterodimeric-variant-Fc-region-bispecific antibodies described herein that bind to any target or combination of these targets could be made using methods described herein.

Nucleic Acids and Vectors Encoding Variant-Fc-region-containing Fusion Proteins and/or Antibodies, and Heterodimeric-Variant-Fc-region-Bispecific Antibodies Provided are nucleic acids, e.g., DNA, encoding the variant-Fc-region-containing fusion proteins and/or antibodies, such as heterodimeric-variant-Fc-region-bispecific antibodies described herein. Numerous nucleic acid sequences encoding immunoglobulin domains, for example Fc-regions, VH, VL, hinge, CH1, CH2, and CH3 domains are known in the art. See, e.g., Kabat et al., supra. Using the guidance provided herein, one of skill in the art could combine known or novel nucleic acid sequences encoding antibodies and modify them by known methods to create nucleic acids encoding the variant-Fc-region-containing fusion proteins and/or antibodies, including heterodimeric-variant-Fc-region-bispecific antibodies described herein, which comprise alterations as described herein.

Methods of modifying nucleic acids are well-known in the art. Perhaps the most straightforward method for creating a modified nucleic acid is to synthesize a nucleic acid having the desired sequence. A number of companies, e.g., Atum (Menlo Park, Calif., USA), BlueHeron (Bothell, Washington), Genewiz (South Plainfield, New Jersey), Gen9 (Cambridge, Massachusetts), and Integrated DNA Technologies (Coralville, lowa; IDT), provide this service. Other known methods of introducing mutations, for example site-directed mutagenesis using polymerase chain reaction (PCR), can also be employed. See, e.g., Zoller (1991), Curr. Opin. Biotechnol. 2(4): 526-531; Reikofski and Tao (1992), Biotechnol. Adv. 10(4): 535-547. For example, Example 2 below describes the use of a commercial kit to introduce specific mutations into a starting DNA.

The DNA vector(s) that contain(s) the DNA encoding the HCs and LCs of the antibodies can be any vector(s) suitable for expression of the antibodies in a chosen host cell. The vector can include a selectable marker for selection of host cell cells containing the vector and/or for maintenance and/or amplification of the vector in the host cell. Such markers include, for example, (1) genes that confer resistance to antibiotics or other toxins, e.g., ampicillin, tetracycline, or kanamycin for prokaryotic host cells, (2) genes that complement auxotrophic deficiencies of the cell, or (3) genes whose operation supplies critical nutrients not available from complex or defined media. Specific selectable markers include the kanamycin resistance gene, the ampicillin resistance gene, and the tetracycline resistance gene. Both neomycin resistance gene and blasticidin S resistance gene may also be used for selection in both prokaryotic and eukaryotic host cells. A dihydrofolate reductase (DHFR) gene and/or a promoterless thymidine kinase gene can be used in mammalian cells, as is known in the art.

In addition, a vector can contain various other sequence elements necessary for the maintenance of the vector and/or the expression of the inserted sequences encoding the variant-Fc-region-containing fusion proteins and/or antibodies, including the heterodimeric-variant-Fc-region-bispecific antibodies described herein, e.g., the HCs and LCs of the antibodies described herein. Such elements include, for example, an origin of replication, a promoter, one or more enhancers, a transcriptional terminator, a ribosome binding site, a polyadenylation site, and a polylinker insertion site for exogenous sequences (such as the DNA encoding the antibody mixtures described herein). These sequence elements can be chosen to function in the desired host cells so as to promote replication and/or amplification of the vector and expression and of the heterologous sequences inserted into the vector. Such sequence elements are well known in the art and available in a large array of commercially available vectors. Many vectors are commercially available from companies including Promega Corporation (Madison, WI, USA) and Agilent Technologies (Santa Clara, CA, USA), among many others.

DNA encoding each of two or more antibodies can be introduced into a population of host cells using any appropriate method including, for example, transfection, transduction, transformation, bombardment with microprojectiles, microinjection, or electroporation. In some embodiments, DNA encoding two full-length IgG antibodies is introduced into the host cells. Such methods are known in the art and described in, e.g., Kaestner et al. (2015), Bioorg. Med. Chem. Lett. 25:1171-1176, which is incorporated herein by reference.

In some embodiments, nucleic acids encoding the variant-Fc-region fusion proteins, variant-Fc-region-antibodies and/or heterodimeric-variant-Fc-region-bispecific-antibodies described herein can be carried on one or more viral vectors. Examples of such viral vectors include adenovirus, adeno-associated virus (AAV), retrovirus, vaccinia virus, modified vaccinia virus Ankara (MVA), herpes virus, lentivirus, or poxvirus vectors. In such embodiments, these viral vectors containing nucleic acids encoding the variant-Fc-region fusion proteins, variant-Fc-region-antibodies and/or heterodimeric-variant-Fc-region-bispecific-antibodies described herein can be administered to patients to treat a disease. In a cancer patient, such viral vectors containing nucleic acids encoding the variant-Fc-region fusion proteins, variant-Fc-region-antibodies and/or heterodimeric-variant-Fc-region-bispecific-antibodies described herein can be administered directly to a tumor or a major site of cancer cells in the patient, for example by injection, inhalation (for a lung cancer), topical administration (for a skin cancer), and/or administration to a mucus membrane (through which the nucleic acids can be absorbed), among many possibilities.

Similarly, nucleic acids encoding the variant-Fc-region fusion proteins, variant-Fc-region-antibodies and/or heterodimeric-variant-Fc-region-bispecific-antibodies described herein as described herein, which can be encased in liposomes, can be administered to a patient suffering from a disease.

Host Cells that Can Produce Variant-Fc-region Fusion Proteins, Variant-Fc-region-Antibodies and Heterodimeric-Variant-Fc-region-Bispecific-Antibodies The host cells into which DNA(s) encoding the variant-Fc-region fusion proteins, variant-Fc-region-antibodies and/or heterodimeric-variant-Fc-region-bispecific-antibodies described herein are introduced can be any of a variety of cells suitable for the expression of a recombinant protein. These include, for example, gram negative or gram positive prokaryotes, for example, bacteria such as *Escherichia coli, Bacillus subtilis*, or *Salmonella typhimurium*. In other embodiments, the host cells can be eukaryotic cells, including such species as *Saccharomyces cerevisiae, Schizosaccharomyces pombe*, or eukaryotes of the genus *Kluyveromyces, Candida*, Spodotera, or any cell capable of expressing heterologous polypeptides. In further embodiments, the host cells can be mammalian cells. Many mammalian cells suitable for expression of heterologous polypeptides are known in the art and can be obtained from a variety of vendors including, e.g., American Type Culture Collection (ATCC). Suitable mammalian cells include, for example, the COS-7 line (ATCC CRL 1651) (Gluzman et al., 1981, Cell 23:175), L cells, C127 cells, 3T3 cells (ATCC CCL 163), Chinese hamster ovary (CHO) cells, or their derivatives such as Veggie CHO and related cell lines which grow in serum-free media (Rasmussen et al., 1998, Cytotechnology 28:31), Hela cells, baby hamster kidney (BHK) cells (e.g., ATCC CRL 10), the CVI/EBNA cell line derived from the African green monkey kidney cell line CVI (ATCC CCL 70) as described by McMahan et al., 1991, EMBO J. 10:2821, human embryonic kidney (HEK) cells such as 293, 293 EBNA or MSR 293, human epidermal A431 cells, human Colo205 cells, HL-60 cells, U937 cells, Hak cells, Jurkat cells, HepG2/3B cells, KB cells, NIH 3T3 cells, or S49 cells. Other mammalian cell types that are capable of expression of a heterologous polypeptide could also be used.

In some embodiments, the variant-Fc-region fusion proteins, variant-Fc-region-antibodies and/or heterodimeric-variant-Fc-region-bispecific-antibodies described herein, can be obtained from a population of host cells into which DNA encoding the variant-Fc-region fusion proteins, variant-Fc-region-antibodies and/or heterodimeric-variant-Fc-region-bispecific-antibodies described herein has been introduced, for example, by transfection. In some embodiments, a single cell is isolated from the population of cells into which the DNA has been introduced. This cell is propagated to create a "host cell line," as defined herein, that can produce the variant-Fc-region fusion proteins, variant-Fc-region-antibodies and/or heterodimeric-variant-Fc-region-bispecific-antibodies described herein.

Methods of Treatment

The variant-Fc-region fusion proteins, variant-Fc-region-antibodies and/or heterodimeric-variant-Fc-region-bispecific-antibodies described herein or nucleic acids encoding them can be used to treat a variety of diseases, optionally human diseases. As would be readily understood by one of skill in the art, the disease that a particular variant-Fc-region fusion proteins, variant-Fc-region-antibodies and/or heterodimeric-variant-Fc-region-bispecific-antibodies described herein, or nucleic acids encoding the antibody or mixture could be used to treat could be determined by a variety of factors including the identity of the target protein to which each antibody in the mixture binds, the particular epitope on each target protein bound by each antibody, the relative amounts of each antibody in the composition, the isotype of each antibody, and the in vivo half life of the variant-Fc-region fusion proteins, variant-Fc-region-antibodies and/or heterodimeric-variant-Fc-region-bispecific-antibodies described herein, among other possible factors. The target proteins bound by the variant-Fc-region fusion proteins, variant-Fc-region-antibodies and/or heterodimeric-variant-Fc-region-bispecific-antibodies described herein may play a direct or indirect role in driving the course of a disease being treated. For example, a target protein may be part of a biological pathway that drives a disease or be a protein that serves as an immune checkpoint, and/or a target protein may serve as a means to target disease cells for destruction by the immune system. Other scenarios are also possible.

In a general sense, the invention variant-Fc-region fusion proteins, variant-Fc-region-antibodies and/or heterodimeric-variant-Fc-region-bispecific-antibodies described herein, or nucleic acids encoding them, can be used to treat diseases driven by multiple biological pathways, diseases driven by a molecule that has multiple mechanisms of action (e.g., HER2 in breast cancer), or diseases driven by multiple molecules that feed into a single biological pathway, among other possibilities. These diseases include, without limitation, cancers, metabolic diseases, infectious diseases, and autoimmune or inflammatory diseases, among many possibilities.

The variant-Fc-region fusion proteins, variant-Fc-region-antibodies and/or heterodimeric-variant-Fc-region-bispecific-antibodies, or nucleic acids encoding them described herein can, for example, be used to treat a cancer. In such a case, the variant-Fc-region fusion proteins, variant-Fc-region-antibodies and/or heterodimeric-variant-Fc-region-bispecific-antibodies described herein can be administered to a cancer patient, optionally directly to a tumor. As is known in the art, different cancers are different and require different treatments. Thus, different variant-Fc-region fusion proteins, variant-Fc-region-antibodies and/or heterodimeric-variant-Fc-region-bispecific-antibodies described herein may be suitable for different cancers. Cancers that can be treated with the variant-Fc-region fusion proteins, variant-Fc-region-antibodies and/or heterodimeric-variant-Fc-region-bispecific-antibodies described herein include, for example, hematolytic cancers, solid tumors including carcinomas and sarcomas, breast cancer, skin cancers including melanoma, lung cancers, pancreatic cancer, prostate cancer, cancer of the head and neck, thyroid cancer, brain cancer, among many others.

The variant-Fc-region fusion proteins, variant-Fc-region-antibodies and/or heterodimeric-variant-Fc-region-bispecific-antibodies described herein, or the nucleic acids encoding them can be formulated, for example, as a liquid, a paste or a cream, or a solid. Oral administration is possible. The variant-Fc-region fusion proteins, variant-Fc-region-antibodies and/or heterodimeric-variant-Fc-region-bispecific-antibodies described herein, or nucleic acids can be administered via parenteral injection. For example, an injection of the variant-Fc-region fusion proteins, variant-Fc-region-antibodies and/or heterodimeric-variant-Fc-region-bispecific-antibodies described herein or nucleic acids can be subcutaneous, intravenous, intra-arterial, intra-lesional (including into a tumor or other major site of a cancer), peritoneal, or intramuscular. Topical administration, e.g., of a liquid, paste, or cream, is possible, especially for diseases of the skin. Administration through contact with a mucus membrane, such as by intra-nasal, sublingual, vaginal, or rectal administration, is also possible. Alternatively, the variant-Fc-region fusion proteins, variant-Fc-region-antibodies and/or heterodimeric-variant-Fc-region-bispecific-antibodies described herein, or nucleic acid(s) encoding an antibody or antibody mixture can be administered as an inhalant.

In some embodiments, the nucleic acids encoding the variant-Fc-region fusion proteins, variant-Fc-region-antibodies and/or heterodimeric-variant-Fc-region-bispecific-antibodies described herein can be carried on one or more viral vectors. In such embodiments, these viral vectors containing nucleic acids encoding the variant-Fc-region fusion proteins, variant-Fc-region-antibodies and/or heterodimeric-variant-Fc-region-bispecific-antibodies described herein can be administered to patients to treat a disease, e.g., by oral administration or by injection (including, for example, subcutaneous, intramuscular, intravenous, intra-tumoral or peritoneal injection), inhalation, topical administration, and/or by administration to a mucus membrane (through which the nucleic acids can be absorbed), among many possibilities. In a cancer patient, such viral vectors containing nucleic acids encoding the variant-Fc-region fusion proteins, variant-Fc-region-antibodies and/or heterodimeric-variant-Fc-region-bispecific-antibodies described herein can be administered directly to a tumor or a major site of cancer cells in the patient, for example by injection, inhalation (for a lung cancer), topical administration (for a skin cancer), and/or administration to a mucus membrane (through which the nucleic acids can be absorbed), among many possibilities. The viral vector(s) can be, for example, adenovirus, adeno-associated virus (AAV), retrovirus, vaccinia virus, modified vaccinia virus Ankara (MVA), herpes virus, lentivirus, or a poxvirus vector(s).

Dosing and frequency of dosing of the variant-Fc-region fusion proteins, variant-Fc-region-antibodies and/or heterodimeric-variant-Fc-region-bispecific-antibodies described herein, or the nucleic acids encoding them can be adjusted by one skilled in the art according to the condition being treated, the concentration of the antibodies or nucleic acids, the binding properties (such as affinity and avidity) of the antibodies, the in vivo abundance and accessibility of the target molecules to which the antibodies bind, and the in vivo half lives of the antibodies, among many other possible considerations. The dose of the variant-Fc-region fusion proteins, variant-Fc-region-antibodies and/or heterodimeric-variant-Fc-region-bispecific-antibodies described herein administered to a patient can be, for example, from about 0.0036 milligrams (mg) to about 450 mg, from about 0.000051 mg/kg to about 6.4 mg/kg, or from about 0.002 mg/mm2 to about 250 mg/mm2. Similarly, dosing of nucleic acids, e.g., DNA, encoding the variant-Fc-region fusion proteins, variant-Fc-region-antibodies and/or heterodimeric-variant-Fc-region-bispecific-antibodies described herein can be, for example, from about 109 to about 1013 copies of the DNA(s) encoding the variant-Fc-region fusion proteins, variant-Fc-region-antibodies and/or heterodimeric-variant-Fc-region-bispecific-antibodies described herein per kilogram of patient weight. Dosing can occur every day, every other day, twice per week, once per week, every other week, once every 3, 4, 5, 6, 7, 8, 9, 10, 11, or 12 weeks, 4 times per year, twice per year, once every nine months, or once per year, among other possible schedules.

Having described the invention in general terms above, the specific Examples described below are offered to exemplify, not limit, the scope of the invention. It is understood that various changes and modifications may be made to the invention that are in keeping with the spirit of the invention described herein and would be apparent to one of skill in the art. Such changes and modifications are within the scope of the invention described herein, including in the appended claims.

EXAMPLES

Example 1: Designing HC-partner-directing alterations to favor the heterodimeric Fc formation Bispecific antibodies can simultaneously recognize two different antigens, neutralize different pathogenic mediators, recruit different types of effector cells, and modulate signal pathways. The development of bispecific antibodies as therapeutic agents for human diseases has great clinical potential. Bispecific heterodimeric antibody comprising two different HCs and two different LCs from two different antibodies keep all features of standard IgG antibody, such as high production, easy purification, long half-life, good stability. However, when co-expressing the HCs and LCs of two different antibodies in the same cell, ten different HC/LC combinations randomly form; whereas only one combination has the desired correct configuration (see Cater, J. Immunol. Methods, 2001; 248:7-15).

To make bispecific heterodimeric IgG antibody, engineering the HC and LC of the two different antibodies is required so that they can assemble exclusively into a heterodimeric antibody without other contaminating species. In one aspect, heterodimeric HC pairing is achieved by engineering the $C_H3$ regions of two HCs so that they form a heterodimer exclusively. Further, cognate LC/HC pairings are achieved by engineering interface residues between the LC and the HC to prevent mispairing of LCs to the non-cognate HCs to form a desired four-chain heterodimeric antibody.

The interaction of two $C_H3$ domains of IgG antibody is very high affinity which is the driving force of forming Fc homodimer. To make bispecific heterodimeric antibody, the first step is to engineer the $C_H3$ interface residues so that only two different HCs can form a complex and secreted from the cells. Strategies such as knob-into-hole (Ridgway et al. 1996), charge-pair (Gunasekaran et al. 2010), IgG1/IgG3 hybrid HCs (Tustian et al, 2016) have been applied to achieve this goal. The knobs-into-holes mutations were also combined with inter-$C_H3$ domain disulfide bond engineering to enhance heterodimer formation (Sowdhamini. Srinivasan et al. 1989: Atwell. Ridgway et al. 1997).

Charge pair strategy is simple because the same polarity causes repulsion and opposite polarity causes attraction. When one (or more) negative charge residue in one Fc chain is replaced with a positive-charged residue (such as a lysine, arginine, or histidine), at the same time the interacting positive charge residue in the other Fc chain is swapped to a negative charge residue (such as aspartic acid and glutamate acid), the two different Fc chains are attractive each other whereas the same Fc chains are repulsive, therefore, favoring the formation of heterodimeric HCs.

The charge pairs identified by Amgen are partly working as intended, but homodimers are not fully prevented. When co-transfecting the LC and HC having E356K and D399K substitutions of anti-EGFR panitumumab, or anti-HER2 trastuzumab, or anti-HER pertuzumab in mammalian HEK293 cells, around half of secreted antibody is full-length homodimer although in theory the E356K and D399K in one Fc chain are supposed to repulse with the second Fc chain having E356K and D399K (see FIG. 5 of Liu et al 2015). The same observation is true for the Fc chain having K392D and K409D substitutions (see FIG. 5 of Liu et al 2015). In addition, the Tm of $C_H3$ domains was decreased as observed by DSC due to the charge pair swapping (see FIG. 6 of Liu et al 2015).

To minimize the homodimer formation and increase the stability of bispecific antibody, new interacting non-charged residues at $C_H3$-$C_H3$ interface were investigated. Existing X-ray crystal structures were used to identify residues on a human IgG1 $C_H3$-$C_H3$ interfaces for modification. Crystal structure of a humanized IgG1 Fc has been reported (available at www.imgt.org/3Dstructure-DB/by searching with the Protein Data Bank accession number 1H3X; see also Cho et al. (2003), Nature 421 (6924): 756-760, which is incorporated herein by reference). The crystal structure of a human IgG4 $C_H3$-$C_H3$ interfaces has also been reported (available at www.imgt.org/3Dstructure-DB/by searching with the Protein Data Bank accession number 4C54; see also Brady et al. (1992), J Mol Biol, 227 (1): 253-264, which is incorporated herein by reference).

To select residues involved in the $C_H3$-$C_H3$ interaction that would be suitable to test as sites for substitution with charged amino acids, physical contact as determined by a distance limit criterion and solvent accessible surface area were considered. Using the physical contact method, interface residues for substitution with charged amino acids were defined as residues whose side chain heavy atoms, i.e., atoms other than hydrogen, are positioned closer than a specified limit (5 Å) from side chain heavy atoms of any residue in the second chain. In some cases, this could mean that the α-carbon atoms (Cα) of the two amino acids, i.e., the carbon in the position adjacent to the carboxyl group of the amino acid, could be as far as about 12 Å away from each other. Such distances were determined using Molecular Operating Environment (MOE) software, obtained from Chemical Computing Group Inc. (1010 Sherbooke St. West, Suite #910, Montreal, QC, Canada, H3A 2R7). The second method involves calculating solvent accessible surface area (ASA) of the residues in the presence and absence of the second chain. See, e.g., Liu et al. (2015), J. Biol. Chem. 290 (12): 7535-7562, the relevant portions of which are incorporated herein by reference. The residues that show difference>1 $Å^2$ in ASA between the two calculations were identified as interface residues. Both the methods identified a similar set of interface residues. The following additional criteria were further applied to select $C_H3$-$C_H3$ interface residue pairs for mutagenesis: (1) Either one or both interacting residues are not charged residue, (2) they are highly conserved among IgG antibody isotypes, and (3) they are mostly solvent inaccessible (i.e., buried or partially buried). To stabilize the engineered $C_H3$ domains, an interchain disulfide bond is introduced by substitutions of Y349C in one $C_H3$ and S354C in the other $C_H3$ domain. This cysteine pair was proved to form a disulfide bond (Atwell et al, 1997). The residues suitable for charge pair substitutions and interchain disulfide bond formation are summarized in Table 15 below.

TABLE 15

IgG1 $C_H3$-$C_H3$ interface residues suitable for charge pair and cysteine pair substitution

| IgG1 $C_H3$-A | | | Cα-Cα | IgG1 $C_H3$-B | | |
|---|---|---|---|---|---|---|
| EU #@ | Location* | Residue | distance (Å) | Residue | Location* | EU #@ |
| 390 | D-strand | N | 7.65 | S | DE-turn | 400 |
| 400 | DE-turn | S | 7.76 | N | D-strand | 390 |
| 362 | B-strand | Q | 12.40 | K | B-strand | 370 |
| 370 | B-strand | K | 12.31 | Q | B-strand | 362 |
| 347 | A-strand | Q | 10.85 | K | B-strand | 360 |
| 360 | B-strand | K | 11.22 | Q | A-strand | 347 |
| 364 | B-strand | S | 9.46 | K | B-strand | 370 |
| 370 | B-strand | K | 9.60 | S | B-strand | 364 |
| 349 | A-strand | Y | 6.17 | S | A-strand | 354 |
| 354 | A-strand | S | 6.17 | Y | A-strand | 349 |

We also hypothesized that an oppositely charged pair of amino acids interacting across a $C_H3$-$C_H3$ interface might have maximum electrostatic steering effect if both oppositely charged residues are located on the inner β-sheet of the $C_H3$ domains, which includes Strand-B, Strand D, and Strand E. Example of such residues include S364 and K370 on the inner β-sheet of the $C_H3$ domain.

Example 2: Testing $C_H3$ Variants to Establish a New Heterodimeric Bispecific Antibody Platform As a starting step, we were especially interested in testing 390N and 400S pair because both residues are located at the edge of folded $C_H3$ structure (partially exposed), charge pair (one is negatively charged, the other is positively charged) can therefor initiates the assembly of whole Fc region. Since 392K residue is located near this pair (390N and 400S), we took the local charge environment into account when designing the Fc variants. For example, when making S400K in one Fc chain, and N390D in the other Fc chain, K392D is also made for possible interaction with S400K in the opposite Fc chain. We also explored making S400D in one Fc chain and N390K and keep K392K in the other Fc chain.

To identify alterations that would achieve the goal of preventing homodimeric HC/HC pairs, a panel of DNAs encoding pairs of proteins including one Fc fragment and one cognate HC/LC pair, which had different alterations in their $C_H3$ domains, were made. These DNAs were introduced into host cells that could express them, and the antibodies produced by the host cells were analyzed by SDS-PAGE electrophoresis and Western blotting as described below to determine the relative amounts of HC-LC/Fc heterodimers, HC-LC/HC-LC homodimers, and Fc/Fc homodimers due to their different size and migration in the SDS-PAGE gel.

DNA constructs encoding Fc fragments and HC/LC pairs with different alterations in the $C_H3$ domain were generated using PCR and Gibson assembly. The resulting DNAs encoding the Fc fragment and the full-length HC and LC, which included different alterations, were co-transfected into EXPI293™ cells (ThermoFisher Scientific, Waltham, MA, USA). Conditioned media, which contained the antibodies produced by the host cells, were harvested from the transfectants after five days of culture.

Supernatants were migrated on 4-15% CRITERION™ TGX STAIN-FREE™ Precast SDS-PAGE gels (Bio-Rad Laboratories, Inc., Hercules, CA, cat no. 567-8085). The antibodies in the media were detected by Western blotting under non-reducing conditions. After visualization using a CHEMIDOC™ XRS+System with IMAGE LAB™ Software from Bio-Rad Laboratories, Inc., IMAGE LAB™ Software was used to visualize the heterodimers produced by the host cells transfected with DNA encoding the various pairs of altered proteins.

FIG. 1 shows Western blots of samples taken from culture media of transfectants containing pairs of DNAs encoding a LC and a wild type human IgG1 HC plus an altered human IgG1 Fc fragment having two or three substitutions at position 390N, 392K, and 400S. Each of these positions is at the $C_H3$-$C_H3$ interface (see, e.g., WO 2015/017548, Table 1 on page 8, which is incorporated herein by reference). Lane 1 contains cell supernatants from control transfections containing IgG1 anti-HER2 antibody 4D5-8 (comprising the amino acid sequences SEQ ID NOs. 2 and 4), lane 2 containing IgG1 anti-HER2 antibody 2C4 (which contains the amino acid sequences of SEQ ID NOs. 12 and 16). Lanes 1 and 2 serve as positive controls to monitor the transfection efficiency. As indicated, all other samples are in groups of three and contain cell supernatants from transfections containing the DNAs encoding combinations of anti-HER2 4D5-8 LC, anti-HER2 4D5-8 HC variants, and dummy Fc variants. These antibodies are either unaltered (designated "WT") or altered in various ways in different lanes as indicated in the FIG. 1. Lane 3 is the identical repeat of lane 1, the main full-length anti-HER2 antibody 4D5-8 at around 150 KDa was detected; lane 5 is the transfectants of dummy Fc, so the Fc homodimer at around 50 KDa was observed; lane 4 is the transfectants of co-transfection of three plasmid DNAs, so by random combinations three protein bands were detected at 150 KDa for anti-HER2 4D5 full-length HC-LC/HC-LC IgG1, and 100 KDa for the HC-LC/Fc heterodimeric product, and 50 KDa for dummy Fc homodimer. Mainly by comparing the intensity of 100 KDa band for other set of transfectants, lane 19 has the highest heterodimer formation while the intensities of both 150 KDa full-length anti-HER2

4D5-8 IgG1 and 50 KDa dummy Fc homodimer were less than those of baseline lane 4, indicating the combined effect of charge pairs and disulfide bond favors the heterodimer formation. It should be noted that the migration of heterodimer in lane 19 is faster than that in lane 4, probably due to the slightly different conformation caused by the extra interchain disulfide bond introduced by Y349C and S354C.

From the first round of exploration, it is obvious that the substitutions in lane 19 are still not optimal to prevent the homodimer formation. After repacking the atoms in Fc variants of lane 19, it was predicted that in one Fc chain the negative charge residue S400D points to the positive charge residue 392K (naturally a Lys at 392) in the other Fc chain whereas the N390K in the other Fc chain is rotated to point to a different direction, therefore, the overall electrostatic steering effect is weakened at the local environment. Similarly, at the other end of local environment, the S400K interacts with K392D whereas the N390D is diverged to a different direction, therefore the overall electrostatic steering effect is also weakened. The modeling suggested that 390N in one Fc chain and 392K in another Fc chain could be both optimized to accommodate the charge environment to obtain the best electrostatic steering effect.

Using Molecular Operating Environment (MOE) software as described above, we set one Fc chain having the substitutions of S354C, K392K, and S400K then randomize the residue at position 390 to any of all 20 possible amino acid residues; similarly, we set the other Fc chain having the substitutions of Y349C, N390D, and S400D then randomize the residue at position 392 to any of all 20 possible amino acid residues. A total of 20*20=400 calculations were carried out to find better Fc variants which lead to stronger $C_H3$-$C_H3$ domain interaction and higher stability. The top 14 variants are summarized in Table 16 below.

TABLE 16

Summary of top Fc variants at position 390 in one Fc chain and at position 392 in the other Fc chain

| mutseq | mutation | dAffinity | dStability |
|---|---|---|---|
| 0 | 1: N390K, 2: K392D | 0.0000 | 0.0000 |
| 1 | 1: N390K, 2: K392A | −1779.7266 | −204.4277 |
| 2 | 1: N390K, 2: K392I | −1782.0625 | −206.0674 |
| 3 | 1: N390A, 2: K392D | −1403.4141 | −176.3311 |
| 4 | 1: N390N, 2: K392D | −1579.2891 | −177.3750 |
| 5 | 1: N390I, 2: K392D | −1592.0625 | −194.3408 |
| 6 | 1: N390P, 2: K392G | −1971.8281 | −243.5303 |
| 7 | 1: N390S, 2: K392F | −2089.0781 | −236.9346 |
| 8 | 1: N390V, 2: K392Q | −2034.7578 | −234.0654 |
| 9 | 1: N390S, 2: K392G | −1975.5781 | −229.7109 |
| 10 | 1: N390T, 2: K392N | −1988.8750 | −228.6729 |
| 11 | 1: N390G, 2: K392S | −1638.8750 | −211.9434 |
| 12 | 1: N390E, 2: K392V | −1793.1484 | −211.5898 |
| 13 | 1: N390W, 2: K392P | −2040.7031 | −208.9990 |
| 14 | 1: N390N, 2: K392T | −1757.2422 | −203.3115 |
| 15 | 1: N390H, 2: K392A | −1432.3359 | −201.1631 |

If setting one Fc chain having S354C, N390K, K392K, and S400K while setting the other Fc chain having Y349C, N390D, K392D, and S400D as the baseline (dAffinity=0 and dStability=0), mutants 1 and 2 have the N390K mutation in one Fc chain, but the K392 is changed to either Ala or 11*e*, the predicted outcome is to have stronger $C_H3$-$C_H3$ interaction (a low dAffinity score predicts higher affinity) and higher stability (a low dStability score predicts higher stability). Mutants 3, 4, and 5 have the residues Ala, λsn, or 11*e* at position 390 in one Fc chain while position 392 of the other Fc chain is fixed to λsp, these 3 mutants are also predicted to have the potential of forming stable Fc heterodimer. Mutants 6~ 15 have substitutions at position 390 in one Fc chain and at position 392 in the other Fc chain.

For the second round of mutagenesis, the above single N390 substitution was individually introduced into the HC of anti-HER2 4D5-8 IgG1 that already has S354C, K392K and S400K. The above single K392 substitution was individually introduced into the dummy Fc that already has Y349C, N390D, and S400D. Mutagenesis reactions were carried out using the QuikChange Lightning mutagenesis kit (Agilent Technologies, cat no. 210516). The plasmid DNAs were sequenced to confirm the mutation. Transient transfections of Expi293 cells with anti-HER2 4D5-8 LC, anti-HER2 4D5-8 HC variants, and Dummy Fc variants were done as described previously. After 5 days of post-transfection, the supernatant was harvested and 5 μl per lane was loaded into the 4-15% CRITERION™ TGX STAIN-FREE™ Precast SDS-PAGE gels (Bio-Rad Laboratories, Inc., Hercules, CA, cat no. 567-8085), Electrophoresis was run for 45 minutes at 200 V. The proteins were transferred onto a nitrocellulose membrane with TRANS-BLOT® TURBO™ Transfer System (Bio-Rad Laboratories, Inc.) and blocked in 3% non-fat milk in 1 X phosphate buffered saline with 0.05% TWEEN® 20 (PBST). The nitrocellulose membrane was washed, and the antibodies were detected with HRP-conjugated polyclonal goat-anti-human IgG (Fc-specific) (Sigma-Aldrich Corporation, St. Louis, MO, cat. no. A0170). The image was visualized with a CHEMIDOC™ XRS+imager from Bio-Rad Laboratories, Inc.

The effect of new Fc variants is shown in FIG. 2 panel A and panel B. Lane 1 is the co-transfection of anti-HER2 IgG1 4D5-8 HC and LC, the main full-length anti-HER2 antibody 4D5-8 at around 150 KDa was detected; lane 3 is the transfectants of dummy Fc without any mutation, so the Fc homodimer at around 50 KDa was observed; lane 2 is the transfectants of co-transfection of three plasmid DNAs, so by random combinations three protein bands were detected at 150 KDa for anti-HER2 4D5 full-length HC-LC/HC-LC IgG1, and 100 KDa for the HC-LC/Fc heterodimeric product, and 50 KDa for dummy Fc homodimer. Lanes 1~ 3 serve as the baseline to determine whether the new Fc variants have improved the heterodimer formation. Criteria are (1): whether the intensity of 100 KDa band for other set of transfectants is stronger than that of lane 2. (2): whether the intensity of both 150 KDa full-length anti-HER2 4D5-8 IgG1 and 50 KDa dummy Fc homodimer were decreased than those in baseline lane 2. If both criteria are met, that means, the new Fc variant favors heterodimer formation. (3): whether the intensity of 150 KDa full-length IgG1 co-transfected with two plasmids of anti-HER2 4D5-8 WT LC and anti-HER2 4D5-8 HC variants was decreased than that in baseline lane 1. (4): whether the intensity of 50 KDa dummy Fc homodimer co-transfected with one plasmid of dummy Fc variants was decreased than that in baseline lane 3.

Careful comparisons illustrate that the lanes 17 and 23 are the most promising, since the intensity of 150 KDa full-length anti-HER2 4D5-8 IgG1 in lane 16 or 22 is slightly less than that in lane 1; the intensity of 50 KDa dummy Fc in lane 18 or 24 is slightly less than that in lane 3, in addition to the two criteria mentioned above. Lane 11 is also interesting, the intensity of 150 KDa full-length anti-HER2 4D5-8 IgG1 is very low, when compared to other transfectants with three plasmid DNAs (i.e. lanes 5, 8, 14, 17, 20, 23, 26, 29, 32).

For the third round of mutagenesis, Q362-K370 pair were added to the Fc variants in lanes 11, 17, and 23. See FIG. 3. Q362K was embedded into the Fc chain already having S354C, K370K, N390K, K392K, S400K; or S354C, K370K, N390N, K392K, S400K; or S354C, K370K, N390P, K392K, S400K, respectively. Q362D and K370D were embedded into the other Fc chain already having Y349C, N390D, K3921, S400D; or Y349C, N390D, K392D, S400D; or Y349C, N390D, K392G, S400D respectively. Co-transfection of ExpiCHO cells with three plasmid DNAs were similarly done as described above. Western blotting was carried out to visualize the protein bands containing the human Fc, see FIG. 3.

When compared with the baseline lane 5, these lanes 8, 11, 14 co-transfected with three plasmid DNAs were shown to have slight improvement regarding the higher heterodimer expression of 100 KDa LC-HC/Fc and lower homodimer expression of LC-HC/LC-HC at 150 KDa and Fc/Fc at 50 KDa, based on the four criteria described above. The results suggested that Q362

K370 pair is not a good addition to the Fc variants generated from the second round of mutagenesis.

Since S364-K370 pair has shorter Cα-Cα distance than that of Q362-K370, see Table 1. Both S364-K370 pairs are face-to-face located at the core of an inner β-sheet (B-strand) of $C_H3$ domain, we hypothesized that the swapping with charge pair at S364-K370 may have better impact of electrostatic steering effect. For the fourth round of mutagenesis, S364-K370 pair were added to the Fc variants in lanes 11, 17, and 23 in FIG. 2. S364K was embedded into the Fc chain already having S354C, K370K, N390K, K392K, S400K; or S354C, K370K, N390N, K392K, S400K; or S354C, K370K, N390P, K392K, S400K, respectively. S364D and K370D were embedded into the other Fc chain already having Y349C, N390D, K3921, S400D; or Y349C, N390D, K392D, S400D; or Y349C, N390D, K392G, S400D respectively. Co-transfection of ExpiCHO cells with three plasmid DNAs were similarly done as described above. Western blotting was carried out to visualize the protein bands containing the human Fc. See FIG. 4.

When compared with the baseline lane 2, lanes 5, 8, 11 co-transfected with three plasmid DNAs were shown to have the best improvement regarding with no or reduced homodimer expression of LC-HC/LC-HC at 150 KDa and Fc/Fc at 50 KDa, with lane 11 being the best since higher heterodimer LC-HC/Fc at ~ 100 KDa size was also observed. Comparing lane 12 with lane 3, the homodimer Fc in lane 12 was completely prevented since no band at ~ 50 KDa was detected. Comparing lane 10 with lane 1, the 150 KDa band of full-length anti-HER2 4D5-8 IgG1 in lane 10 was also dramatically decreased. The results suggested that S364K/D-K370K/D charge pair is a good addition to the Fc variants generated from the second round of mutagenesis.

Taken together, we did four rounds of Fc engineering, we have identified Fc variants which strongly favor the formation of heterodimeric Fc protein which can be used for making bispecific antibodies. In one Fc chain, the substitutions are S354C, S364K, K370K, N390P, K392K, S400K (where the Lys at positions 370 and 392 are not changed but listed here to indicate they are involved in the interaction with negatively charged residues in other Fc chain), these residues together are referred as "CKKPKK" in short in this patent application; in the other Fc chain, the substitutions are Y349C, S364D, K370D, N390D, K392G, S400D, these five substitutions are referred as "CDDDGD" in short in this patent application.

Example 3: Making Anti-CD20×CD37 Bispecific Antibody to Validate the New Heterodimeric Bispecific Antibody Platform The natural LC/HC preference of humanized anti-CD20 and anti-CD37 IgG1 antibodies was tested by transient transfection of Expi293 cells. See FIG. 18 of our WO 2021/041678 A1 patent application. Western blot of supernatants from transiently transfected EXPI293™ cells to assess extent of non-cognate LC/HC pairing among the HCs and LCs of anti-hCD20 Ab 1.2.2 and anti-hCD37 Ab1.A1. The left blot and the right blot contain duplicate samples (1 is the duplicate of 1', etc.) run in parallel. Transfected cell supernatants in lanes 1 and 1' came from cells containing plasmid DNAs encoding the LC and HC of anti-hCD20 Ab1.2.2 (LC1 and HC1). Transfected cell supernatants in lanes 2 and 2' came from cells containing plasmid DNAs encoding HC1 and LC2. Transfected cell supernatants in lanes 3 and 3' came from cells containing plasmid DNAs encoding LC1 and HC2. Transfected cell supernatants in lanes 4 and 4' came from cells containing plasmid DNAs encoding the LC and HC of anti-hCD37 Ab1.A1 (LC2 and HC2). Transfected cell supernatants in lanes 5 and 5' came from cells containing plasmid DNAs encoding LC and HC of anti-HER2 antibody trastuzumab.

Results showed that the anti-hCD20 Ab1.2.2 (lanes 1 and 1') and anti-hCD37 Ab1.A1 (lanes 4 and 4') antibodies are expressed well, although the expression is slightly lower than the expression of the anti-HER2 antibody trastuzumab (lanes 5 and 5'). The antibody resulting from the cognate HC1/LC1 pair of anti-hCD20 Ab1.2.2 (lanes 1 and 1') was expressed at approximately the same level as the antibody resulting from the non-cognate pair of HC1 (from anti-hCD20 Ab1.2.2) and LC2 (from anti-hCD37 Ab1.A1) by comparing lanes 1 and 1' to lanes 2 and 2'. This suggests that the HC1 of anti-hCD20 Ab1.2.2 can express equally well with its own LC1 or non-cognate LC2 from anti-hCD37 Ab1.A1. Interestingly, the non-cognate pairing of LC1 (from anti-hCD20 Ab1.2.2) and HC2 (from anti-hCD37 Ab1.A1) is expressed at much lower levels than the cognate HC2/LC2 pair by comparing lanes 3 and 3' to lanes 4 and 4'. These data suggest that the HC2 of anti-hCD37 Ab1.A1 prefers its own LC2 for expression over the non-cognate anti-hCD20 LC1. Therefore, the main issue to address in engineering these two antibodies to express only cognate HC/LC pairs when expressed in the same host cell is the mispairing of HC1 from anti-hCD20 Ab1.2.2 and LC2 from anti-hCD37 Ab1.A1.

In the following experiment, the antibodies were altered to strengthen cognate HC/LC pairs, prevent non-cognate HC/LC pairs, and promote HC/HC heterodimers. The parental antibodies anti-hCD20 Ab1.2 and anti-hCD37 Ab1.A1 are used for making bispecific antibodies as follows. Substitutions Y349C, S364D, K370D, N390D, K392G, and S400D (CDDDGD) in $C_H3$ region were introduced into the HC of anti-hCD20 Ab1.2 by designing appropriate mutations into DNA gBlocks encoding these HCs by the methods described above, SEQ ID NOs: 29 and 30 show the nucleic acid sequence and the amino acid sequence of anti-hCD20 Ab1.2.5 HC, respectively. Substitutions S354C, S364K, N390P, and S400K (CKKPKK) in $C_H3$ region were introduced into the HC of anti-hCD20 Ab1.2 by designing appropriate mutations into DNA gBlocks encoding these HCs by the methods described above, SEQ ID NOs: 31 and 32 show the nucleic acid sequence and the amino acid sequence of anti-hCD20 Ab1.2.6 HC, respectively. The LC of anti-hCD20 Ab1.2 (SEQ ID NOs: 35 and 36) can also pair with either anti-hCD20 Ab1.2.5 or Ab1.2.6 HC to produce the bispecific antibodies when co-transfected with DNAs encoding the anti-hCD37 HC and LC described below.

Substitutions K147D, F170C, and V173C in $C_H1$ region; C220G in upper hinge region; S354C, S364K, N390P, and S400K in $C_H3$ region were introduced into the HC of anti-hCD37 Ab1.A1 by designing appropriate mutations (DCCG+CKKPKK) into DNA gBlocks encoding the HC by the methods described above, SEQ ID NOs: 41 and 42 show the nucleic acid sequence and the amino acid sequence of anti-hCD37 Ab1.A1.2 HC, respectively. Substitutions K147D, F170C, and V173C in $C_H1$ region; C220G in upper hinge region; Y349C, S364D, K370D, N390D, K392G, and S400D in $C_H3$ region were introduced into the HC of anti-hCD37 Ab1.A1 by designing appropriate mutations (DCCG+CDDDGD) into DNA gBlocks encoding these HCs by the methods described above, SEQ ID NOs: 43 and 44 show the nucleic acid sequence and the amino acid sequence of anti-hCD37 Ab1.A1.3 HC, respectively. Accordingly, substitutions S131K, Q160C, S162C, and C214S (KCCS) were incorporated into the LC of anti-CD37 Ab1. A1 by the method described above. The new variant is named as anti-hCD37 Ab1.A1.1 LC. SEQ ID NOs: 49 and 50 show the nucleic acid sequence and amino acid sequence of anti-hCD37 Ab1.A1.1 LC, respectively.

Plasmid DNAs encoding HCs and LCs, which made up one antibody, were put into a series of EPPENDORF tubes. The tubes contained DNAs encoding the following antibodies: (1) trastuzumab IgG1 (an anti-HER2 antibody used as a control to monitor transfection efficiency) with corresponding LC; (2) anti-hCD20 IgG Ab1.2 (SEQ ID NO:28) with corresponding LC (SEQ ID NO: 36); (3) anti-hCD37 Ab1.A1 HC (SEQ ID NO:40) with corresponding LC (SEQ ID NO:48); (4) the bispecific anti-hCD20 (Ab1.2.5)×hCD37 (Ab1.A1.2) in which the CDDDGD are embedded in the HC of anti-CD20 antibody (SEQ ID NO:30) pairing with the original anti-CD20 LC (SEQ ID NO: 36); and DCCG+CKKPKK are embedded in the HC of anti-CD37 antibody (SEQ ID NO:42) pairing with anti-CD37 LC having the KCCS substitutions (SEQ ID NO:50); (5) the bispecific anti-hCD20 (Ab1.2.6)×CD37 (Ab1.A1.3) in which the CKKPKK are embedded in the HC of anti-hCD20 antibody (SEQ ID NO:32) pairing with the original anti-CD20 LC (SEQ ID NO:36); and DCCG+CDDDGD are embedded in the HC of anti-hCD37 antibody (SEQ ID NO:44) pairing with the anti-CD37 LC having KCCS substitutions (SEQ ID NO:50). The mixed plasmid DNAs were used to transfect 30 mL of EXPICHO™ cells. The flasks containing the transfected EXPICHO™ cells were shaken at 37° C. at 10% $CO_2$ for 12 days. Antibodies were harvested from the culture supernatants and purified by Protein A affinity chromatography.

To roughly determine the size of the antibody preparations described immediately above, the purified antibody preparations by Protein A resin were subjected to electrophoresis on SDS-PAGE gels. Each sample contained 2 μg of each antibody in a total volume of 20 μl that contained 10 ul of 2× Laemmli Sample Buffer (65.8 mM Tris-HC1, pH 6.8, 2.1% sodium lauryl sulfate (SDS), 26.3% (w/v) glycerol, 0.01% bromophenol blue) in the absence (for non-reduced samples) or presence (for reduced samples) of 100 mM dithiothreitol (DTT). Samples were heated at 70° C. for 10 minutes, then loaded onto a 4-15% CRITERION™ TGX STAIN-FREE™ Precast SDS-PAGE gels (Bio-Rad Laboratories, Inc., Hercules, CA, cat no. 567-8085). Electrophoresis was run for 45 minutes at 200 V. The image was visualized with a CHEMIDOC™ XRS+imager from Bio-Rad Laboratories, Inc. after light activation.

As shown in FIG. 5 (left panel), the monoclonal antibodies trastuzumab (lane 1), anti-hCD20 Ab1.2 (lane 2), and anti-hCD37 IgG1 Ab1.A1 (lane 3) migrate at around 150 KDa under non-reduced conditions. When plasmid DNAs encoding HC1 and LC1 from anti-hCD20 Ab1.2.5 and HC2 and LC2 from anti-hCD37 Ab1.A1.2 were used to transfect the cells, a band at around 150 KDa (lane 4) was observed on the SDS-PAGE gel. When plasmid DNAs encoding HC1 and LC1 from anti-hCD20 Ab1.2.6 and HC2 and LC2 from anti-hCD37 Ab1.A1.3 were used to transfect the cells, a band at around 150 KDa (lane 5) was also observed on the SDS-PAGE gel. Under reducing conditions (FIG. 5, right panel), an HC band with a size of about 50 KDa and a LC band with a size of 25 KDa were observed for trastuzumab (lane 1'), anti-hCD20 Ab1.2 (lane 2'), and anti-hCD37 Ab1.A1 (lane 3'), whereas two HC bands and two LC bands were well separated for the anti-hCD20 (Ab1.2.5)×hCD37 (Ab1.A1.2) bispecific antibody (lane 4'). These results indicate that IgG antibody consisting of two different HCs and two different LCs is produced in host cells. Two LC bands were clearly observed for the anti-hCD20 (Ab1.2.6)×hCD37 (Ab1.A1.3) bispecific antibody (lane 5') but the two HCs migrated very closely. Taken together, these results suggested that the charge residues (negative charge vs positive charge) in HC can impact the migration under reducing conditions, by comparing HC bands at around 50 KDa in lanes 4' and 5'. Both anti-hCD20(Ab1.2.5)×hCD37 (Ab1.A1.2) and anti-hCD20 (Ab1.2.6)×hCD37 (Ab1.A1.3) bispecific antibodies looked to contain four different chains as expected.

Example 4: Characterizations of Anti-CD20×CD37 Bispecific Antibodies to Assess the Integrity and Fidelity by Mass Spectrometry Mass spectrometry was performed to determine whether the bispecific antibodies produced by the host cells containing DNAs encoding anti-hCD20 (Ab1.2.5)×hCD37 (Ab1.A1.2) shown in lanes 4 and 4' of FIG. 5, and anti-hCD20 (Ab1.2.6)×hCD37 (Ab1.A1.3) shown in lanes 5 and 5' of FIG. 5 have (1) two different HCs and two different LCs; (3) HC1 of anti-CD20 part forms heterodimer with HC2 of anti-CD37 part; (3) the LC1 of anti-CD20 correctly pairs with the HC1 of anti-CD20, vice versa, the LC2 of anti-CD37 correctly pairs with the HC2 of anti-CD37. This means, fully cognate HC/LC pairings for both Fab arms in the context of bispecific antibodies. Mass spectrometry methods used are described by Thompson et al. (2014), mAbs 6:1: 197-203, which is incorporated herein in its entirety, and in WO 2017/205014, page 92, line 31 to page 94, line 10 and FIG. 19, which portions of WO 2017/205014 are incorporated herein by reference.

To do this analysis, 20 μg of the purified bispecific antibody anti-hCD20 (Ab1.2.5)×hCD37 (Ab1.A1.2) or (Ab1.2.6)×hCD37 (Ab1.A1.3) was incubated at 37° C. with 1 μl of PNGase F endopeptidase (New England Biolabs) in 20 ul of 50 mM Tris pH 7.5 for 16 hr. After deglycosylation by PNGase F, half of the sample was reduced by incubation at 55° C. in a buffer containing 4 M Guanidine Hydrochloride, 50 mM Tris pH8.0 with 50 mM DTT for 30 minutes. HPLC-MS analysis of the reduced samples was performed using an Agilent 6224 accurate-mass TOF mass spectrometer equipped with an ESI source and coupled to an Agilent 1200 HPLC. An Agilent Pursuit Diphenyl column (2.0×150 mm, 3 μm) was used with a column temperature of 80° C. and a flow rate of 0.4 μl/min. Mobile phase A consisted of water with 0.1% trifluoroacetic acid (TFA), and mobile phase B consisted of isopropyl alcohol (IPA): acetonitrile (ACN): water (70:30:10) with 0.9% TFA. Mobile phase B was held initially at 10%, then raised to 32% B over 5 minutes, and then increased to 42% over 35 minutes. The solvent was then changed to 90% B and held for 4 minutes to clean up the column. Finally, the solvent was reverted to 10% B and held for 4 minutes for re-equilibration of the column. MS instrumental parameters were as follows: the drying gas temperature, drying gas flow and nebulizer were set at 300° C., 12 L/min and 40 psig, respectively. The capillary, fragmentor, skimmer1 and Oct RF Vpp were set at 4500V, 250V, 60V and 750V, individually. The instrument was calibrated in m/z range of 100 to 3000 at 4 GHz high resolution. Data from HPLC-MS were analyzed using Agilent MassHunter Qualitative and BioConfirm software. Theoretical sizes of all deglyosylated antibody species that could potentially be formed in cells containing DNAs encoding anti-hCD20 (Ab1.2.5)×anti-hCD37 (Ab1.A1.2) or anti-hCD20 (Ab1.2.6)×anti-hCD37 (Ab1.A1.3) are shown in Table 17 below.

TABLE 17

Theoretical sizes for deglycosylated antibodies.

| Combination of HCs and LCs | Theoretical mass (Daltons)<br>aCD20 with Y349C, S364D, K370D, N390D, K392G, S400D (HC1, LC1)<br>aCD37 with S354C, S364K, N390P, S400K (HC2, LC2) | aCD20 with S354C, S364K, N390P, S400K (HC1, LC1)<br>aCD37 with Y349C, S364D, K370D, N390D, K392G, S400D (HC2, LC2) |
|---|---|---|
| LC1/HC1/HC1/LC1 | 145525.78 | 145188.78 |
| LC2/HC2/HC2/LC2 | 144187.78 | 144524.78 |
| LC1/HC2/HC2/LC1 | 143955.42 | 144292.42 |
| LC2/HC1/HC1/LC2 | 145758.14 | 145421.14 |
| LC1/HC2/HC1/LC2 | 144856.78 | 144856.78 |
| LC1/HC1/HC2/LC2 | 144856.78 | 144856.78 |
| LC1/HC1/HC1/LC2 | 145642.96 | 145305.96 |
| LC1/HC2/HC2/LC2 | 144072.6 | 144409.6 |
| LC1/HC1/HC2/LC1 | 144741.6 | 144741.6 |
| LC2/HC1/HC2/LC2 | 144973.96 | 144973.96 |

FIG. 6, panel A and B show data from deglycosylated antibody produced by host cells containing DNAs encoding anti-hCD20 (Ab1.2.5)×anti-hCD37 (Ab1.A1.2) bispecific antibody. λs indicated, the actual mass of the major peak detected was 144867.63 daltons (Da), which is 75 parts per million (ppm) from the theoretical mass of 144856.78 Da. FIG. 6, panel C and D show data from deglycosylated antibody produced by host cells containing DNAs encoding anti-hCD20 (Ab1.2.6)×anti-hCD37 (Ab1.A1.3). The actual mass of the main peak detected is 144867.71 Da, which is also 75 ppm from the theoretical size of 144856.78 Da. Since both variations in size from the theoretical sizes are less than 100 ppm, these experimentally determined masses suggested that the major peaks observed could result from antibodies with cognate HC/LC pairs and heterodimeric HC1/HC2 pairings, i.e., anti-hCD20 Ab1.2.5 with anti-hCD37 Ab1.A1.2, or anti-hCD20 Ab1.2.6 with anti-hCD37 Ab1.A1.3 to form bispecific antibodies. As shown in the table above, other 8 mis-paired antibody species have masses quite distant from the theoretical mass of 144856.78 Da.

Under reducing condition, anti-hCD20 (Ab1.2.5)×anti-hCD37 (Ab1.A1.2) bispecific antibody contains an anti-CD20 LC (FIG. 7, panel A) with a mass of 23378.00 Da, which is 9.4 ppm away from the theoretical mass of 23378.22 Da; an anti-CD37 LC (FIG. 7, panel B) with a mass of 23495.11 Da, which is 1.7 ppm away from the theoretical mass of 23495.15 Da; an anti-CD37 HC (FIG. 7, panel C) with a mass of 48785.54 Da, which is 14.3 ppm away from the theoretical mass of 48786.24 Da; an anti-CD20 HC (FIG. 7, panel D) with a mass of 49232.79 Da, which is 8.3 ppm away from the theoretical mass of 49233.42 Da. All experimental errors are far below the allowable error of 100 ppm. These results clearly demonstrate that the anti-hCD20 (Ab1.2.5)×anti-hCD37 (Ab1.A1.2) bispecific antibody consists of four different chains with expected masses.

Under reducing condition, anti-hCD20 (Ab1.2.6)×anti-hCD37 (Ab1.A1.3) bispecific antibody contains an anti-CD20 LC (FIG. 8, panel A) with a mass of 23378.00 Da, which is 9.4 ppm away from the theoretical mass of 23378.22 Da; an anti-CD37 LC (FIG. 8, panel B) with a mass of 23495.11 Da, which is 1.7 ppm away from the theoretical mass of 23495.15 Da; an anti-CD37 HC (FIG. 8, panel C) with a mass of 48617.13 Da, which is 12.5 ppm away from the theoretical mass of 48617.74 Da; an anti-CD20 HC (FIG. 8, panel D) with a mass of 49401.16 Da, which is 13.3 ppm away from the theoretical mass of 49401.92 Da. All experimental errors are far below the allowable error of 100 ppm. These results clearly demonstrate that the anti-hCD20 (Ab1.2.6)×anti-hCD37 (Ab1.A1.3) bispecific antibody consists of four different chains with the expected masses.

However, one mis-paired HCs/LCs antibody, when LC1 pairs with HC2 and LC2 pairs with HC1, the theoretical mass of such mis-paired antibody (LC1/HC2/HC1/LC2) has an identical mass of 144856.78 Da as the correctly paired bispecific antibody (LC1/HC1/HC2/LC2). Therefore, the anti-hCD20×hCD37 bispecific antibodies described above were further analyzed by high performance liquid chromatograph-mass spectrometry (HPLC-MS) to identify the cognate HC/LC pairings as follows.

To generate Fab fragments, 20 μg of the antibody preparations purified from host cells containing DNAs encoding anti-hCD20 (Ab1.2.5)×hCD37 (Ab1.A1.2) or anti-hCD20 (Ab1.2.6)×hCD37 (Ab1.A1.3) bispecific antibodies were treated with IgG degrading enzyme of *Streptococcus pyogenes* (IdeS Protease; Promega, cat no. V7511, which cleaves an IgG antibody at a single site below the hinge region, yielding F(ab')2 fragments and fragments comprising the $C_H2$ and $C_H3$ domains) followed by partial reduction in the presence of 2-mercaptoethyl amine (2-MEA) and ethylenediaminetetraacetic acid (EDTA). The treatment with 2-MEA and EDTA reduces hinge region disulfide bridges without substantially affecting HC/LC disulfide bridges. Thus, this treatment would be expected to yield Fab' fragments and fragments comprising the $C_H2$ and $C_H3$ domains, possibly accompanied by minor quantities of Fd fragments (comprising the $V_H$ and $C_H1$) and LCs.

Table 18 below shows the calculated masses of Fab fragments resulting from the four possible Fd/LC pairings from a bispecific antibody comprising anti-hCD20 Ab1.2.5 and anti-hCD37 Ab1.A1.2, including cognate and non-cognate pairs.

TABLE 18

Calculated masses of Fab fragments

| Fd/LC combination* | Calculated mass of Fab (Da) |
|---|---|
| Fd1/LC1 | 48,912.71 |
| Fd2/LC2 | 48,412.21 |
| Fd1/LC2 | 49,029.89 |
| Fd2/LC1 | 48,297.03 |

*Fd1 and LC1 are from the anti-hCD20 Ab1.2.5 antibody, and Fd2 and LC2 are from the anti-hCD37 Ab1.A1.2 antibody.

Analysis of the IdeS protease-digested and 2-MEA plus EDTA-treated pair of antibodies by mass spectrometry (FIG. 9) yielded peaks at 48,415.74 Da and 48,915.13 Da, which matched the calculated Fd2/LC2 mass and Fd1/LC1 Fab mass with an error of 73 ppm and 50 ppm, respectively, see Table 18 and FIG. 9. No peak at around 49029.89 Da or 48297.03 Da was found. A very minor peak at 49074.74 Da was observed, it is the O-glycosylation modified anti-hCD37 Fd2/LC2 fragment due to the exposed Ser residue at position 219 after the C220G substitution has abolished the natural disulfide bond between 220C at the upper hinge region and 214C at the end of kappa LC. The O-glycosylation of anti-CD37 antibody was well described in our previous patent application WO2021041678 ANTI-CD20 ANTIBODIES, ANTI-CD37 ANTIBODIES, AND MIXTURES THEREOF.

The Mass spectrometry analysis of Fab fragments from the other anti-hCD20 (Ab1.2.6)×CD37 (Ab1.A1.3) bispecific antibody was carried out in the same way, and the same results were obtained (not shown) because these two bispecific antibodies contain the same Fab fragments but differ in the Fc regions only.

Taken together, these data clearly indicated that both anti-hCD20 (Ab1.2.5)×CD37 (Ab1.A1.2) and anti-hCD20 (Ab1.2.6)×CD37 (Ab1.A1.3) bispecific antibodies have the cognate LC/HC pairings; HC1 from anti-CD20 and HC2 from anti-CD37 completely form heterodimer as we designed.

Example 5: In Vitro Bioassay to Test the Killing Activity of Anti-CD20×CD37 Bispecific Antibodies Using B-Cell Lymphoma Cell Lines To assess whether the anti-hCD20 (Ab1.2.5)×hCD37 (Ab1.A1.2) bispecific antibody retains the activity of the parental antibodies, a killing assay was performed using either WSU-DLCL2 or Ramos cells. Both cell lines are from human B-cell lymphomas expressing both CD20 and CD37 on cell surface. Firstly, prepare antibody dose titrations by diluting the concentrated antibody in a 3× serial dilutions in assay medium (RPMI+10% FBS), the diluted antibody was added to wells in a round bottom 96-well tissue culture plate at 100 μl per well. Secondly, WSU-DLCL2 and Ramos tumor cells were collected and transferred to a 50-ml conical tube, the tube of cells is pelleted by centrifugation at room temperature for 5 minutes at 200× g, the medium is removed from the tube by aspiration and the cells are then resuspended in assay medium, tumor cells were seeded into plate at 200 μL per well with cell density at $1\times10^5$ cells per well for a total volume 300 μL per well. Tumor cells were continuously incubated in a humidified CO2 incubator set to 37° C. and 5% $CO_2$ for 24 hours. Thirdly, mix tumor cells with multi-channel pipette to break cell aggregation. Add 10 μL of 37% formaldehyde to make 1.2% final and gently mix cells in wells, incubate plate at 4° C. for half hour. Fourthly, run samples with BD LSRII flow cytometry with autosampler at 60 μl/well at rate of 1 μl/second. Finally, data were analyzed with FlowJo software to determine the blast cell numbers in blast gated populations as measures of antibody induced killing activity. The data are plotted as "BlastCell #" in Y-axis and analyzed using linear regression calculations in GraphPrism software to determine the $IC_{50}$ values for relative efficacy. Results are expressed as the mean and standard error of the mean (SEM) for duplicated measurements.

The activity of the bispecific antibody was compared to that of parental anti-CD20 alone or anti-CD37 alone, see FIG. 10. In panel A with WSU-DLCL2 cells, the anti-CD37 parental antibody had low killing activity with approximately 15% reduction of the number of cells at the highest concentration (33.3 nM or 5 μg/ml), when compared to the IgG1 isotype control. This result reflects a much lower CD37 expression than CD20 expression on WSU-DLCL2 cell surface (in-house data, not shown). Both the parental anti-CD20 antibody and the anti-hCD20 (Ab1.2.5)×hCD37 (Ab1.A1.2) bispecific antibody reduced the cell number by roughly 62% at the highest concentration. Although the maximum activity is the same for both parental anti-CD20 antibody and the anti-hCD20 (Ab1.2.5)×hCD37 (Ab1.A1.2) bispecific antibody, but at lower concentration, especially between 0.1 nM and 10 nM, the bispecific antibody outperformed over both the parental anti-CD20 antibody alone and anti-CD37 antibody alone. This suggests that co-engagement of CD20 and CD37 simultaneously by bispecific antibody can lead to an increased killing activity.

In the case of Ramos cells (FIG. 10, panel B), the parental anti-CD37 alone showed higher killing than the parental the anti-CD20 alone with roughly 40% more killing at the highest dose, this reflects the fact that Ramos cells express higher CD37 than CD20 (Oksvold M. P. et al. *Clin Ther.* 2014; 36 (6): 847-862.e1) on cell surface, it was well documented that Ramos cells are resistant to the treatment by anti-CD20 antibody (Takei K. et al. *Leuk Res.* 2006;30 (5): 625-631). The anti-hCD20 (Ab1.2.5)×hCD37 (Ab1.A1.2) bispecific antibody again showed the most potent killing activity with approximately 62% of cells killed at the highest concentration tested. The anti-CD20×CD37 bispecific antibody outperforms either parental anti-CD20 alone or anti-CD37 antibody alone, suggesting that there could be a big potential of treating human B-cell lymphomas using anti-CD20×CD37 bispecific antibody to engage CD20 and CD37 simultaneously.

Tumor cells can express targets CD20 and CD37 at different levels at surface. For WSU-DLCL2 cells, CD20 expression is higher; for Ramos cells, CD37 is predominantly expressed and the expression of CD20 is much lower. This fact exemplifies well the advantage of bispecific antibodies as the patient population are generally heterogenous in terms of what target is expressed on the surface of their cancerous cells. Bispecific antibodies such as the ones described here can retain high levels of activity, even if one of the targets has a low level of expression. When both targets are expressed, the activity of the bispecific antibody can outperform either single antibody, suggesting the co-engagement of CD20 and CD37 could bring additive or synergistic potential for treating B-cell lymphomas.

Example 6: Making Anti-hSIRPα×Anti-hCLDN18.2 Bispecific Antibody to Further Validate the New Heterodimeric Bispecific Antibody Platform The human Claudin 18 splice variant 2 (hCLDN18.2) belongs to the tight junction family, its expression in normal tissues is strictly confined to differentiated epithelial cells of the gastric mucosa, but it is absent from the gastric stem cell zone. hCLDN18.2 is retained on malignant transformation and is expressed in a significant proportion of primary gastric cancers and the metastases thereof. In addition to its orthotopic expression, frequent ectopic activation of hCLDN18.2 in human pancreatic, esophageal, ovarian, and lung tumors were observed by many researchers (Sahin et al, 2008; Moentenich et al, 2020; Li et al, 2020). Therefore, hCLDN18.2 could serve as a highly selective cell lineage marker. The activation of hCLDN18.2 depends on the binding of the transcription factor cyclic AMP-responsive element binding protein to its unmethylated consensus site. Monoclonal antibodies that bind to hCLDN18.2 but not to its lung-specific splice variant (hCLDN18.1) may have a significant therapeutical potential for treating multiple human solid tumors expressing hCLDN18.2 antigen on the surface of cancer cells.

The human CD47 represents a "don't eat me" signal for phagocytic cells. Analysis of patient tumor and matched adjacent normal (nontumor) tissue revealed that CD47 is overexpressed on cancer cells (Huang et al, 2020). CD47 mRNA expression levels correlated with a decreased probability of survival for multiple types of cancer (Li et al, 2017; Yuan et al, 2019; Huang et al, 2020). CD47 is a ligand for SIRPa, the signal-regulatory-protein a (hSIRPα), a protein expressed on macrophages and dendritic cells. There are two alleles (V1 and V2) for hSIRPα in human populations (Deborah Hatherley et al, 2014). Interaction of SIRPα expressed on the surface of macrophages with its ligand CD47 expressed on target cells negatively regulates phagocytosis of the latter cells by the former. It was reported that blocking antibodies to mouse SIRPα enhanced both the Ab-dependent cellular phagocytosis (ADCP) activity of mouse macrophages for Burkitt's lymphoma Raji cells opsonized with an antibody to CD20 (rituximab) in vitro, as well as the inhibitory effect of rituximab on the growth of tumors formed by Raji cells in nonobese diabetic (NOD)/SCID mice (Murata et al, 2018). The anti-human SIRPα antibody also markedly enhanced the inhibitory effect of rituximab on the growth of tumors formed by Raji cells in hSIRPα-DKO mice (Murata et al, 2018). These results suggested that the combination of antibodies to human SIRPα with therapeutic antibodies specific for tumor antigens warrants further investigation for potential application to cancer immunotherapy. We aimed to make anti-hSIRPα× anti-hCLDN18.2 bispecific antibody to engage macrophages to phagocyte or kill tumor cells highly expressing hCLDN18.2 antigen by the enhanced ADCP mechanism.

CHO cells stably expressing hCLDN18.2 was used to immunize Balb/c mice to generate hybridomas. The process has been well known in many prior arts. Individual clones were screened for (1) strong binding to stable CHO cells which express hCLDN18.2 but no binding to blank CHO cells; (2) strong ADCC killing activity of tumor cells induced by hybridoma antibody and PBMCs; (3) high CDC killing activity of tumor cells induced by hybridoma antibody and complements. One of hybridomas, clone 59F9E1, met all above 3 criteria. The mRNA from hybridoma clone 59F9E1 was isolated and reverse transcribed to cDNA. The DNA sequences encoding the VL and VH were sequenced to deduce the amino acid sequences of clone 59F9E1. The mouse antibody 59F9E1 was humanized according to procedure in our previous patent application WO2021041678 ANTI-CD20 ANTIBODIES, ANTI-CD37 ANTIBODIES, AND MIXTURES THEREOF. Similarly, a mouse anti-hSIRPα antibody which blocks the interaction between hSIRPα (both V1 and V2 alleles) and CD47 was humanized and engineered by yeast display technology, which was well described in our previous patent application WO-2020180811-A1 ANTI-SIRP-ALPHA ANTIBODIES.

To figure out how to force the cognate HC/LC pairings when making anti-hSIRPα×anti-hCLDN18.2 bispecific antibody, the HC/LC pairing preference of anti-SIRPα and anti-hCLDN18.2 antibodies was assessed by transient transfection in Expi293 cells (FIG. 11, panels A and B), similarly to what was done for anti-hCD20×hCD37 bispecific antibody. Mixture of plasmids corresponding to cognately paired HC and LC as well as mis-paired chains were used for transient transfection as described in Example 3. After transfection, supernatants were analyzed on an SDS-PAGE stain-free protein gel (4-15% CRITERION™ TGX STAIN-FREE™ Precast SDS-PAGE gels, Bio-Rad, cat no. 567-8085). Lanes 1 to 6 and lanes 7 to 12 are technical duplicates and contain the same mixture of HC and LC plasmids. Overall, when HC and LC are cognately paired (lanes 1 and 7 for anti-hCLDN18.2 and lanes 4 and 10 for anti-SIRPa), both antibodies are produced since a band at around 150 KDa was observed in the SDS-PAGE gel, anti-hCLDN18.2 expression appears to be higher than that of anti-hSIRPα. When the LC1 of anti-hCLDN 18.2 is paired with the HC2 of anti-hSIRPα (lanes 3 and 9), the resulting antibody has even higher expression than the mis-paired LC2 of anti-hSIRPα with the HC1 of anti-hCLDN18.2 (lanes 2 and lane 8). Another interesting observation is the high amount of anti-hCLDN18.2 LC expressed whenever it is present, free LC at size of about 25 KDa can be observed in lanes 1, 3, 7 and 9. In this case, a serious problem that needs to be addressed is the strong compatibility between the LC1 of anti-hCLDN18.2 and the HC2 of anti-hSIRPα antibody.

Based on the results described above, we chose to introduce the pairing mutations controlling the proper pairing of the LC and HC together in anti-hCLDN18.2. S131K, Q160C, S162C and C214S (KCCS) were introduced on the LC of anti-hCLDN18.2 (SEQ ID NO:64) while K147D, F170C, V73C in CH1 and C220G in upper hinge region (DCCG) were introduced on the HC of anti-hCLDN18.2 IgG1 (SEQ ID NO:56). No change was introduced in the LC and HC of anti-hSIRPα antibody (SEQ ID NO:68 and 74). To test the impact of such mutations, the pairing test described above was repeated with the plasmids encoding the new HC and LC (FIG. 11, panels C and D, lanes 13 to 24). Lanes 13 to 18 and lanes 19 to 24 are technical duplicates and contain the same mixture of HC and LC. Expression in lanes 13 and 19 containing the HC1 and LC1 of anti-hCLDN18.2 did not significantly change after the introduction of the pairing mutations. However, lanes 14 and 20 which contain the mis-paired HC1 from anti-hCLDN18.2 and LC2 from anti-hSIRPα; as well as lanes 15 and 21 containing mis-paired HC2 from anti-hSIRPα and LC1 from anti-hCLDN18.2 no longer produce a full-length antibody, since no band with a size of around 150 KDa was observed. The anti-hSIRPα IgG expression is unchanged (comparing lanes 16 and 22). Because the LC of anti-hCLDN18.2 has such a high level of expression, it can easily accommodate the introduced substitutions without much change in antibody production as demonstrated in this SDS-PAGE gel.

The Y349C, S364D, K370D, N390D, K392G and S400D substitutions were further introduced in CH3 region of the HC1 of anti-hCLDN18.2 ((DCCG+CDDDGD, SEQ ID NO:58) while the S354C, S364K, N390P and S400K (CKKPKK) substitutions were further introduced in the CH3 region of HC2 of anti-hSIRPα (SEQ ID NO:70) to form HC1/HC2 heterodimers. Accordingly, the LC1 of anti-hCLDN18.2 antibody having S131K, Q160C, S162C and C214S (KCCS) substitutions (SEQ ID NO:64) was used to pair with the anti-hCLDN18.2 having DCCG+CDDDGD substitutions (SEQ ID NO:58), the LC2 of anti-hSIRPα is unchanged (SEQ ID NO:74). After these final modifications, the resulting plasmids for the 2 HCs and 2 LCs were mixed and transfected in ExpiCHO cells at the 30 ml scale. Antibodies were purified using a protein A column coupled with an AKTA HPLC purifier system (Cytiva). The resulting purified protein was loaded on a 4-15% Tris-Glycine SDS-PAGE gel under non-reducing (FIG. 12, panel A) and reducing (FIG. 12, panel B) conditions. Each sample was loaded at 2 μg per lane. Lane 1 corresponds to an irrelevant anti-DNP IgG1 antibody for size reference. Lane 2 corresponds to anti-hCLDN18.2 IgG1 WT. Lane 3 corresponds to anti-hSIRPα IgG WT antibody. Lane 4 corresponds to the anti-hCLDN18.2×hSIRPα bispecific antibody. Under non-reducing conditions, all antibodies showed a band at a size of around 150 KDa. Under non-reducing condition, a HC band at a size of around 50 KDa and a LC band at around 25 KDa were observed for anti-DNP IgG1 WT, anti-hCLDN18.2 IgG1 WT, and anti-hSIRPα IgG WT antibodies. Two HC bands well separated at around 50 KDa were observed in anti-hCLDN18.2×hSIRPα bispecific antibody, however, the LCs in anti-hCLDN18.2×hSIRPα bispecific antibody co-migrated very closely.

Example 7: Characterization of Anti-hSIRPα×Anti-hCLDN18.2 Bispecific Antibody to Assess Integrity and Fidelity by Mass Spectrometry Mass spectrometry was performed to determine whether the anti-hSIRPα×anti-hCLDN18.2 bispecific antibody has the expected heterodimeric HC1/HC2 pairings and cognate HC1/LC1 and HC2/LC2 pairings. Intact anti-hSIRPα×anti-hCLDN18.2 bispecific antibody comprising of the SEQ ID NOs 70, 74, 58, and 64 was deglycosylated by PNGase F as previously described in Example 4. FIG. 13 shows the intact (Panel A) and reduced (Panel B) fragments. The observed intact size is 146009.69 Da in FIG. 13A matches the theoretical size (146003.2 Da) of the expected bispecific antibody with an error of 44 ppm, well below the allowed technical error of 100 ppm, suggesting that the purified anti-hSIRPα×anti-hCLDN18.2 bispecific antibody contains four different chains (HC1, LC1, HC2, LC2).

Under reducing condition (FIG. 13 panel B), anti-hSIRPα×anti-hCLDN18.2 bispecific antibody contains an anti-hCLDN18.2 LC with a mass of 24274.34 Da, which is 21.8 ppm away from the theoretical mass of 24273.81 Da; an anti-hSIRPα LC with a mass of 24022.03 Da, which is 24.5 ppm away from the theoretical mass of 24021.44 Da; an anti-hCLDN18.2 HC with a mass of 48935.55 Da, which is 39.4 ppm away from the theoretical mass of 48933.62 Da; an anti-hSIRPα HC with a mass of 48812.99 Da, which is 47.7 ppm away from the theoretical mass of 48810.66 Da. All experimental errors are below the maximum acceptable error of 100 ppm. These results clearly demonstrate that the anti-hSIRPα×anti-hCLDN18.2 bispecific antibody consists of four different chains with the expected masses.

The anti-hSIRPα×anti-hCLDN18.2 bispecific antibody was further treated with IdeS Protease and followed by 2-MEA/EDTA treatment to generate Fab fragments, which are well separated under UV trace (FIG. 14, panel A). The expected Fab mass for the anti-hCLDN18.2 arm is 49510.60 Da and a fragment with a actual size of 49510.55 Da was indeed observed (FIG. 14B, error=1 ppm). Similarly, the expected mass for the Fab of the anti-hSIRPα arm is 48968.75 Da and a fragment with a size of 48968.31 Da was also observed (FIG. 14C, error=9 ppm). The results suggested that the LC1 of anti-hCLDN18.2 is pairing with the HC1 of anti-hCLDN18.2 antibody and LC2 of anti-hSIRPα is pairing with the HC2 of anti-hSIRPα antibody.

Finally, F(ab')2 was also generated as described previously in our grant patents U.S. Pat. Nos. 11,130,808 and 11,124,570. Two main peaks comprising the Fc fragment and F(ab')2 fragment with minor shoulder peaks were detected under UV trace (FIG. 14, panel D). The observed F(ab')2 mass at 98480.15 Da (FIG. 14F) of the main peak matches the theoretical mass of the properly paired F(ab')2 (98475.35 Da) with an error of 49 ppm, while the minor peak observed for the F(ab')2 (FIGS. 14D and 14E) has a mass of 98521.69 Da and is compatible with post-translational trisulfide modification of the expected F(ab')2. The F(ab')2 homodimer of anti-hCLDN18.2 antibody would be expected at a mass of 99017.20 Da, and the F(ab')2 homodimer of anti-hSIRPα antibody would be expected at a mass of 97931.50 Da, however, none of the observed peaks were compatible with those masses. Similarly, an Fc fragment with a mass of 47569.32 Da was observed (FIG. 14H), which matches the theoretical mass of 47567.88 Da of an HC1 and HC2 heterodimeric Fc fragment with an experimental error of 30 ppm. The mass of homodimeric Fc of anti-hCLDN18.2 and anti-hSIRPα antibody is expected to be 47399.38 Da and 47736.38 Da, respectively, however, such homodimeric Fc fragments were not observed. A second minor Fc peak was also observed (FIGS. 14D and 14G). This minor peak has a mass of 47587.13 Da which is compatible with post-translational oxidation of the heterodimeric Fc. These results clearly demonstrated that HC1 of anti-hCLDN 18.2 antibody forms a heterodimer with HC2 of anti-hSIRPα antibody.

All experimental results are below acceptable 100 ppm mass error. Taken together, those results indicate that the expected bispecific antibody was properly produced with (1) heterodimerization of HC1 with HC2; (2) cognate pairing of HC1 and LC1 for anti-hCLDN18.2 antibody; (3) cognate pairing of HC2 and LC2 for anti-hSIRPα antibody.

Example 8: Characterization of Anti-hSIRPα×Anti-hCLDN18.2 Bispecific Antibody to Assess Binding Affinity to hSIRPα v1 and v2 Antigens by Biacore Assay The His6 tagged soluble monomeric extracellular domain (ECD) of hSIRPα v1 and v2 were made by transient transfection in Expi293 cells. Kinetic analysis was performed using surface plasmon resonance (T200, Cytiva) to compare the binding of the anti-hSIRPα×anti-hCLDN18.2 bispecific antibody (SEQ ID NOs: 70 and 74) and the parental anti-hSIRPα #24 IgG antibody (SEQ ID NOs: 68 and 74) to antigens hSIRPα v1 and hSIRPα v2 (FIG. 15). Either antibody was captured to the CM5 chip surface (Cytiva) by the immobilized goat-anti-human Fc polyclonal antibody, monomeric antigen hSIRPα v1 or v2 was sequentially injected at 6 different concentrations: huSIRPα v1 at 3.13, 6.25, 12.5, 25, 50, 100 nM while hSIPRa v2 at 0.78, 1.56, 3.13, 12.5, 25 nM with regeneration by 10 mM Glycine-HCl pH1.5 (FIG. 15, panels A-D) for multi-cycle kinetics or without regeneration (FIG. 15, panels E-H) for single-cycle kinetics. The anti-hSIRPα Fab arm in the context of the anti-hSIRPα×anti-hCLDN18.2 bispecific antibody showed similar Kon and Koff as the parental anti-hSIRPα #24 IgG antibody to antigen hSIRPα v1 (comparing FIG. 15 panels A and B and Table 19) and antigen hSIRPα v2 (comparing FIG. 15 panels C and D and Table 19). The overall binding affinity (KD) of the bispecific antibody is 2.32×10-8 M for hSIRPα v1 and 8.8×10-10 M for hSIRPα v2; the overall binding affinity (KD) of the parental anti-hSIRPα #24 IgG antibody is 2.23×10-8 M for hSIRPα v1 and 9.08×10-10 M for hSIRPα v2, respectively. The results suggested that the introduced substitutions in the HC of anti-hSIRPα antibody in the context of bispecific antibody do not impact the antibody's binding capability to its targets. While the same amount of ligand is bound to the chip, the Rmax of the bispecific antibody is approximately half of parental anti-hSIRPα #24 IgG antibody (comparing FIG. 15A versus 15B; FIG. 15E versus 15F) in terms of binding to hSIRPα v1 antigen. Similarly, the Rmax of the bispecific antibody is approximately half of parental anti-hSIRPα #24 IgG antibody (comparing FIG. 15C versus 15D; FIG. 15G versus 15H) in terms of binding to hSIRPα v2 antigen. These results are expected given the fact that the parental antibody is bivalent while the bispecific antibody has only one Fab arm binding to hSIRPα v1 or hSIRPα v2. Because hCLDN18.2 is a tetra-spanning membrane protein, it is not soluble, the measurement of binding affinity of the anti-hSIRPα×anti-hCLDN18.2 bispecific antibody is not feasible by Biacore measurement. Therefore, flow-based binding was carried out in place of surface plasmon resonance analysis.

TABLE 19

Biacore measurement of anti-hSIRPα in the context of bispecific antibody or mAb with monomeric hSIRPα V1 or hSIRPα V2 antigen

| | Format | ka (1/Ms) | Kd (1/s) | KD (M) |
|---|---|---|---|---|
| huSIRPαv1 | bispecific | 3.29E+05 | 7.32E−03 | 2.32E−08 |
| | anti-SIRPα mAb | 3.46E+05 | 7.70E−03 | 2.23E−08 |
| huSIRPαv2 | bispecific | 1.18E+06 | 1.04−03 | 8.80E−10 |
| | anti-SIRPα mAb | 1.21E+06 | 1.09E−03 | 9.08E−10 |

Example 9: Characterization of Anti-hSIRPα×Anti-hCLDN18.2 Bispecific Antibody to Assess the Binding to the Antigen hCLDN18.2 by Flow Cytometry To investigate whether the anti-hCLDN18.2 arm of the anti-hSIRPα×anti-hCLDN18.2 bispecific antibody has changed the binding to target after multiple substitutions have been introduced in the anti-hCLDN18.2 antibody, a cell line stably expressing hCLDN18.2 was generated. pEF1a/V5-His A vector (from ThermoFisher) was digested using the restriction enzymes BamHI-HF and Xbal (New England Biolabs, cat no. R3136T and R0145T, respectively). The cDNA encoding full-length hCLDN18.2 was inserted into the vector using Gibson reaction (New England Biolabs, cat no. E2611L). The resulting plasmid was prepared and transfected into Expi293 cells using Expi-Fectamine 293 Transfection Kit (ThermoFisher, cat no. A14524). After transfection, cells were cultured without selection pressure in RPMI 1640, 1×(Corning, MT10104CV) medium for 4 days for recovery, then a final concentration at 500 ng/ml of G418 (Corning, 30234Cl) was added to the culture media for selection. A rapid drop in cell viability was observed since most cells did not incorporate the plasmid DNA and could therefore not resist the selection pressure. After 3 weeks of continued growth, the cell viability recovered to around 98%, cells stained positively for hCLDN18.2 expression were sorted on a FACSaria sorter (BD Biosciecnes) at the Pathology Flow Cytometry Core Facility (University of Washington, Seattle). The sorted cells were spun down and further cultured for 2 weeks before the binding assay was conducted.

Cells stably expressing hCLDN18.2 were spun down at 1500 rpm at room temperature for 5 minutes and resuspended in 1×PBS/1% BSA (washing buffer), antibodies at a 1:3 series dilution ranging from 100 nM to 24 pM were added, cells were incubated at RT with shaking for 1 hour. After 3 washes with 1×PBS/1% BSA, 10 μg/ml Allophycocyanin (APC) conjugated AffiniPure F(ab')2 fragments of goat anti-human IgG (Jackson ImmunoResearch Laboratories, catalog no. 109-136-170) was added and cells were incubated at RT with shaking for 1 hour. Three additional washes were performed to get rid of unbound antibodies, treated samples were run on an LSRII flow cytometer (BD Biosciences) and signal intensity was determined using the geometric MFI of APC using Flow Jo software (BD Biosciences). Curve fitting and $EC_{50}$ values were obtained using GraphPad Prism 6 software.

Isotype control IgG1 antibody and growth media alone (no mAb) did not have any binding to the cells as expected, the parental anti-hCLDN18.2 59F9E1 IgG1 antibody (aCLDN18.2) comprising SEQ ID NOs: 54 and 62 had a very strong binding with a $EC_{50}$ of 4.52 nM, the anti-hCLDN18.2 Fab arm in the context of anti-hSIRPα×anti-hCLDN18.2 bispecific antibody (Bispecific, SEQ ID NOs: 58 and 64) showed a binding curve with an $EC_{50}$ of 16.92 nM (FIG. 16). The parental anti-hCLDN18.2 59F9E1 IgG1 antibody has two Fab arms that can bind to target hCLDN18.2 whereas the anti-hSIRPα×anti-hCLDN18.2 bispecific antibody has only one Fab arm available for target binding. Thus, the binding difference between the parental antibody and bispecific antibody can be explained by different valency (two Fab arms versus one Fab arm) and avidity effects (tighter binding when 2 Fab arms are simultaneously engaged with antigens).

Example 10: Characterization of Anti-hSIRPα×Anti-hCLDN18.2 Bispecific Antibody to Assess the Killing of Tumor Cells Induced by Macrophages and Antibodies After anti-hSIRPα×anti-hCLDN18.2 bispecific antibody was demonstrated to bind to the targets hSIRPα v1 and v2 (Example 8) and hCLDN18.2 (Example 9), a killing assay was conducted to investigate whether the anti-hSIRPα×anti-hCLDN18.2 bispecific antibody can induce antibody dependent cell phagocytosis (ADCP). Human PBMCs from a donor which was hSIRPα V1/V2 heterozygote were incubated in the attachment media (Sigma Aldrich, cat no. C-28051) at 37° C. at 10% $CO_2$ for 1.5 hours. Non-adherent cells were removed after 3 successive washes with the attachment media while adherent cells were further cultured in the presence of M-CSF at 20 ng/ml for 7 days. These monocytes-derived macrophages were confirmed to show differentiation under microscopy and used for ADCP assay as described below.

On day 7, PaTu 8988s cells from a pancreatic adenocarcinoma cell line (from the German Collection of Microorganisms and Cell Cultures) were added to the wells containing the differentiated macrophages at a 2:1 ratio (adenocarcinoma cells: macrophages) in the presence of serially diluted parental anti-hCLDN18.2 IgG1 antibody (aCLDN18.2 alone), parental anti-SIRPα IgG antibody (aSIRPα alone), a 1:1 mixed both parental antibodies (aSIRPa+aCLDN18.2), or anti-hSIRPα×anti-hCLDN18.2 bispecific antibody (Bispecific). An isotype IgG1 antibody control was added at 100 nM, the highest concentration tested in this assay. After overnight culture, the remaining adenocarcinoma cells and macrophages in each well were detached using 0.05% Trypsin/EDTA (Thermo Fisher catalog no. 2530054). The cell mixtures were then stained with a PE-conjugated anti-CD45 antibody (BD Biosciences, Clone HI30, 555483) and subject to FACS analysis on a LSRII flow cytometer (BD Biosciecnes). Since macrophages express CD45 on cell surface whereas Patu 8988S tumor cells do not express CD45, macrophages were easily distinguishable from adenocarcinoma cells by the positive staining of CD45 surface marker. The number of remaining Patu 8988S tumor cells were counted. Lower Patu 8988S cells number translates to higher ADCP activity after the Patu 8988S tumor cells are engulfed by macrophages.

As shown in FIG. 17, the isotype IgG1 antibody control at the highest concentration did not have ADCP killing activity, the serially diluted parental anti-hCLDN18.2 antibody (aCLDN18.2 alone) or parental anti-SIRPα antibody (aSIRPα alone) did not show ADCP killing activity either. The combination of parental anti-hCLDN18.2 antibody and parental anti-SIRPα antibody (aSIRPa+aCLDN18.2) showed good killing activity with an $EC_{50}$ at 0.223 nM. The anti-hSIRPα×anti-hCLDN18.2 bispecific antibody showed similar killing activity as the combination of two parental antibodies, with an $EC_{50}$ at 0.172 nM. These results indicate that the anti-hSIRPα×anti-hCLDN18.2 bispecific antibody can trigger ADCP killing as comparable as the combination of two parental antibodies.

Example 11: Using the Hetero-Fc Design to Generate Fc-IL15×Fc-IL15Rα Sushi Domain Fusion Protein The Hetero-Fc mutations described herein are used to make constructs to fuse on the C-terminus with human Interleukin 15 (IL-15) on one chain and with the sushi domain of human IL-15 receptor alpha (IL-15Ra) on the other chain (FIG. 18).

IL-15 is a well-known cytokine that is involved in many biological functions such as T cell response, NK cell activation, and the development of inflammatory responses more broadly (Dalai, 2016; Rautela and Huntington, 2017). With the recent renewed interest in the use of cytokines to treat cancer, several clinical trials using IL-15 are ongoing (Xiong et al, 2015, Waldman et al, 2020). However, IL-15 related toxicity limits the dosing and frequency at which the cytokine can be given to the patient which in turn reduces the anti-tumor efficacy (Conlon et al, 2019). Patient treatment with IL-15 can cause hypotension, thrombocytopenia, liver injury, fever, and rigors. However, unlike IL-2 treatment, IL-15 does not cause vascular leak syndrome (Schwartz et al, 2002; Conlon et al, 2015; Guo et al, 2015). This is in part because, although IL-15 binds to two subunits CD122 and CD132 of IL-2R, it does not bind to CD25. Instead, IL-15 binds to a different subunit, IL-15 receptor alpha (IL-15Ra). IL15/IL-15Ra complex can bind to CD122 and CD132 on immune cells in trans to form a tetrameric complex with a high affinity (Stonier and Schluns, 2010). This presents an opportunity to design a construct that could provide both the IL-15 cytokine and IL-15Ra to activate T cells and NK cells. Such construct could bind CD122 and CD132 with higher affinity than IL-15 alone. However, proper formation of the heterodimer is essential to ensure that the cytokine IL15 is only present in conjunction with IL-15Rα. This can be achieved with our Hetero-Fc mutations described herein. This approach can also extend IL-15's half-life as the fusion protein would benefit from the extended half-life provided by the interaction between the Fc portion of the fusion protein and the neonatal Fc receptor (Unverdorben et al, 2016) on endothelial cells.

A portion of the IL-15Ra that is responsible for the interaction with IL-15 was identified (Wei et al, 2001). It contains a Sushi domain and has been used previously to generate similar constructs (Han et al, 2011). However, without a heterodimeric Fc, those types of constructs present a couple of additional challenges: (1) because the cytokine is fused to an Fc that forms a homodimer, each molecule comprises 2 IL15 cytokines which is undesirable. One IL15 molecule fused to one Fc molecule is preferred to reduce the potential toxicity. (2) the IL-15Rα sushi domain needs to be covalently linked to IL-15 to stabilize the IL15's secretion and activity. Our design could help address both issues and offer a new type of molecule that could safely harness the potential of IL-15 therapy. We made Fc-IL15 construct (SEQ ID 107) in which 6 substitutions (Y349C, K370D, S364D, N390D, K392G, S400D) are incorporated and Fc-IL15Rα construct (SEQ ID 109) in which 4 substitutions (S354C, S364K, N390P, S400K)) are incorporated for making the heterodimeric Fc fusion molecules, see FIG. 18. The plasmid DNAs encoding both Fc-IL15 and Fc-IL15Rα were co-transfected to make the Fc-IL15×Fc-IL15Rα heterodimeric fusion protein by transient transfection as described below.

Example 12: Characterization of Fc-IL15×Fc-IL15Rα Sushi Domain Construct

As previously described, ExpiCHO cells were transfected with plasmids encoding SEQ ID 108 and SEQ ID 110 and the resulting Fc fusion protein was purified by protein A purification. An "unarmed" Fc consisting of only the Fc portions with the heterodimeric mutations (but without IL15 and IL15Rα) was also produced in parallel to be used as a control in the reporter assay (SEQ ID 112 and SEQ ID 114).

The resulting purified Fc-IL15×Fc-IL15Rα fusion proteins were loaded on an SDS-PAGE gel to assess purity (FIG. 19). Panel A shows a picture of the stain-free gel under nonreducing conditions. Panel B shows a picture of the stain-free gel under reducing conditions. Lane 1 and lane 4 contain an anti-HER2 IgG1 antibody used for reference and quality control. Lane 2 and lane 5 contain the Fc-IL15×Fc-IL15Rα sushi domain. Two main bands of similar intensity below 75 KDa were observed under nonreducing condition (FIG. 19, panel A, lane 2). This reflects heterogeneous glycosylation pattern in IL15 which contains three N-glycosylation sites (N—X-S/T) (Thaysen-Anderson et al 2016). Under reducing condition (FIG. 19, panel B, lane 5), the band of Fc-IL15Rα chain at 33 KDa was clearly observed, whereas three bands of Fc-IL15 at the range of 40~ 50 KDa were also observed, reflecting the heterogeneous glycosylation pattern in IL15. Lanes 3 and 6 correspond to the dummy hetero-Fc construct which doesn't have cytokine, the reduced profile shows 2 clear bands corresponding to the 2 different chains of Fc having different mutations (SEQ ID NOs: 112 and 114).

Example 13: Validation of the IL15-IL15Rα Sushi Domain Construct in a Reporter Assay To confirm that the activity of IL-15 was conserved, a reporter assay from InvivoGen (cat no. hkb-IL2) was used. In this reporter assay, an HEK 293 cell line containing CD25, CD122, and CD132 as well as STAT5 and a SEAP based reporter gene which is expressed in response to STAT5 phosphorylation. The assay was carried out according to the supplier's recommendations. Briefly, cells were grown in DMEM media with the proper selection agents and resuspended at 280,000 cells per ml on day 1 of the experiment. 180 μl of cell suspension was distributed in a 96 well plate and the cytokine treatment was administered at various concentrations (from 100 nM down to 0.4 pM) in a volume of 20 ul. The cells with the treatment were incubated at 37° C. in an incubator with 5% CO2 overnight. The next day, cells were spun down at 1500 rpm for 5 minutes and 20 ul of supernatant were added to 180 ul of QUANTI-Blue solution in a new plate. The new plate was incubated at 37° C. for 1 hour and the activity was determined based on absorbance at 650 nm using a plate spectrophotometer (FIG. 20) following the provided protocol.

IL-15 does not bind CD25 but binds CD122 and CD132. As expected, the control construct (Hetero-Fc alone), did not have any activity, both the recombinant IL-15 (PeproTech 200-15) and the Fc-IL15×Fc-IL15Rα sushi domain fusion protein generated a clear signal with an EC50 of 21 and 66 pM respectively. Interestingly, the fusion protein had lower activity than IL-15 alone. A possible explanation is that CD25 is highly expressed on this cell line which might lead to competition between CD25 and IL15Rα for binding to the CD122/CD132 complex.

Taken together, those results demonstrate the application for making cytokine fusions using our heterodimeric mutations described herein. Other applications include the potential fusion of our heterodimeric Fc with extracellular domains of receptors, other cytokines, ligands, enzymes, antibody domains, or peptides, and more.

Example 14: Mechanisms of Action about how to Precisely Control the Formation of HC Heterodimers and Cognate HC-LC Pairings To explain how to precisely control the chain pairings when making heterodimeric bispecific antibody from 2 pre-existing antibodies, we took 2 steps to achieve our design goals, see Table 15 and FIG. 21.

The first step is to form heterodimeric HCs and exclude the homodimeric HCs.

(A). 364S in one Fc chain (referred as Fc-A chain) is spatially close to 370K in the other Fc chain (referred as Fc-B chain); similarly, 370K in Fc-A chain is also spatially close to the 364S in Fc-B chain. All these 4 amino acid residues are buried (in B-strand) and located in the core of CH3 region. Substitution S364K in Fc-A chain can form a salt bridge with K370D in Fc-B chain, while S364D in Fc-B chain can also form a salt bridge with native 370K in Fc-A chain. However, when 2 identical HCs containing the same charge polarity, i.e. 2 Fc-A chains both containing S364K and native 370K, come closely, they are repulsive to each other. Similarly, 2 Fc-B chains both containing S364D and K370D are repulsive due to the same charge polarity.

(B). 392K in Fc-A chain spatially points to 400S in Fc-B chain, whereas 400S in Fc-A chain points to 390N in Fc-B chain. Two pairs of substitutions are required to introduce the desired electrostatic steering. Native 392K in Fc-A chain forms a salt bridge with S400D in Fc-B chain; S400K in Fc-A chain forms a salt bridge with N390D in Fc-B chain. As explained above, Fc chains containing the same charge polarity are repulsive to decrease the formation of homodimeric HCs, whereas Fc-A and Fc-B chains are attractive to help the formation of heterodimeric HCs.

(C). Residue Proline generally locates at the turn of β-sheet and residue Glycine is quite flexible, so substitutions N390P in Fc-A chain and K392G in Fc-B chain could separately offer flexibility to help antibody folding.

(D). Substitutions S354C in Fc-A chain and Y349C in Fc-B chain are spatially close to form a new disulfide bond. However, when 2 identical Fc chains come closely, i.e. S354C in Fc-A chain can't form a disulfide bond with S354C in another Fc-A chain because they are spatially far away; Y349C in Fc-B chain can't form a disulfide bond with Y349C in another Fc-B chain because they are spatially far away either. The new disulfide bond between the S354C in Fc-A and the Y349C in Fc-B can lock and stabilize the heterodimer Fc chains.

In total, 1 cysteine pair and 4 charge pairs work together to allow the formation of heterodimeric HCs and prevent the formation of homodimeric HCs.

The second step is to precisely control the cognate HC-LC pairings.

(A). The substitutions C214S at the end of Cκ region and C220G in upper hinge region together abolish the naturally occurring disulfide bond in IgG1 of anti-target-X antibody. Without an inter-chain disulfide bond, LC of anti-target-X antibody is not stable with the HC of anti-target-Y antibody, vice versa, LC of anti-target-Y antibody is not stable with the HC of anti-target-X antibody either.

(B). In anti-target-X antibody, the substitutions Q160C in Cκ region and V173C in CH1 region are spatially close to form a new disulfide bond; similarly, the substitutions S162C in Cκ region and F170C in CH1 region of anti-target-X antibody are also spatially close to form a new disulfide bond. The two new disulfide bonds help stabilize the Fab arm of anti-target-X antibody. The Fab arm of anti-target-Y antibody is kept as wild type without any change. When LC of anti-target-X antibody comes closely to the HC of anti-target-Y antibody, Q160C and S162C in anti-target-X antibody can't form disulfide bonds with native 173V and native 170F in anti-target-Y antibody, respectively. Similarly, when LC of anti-target-Y antibody comes closely to the HC of anti-target-X antibody, native 160Q and native 162S in Cκ region of anti-target-Y antibody can't form disulfide bonds with V173C and F170C in CH1 region of anti-target-X antibody, respectively.

(C). The introduced charge pair S131K in Cκ and K147D in CH1 of anti-target-X antibody can form a salt bridge and are well accommodated in the Fab arm of anti-target-X antibody, because the residue S (Ser) has a similar size as D (Asp). However, the S131K in anti-target-X antibody is repulsive to the naturally occurring 147K in the CH1 region of the HC of the anti-target-Y antibody, to increase the stringency for cognate LC-HC pairings.

Because all substitutions are introduced in constant regions (Cκ and CH1) only, not in the variable regions (VH and VL), the binding affinity of each Fab arm of anti-target-X and anti-target-Y antibodies are not significantly impacted, therefore, the activity of each Fab arm is well maintained.

In conclusion, our novel platform can generate bispecific antibody with the desired HC heterodimers and the cognate HC-LC pairings from two pre-existing antibodies. The bispecific antibody retains the configuration of standard IgG antibody, is produced as robust as standard IgG antibodies. No artificial linker is used. Each Fab arm in the context of a bispecific antibody is as functional as that of the parental antibodies. The bispecific antibody can be processed as standard monoclonal antibodies. Thus, our bispecific antibody platform may have a significant potential for making novel bispecific antibodies for treating life threatening diseases, such as cancers and infectious diseases.

SPECIFICATON LISTING OF SEQUENCES:

anti-HER2 humAb4D5-8 VL (WT)

SEQ ID NO: 1 gatattcagatgacccagagcccgagcagcctgagcgcgagcgtg ggcgatcgcgtgaccattacctgccgcgcgagccaggatgtgaac accgcggtggcgtggtatcagcagaaaccaggcaaagcgccgaaa ctgctgatttatagcgcgagcttcctgtatagcggcgtgccgagc cgcttcagcggcagccgcagcggcaccgatttcaccctgaccatt agcagcctgcagccggaagatttcgcgacctattattgccagcag cattataccaccccgccgaccttcggccagggcaccaaagtggaa attaaa anti-HER2 humAb4D5-8 VL (WT)

SEQ ID NO: 2

DIQMTQSPSSLSASVGDRVTITCRASQDVNTAVAWYQQKPGKAPK

LLIYSASFLYSGVPSRFSGSRSGTDFTLTISSLQPEDFATYYCQQ

HYTTPPTFGQGTKVEIK anti-HER2 humAb4D5-8 LC (WT)

SEQ ID NO: 3 gatattcagatgacccagagcccgagcagcctgagcgcgagcgtg ggcgatcgcgtgaccattacctgccgcgcgagccaggatgtgaac accgcggtggcgtggtatcagcagaaaccaggcaaagcgccgaaa ctgctgatttatagcgcgagcttcctgtatagcggcgtgccgagc cgcttcagcggcagccgcagcggcaccgatttcaccctgaccatt agcagcctgcagccggaagatttcgcgacctattattgccagcag cattataccaccccgccgaccttcggccagggcaccaaagtggaa attaaacgtacggtggctgcaccatctgtcttcatcttcccgcca tctgatgagcagttgaaatctggaactgcctctgttgtgtgcctg ctgaataacttctatcccagagaggccaaagtacagtggaaggtg gataacgccctccaatcgggtaactcccaggagagtgtcacagag caggacagcaaggacagcacctacagcctcagcagcaccctgacg ctgagcaaagcagactacgagaaacacaaagtctacgcctgcgaa gtcacccatcagggcctgagctcgcccgtcacaaagagcttcaac aggggagagtgttag anti-HER2 humAb4D5-8 LC (WT)

SEQ ID NO: 4

DIQMTQSPSSLSASVGDRVTITCRASQDVNTAVAWYQQKPGKAPK

LLIYSASFLYSGVPSRFSGSRSGTDFTLTISSLQPEDFATYYCQQ

HYTTPPTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC anti-HER2 humAb4D5-8 VH (WT)

SEQ ID NO: 5 gaagtccaactggtagagtcgggaggtggcttggtacagcccggt gggtccttgcgactcagctgcgccgcttcgggattcaacatcaaa gacacttacattcactgggtgcggcaggcaccggggaaggggctt gagtgggtcgccagaatctaccctacgaatggctatacgcgctac -continued gcggattcagtgaaagggaggtttaccatttcggcggacacatcg aagaatacagcatatctccagatgaacagccttcgggccgaagat accgcggtgtattactgttccagatggggaggagatgggttctat gcgatggactactggggacagggaacactggtaaccgtctctagt anti-HER2 humAb4D5-8 VH (WT)

SEQ ID NO: 6

EVQLVESGGGLVQPGGSLRLSCAASGFNIKDTYIHWVRQAPGKGL

EWVARIYPTNGYTRYADSVKGRFTISADTSKNTAYLQMNSLRAED

TAVYYCSRWGGDGFYAMDYWGQGTLVTVSS anti-HER2 humAb4D5-8 IgG1 HC (WT)

SEQ ID NO: 7 gaagtccaactggtagagtcgggaggtggcttggtacagcccggt gggtccttgcgactcagctgcgccgcttcgggattcaacatcaaa gacacttacattcactgggtgcggcaggcaccggggaaggggctt gagtgggtcgccagaatctaccctacgaatggctatacgcgctac gcggattcagtgaaagggaggtttaccatttcggcggacacatcg aagaatacagcatatctccagatgaacagccttcgggccgaagat accgcggtgtattactgttccagatggggaggagatgggttctat gcgatggactactggggacagggaacactggtaaccgtctctagt gctagcaccaagggcccatcggtcttccccctggcaccctcctcc aagagcacctctgggggcacagcggccctgggctgcctggtcaag gactacttccccgaaccggtgacggtgtcgtggaactcaggcgcc ctgaccagcggcgtgcacaccttcccggctgtcctacagtcctca ggactctactccctcagcagcgtggtgaccgtgccctccagcagc ttgggcacccagacctacatctgcaacgtgaatcacaagcccagc aacaccaaggtggacaagaaagttgagcccaaatcttgtgacaaa actcacacatgcccaccgtgcccagcacctgaactcctgggggga ccgtcagtcttcctcttccccccaaaacccaaggacaccctcatg atctcccggacccctgaggtcacatgcgtggtggtggacgtgagc cacgaagaccctgaggtcaagttcaactggtacgtggacggcgtg gaggtgcataatgccaagacaaagccgcgggaggagcagtacaac agcacgtaccgtgtggtcagcgtcctcaccgtcctgcaccaggac tggctgaatggcaaggagtacaagtgcaaggtctccaacaaagcc ctcccagcccccatcgagaaaaccatctccaaagccaaagggcag ccccgagaaccacaggtgtacaccctgcccccatcccgggaggag atgaccaagaaccaggtcagcctgacctgcctggtcaaaggcttc tatcccagcgacatcgccgtggagtgggagagcaatgggcagccg gagaacaactacaagaccacgcctcccgtgctggactccgacggc tccttcttcctctatagcaagctcaccgtggacaagagcaggtgg cagcaggggaacgtcttctcatgctccgtgatgcatgaggctctg cacaaccactacacgcagaagagcctctccctgtctccgggtaaa tga -continued anti-HER2 humAb4D5-8 IgG1 HC (WT)

SEQ ID NO: 8

EVQLVESGGGLVQPGGSLRLSCAASGFNIKDTYIHWVRQAPGKGL

EWVARIYPTNGYTRYADSVKGRFTISADTSKNTAYLQMNSLRAED

TAVYYCSRWGGDGFYAMDYWGQGTLVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYNSTYRVVSVLTVLHQD

WLNGKEYKCKVSNKALPAPIEKTISKAKGQPREPQVYTLPPSREE

MTKNQVSLTCLVKGFYPSDIAVEWESNGQPENNYKTTPPVLDSDG

SFFLYSKLTVDKSRWQQGNVFSCSVMHEALHNHYTQKSLSLSPGK

Nucleotide sequence encoding the VL domain of the anti-HER2 humAb2C4 (WT)

SEQ ID NO: 9 gacatccagatgacccagagccccagcagcctgtctgccagcgtg ggcgacagagtgaccatcacatgcaaggccagccaggacgtgtcc atcggcgtggcctggtatcagcagaagcccggcaaggcccccaag ctgctgatctacagcgccagctaccggtacaccggcgtgcccagc agattttctggcagcggctccggcaccgacttcaccctgacaatc agctccctgcagcccgaggacttcgccacctactactgccagcag tactacatctacccctacaccttcggccagggcaccaaggtggaa atcaag Amino acid sequence of the VL domain of the anti-HER2 humAb2C4 (WT)

SEQ ID NO: 10

DIQMTQSPSSLSASVGDRVTITCKASQDVSIGVAWYQQKPGKAPK

LLIYSASYRYTGVPSRFSGSGSGTDFTLTISSLQPEDFATYYCQQ

YYIYPYTFGQGTKVEIK

Nucleotide sequence encoding the LC of the anti-HER2 humAb2C4 (WT)

SEQ ID NO: 11 gacatccagatgacccagagccccagcagcctgtctgccagcgtg ggcgacagagtgaccatcacatgcaaggccagccaggacgtgtcc atcggcgtggcctggtatcagcagaagcccggcaaggcccccaag ctgctgatctacagcgccagctaccggtacaccggcgtgcccagc agattttctggcagcggctccggcaccgacttcaccctgacaatc agctccctgcagcccgaggacttcgccacctactactgccagcag tactacatctacccctacaccttcggccagggcaccaaggtggaa atcaagcgtacggtggctgcaccatctgtcttcatcttcccgcca tctgatgagcagttgaaatctggaactgcctctgttgtgtgcctg ctgaataacttctatcccagagaggccaaagtacagtggaaggtg gataacgccctccaatcgggtaactcccaggagagtgtcacagag caggacagcaaggacagcacctacagcctcagcagcaccctgacg ctgagcaaagcagactacgagaaacacaaagtctacgcctgcgaa gtcacccatcagggcctgagctcgcccgtcacaaagagcttcaac aggggagagtgttag Amino acid sequence of the LC of the anti-HER2 humAb2C4 (WT)

SEQ ID NO: 12

DIQMTQSPSSLSASVGDRVTITCKASQDVSIGVAWYQQKPGKAPK

LLIYSASYRYTGVPSRFSGSGSGTDFTLTISSLQPEDFATYYCQQ

YYIYPYTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

Nucleotide sequence encoding the VH domain of the anti-HER2 humAb2C4 (WT)

SEQ ID NO: 13 gaagtgcagctggtggaatctggcggcggactggtgcagcctggc ggatctctgagactgagctgtgccgccagcggcttcaccttcacc gactacaccatggactgggtgcgccaggcccctggcaagggcctg gaatgggtggccgacgtgaaccccaatagcggcggcagcatctac aaccagcggttcaagggccggttcaccctgagcgtggacagaagc aagaacaccctgtacctgcagatgaacagcctgcgggccgaggac accgccgtgtactactgcgccagaaacctgggccccagcttctac ttcgactactggggccagggcaccctcgtgaccgtgtcatct Amino acid sequence of the VH domain of the anti-HER2 humAb2C4 (WT)

SEQ ID NO: 14

EVQLVESGGGLVQPGGSLRLSCAASGFTFTDYTMDWVRQAPGKGL

EWVADVNPNSGGSIYNQRFKGRFTLSVDRSKNTLYLQMNSLRAED

TAVYYCARNLGPSFYFDYWGQGTLVTVSS

Nucleotide sequence encoding the HC of the anti-HER2 humAb2C4 IgG1 (WT)

SEQ ID NO: 15 gaagtgcagctggtggaatctggcggcggactggtgcagcctggc ggatctctgagactgagctgtgccgccagcggcttcaccttcacc gactacaccatggactgggtgcgccaggcccctggcaagggcctg gaatgggtggccgacgtgaaccccaatagcggcggcagcatctac aaccagcggttcaagggccggttcaccctgagcgtggacagaagc aagaacaccctgtacctgcagatgaacagcctgcgggccgaggac accgccgtgtactactgcgccagaaacctgggccccagcttctac ttcgactactggggccagggcaccctcgtgaccgtgtcatctgct agcaccaagggcccatcggtcttccccctggcaccctcctccaag agcacctctgggggcacagcggccctgggctgcctggtcaaggac tacttccccgaaccggtgacggtgtcgtggaactcaggcgccctg accagcggcgtgcacaccttcccggctgtcctacagtcctcagga ctctactccctcagcagcgtggtgaccgtgccctccagcagcttg ggcacccagacctacatctgcaacgtgaatcacaagcccagcaac accaaggtggacaagaaagttgagcccaaatcttgtgacaaaact cacacatgcccaccgtgcccagcacctgaactcctggggggaccg -continued tcagtcttcctcttccccccaaaacccaaggacaccctcatgatc tcccggacccctgaggtcacatgcgtggtggtggacgtgagccac gaagaccctgaggtcaagttcaactggtacgtggacggcgtggag gtgcataatgccaagacaaagccgcgggaggagcagtacaacagc acgtaccgtgtggtcagcgtcctcaccgtcctgcaccaggactgg ctgaatggcaaggagtacaagtgcaaggtctccaacaaagccctc ccagcccccatcgagaaaaccatctccaaagccaaagggcagccc cgagaaccacaggtgtacaccctgcccccatcccgggaggagatg accaagaaccaggtcagcctgacctgcctggtcaaaggcttctat cccagcgacatcgccgtggagtgggagagcaatgggcagccggag aacaactacaagaccacgcctcccgtgctggactccgacggctcc ttcttcctctatagcaagctcaccgtggacaagagcaggtggcag caggggaacgtcttctcatgctccgtgatgcatgaggctctgcac aaccactacacgcagaagagcctctccctgtctccgggtaaatga Amino acid sequence of the HC of the anti-HER2 humAb2C4 IgG1 (WT)

SEQ ID NO: 16

EVQLVESGGGLVQPGGSLRLSCAASGFTFTDYTMDWVRQAPGKGL

EWVADVNPNSGGSIYNQRFKGRFTLSVDRSKNTLYLQMNSLRAE

DTAVYYCARNLGPSFYFDYWGQGTLVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYNSTYRVVSVLTVLHQD

WLNGKEYKCKVSNKALPAPIEKTISKAKGQPREPQVYTLPPSREE

MTKNQVSLTCLVKGFYPSDIAVEWESNGQPENNYKTTPPVLDSDG

SFFLYSKLTVDKSRWQQGNVFSCSVMHEALHNHYTQKSLSLSPGK

DNA sequence encoding anti-HER2 humAb4D5-8 IgG1 HC (CDDDGD)

SEQ ID NO: 17 gaagtccaactggtagagtcgggaggtggcttggtacagcccggt gggtccttgcgactcagctgcgccgcttcgggattcaacatcaaa gacacttacattcactgggtgcggcaggcaccggggaaggggctt gagtgggtcgccagaatctaccctacgaatggctatacgcgctac gcggattcagtgaaagggaggtttaccatttcggcggacacatcg aagaatacagcatatctccagatgaacagccttcgggccgaagat accgcggtgtattactgttccagatggggaggagatgggttctat gcgatggactactggggacagggaacactggtaaccgtctctagt gctagcaccaagggcccatcggtcttccccctggcaccctcctcc aagagcacctctgggggcacagcggccctgggctgcctggtcaag gactacttccccgaaccggtgacggtgtcgtggaactcaggcgcc ctgaccagcggcgtgcacaccttcccggctgtcctacagtcctca ggactctactccctcagcagcgtggtgaccgtgccctccagcagc -continued ttgggcacccagacctacatctgcaacgtgaatcacaagcccagc aacaccaaggtggacaagaaagttgagcccaaatcttgtgacaaa actcacacatgcccaccgtgcccagcacctgaactcctgggggga ccgtcagtcttcctcttccccccaaaacccaaggacaccctcatg atctcccggacccctgaggtcacatgcgtggtggtggacgtgagc cacgaagaccctgaggtcaagttcaactggtacgtggacggcgtg gaggtgcataatgccaagacaaagccgcgggaggagcagtacaac agcacgtaccgtgtggtcagcgtcctcaccgtcctgcaccaggac tggctgaatggcaaggagtacaagtgcaaggtctccaacaaagcc ctcccagcccccatcgagaaaaccatctccaaagccaaagggcag ccccgagaaccacaggtgtgcaccctgcccccatcccgggaggag atgaccaagaaccaggtcgacctgacctgcctggtcgacggcttc tatcccagcgacatcgccgtggagtgggagagcaatgggcagccg gagaacgactacggcaccacgcctcccgtgctggacgacgacggc tccttcttcctctatagcaagctcaccgtggacaagagcaggtgg cagcaggggaacgtcttctcatgctccgtgatgcatgaggctctg cacaaccactacacgcagaagagcctctccctgtctccgggtaaa tga Amino acid sequence of anti-HER2 humAb4D5-8 IgG1 HC (CDDDGD)

SEQ ID NO: 18

EVQLVESGGGLVQPGGSLRLSCAASGFNIKDTYIHWVRQAPGKGL

EWVARIYPTNGYTRYADSVKGRFTISADTSKNTAYLQMNSLRAED

TAVYYCSRWGGDGFYAMDYWGQGTLVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYNSTYRVVSVLTVLHQD

WLNGKEYKCKVSNKALPAPIEKTISKAKGQPREPQVCTLPPSREE

MTKNQVDLTCLVDGFYPSDIAVEWESNGQPENDYGTTPPVLDDDG

SFFLYSKLTVDKSRWQQGNVFSCSVMHEALHNHYTQKSLSLSPGK

Nucleotide sequence encoding the anti-HER2 humAb4D5-8 IgG1 HC (CKKPKK)

SEQ ID NO: 19 gaagtccaactggtagagtcgggaggtggcttggtacagcccggt gggtccttgcgactcagctgcgccgcttcgggattcaacatcaaa gacacttacattcactgggtgcggcaggcaccggggaaggggctt gagtgggtcgccagaatctaccctacgaatggctatacgcgctac gcggattcagtgaaagggaggtttaccatttcggcggacacatcg aagaatacagcatatctccagatgaacagccttcgggccgaagat accgcggtgtattactgttccagatggggaggagatgggttctat gcgatggactactggggacagggaacactggtaaccgtctctagt gctagcaccaagggcccatcggtcttccccctggcaccctcctcc aagagcacctctgggggcacagcggccctgggctgcctggtcaag gactacttccccgaaccggtgacggtgtcgtggaactcaggcgcc ctgaccagcggcgtgcacaccttcccggctgtcctacagtcctca ggactctactccctcagcagcgtggtgaccgtgccctccagcagc ttgggcacccagacctacatctgcaacgtgaatcacaagcccagc aacaccaaggtggacaagaaagttgagcccaaatcttgtgacaaa actcacacatgcccaccgtgcccagcacctgaactcctgggggga ccgtcagtcttcctcttccccccaaaacccaaggacaccctcatg atctcccggacccctgaggtcacatgcgtggtggtggacgtgagc cacgaagaccctgaggtcaagttcaactggtacgtggacggcgtg gaggtgcataatgccaagacaaagccgcgggaggagcagtacaac agcacgtaccgtgtggtcagcgtcctcaccgtcctgcaccaggac tggctgaatggcaaggagtacaagtgcaaggtctccaacaaagcc ctcccagcccccatcgagaaaaccatctccaaagccaaagggcag ccccgagaaccacaggtgtacaccctgcccccatgccgggaggag atgaccaagaaccaggtcaagctgacctgcctggtcaagggcttc tatcccagcgacatcgccgtggagtgggagagcaatgggcagccg gagaacccctacaagaccacgcctcccgtgctggacaaggacggc tccttcttcctctatagcaagctcaccgtggacaagagcaggtgg cagcaggggaacgtcttctcatgctccgtgatgcatgaggctctg cacaaccactacacgcagaagagcctctccctgtctccgggtaaa tga anti-HER2 humAb4D5-8 IgG1 HC (CKKPKK)

SEQ ID NO: 20

EVQLVESGGGLVQPGGSLRLSCAASGFNIKDTYIHVRQAPGKGLE

WARIYPTNGYTRYADSVKGRFTISADTSKNTAYLQMNSLRAEDTA

VYYCSRWGGDGFYAMDYWGQGTLVTVSSASTKGPSVFPLAPSSKS

TSGGTAALGCLVKDYFPEPVTVSWNSGALTSGVHTFPAVLQSSGL

YSLSSVVTVPSSSLGTQTYICNVNHKPSNTKVDKKVEPKSCDKTH

TCPPCPAPELLGGPSVFLFPPKPKDTLMISRTPEVTCVVVDVSHE

DPEVKFNWYVDGVEVHNAKTKPREEQYNSTYRVVSVLTVLHQDWL

NGKEYKCKVSNKALPAPIEKTISKAKGQPREPQVYTLPPCREEMT

KNQVKLTCLVKGFYPSDIAVEWESNGQPENPYKTTPPVLDKDGSF

FLYSKLTVDKSRWQQGNVFSCSVMHEALHNHYTQKSLSLSPGK

Dummy Fc (C220G and CDDDGD)

SEQ ID NO: 21 gagcccaaatctggtgacaaaactcacacatgcccaccgtgccca gcacctgaactcctggggggaccgtcagtcttcctcttccccca aaacccaaggacaccctcatgatctcccggacccctgaggtcaca tgcgtggtggtggacgtgagccacgaagaccctgaggtcaagttc aactggtacgtggacggcgtggaggtgcataatgccaagacaaag ccgcgggaggagcagtacaacagcacgtaccgtgtggtcagcgtc ctcaccgtcctgcaccaggactggctgaatggcaaggagtacaag tgcaaggtctccaacaaagccctcccagcccccatcgagaaaacc atctccaaagccaaagggcagccccgagaaccacaggtgtgcacc ctgcccccatcccgggaggagatgaccaagaaccaggtcgacctg acctgcctggtcgatggcttctatcccagcgacatcgccgtggag tgggagagcaatgggcagccggagaacgactacgggaccacgcct cccgtgctggacgacgacggctccttcttcctctatagcaagctc accgtggacaagagcaggtggcagcaggggaacgtcttctcatgc tccgtgatgcatgaggctctgcacaaccactacacgcagaagagc ctctccctgtctccgggtaaatga Dummy Fc (C220G and CDDDGD)

SEQ ID NO: 22

EPKSGDKTHTCPPCPAPELLGGPSVFLFPPKPKDTLMISRTPEVT

CVWDVSHEDPEVKFNWYVDGVEVHNAKTKPREEQYNSTYRVVSVL

TVLHQDWLNGKEYKCKVSNKALPAPIEKTISKAKGQPREPQVCTL

PPSREEMTKNQVDLTCLVDGFYPSDIAVEWESNGQPENDYGTTPP

VLDDDGSFFLYSKLTVDKSRWQQGNVFSCSVMHEALHNHYTQKSL

SLSPGK

Dummy Fc (C220G and CKKPKK)

SEQ ID NO: 23 gagcccaaatctggtgacaaaactcacacatgcccaccgtgccca gcacctgaactcctggggggaccgtcagtcttcctcttcccccca aaacccaaggacaccctcatgatctcccggacccctgaggtcaca tgcgtggtggtggacgtgagccacgaagaccctgaggtcaagttc aactggtacgtggacggcgtggaggtgcataatgccaagacaaag ccgcgggaggagcagtacaacagcacgtaccgtgtggtcagcgtc ctcaccgtcctgcaccaggactggctgaatggcaaggagtacaag tgcaaggtctccaacaaagccctcccagcccccatcgagaaaacc atctccaaagccaaagggcagccccgagaaccacaggtgtacacc ctgcccccatgccgggaggagatgaccaagaaccaggtcaagctg acctgcctggtcaagggcttctatcccagcgacatcgccgtggag tgggagagcaatgggcagccggagaacccctacaagaccacgcct cccgtgctggacaaggacggctccttcttcctctatagcaagctc accgtggacaagagcaggtggcagcaggggaacgtcttctcatgc tccgtgatgcatgaggctctgcacaaccactacacgcagaagagc ctctccctgtctccgggtaaatga Dummy Fc (C220G and CKKPKK)

SEQ ID NO: 24

EPKSGDKTHTCPPCPAPELLGGPSVFLFPPKPKDTLMISRTPEVT

CVVVDVSHEDPEVKFNWYVDGVEVHNAKTKPREEQYNSTYRVVSV

LTVLHQDWLNGKEYKCKVSNKALPAPIEKTISKAKGQPREPQVYT

LPPCREEMTKNQVKLTCLVKGFYPSDIAVEWESNGQPENPYKTTP

PVLDKDGSFFLYSKLTVDKSRWQQGNVFSCSVMHEALHNHYTQKS

LSLSPGK

-continued

Nucleotide sequence encoding the VH of anti-hCD20 antibodies Ab1.2, Ab1.2.2.1, Ab1.2.5, Ab1.2.6

SEQ ID NO: 25 caggtgcagctggtgcagtctggcgccgaggtgaagaaacctggc
tcttcagtgaaggtgtcctgcaaggcttccggctacacattcacc
agctacaacatgcactgggtccggcaggcccctggacaaggatta
gaatggatgggcgctatctaccccggcaacggcgacacctcttac
aaccagaaattccagggcagagtgaccctgaccgtggacaagtcc
tcttccaccgcctacatggaactgagctccctgagatccgaggat
accgccgtgtacttctgtgccagagtggtgtactactccaactcc
tactggtacttcgacgtgtggggcaccggcactatggtcacagtt
tcctct Amino acid sequence of the VH of anti-hCD20 antibodies Ab1.2, Ab1.2.2.1, Ab1.2.5, Ab1.2.6

SEQ ID NO: 26

QVQLVQSGAEVKKPGSSVKVSCKASGYTFTSYNMHWWRQAPGQGL
EWMGAIYPGNGDTSYNQKFQGRVTLTVDKSSSTAYMELSSLRSED
TAVYFCARVVYYSNSYWYFDVWGTGTMVTVSS

Nucleotide sequence encoding the HC of anti-hCD20 Ab1.2 IgG (WT), having CH1 domain and upper hinge from IgG4, and hinge, CH2, CH3 from IgG1

SEQ ID NO: 27 caggtgcagctggtgcagtctggcgccgaagtgaagaaacccggc
tcctccgtgaaggtgtcctgcaaggcctccggctacacctttacc
agctacaacatgcactgggtgcgacaggcccctggacagggcctg
gaatggatgggcgctatctaccctggcaacggcgacacctcctac
aaccagaaattccagggcagagtgaccctgaccgtggacaagtcc
tcctccaccgcctacatggaactgtcctccctgcggagcgaggat
accgccgtgtacttctgtgcccgggtggtgtactactccaactcc
tactggtacttcgacgtgtggggcaccggcacaatggtcaccgtg
tcctccgctagcaccaaggggccatccgtcttccccctggcgccc
tgctccaggagcacctccgagagcacagccgccctgggctgcctg
gtcaaggactacttccccgaaccggtgacggtgtcgtggaactca
ggcgccctgaccagcggcgtgcacaccttcccggctgtcctacag
tcctcaggactctactccctcagcagcgtggtgaccgtgccctcc
agcagcttgggcacgaagacctacacctgcaacgtagatcacaag
cccagcaacaccaaggtggacaagagagttgagtccaaatatggc
cccccatgcccaccgtgcccagcacctgaactcctggggggaccg
tcagtcttcctcttccccccaaaacccaaggacaccctcatgatc
tcccggacccctgaggtcacatgcgtggtggtggacgtgagccac
gaagaccctgaggtcaagttcaactggtacgtggacggcgtggag
gtgcataatgccaagacaaagccgcgggaggagcagtacaacagc
acgtaccgtgtggtcagcgtcctcaccgtcctgcaccaggactgg
ctgaatggcaaggagtacaagtgcaaggtctccaacaaagccctc
ccagcccccatcgagaaaaccatctccaaagccaaagggcagccc
cgagaaccacaggtgtacaccctgcccccatcccgggaggagatg
accaagaaccaggtcagcctgacctgcctggtcaaaggcttctat
cccagcgacatcgccgtggagtgggagagcaatgggcagccggag
aacaactacaagaccacgcctcccgtgctggactccgacggctcc
ttcttcctctatagcaagctcaccgtggacaagagcaggtggcag
caggggaacgtcttctcatgctccgtgatgcatgaggctctgcac
aaccactacacgcagaagagcctctccctgtctccgggtaaatga Amino acid sequence of the HC of anti-hCD20 Ab1.2 IgG (WT), having CH1 domain and upper hinge from IgG4, and hinge, CH2, CH3 from IgG1

SEQ ID NO: 28

QVQLVQSGAEVKKPGSSVKVSCKASGYTFTSYNMHWVRQAPGQGL
EWMGAIYPGNGDTSYNQKFQGRVTLTVDKSSSTAYMELSSLRSED
TAVYFCARVVYYSNSYWYFDVWGTGTMVTVSSASTKGPSVFPLAP
CSRSTSESTAALGCLVKDYFPEPVTVSWNSGALTSGVHTFPAVLQ
SSGLYSLSSVVTVPSSSLGTKTYTCNVDHKPSNTKVDKRVESKYG
PPCPPCPAPELLGGPSVFLFPPKPKDTLMISRTPEVTCVVVDVSH
EDPEVKFNWYVDGVEVHNAKTKPREEQYNSTYRVVSVLTVLHQDW
LNGKEYKCKVSNKALPAPIEKTISKAKGQPREPQVYTLPPSREEM
TKNQVSLTCLVKGFYPSDIAVEWESNGQPENNYKTTPPVLDSDGS
FFLYSKLTVDKSRWQQGNVFSCSVMHEALHNHYTQKSLSLSPGK

Nucleotide sequence encoding the HC of anti-hCD20 Ab1.2.5 IgG (CDDDGD), having CH1 domain and upper hinge from IgG4, and substitutions CDDDGD in IgG1 CH3 for heterodimer formation

SEQ ID NO: 29 caggtgcagctggtgcagtctggcgccgaggtgaagaaacctggc
tcttcagtgaaggtgtcctgcaaggcttccggctacacattcacc
agctacaacatgcactgggtccggcaggcccctggacaaggatta
gaatggatgggcgctatctaccccggcaacggcgacacctcttac
aaccagaaattccagggcagagtgaccctgaccgtggacaagtcc
tcttccaccgcctacatggaactgagctccctgagatccgaggat
accgccgtgtacttctgtgccagagtggtgtactactccaactcc
tactggtacttcgacgtgtggggcaccggcactatggtcacagtt
tcctctgccagcaccaagggacccagcgttttccctctggctcct
tgctccagatccacctctgagtccacagctgctctgggctgcctg
gtcaaggactactttccagagccagtgaccgtgtcctggaactct
ggcgctctgacatctggcgtgcacacattccctgctgtgctgcag
tcatctggcctgtactctctgtcctctgtcgtgaccgtgcctagc
tcctccctgggcaccaagacctacacctgtaatgtggaccacaag
ccttccaacaccaaggtggacaagcgcgtggaatctaagtacggc
ccaccatgcccaccgtgcccagcacctgaactcctgggcggaccg
tcagtcttcctcttccctccaaaacccaaggacaccctcatgatc -continued tcccggacccctgaggtcacatgcgtggtggtggacgtgagccac gaagaccctgaggtcaagttcaactggtacgtggacggcgtggag gtgcataatgccaagacaaagccgcgggaggagcagtacaacagc acgtaccgtgtggtcagcgtcctcaccgtcctgcaccaggactgg ctgaatggcaaggagtacaagtgcaaggtctccaacaaagccctc ccagcccccatcgagaaaaccatctccaaagccaaagggcagccc cgagaaccacaggtgtgcaccctgcccccatcccgggaggagatg accaagaaccaggtggacctgacctgcctggtggacggcttctat cccagcgacatcgccgtggagtgggagagcaatgggcagccggag aacgactacggcaccacgcctcccgtgctggacgacgacggctcc ttcttcctctatagcaagctcaccgtggacaagagcaggtggcag caggggaacgtcttctcatgctccgtgatgcatgaggctctgcac aaccactacacgcagaaaagcctctccctgtctccgggtaaataa Amino acid sequence of the HC of anti-hCD20 Ab1.2.5 IgG (CDDDGD), having CH1 domain and upper hinge from IgG4, and substitutions CDDDGD in IgG1 CH3 for heterodimer formation

SEQ ID NO: 30

QVQLVQSGAEVKKPGSSVKVSCKASGYTFTSYNMHWVRQAPGQGL

EWMGAIYPGNGDTSYNQKFQGRVTLTVDKSSSTAYMELSSLRSED

TAVYFCARVVYYSNSYWYFDVWGTGTMVTVSSASTKGPSVFPLAP

CSRSTSESTAALGCLVKDYFPEPVTVSWNSGALTSGVHTFPAVLQ

SSGLYSLSSVVTVPSSSLGTKTYTCNVDHKPSNTKVDKRVESKYG

PPCPPCPAPELLGGPSVFLFPPKPKDTLMISRTPEVTCVVVDVSH

EDPEVKFNWYVDGVEVHNAKTKPREEQYNSTYRVVSVLTVLHQDW

LNGKEYKCKVSNKALPAPIEKTISKAKGQPREPQVCTLPPSREEM

TKNQVDLTCLVDGFYPSDIAVEWESNGQPENDYGTTPPVLDDDGS

FFLYSKLTVDKSRWQQGNVFSCSVMHEALHNHYTQKSLSLSPGK

Nucleotide sequence encoding the HC of anti-hCD20 Ab1.2.6 IgG (CKKPKK), having CH1 domain and upper hinge from IgG4, and substitutions CKKPKK in IgG1 CH3 for heterodimer formation

SEQ ID NO: 31 caggtgcagctggtgcagtctggcgccgaggtgaagaaacctggc tcttcagtgaaggtgtcctgcaaggcttccggctacacattcacc agctacaacatgcactgggtccggcaggcccctggacaaggatta gaatggatgggcgctatctaccccggcaacggcgacacctcttac aaccagaaattccagggcagagtgaccctgaccgtggacaagtcc tcttccaccgcctacatggaactgagctccctgagatccgaggat accgccgtgtacttctgtgccagagtggtgtactactccaactcc tactggtacttcgacgtgtggggcaccggcactatggtcacagtt tcctctgccagcaccaagggacccagcgttttccctctggctcct tgctccagatccacctctgagtccacagctgctctgggctgcctg gtcaaggactactttccagagccagtgaccgtgtcctggaactct ggcgctctgacatctggcgtgcacacattccctgctgtgctgcag -continued tcatctggcctgtactctctgtcctctgtcgtgaccgtgcctagc tcctccctgggcaccaagacctacacctgtaatgtggaccacaag ccttccaacaccaaggtggacaagcgcgtggaatctaagtacggc ccaccatgtcctccatgtcctgctccagaactgctcggcggacct tccgtgttcctgtttcctccaaagcctaaggacaccctgatgatc tctcggacccctgaagtgacctgcgtggtggtggatgtgtctcac gaggatcccgaagtgaagttcaattggtacgtggacggcgtggaa gtgcacaacgccaagaccaagcctagagaggaacagtacaactcc acctacagagtggtgtccgtgctgaccgtgctgcaccaggattgg ctgaacggcaaagagtacaagtgcaaggtgtccaacaaggccctg cctgctcctatcgaaaagaccatcagcaaggccaagggccagccc agggaaccccaggtttacaccctgcctccatgccgggaagagatg accaagaatcaagtgaagctgacctgtctcgtgaagggcttctac ccctccgacatcgccgtggaatgggagtctaatggccagcctgag aatccctacaagacaacccctcctgtgctggacaaggacggctca ttcttcctgtactccaagctgacagtggacaagtccagatggcag cagggcaacgtgttctcctgctccgtgatgcacgaggccctgcac aatcactacacccagaagtccctgtctctgtcccctggcaaataa Amino acid sequence of the HC of anti-hCD20 Ab1.2.6 IgG (CKKPKK), having CH1 domain from IgG4, upper hinge from IgG4, and substitutions CKKPKK for heterodimer formation

SEQ ID NO: 32

QVQLVQSGAEVKKPGSSVKVSCKASGYTFTSYNMHWRQAPGQGLE

WMGAIYPGNGDTSYNQKFQGRVTLTVDKSSSTAYMELSSLRSEDT

AVYFCARVVYYSNSYWYFDVWGTGTMVTVSSASTKGPSVFPLAPC

SRSTSESTAALGCLVKDYFPEPVTVSWNSGALTSGVHTFPAVLQS

SGLYSLSSVVTVPSSSLGTKTYTCNVDHKPSNTKVDKRVESKYGP

PCPPCPAPELLGGPSVFLFPPKPKDTLMISRTPEVTCVVVDVSHE

DPEVKFNWYVDGVEVHNAKTKPREEQYNSTYRVVSVLTVLHQDWL

NGKEYKCKVSNKALPAPIEKTISKAKGQPREPQVYTLPPCREEMT

KNQVKLTCLVKGFYPSDIAVEWESNGQPENPYKTTPPVLDKDGSF

FLYSKLTVDKSRWQQGNVFSCSVMHEALHNHYTQKSLSLSPGK

Nucleotide sequence encoding the VL of the humanized anti-hCD20 antibodies Ab1.2, Ab1.2.2.1, Ab1.2.5, Ab1.2.6

SEQ ID NO: 33

GAGATCGTGCTGACCCAGTCCCCCGACTTCCAGTCCGTGACCCCC

AAAGAAAAAGTGACAATTACCTGCCGGGCCTCCTCCTCCGTGTCC

TACATGCACTGGTATCAGCAGAAGCCCGACCAGTCCCCTAAGCCC

CTGATCTACGCCCCTTCCAACCTGGCCTCTGGCGTGCCCTCTAGA

TTCTCCGGCTCTGGCTCTGGCACCGACTACACCCTGACCATCAAC

TCCCTGGAAGCCGAGGACGCCGCCACCTACTACTGCCAGCAGTGG

TCCTTCAACCCCCCCACCTTTGGCGCTGGCACCAAGCTGGAAATC

AAG

Amino acid sequence of the VL of the humanized anti-hCD20 antibodies Ab1.2, Ab1.2.2.1, Ab1.2.5, Ab1.2.6

SEQ ID NO: 34

EIVLTQSPDFQSVTPKEKVTITCRASSSVSYMHWYQQKPDQSPKP

LIYAPSNLASGVPSRFSGSGSGTDYTLTINSLEAEDAATYYCQQW

SFNPPTFGAGTKLEIK

Nucleotide sequence encoding the LC of the humanized anti-hCD20 antibodies Ab1.2, Ab1.2.2.1, Ab1.2.5, Ab1.2.6

SEQ ID NO: 35

GAGATCGTGCTGACCCAGTCCCCCGACTTCCAGTCCGTGACCCCC

AAAGAAAAAGTGACAATTACCTGCCGGGCCTCCTCCTCCGTGTCC

TACATGCACTGGTATCAGCAGAAGCCCGACCAGTCCCCTAAGCCC

CTGATCTACGCCCCTTCCAACCTGGCCTCTGGCGTGCCCTCTAGA

TTCTCCGGCTCTGGCTCTGGCACCGACTACACCCTGACCATCAAC

TCCCTGGAAGCCGAGGACGCCGCCACCTACTACTGCCAGCAGTGG

TCCTTCAACCCCCCCACCTTTGGCGCTGGCACCAAGCTGGAAATC

AAGCGGACCGTGGCCGCTCCCTCCGTGTTCATCTTCCCACCTTCC

GACGAGCAGCTGAAGTCCGGCACCGCTTCTGTCGTGTGCCTGCTG

AACAACTTCTACCCCCGCGAGGCCAAGGTGCAGTGGAAGGTGGAC

AACGCCCTGCAGTCCGGCAACTCCCAGGAATCCGTGACCGAGCAG

GACTCCAAGGACAGCACCTACTCCCTGTCCTCTACCCTGACCCTG

TCCAAGGCCGACTACGAGAAGCACAAGGTGTACGCCTGCGAAGTG

ACCCACCAGGGCCTGTCTAGCCCCGTGACCAAGTCTTTCAACCGG

GGCGAGTGCTGA

Amino acid sequence of the LC of the humanized anti-hCD20 antibodies Ab1.2, Ab1.2.2.1, Ab1.2.5, Ab1.2.6

SEQ ID NO: 36

EIVLTQSPDFQSVTPKEKVTITCRASSSVSYMHWYQQKPDQSPKP

LIYAPSNLASGVPSRFSGSGSGTDYTLTINSLEAEDAATYYCQQW

SFNPPTFGAGTKLEIKRTVAAPSVFIFPPSDEQLKSGTASVVCLL

NNFYPREAKVQWKVDNALQSGNSQESVTEQDSKDSTYSLSSTLTL

SKADYEKHKVYACEVTHQGLSSPVTKSFNRGEC

Nucleotide sequence encoding the VH of anti-hCD37 antibodies Ab1.A1, Ab1.A1.1, Ab1.A1.2 and Ab1.A1.3

SEQ ID NO: 37 caggtgcagctggttcagtctggcgccgaagtgaagaaacctggc gcctctgtgaaggtgtcctgcaaggcttctggctacacctttacc ggctacaacgtgaactgggtccgacagaacaacggccagcggctg gaatggatgggcaacatcgatccttactacggcggcaccacctac aaccggaagttcaagggcagagtgaccatcaccgtggacacctct gcctccaccgcctacatggaactgaagtccctgagatccgaggac accgccgtgtactactgcgctaggtctgtgggccctatggactat tggggccagggaacactggtcaccgtgtcctct Amino acid sequence of the VH of anti-hCD37 antibodies Ab1.A1, Ab1.A1.1, AM.A1.2 and Ab1.A1.3

SEQ ID NO: 38

QVQLVQSGAEVKKPGASVKVSCKASGYTFTGYNVNWWRQNNGQRL

EWMGNIDPYYGGTTYNRKFKGRVTITVDTSASTAYMELKSLRSED

TAVYYCARSVGPMDYWGQGTLVTVSS

Nucleotide sequence encoding the HC of anti-hCD37 Ab1.A1 IgG1 (WT)

SEQ ID NO: 39 caagtgcagctcgtccagtccggggcagaggttaagaagcccggc gctagtgtgaaggtgagctgcaaggcctctggctatactttcaca gggtacaacgtgaactgggtgcgccagaacaacggccaacggttg gagtggatgggtaacatcgatccctactacgggggtactacctac aacaggaaattcaaaggacgggtgactatcaccgtggacacatct gcttctaccgcctacatggagctgaagtctttgcggtctgaggac accgccgtctattactgtgccagatccgtgggccctatggattat tggggtcaagggaccctggtgaccgtcagctccgctagcaccaag ggcccatccgtcttccccctggcgccctcctccaagagcacctct gggggcacagcggccctgggctgcctggtcaaggactacttcccc gaaccggtgacggtgtcgtggaactcaggcgccctgaccagcggc gtgcacaccttcccggctgtcctacagtcctcaggactctactcc ctcagcagcgtggtgaccgtgccctccagcagcttgggcacccag acctacatctgcaacgtgaatcacaagcccagcaacaccaaggtg gacaagaaagttgagcccaaatcttgtgacaaaactcacacatgc ccaccgtgcccagcacctgaactcctggggggaccgtcagtcttc ctcttccccccaaaacccaaggacaccctcatgatctcccggacc cctgaggtcacatgcgtggtggtggacgtgagccacgaagaccct gaggtcaagttcaactggtacgtggacggcgtggaggtgcataat gccaagacaaagccgcgggaggagcagtacaacagcacgtaccgt gtggtcagcgtcctcaccgtcctgcaccaggactggctgaatggc aaggagtacaagtgcaaggtctccaacaaagccctcccagccccc atcgagaaaaccatctccaaagccaaagggcagccccgagaacca caggtgtacaccctgcccccatcccgggaggagatgaccaagaac caggtcagcctgacctgcctggtcaaaggcttctatcccagcgac atcgccgtggagtgggagagcaatgggcagccggagaacaactac aagaccacgcctcccgtgctggactccgacggctccttcttcctc tatagcaagctcaccgtggacaagagcaggtggcagcaggggaac gtcttctcatgctccgtgatgcatgaggctctgcacaaccactac acgcagaagagcctctccctgtctccgggtaaatga -continued Amino acid sequence of the HC of anti-hCD37 Ab1.A1 IgG1 (WT)

SEQ ID NO: 40

QVQLVQSGAEVKKPGASVKVSCKASGYTFTGYNVNWVRQNNGQRL

EWMGNIDPYYGGTTYNRKFKGRVTITVDTSASTAYMELKSLRSED

TAVYYCARSVGPMDYWGQGTLVTVSSASTKGPSVFPLAPSSKSTS

GGTAALGCLVKDYFPEPVTVSWNSGALTSGVHTFPAVLQSSGLYS

LSSVVTVPSSSLGTQTYICNVNHKPSNTKVDKKVEPKSCDKTHTC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSKLTVDKSRWQQGNVFSCSVMHEALHNHYTQKSLSLSPG
K

Nucleotide sequence encoding the HC of anti-hCD37 Ab1.A1.2 IgG1 (DCCG CKKPKK), having DCCG mutations in CH1 domain for cognate LC/HC pairings and substitutions CKKPKK in CH3 domain for heterodimeric Fc formation

SEQ ID NO: 41 caggtgcagctggttcagtctggcgccgaagtgaagaaacctggc gcctctgtgaaggtgtcctgcaaggcttctggctacacctttacc ggctacaacgtgaactgggtccgacagaacaacggccagcggctg gaatggatgggcaacatcgatccttactacggcggcaccacctac aaccggaagttcaagggcagagtgaccatcaccgtggacacctct gcctccaccgcctacatggaactgaagtccctgagatccgaggac accgccgtgtactactgcgctaggtctgtgggccctatggactat tggggccagggaacactggtcaccgtgtcctctgctagcaccaag ggcccatccgtcttccccctggcgccctcctccaagagcacctct gggggcacagcggccctgggctgcctggtcgatgactacttcccc gaaccggtgacggtgtcgtggaactcaggcgccctgaccagcggc gtgcacacatgccccgcctgcctacagtcctcaggactctactcc ctcagcagcgtggtgaccgtgccctccagcagcttgggcacccag acctacatctgcaacgtgaatcacaagcccagcaacaccaaggtg gacaagaaagttgagcccaaatctggtgacaaaactcacacatgt cctccatgtcctgctccagaactgctcggcggaccttccgtgttc ctgtttcctccaaagcctaaggacaccctgatgatctctcggacc cctgaagtgacctgcgtggtggtggatgtgtctcacgaggatccc gaagtgaagttcaattggtacgtggacggcgtggaagtgcacaac gccaagaccaagcctagagaggaacagtacaactccacctacaga gtggtgtccgtgctgaccgtgctgcaccaggattggctgaacggc aaagagtacaagtgcaaggtgtccaacaaggccctgcctgctcct atcgaaaagaccatcagcaaggccaagggccagcccagggaaccc caggtttacaccctgcctccatgccgggaagagatgaccaagaat caagtgaagctgacctgtctcgtgaagggcttctacccctccgac atcgccgtggaatgggagtctaatggccagcctgagaatccctac aagacaacccctcctgtgctggacaaggacggctcattcttcctg tactccaagctgacagtggacaagtccagatggcagcagggcaac gtgttctcctgctccgtgatgcacgaggccctgcacaatcactac acccagaagtccctgtctctgtcccctggcaaataa Amino acid sequence encoding the HC of anti-hCD37 Ab1.A1.2 IgG1 (DCCG CKKPKK), having DCCG mutations in CH1 domain for cognate LC/HC pairings and substitutions CKKPKK in CH3 domain for heterodimer formation

SEQ ID NO: 42

QVQLVQSGAEVKKPGASVKVSCKASGYTFTGYNVNWVRQNNGQRL

EWMGNIDPYYGGTTYNRKFKGRVTITVDTSASTAYMELKSLRSED

TAVYYCARSVGPMDYWGQGTLVTVSSASTKGPSVFPLAPSSKSTS

GGTAALGCLVDDYFPEPVTVSWNSGALTSGVHTCPACLQSSGLYS

LSSVVTVPSSSLGTQTYICNVNHKPSNTKVDKKVEPKSGDKTHTC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPCREEMTKN

QVKLTCLVKGFYPSDIAVEWESNGQPENPYKTTPPVLDKDGSFFL

YSKLTVDKSRWQQGNVFSCSVMHEALHNHYTQKSLSLSPGK

Nucleotide sequence encoding the HC of anti-hCD37 Ab1.A1.3 IgG1 (DCCG + CDDDGD), having DCCG mutations in CH1 domain for cognate LC/HC pairings and substitutions CDDDGD in CH3 domain for heterodimeric Fc formation

SEQ ID NO: 43 caggtgcagctggttcagtctggcgccgaagtgaagaaacctggc gcctctgtgaaggtgtcctgcaaggcttctggctacacctttacc ggctacaacgtgaactgggtccgacagaacaacggccagcggctg gaatggatgggcaacatcgatccttactacggcggcaccacctac aaccggaagttcaagggcagagtgaccatcaccgtggacacctct gcctccaccgcctacatggaactgaagtccctgagatccgaggac accgccgtgtactactgcgctaggtctgtgggccctatggactat tggggccagggaacactggtcaccgtgtcctctgctagcaccaag ggcccatccgtcttccccctggcgccctcctccaagagcacctct gggggcacagcggccctgggctgcctggtcgatgactacttcccc gaaccggtgacggtgtcgtggaactcaggcgccctgaccagcggc gtgcacacatgccccgcctgcctacagtcctcaggactctactcc ctcagcagcgtggtgaccgtgccctccagcagcttgggcacccag acctacatctgcaacgtgaatcacaagcccagcaacaccaaggtg gacaagaaagttgagcccaaatctggtgacaaaactcacacatgc ccaccgtgcccagcacctgaactcctgggcggaccgtcagtcttc ctcttccctccaaaacccaaggacaccctcatgatctcccggacc cctgaggtcacatgcgtggtggtggacgtgagccacgaagaccct gaggtcaagttcaactggtacgtggacggcgtggaggtgcataat -continued gccaagacaaagccgcgggaggagcagtacaacagcacgtaccgt gtggtcagcgtcctcaccgtcctgcaccaggactggctgaatggc aaggagtacaagtgcaaggtctccaacaaagccctcccagcccccc atcgagaaaaccatctccaaagccaaagggcagccccgagaacca caggtgtgcaccctgcccccatcccgggaggagatgaccaagaac caggtggacctgacctgcctggtggacggcttctatcccagcgac atcgccgtggagtgggagagcaatgggcagccggagaacgactac ggcaccacgcctcccgtgctggacgacgacggctccttcttcctc tatagcaagctcaccgtggacaagagcaggtggcagcaggggaac gtcttctcatgctccgtgatgcatgaggctctgcacaaccactac acgcagaaaagcctctccctgtctccgggtaaataa Amino acid sequence of the HC of anti-hCD37 Ab1.A1.3 IgG1 (DCCG + CDDDGD), having DCCG mutations in CH1 domain for cognate LC/HC pairings and substitutions CDDDGD in CH3 domain for heterodimeric Fc formation

SEQ ID NO: 44

QVQLVQSGAEVKKPGASVKVSCKASGYTFTGYNVNWVRQNNGQRL

EWMGNIDPYYGGTTYNRKFKGRVTITVDTSASTAYMELKSLRSED

TAVYYCARSVGPMDYWGQGTLVTVSSASTKGPSVFPLAPSSKSTS

GGTAALGCLVDDYFPEPVTVSWNSGALTSGVHTCPACLQSSGLYS

LSSVVTVPSSSLGTQTYICNVNHKPSNTKVDKKVEPKSGDKTHTC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVCTLPPSREEMTKN

QVDLTCLVDGFYPSDIAVEWESNGQPENDYGTTPPVLDDDGSFFL

YSKLTVDKSRWQQGNVFSCSVMHEALHNHYTQKSLSLSPGK

Nucleotide sequence encoding the VL of the humanized anti-hCD37 antibodies Ab1.A1, Ab1.A1.1, Ab1.A1.2, Ab1.A1.3

SEQ ID NO: 45

Gacatccagatgacccagtccccgtcctctctgagcgccagtgtc ggggaccgcgtcaccattacctgtcgtaccagtgagaacgtctac aactatctggcctggtatcagcagaaaccaggcaaggcccctaag ctgttgatctattttgcaaagaccctggctgaaggcgtcccctcc cggtttagcgggagtggctccggtacacagtttaccttgacaatt agcagcctgcagccggaagactccgcctcctattactgtcagcat cacagcgataacccctggacatttggtgggggcaccgagctggag atcaag Amino acid sequence of the VL of the humanized anti-hCD37 antibodies Ab1.A1, Ab1.A1.1, Ab1.A1.2, Ab1.A1.3

SEQ ID NO: 46

DIQMTQSPSSLSASVGDRVTITCRTSENVYNYLAWYQQKPGKAPK

LLIYFAKTLAEGVPSRFSGSGSGTQFTLTISSLQPEDSASYYCQH

HSDNPWTFGGGTELEIK

-continued

Nucleotide sequence encoding the LC of the humanized anti-hCD37 Ab1.A1 (WT)

SEQ ID NO: 47 gacatccagatgacccagtccccgtcctctctgagcgccagtgtc ggggaccgcgtcaccattacctgtcgtaccagtgagaacgtctac aactatctggcctggtatcagcagaaaccaggcaaggcccctaag ctgttgatctattttgcaaagaccctggctgaaggcgtcccctcc cggtttagcgggagtggctccggtacacagtttaccttgacaatt agcagcctgcagccggaagactccgcctcctattactgtcagcat cacagcgataacccctggacatttggtgggggcaccgagctggag atcaagcgtacggtggctgcaccatctgtcttcatcttcccgcca tctgatgagcagttgaaatctggaactgcctctgttgtgtgcctg ctgaataacttctatcccagagaggccaaagtacagtggaaggtg gataacgccctccaatcgggtaactcccaggagagtgtcacagag caggacagcaaggacagcacctacagcctcagcagcaccctgacg ctgagcaaagcagactacgagaaacacaaagtctacgcctgcgaa gtcacccatcagggcctgagctcgcccgtcacaaagagcttcaac aggggagagtgttga Amino acid sequence of the LC of the humanized anti-hCD37 Ab1.A1 (WT)

SEQ ID NO: 48

DIQMTQSPSSLSASVGDRVTITCRTSENVYNYLAWYQQKPGKAPK

LLIYFAKTLAEGVPSRFSGSGSGTQFTLTISSLQPEDSASYYCQH

HSDNPWTFGGGTELEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

Nucleotide sequence encoding the LC of the humanized anti-hCD37 Ab1.A1.1, Ab1.A1.2, Ab1.A1.3 (KCCS)

SEQ ID NO: 49 gacatccagatgacccagtccccgtcctctctgagcgccagtgtc ggggaccgcgtcaccattacctgtcgtaccagtgagaacgtctac aactatctggcctggtatcagcagaaaccaggcaaggcccctaag ctgttgatctattttgcaaagaccctggctgaaggcgtcccctcc cggtttagcgggagtggctccggtacacagtttaccttgacaatt agcagcctgcagccggaagactccgcctcctattactgtcagcat cacagcgataacccctggacatttggtgggggcaccgagctggag atcaagcgtacggtggctgcaccatctgtcttcatcttcccgcca tctgatgagcagttgaaatctggaactgccaaggttgtgtgcctg ctgaataacttctatcccagagaggccaaagtacagtggaaggtg gataacgccctccaatcgggtaactcctgcgagtgtgtcacagag caggacagcaaggacagcacctacagcctcagcagcaccctgacg ctgagcaaagcagactacgagaaacacaaagtctacgcctgcgaa gtcacccatcagggcctgagctcgcccgtcacaaagagcttcaac aggggagagagctga -continued Amino acid sequence of the LC of the humanized anti-hCD37 Ab1.A1.1, Ab1.A1.2, Ab1.A1.3 (KCCS)

SEQ ID NO: 50

DIQMTQSPSSLSASVGDRVTITCRTSENVYNYLAWYQQKPGKAPK

LLIYFAKTLAEGVPSRFSGSGSGTQFTLTISSLQPEDSASYYCQH

HSDNPWTFGGGTELEIKRTVAAPSVFIFPPSDEQLKSGTAKVVCL

LNNFYPREAKVQWKVDNALQSGNSCECVTEQDSKDSTYSLSSTLT

LSKADYEKHKVYACEVTHQGLSSPVTKSFNRGES

Nucleotide sequence encoding the VH of anti-hCLDN18.2 59F9E1

SEQ ID NO: 51 caggttcagctggttcagtctggcgccgaagtgaagaaacctggc tcctccgtgaaggtgtcctgcaaggcttctggctataccctgacc ggctactggatcgagtggctgagacagaggcctggacagggactt gagtggatgggagagatcctgctcggctccggctccatcaagtac aacgtgaagttcaaggaccgcgtgaccatcaccgccgacgagtct acctctaccgcctacatggaactgtccagcctgagatctgaggac accgccgtgtactactgcgccagaaagggcctgagaggcaactcc ttcgattactggggccagggcacactggtcaccgtgtcctct Amino acid sequence of the VH of anti-hCLDN18.2 clone 59F9E1

SEQ ID NO: 52

QVQLVQSGAEVKKPGSSVKVSCKASGYTLTGYWIEWLRQRPGQGL

EWMGEILLGSGSIKYNVKFKDRVTITADESTSTAYMELSSLRSED

TAVYYCARKGLRGNSFDYWGQGTLVTVSS

Nucleotide sequence encoding the HC of humanized anti-hCLDN18.2 clone 59F9E1 IgG1 (WT)

SEQ ID NO: 53

CAGGTTCAGCTGGTTCAGTCTGGCGCCGAAGTGAAGAAACCTGGC

TCCTCCGTGAAGGTGTCCTGCAAGGCTTCTGGCTATACCCTGACC

GGCTACTGGATCGAGTGGCTGAGACAGAGGCCTGGACAGGGACTT

GAGTGGATGGGAGAGATCCTGCTCGGCTCCGGCTCCATCAAGTAC

AACGTGAAGTTCAAGGACCGCGTGACCATCACCGCCGACGAGTCT

ACCTCTACCGCCTACATGGAACTGTCCAGCCTGAGATCTGAGGAC

ACCGCCGTGTACTACTGCGCCAGAAAGGGCCTGAGAGGCAACTCC

TTCGATTACTGGGGCCAGGGCACACTGGTCACCGTGTCCTCTGCT

AGCACCAAGGGACCCAGCGTGTTCCCTCTGGCTCCTTCCAGCAAG

TCTACATCCGGCGGAACAGCTGCTCTGGGCTGCCTGGTCAAGGAC

TACTTTCCTGAGCCTGTGACCGTGTCTTGGAACTCTGGCGCTCTG

ACAAGCGGCGTGCACACCTTTCCAGCTGTGCTGCAATCCTCCGGC

CTGTACTCTCTGTCCTCCGTCGTGACCGTGCCTTCTAGCTCTCTG

GGCACCCAGACCTACATCTGCAATGTGAACCACAAGCCTTCCAAC

ACCAAGGTGGACAAGAAGGTGGAACCCAAGTCCTGCGACAAGACC

CACACCTGTCCTCCATGTCCTGCTCCAGAACTCCTGGGGGGACCG

TCAGTCTTCCTCTTCCCCCCAAAACCCAAGGACACCCTCATGATC

TCCCGGACCCCTGAGGTCACATGCGTGGTGGTGGACGTGAGCCAC

-continued

GAAGACCCTGAGGTCAAGTTCAACTGGTACGTGGACGGCGTGGAG

GTGCATAATGCCAAGACAAAGCCGCGGGAGGAGCAGTACAACAGC

ACGTACCGTGTGGTCAGCGTCCTCACCGTCCTGCACCAGGACTGG

CTGAATGGCAAGGAGTACAAGTGCAAGGTCTCCAACAAAGCCCTC

CCAGCCCCCATCGAGAAAACCATCTCCAAAGCCAAAGGGCAGCCC

CGAGAACCACAGGTGTACACCCTGCCCCCATCCCGGGAGGAGATG

ACCAAGAACCAGGTCAGCCTGACCTGCCTGGTCAAAGGCTTCTAT

CCCAGCGACATCGCCGTGGAGTGGGAGAGCAATGGGCAGCCGGAG

AACAACTACAAGACCACGCCTCCCGTGCTGGACTCCGACGGCTCC

TTCTTCCTCTATAGCAAGCTCACCGTGGACAAGAGCAGGTGGCAG

CAGGGGAACGTCTTCTCATGCTCCGTGATGCATGAGGCTCTGCAC

AACCACTACACGCAGAAGAGCCTCTCCCTGTCTCCGGGTAAATGA

TAG

Amino acid sequence of the HC of humanized anti-hCLDN18.2 clone 59F9E1 IgG1 (WT)

SEQ ID NO: 54

QVQLVQSGAEVKKPGSSVKVSCKASGYTLTGYWEWLRQRPGQGLE

WMGELLGSGSIKYNVKFKDRVTITADESTSTAYMELSSLRSEDTA

VYYCARKGLRGNSFDYWGQGTLVTVSSASTKGPSVFPLAPSSKST

SGGTAALGCLVKDYFPEPVTVSWNSGALTSGVHTFPAVLQSSGLY

SLSSVVTVPSSSLGTQTYICNVNHKPSNTKVDKKVEPKSCDKTHT

CPPCPAPELLGGPSVFLFPPKPKDTLMISRTPEVTCVVVDVSHED

PEVKFNWYVDGVEVHNAKTKPREEQYNSTYRVVSVLTVLHQDWLN

GKEYKCKVSNKALPAPIEKTISKAKGQPREPQVYTLPPSREEMTK

NQVSLTCLVKGFYPSDIAVEWESNGQPENNYKTTPPVLDSDGSFF

LYSKLTVDKSRWQQGNVFSCSVMHEALHNHYTQKSLSLSPGK

Nucleotide sequence encoding the HC of anti-hCLDN18.2 59F9E1 IgG1 with substitutions 147D, F170C, V173C in CH1 region and C220G in upper hinge region for cognate HC/LC pairing (DCCG)

SEQ ID NO: 55 caggttcagctggttcagtctggcgccgaagtgaagaaacctggc tcctccgtgaaggtgtcctgcaaggcttctggctataccctgacc ggctactggatcgagtggctgagacagaggcctggacagggactt gagtggatgggagagatcctgctcggctccggctccatcaagtac aacgtgaagttcaaggaccgcgtgaccatcaccgccgacgagtct acctctaccgcctacatggaactgtccagcctgagatctgaggac accgccgtgtactactgcgccagaaagggcctgagaggcaactcc ttcgattactggggccagggcacactggtcaccgtgtcctctgct agcaccaagggacccagcgtgttccctctggctccttccagcaag tctacatccggcggaacagctgctctgggctgcctggtcgacgac tactttcctgagcctgtgaccgtgtcttggaactctggcgctctg acaagcggcgtgcacacctgcccagcttgcctgcaatcctccggc -continued ctgtactctctgtcctccgtcgtgaccgtgccttctagctctctg
ggcacccagacctacatctgcaatgtgaaccacaagccttccaac
accaaggtggacaagaaggtggaacccaagtccggcgacaagacc
cacacctgtcctccatgtcctgctccagaactcctggggggaccg
tcagtcttcctcttccccccaaaacccaaggacaccctcatgatc
tcccggacccctgaggtcacatgcgtggtggtggacgtgagccac
gaagaccctgaggtcaagttcaactggtacgtggacggcgtggag
gtgcataatgccaagacaaagccgcgggaggagcagtacaacagc
acgtaccgtgtggtcagcgtcctcaccgtcctgcaccaggactgg
ctgaatggcaaggagtacaagtgcaaggtctccaacaaagccctc
ccagcccccatcgagaaaaccatctccaaagccaaagggcagccc
cgagaaccacaggtgtacaccctgcccccatcccgggaggagatg
accaagaaccaggtcagcctgacctgcctggtcaaaggcttctat
cccagcgacatcgccgtggagtgggagagcaatgggcagccggag
aacaactacaagaccacgcctcccgtgctggactccgacggctcc
ttcttcctctatagcaagctcaccgtggacaagagcaggtggcag
caggggaacgtcttctcatgctccgtgatgcatgaggctctgcac
aaccactacacgcagaagagcctctccctgtctccgggtaaatga
tag Amino acid sequence of the HC of anti-hCLDN18.2 59F9E1 IgG 1 with substitutions 147D, F170C, V173C in CH1 region and C220G in upper hinge region for cognate HC/LC pairing (DCCG)

SEQ ID NO: 56

QVQLVQSGAEVKKPGSSVKVSCKASGYTLTGYWIEWLRQRPGQGL
EWMGEILLGSGSIKYNVKFKDRVTITADESTSTAYMELSSLRSED
TAVYYCARKGLRGNSFDYWGQGTLVTVSSASTKGPSVFPLAPSSK
STSGGTAALGCLVDDYFPEPVTVSWNSGALTSGVHTCPACLQSSG
LYSLSSVVTVPSSSLGTQTYICNVNHKPSNTKVDKKVEPKSGDKT
HTCPPCPAPELLGGPSVFLFPPKPKDTLMISRTPEVTCVVVDVSH
EDPEVKFNWYVDGVEVHNAKTKPREEQYNSTYRVVSVLTVLHQDW
LNGKEYKCKVSNKALPAPIEKTISKAKGQPREPQVYTLPPSREEM
TKNQVSLTCLVKGFYPSDIAVEWESNGQPENNYKTTPPVLDSDGS
FFLYSKLTVDKSRWQQGNVFSCSVMHEALHNHYTQKSLSLSPGK

Nucleotide sequence encoding the HC of anti-hCLDN18.2 59F9E1 IgG1 with substitutions 147D, F170C, V173C, C220G for cognate LC/HC pairing and substitutions Y349C, S364D, K370D, N390D, K392G, S400D to force heterodimer formation (DCCG + CDDDGD)

SEQ ID NO: 57 caggttcagctggttcagtctggcgccgaagtgaagaaacctggc
tcctccgtgaaggtgtcctgcaaggcttctggctataccctgacc
ggctactggatcgagtggctgagacagaggcctggacagggactt
gagtggatgggagagatcctgctcggctccggctccatcaagtac
aacgtgaagttcaaggaccgcgtgaccatcaccgccgacgagtct
acctctaccgcctacatggaactgtccagcctgagatctgaggac
accgccgtgtactactgcgccagaaagggcctgagaggcaactcc
ttcgattactggggccagggcacactggtcaccgtgtcctctgct
agcaccaagggacccagcgtgttccctctggctccttccagcaag
tctacatccggcggaacagctgctctgggctgcctggtcgacgac
tactttcctgagcctgtgaccgtgtcttggaactctggcgctctg
acaagcggcgtgcacacctgcccagcttgcctgcaatcctccggc
ctgtactctctgtcctccgtcgtgaccgtgccttctagctctctg
ggcacccagacctacatctgcaatgtgaaccacaagccttccaac
accaaggtggacaagaaggtggaacccaagtccggcgacaagacc
cacacctgtcctccatgtcctgctccagaactgctcggcggaccc
agcgtgttcctgtttcctccaaagcctaaggacaccctgatgatc
tctcggacccctgaagtgacctgcgtggtggtggatgtgtctcac
gaggacccagaagtgaagtttaattggtacgtggacggcgtggag
gtgcataatgccaagacaaagccgcgggaggagcagtacaacagc
acgtaccgtgtggtcagcgtcctcaccgtcctgcaccaggactgg
ctgaatggcaaggagtacaagtgcaaggtctccaacaaagccctc
ccagcccccatcgagaaaaccatctccaaagccaaagggcagccc
cgagaaccacaggtgtgcaccctgcccccatcccgggaggagatg
accaagaaccaggtcgacctgacctgcctggtcgacggcttctat
cccagcgacatcgccgtggagtgggagagcaatgggcagccggag
aacgactacggcaccacgcctcccgtgctggacgacgacggctcc
ttcttcctctatagcaagctcaccgtggacaagagcaggtggcag
caggggaacgtcttctcatgctccgtgatgcatgaggctctgcac
aaccactacacgcagaagagcctctccctgtctccgggcaaatga
taa Amino acid sequence of the HC of anti-hCLDN18.2 59F9E1 IgG 1 with substitutions 147D, F170C, V173C, C220G for cognate LC/HC pairing and substitutions Y349C, S364D, K370D, N390D, K392G, S400D to force heterodimeric Fc formation (DCCG + CDDDGD)

SEQ ID NO: 58

QVQLVQSGAEVKKPGSSVKVSCKASGYTLTGYWIEWLRQRPGQGL
EWMGELLGSGSIKYNVKFKDRVTITADESTSTAYMELSSLRSEDT
AVYYCARKGLRGNSFDYWGQGTLVTVSSASTKGPSVFPLAPSSKS
TSGGTAALGCLVDDYFPEPVTVSWNSGALTSGVHTCPACLQSSGL
YSLSSVVTVPSSSLGTQTYICNVNHKPSNTKVDKKVEPKSGDKTH
TCPPCPAPELLGGPSVFLFPPKPKDTLMISRTPEVTCVVVDVSHE
DPEVKFNWYVDGVEVHNAKTKPREEQYNSTYRVVSVLTVLHQDWL
NGKEYKCKVSNKALPAPIEKTISKAKGQPREPQVCTLPPSREEMT
KNQVDLTCLVDGFYPSDIAVEWESNGQPENDYGTTPPVLDDDGSF
FLYSKLTVDKSRWQQGNVFSCSVMHEALHNHYTQKSLSLSPGK

-continued

Nucleotide sequence encoding the VL of the humanized anti-hCLDN18.2 59F9E1

SEQ ID NO: 59 gatatcgtaatgacacaatcaccttcatcactgaccgtgagtctc
ggggaaaaagctactatatcctgtaaatcctcccaatcacttctt
aacgctgggaaccaaaagtcttatcttacttggtaccagcaaaag
cccggtcaaccacctaagcggctcatttattgggcttccaccaga
gagtctggggtaccagaccgcttctctggaagcggcagtgggact
gactttactttgaccatttcatctctgcaagcagaagacttggca
gtttattattgtcaaaacgattactattacccatttacattcggt
caaggaactaaagtggaaataaaa Amino acid sequence of the VL of the humanized anti-hCLDN18.2 59F9E1

SEQ ID NO: 60

DIVMTQSPSSLTVSLGEKATISCKSSQSLLNAGNQKSYLTWYQQK
PGQPPKRLIYWASTRESGVPDRFSGSGSGTDFTLTISSLQAEDLA
VYYCQNDYYYPFTFGQGTKVEIK

Nucleotide sequence encoding the LC of the humanized anti-hCLDN18.2 clone 59F9E1 (WT)

SEQ ID NO: 61

Gatatcgtaatgacacaatcaccttcatcactgaccgtgagtctc
ggggaaaaagctactatatcctgtaaatcctcccaatcacttctt
aactctgggaaccaaaagtcttatcttacttggtaccagcaaaag
cccggtcaaccacctaagcggctcatttattgggcttccaccaga
gagtctggggtaccagaccgcttctctggaagcggcagtgggact
gactttactttgaccatttcatctctgcaagcagaagacttggca
gtttattattgtcaaaacgattactattacccatttacattcggt
caaggaactaaagtggaaataaaacgtacggtggctgcaccatct
gtcttcatcttcccgccatctgatgagcagttgaaatctggaact
gcctctgttgtgtgcctgctgaataacttctatcccagagaggcc
aaagtacagtggaaggtggataacgccctccaatcgggtaactcc
caggagagtgtcacagagcaggacagcaaggacagcacctacagc
ctcagcagcaccctgacgctgagcaaagcagactacgagaaacac
aaagtctacgcctgcgaagtcacccatcagggcctgagctcgccc
gtcacaaagagcttcaacaggggagagtgttgatag Amino acid sequence of the LC of the humanized anti-hCLDN18.2 clone 59F9E1 (WT)

SEQ ID NO: 62

DIVMTQSPSSLTVSLGEKATISCKSSQSLLNSGNQKSYLTWYQQK
PGQPPKRLIYWASTRESGVPDRFSGSGSGTDFTLTISSLQAEDLA
VYYCQNDYYYPFTFGQGTKVEIKRTVAAPSVFIFPPSDEQLKSGT
ASVVCLLNNFYPREAKVQWKVDNALQSGNSQESVTEQDSKDSTYS
LSSTLTLSKADYEKHKVYACEVTHQGLSSPVTKSFNRGEC

Nucleotide sequence encoding the LC of the humanized anti-hCLDN18.2 clone 59F9E1 with mutations S131K, Q160C, S162C, and C214S (KCCS)

SEQ ID NO: 63 gatatcgtaatgacacaatcaccttcatcactgaccgtgagtctc
ggggaaaaagctactatatcctgtaaatcctcccaatcacttctt
aacgctgggaaccaaaagtcttatcttacttggtaccagcaaaag
cccggtcaaccacctaagcggctcatttattgggcttccaccaga
gagtctggggtaccagaccgcttctctggaagcggcagtgggact
gactttactttgaccatttcatctctgcaagcagaagacttggca
gtttattattgtcaaaacgattactattacccatttacattcggt
caaggaactaaagtggaaataaaacgtacggtggctgcaccatct
gtcttcatcttcccgccatctgatgagcagttgaaatctggaact
gccaaggttgtgtgcctgctgaataacttctatcccagagaggcc
aaagtacagtggaaggtggataacgccctccaatcgggtaactcc
tgcgagtgtgtcacagagcaggacagcaaggacagcacctacagc
ctcagcagcaccctgacgctgagcaaagcagactacgagaaacac
aaagtctacgcctgcgaagtcacccatcagggcctgagctcgccc
gtcacaaagagcttcaacaggggagagagctaatga Amino acid sequence of the LC of the humanized anti-hCLDN18.2 clone 59F9E1 with mutations S131K, Q160C, S162C, and C214S (KCCS)

SEQ ID NO: 64

DIVMTQSPSSLTVSLGEKATISCKSSQSLLNAGNQKSYLTWYQQK
PGQPPKRLIYWASTRESGVPDRFSGSGSGTDFTLTISSLQAEDLA
VYYCQNDYYYPFTFGQGTKVEIKRTVAAPSVFIFPPSDEQLKSGT
AKVVCLLNNFYPREAKVQWKVDNALQSGNSCECVTEQDSKDSTYS
LSSTLTLSKADYEKHKVYACEVTHQGLSSPVTKSFNRGES

Nucleotide sequence encoding the VH of anti-hSIRPa clone #24

SEQ ID NO: 65 gaggtgcagctggtggaatctggcggaggacttgtgaagcctggc
ggctctctgagactgtcttgtgccgcttccggcttcaccttctcc
agctacgtgatgtcctgggtccgacagacccctggcaaaggactg
gaatgggtcgccacaatctcctccggcggcacctacacctactat
cccgactctgtgaagggcagattcaccctgtccagagacaacgcc
aagaactccctgtacctgcagatgaacagcctgagagccgaggac
accgccgtgtactactgtgcttctcagctgaccggctccgagttc
gattattggggccagggcaccaccgtgaccgtgtcctct Amino acid sequence of the VH of anti-hSIRPa clone #24

SEQ ID NO: 66

EVQLVESGGGLVKPGGSLRLSCAASGFTFSSYVMSWVRQTPGKGL
EWVATISSGGTYTYYPDSVKGRFTLSRDNAKNSLYLQMNSLRAED
TAVYYCASQLTGSEFDYWGQGTTVTVSS

-continued

Nucleotide sequence encoding the HC of anti-hSIRPa clone #24 IgG (WT)

SEQ ID NO: 67

ATGGACATGAGAGTGCCCGCTCAGCTGCTGGGACTGCTGCTGTTG

TGGTTGAGAGGCGCTAGATGCGAGGTGCAGCTGGTGGAATCTGGC

GGAGGACTTGTGAAGCCTGGCGGCTCTCTGAGACTGTCTTGTGCC

GCTTCCGGCTTCACCTTCTCCAGCTACGTGATGTCCTGGGTCCGA

CAGACCCCTGGCAAAGGACTGGAATGGGTCGCCACAATCTCCTCC

GGCGGCACCTACACCTACTATCCCGACTCTGTGAAGGGCAGATTC

ACCCTGTCCAGAGACAACGCCAAGAACTCCCTGTACCTGCAGATG

AACAGCCTGAGAGCCGAGGACACCGCCGTGTACTACTGTGCTTCT

CAGCTGACCGGCTCCGAGTTCGATTATTGGGGCCAGGGCACCACC

GTGACCGTGTCCTCTGCTTCTACCAAGGGACCCAGCGTGTTCCCT

CTGGCTCCTTGCTCCAGATCCACCTCCGAGTCTACAGCTGCTCTG

GGCTGCCTGGTCAAGGACTACTTTCCTGAGCCTGTGACAGTGTCC

TGGAACTCTGGCGCTCTGACATCCGGCGTGCACACATTTCCAGCT

GTGCTGCAGTCCTCCGGCCTGTACTCTCTGTCCTCTGTCGTGACA

GTGCCCTCCTCTAGCCTGGGCACCAAGACCTATACCTGCAATGTG

GACCACAAGCCTTCCAACACCAAGGTGGACAAGCGCGTGGAATCT

AAGTACGGCCCTCCTTGTCCTCCATGTCCTGCTCCTCCAGTGGCT

GGCCCTTCCGTGTTTCTGTTCCCTCCAAAGCCTAAGGACACCCTG

ATGATCTCTCGGACCCCTGAAGTGACCTGCGTGGTGGTGGATGTG

TCTCACGAGGATCCTGAGGTGCAGTTCAATTGGTACGTGGACGGC

GTGGAAGTGCACAATGCCAAGACCAAGCCTAGAGAGGAACAGTTC

AACTCCACCTTCAGAGTGGTGTCCGTGCTGACCGTGGTGCATCAG

GATTGGCTGAACGGCAAAGAGTACAAGTGCAAGGTGTCCAACAAA

GGCCTGGCCGCTCCTATCGAAAAGACCATCTCTAAGACCAAGGGG

CAGCCCCGGGAACCTCAGGTTTACACACTGCCTCCAAGCCGGGAA

GAGATGACCAAGAACCAGGTGTCCCTGACCTGCCTCGTGAAGGGC

TTCTACCCTTCCGATATCGCCGTGGAATGGGAGTCCAATGGCCAG

CCAGAGAACAACTACAAGACCACACCTCCTATGCTGGACTCCGAC

GGCTCATTCTTCCTGTACTCCAAGCTGACAGTGGACAAGTCCAGA

TGGCAGCAGGGCAACGTGTTCTCCTGCAGCGTGATGCACGAGGCC

CTGCACAATCACTACACCCAGAAGTCCCTGTCTCTGAGCCCTGGC

AAGTAATGA

Amino acid sequence of the HC of anti-hSIRPa clone #24 IgG (WT)

SEQ ID NO: 68

EVQLVESGGGLVKPGGSLRLSCAASGFTFSSYVMSWVRQTPGKGL

EWVATISSGGTYTYYPDSVKGRFTLSRDNAKNSLYLQMNSLRAED

TAVYYCASQLTGSEFDYWGQGTTVTVSSASTKGPSVFPLAPCSRS

TSESTAALGCLVKDYFPEPVTVSWNSGALTSGVHTFPAVLQSSGL

YSLSSVVTVPSSSLGTKTYTCNVDHKPSNTKVDKRVESKYGPPCP

PCPAPPVAGPSVFLFPPKPKDTLMISRTPEVTCVVVDVSHEDPEV

-continued

QFNWYVDGVEVHNAKTKPREEQFNSTFRVVSVLTVVHQDWLNGKE

YKCKVSNKGLAAPIEKTISKTKGQPREPQVYTLPPSREEMTKNQV

SLTCLVKGFYPSDIAVEWESNGQPENNYKTTPPMLDSDGSFFLYS

KLTVDKSRWQQGNVFSCSVMHEALHNHYTQKSLSLSPGK

Nucleotide sequence encoding the HC of anti-hSIRPa clone #24 IgG with S354C, S364K, N390P and S400K in CH3 region for heterodimeric Fc formation (CKKPKK)

SEQ ID NO: 69 gaggtgcagctggtggaatctggcggaggacttgtgaagcctggc ggctctctgagactgtcttgtgccgcttccggcttcaccttctcc agctacgtgatgtcctgggtccgacagacccctggcaaaggactg gaatgggtcgccacaatctcctccggcggcacctacacctactat cccgactctgtgaagggcagattcaccctgtccagagacaacgcc aagaactccctgtacctgcagatgaacagcctgagagccgaggac accgccgtgtactactgtgcttctcagctgaccggctccgagttc gattattggggccagggcaccaccgtgaccgtgtcctctgctagc accaagggcccatccgtcttccccctggcgccctcctccaagagc acctctgggggcacagcggccctgggctgcctggtcaaggactac ttccccgaaccggtgacggtgtcgtggaactcaggcgccctgacc agcggcgtgcacaccttcccggctgtcctacagtcctcaggactc tactccctcagcagcgtggtgaccgtgccctccagcagcttgggc acccagacctacatctgcaacgtgaatcacaagcccagcaacacc aaggtggacaagaaagttgagcccaaatcttgtgacaaaactcac acatgcccaccgtgcccagcacctgaactcctggggggaccgtca gtcttcctcttccccccaaaacccaaggacaccctcatgatctcc cggacccctgaggtcacatgcgtggtggtggacgtgagccacgaa gaccctgaggtcaagttcaactggtacgtggacggcgtggaggtg cataatgccaagacaaagccgcgggaggagcagtacaacagcacg taccgtgtggtcagcgtcctcaccgtcctgcaccaggactggctg aatggcaaggagtacaagtgcaaggtctccaacaaagccctccca gcccccatcgagaaaaccatctccaaagccaaagggcagccccga gaaccacaggtgtacaccctgcccccatgccgggaggagatgacc aagaaccaggtcaagctgacctgcctggtcaaaggcttctatccc agcgacatcgccgtggagtgggagagcaatgggcagccggagaac ccttacaagaccacgcctcccgtgctggacaaggacggctccttc ttcctctatagcaagctcaccgtggacaagagcaggtggcagcag gggaacgtcttctcatgctccgtgatgcatgaggctctgcacaac cactacacgcagaagagcctctccctgtctccgggcaaatgataa -continued Amino acid sequence of the HC of anti-hSIRPa clone #24 IgG with S354C, S364K, N390P and S400K for heterodimeric Fc formation (CKKPKK)

SEQ ID NO: 70

EVQLVESGGGLVKPGGSLRLSCAASGFTFSSYVMSWRQTPGKGLE
WVATISSGGTYTYYPDSVKGRFTLSRDNAKNSLYLQMNSLRAEDT
AVYYCASQLTGSEFDYWGQGTTVTVSSASTKGPSVFPLAPSSKST
SGGTAALGCLVKDYFPEPVTVSWNSGALTSGVHTFPAVLQSSGLY
SLSSVVTVPSSSLGTQTYICNVNHKPSNTKVDKKVEPKSCDKTHT
CPPCPAPELLGGPSVFLFPPKPKDTLMISRTPEVTCVVVDVSHED
PEVKFNWYVDGVEVHNAKTKPREEQYNSTYRVVSVLTVLHQDWLN
GKEYKCKVSNKALPAPIEKTISKAKGQPREPQVYTLPPCREEMTK
NQVKLTCLVKGFYPSDIAVEWESNGQPENPYKTTPPVLDKDGSFF
LYSKLTVDKSRWQQGNVFSCSVMHEALHNHYTQKSLSLS
PGK

Nucleotide sequence encoding the VL of the humanized anti-hSIRPa clone #24

SEQ ID NO: 71 gacattgtcttgacccaatcacctgcaagcctcgccgtatctctc
ggggagcgggccacaatttcttgccgggcatcagaaagtgtagac
ttgtatggcacttcctttatgcattggtatcaacaaaaacccggc
caacctcctaaactcttgatttatcgggcctccaacctcgaatcc
ggtgtgcctgatcgtttttcaggttcaggaagcagaacagacttc
acactcaccataaaccccctccaggctgaagacgtcgccacttac
tattgtcaccagtcttcagacgagctgccttggacatttggaggt
ggaactaaggttgagatcaaa Amino acid sequence of the VL of the humanized anti-hSIRPa clone #24

SEQ ID NO: 72

DIVLTQSPASLAVSLGERATISCRASESVDLYGTSFMHWYQQKPG
QPPKLLIYRASNLESGVPDRFSGSGSRTDFTLTINPLQAEDVATY
YCHQSSDELPWTFGGGTKVEIK

Nucleotide sequence encoding the LC of the humanized anti-hSIRPa clone #24 (WT)

SEQ ID NO: 73 gacattgtcttgacccaatcacctgcaagcctcgccgtatctctc
ggggagcgggccacaatttcttgccgggcatcagaaagtgtagac
ttgtatggcacttcctttatgcattggtatcaacaaaaacccggc
caacctcctaaactcttgatttatcgggcctccaacctcgaatcc
ggtgtgcctgatcgtttttcaggttcaggaagcagaacagacttc
acactcaccataaacccccctccaggctgaagacgtcgccacttac
tattgtcaccagtcttcagacgagctgccttggacatttggaggt
ggaactaaggttgagatcaaacgtacggtggctgcaccatctgtc
ttcatcttcccgccatctgatgagcagttgaaatctggaactgcc
tctgttgtgtgcctgctgaataacttctatcccagagaggccaaa
gtacagtggaaggtggataacgccctccaatcgggtaactcccag
gagagtgtcacagagcaggacagcaaggacagcacctacagcctc
agcagcaccctgacgctgagcaaagcagactacgagaaacacaaa
gtctacgcctgcgaagtcacccatcagggcctgagctcgcccgtc
acaaagagcttcaacaggggagagtgttgataa Amino acid sequence of the LC of the humanized anti-hSIRPa clone #24 (WT)

SEQ ID NO: 74

DIVLTQSPASLAVSLGERATISCRASESVDLYGTSFMHWYQQKPG
QPPKLLIYRASNLESGVPDRFSGSGSRTDFTLTINPLQAEDVATY
YCHQSSDELPWTFGGGTKVEIKRTVAAPSVFIFPPSDEQLKSGTA
SVVCLLNNFYPREAKVQWKVDNALQSGNSQESVTEQDSKDSTYSL
SSTLTLSKADYEKHKVYACEVTHQGLSSPVTKSFNRGEC

Nucleotide sequence encoding the HC of the humanized anti-hCD20 Ab1.2.2.1

SEQ ID NO: 75 caggtgcagctggtgcagtctggcgccgaagtgaagaaacccggc
tcctccgtgaaggtgtcctgcaaggcctccggctacacctttacc
agctacaacatgcactgggtgcgacaggcccctggacagggcctg
gaatggatgggcgctatctaccctggcaacggcgacacctcctac
aaccagaaattccagggcagagtgaccctgaccgtggacaagtcc
tcctccaccgcctacatggaactgtcctccctgcggagcgaggat
accgccgtgtacttctgtgcccgggtggtgtactactccaactcc
tactggtacttcgacgtgtggggcaccggcacaatggtcaccgtg
tcctccgctagcaccaaggggccatccgtcttcccccctggcgccc
tgctccaggagcacctccgagagcacagccgccctgggctgcctg
gtcaaggactacttccccgaaccggtgacggtgtcgtggaactca
ggcgccctgaccagcggcgtgcacaccttcccggctgtcctacag
tcctcaggactctactccctcagcagcgtggtgaccgtgccctcc
agcagcttgggcacgaagacctacacctgcaacgtagatcacaag
cccagcaacaccaaggtggacaagagagttgagtccaaatatggc
cccccatgcccaccgtgcccagcacctgaactcctggggggaccg
gacgtcttcctcttccccccaaaacccaaggacaccctcatgatc
tcccggacccctgaggtcacatgcgtggtggtggacgtgagccac
gaagaccctgaggtcaagttcaactggtacgtggacggcgtggag
gtgcataatgccaagacaaagccgcgggaggagcagtacaacgcc
acgtaccgtgtggtcagcgtcctcaccgtcctgcaccaggactgg
ctgaatggcaaggagtacaagtgcaaggtctccaacaaagccctc
ccagcccccatcgagaaaaccatctccaaagccaaagggcagccc
cgagaaccacaggtgtacaccctgcccccatcccgggaggagatg
accaagaaccaggtcagcctgacctgcctggtcaaaggcttctat
cccagcgacatcgccgtggagtgggagagcaatgggcagccggag
aacaactacaagaccacgcctcccgtgctgcgctccgacggctcc ttcttcctctatagcgagctcaccgtggacaagagcaggtggcag caggggaacgtcttctcatgctccgtgatgcatgaggctctgcac aaccactacacgcagaagagcctctccctgtctccgggtaaatga Amino acid sequence of the HC of the humanized anti-hCD20 Ab1.2.2.1

SEQ ID NO: 76

QVQLVQSGAEVKKPGSSVKVSCKASGYTFTSYNMHWVRQAPGQGL

EWMGAIYPGNGDTSYNQKFQGRVTLTVDKSSSTAYMELSSLRSED

TAVYFCARVVYYSNSYWYFDVWGTGTMVTVSSASTKGPSVFPLAP

CSRSTSESTAALGCLVKDYFPEPVTVSWNSGALTSGVHTFPAVLQ

SSGLYSLSSVVTVPSSSLGTKTYTCNVDHKPSNTKVDKRVESKYG

PPCPPCPAPELLGGPDVFLFPPKPKDTLMISRTPEVTCVVVDVSH

EDPEVKFNWYVDGVEVHNAKTKPREEQYNATYRVVSVLTVLHQDW

LNGKEYKCKVSNKALPAPIEKTISKAKGQPREPQVYTLPPSREEM

TKNQVSLTCLVKGFYPSDIAVEWESNGQPENNYKTTPPVLRSDGS

FFLYSELTVDKSRWQQGNVFSCSVMHEALHNHYTQKSLSLSPGK

Nucleotide sequence encoding the HC of the humanized anti-hCD37 Ab1.A1.1

SEQ ID NO: 77 caagtgcagctcgtccagtccggggcagaggttaagaagcccggc gctagtgtgaaggtgagctgcaaggcctctggctatactttca
cagggtacaacgtgaactgggtgcgccagaacaacggccaacggt tggagtggatgggtaacatcgatccctactacggggggtactacct acaacaggaaattcaaaggacgggtgactatcaccgtggacacat ctgcttctaccgcctacatggagctgaagtctttgcggtctgagg acaccgccgtctattactgtgccagatccgtgggccctatggatt attggggtcaagggaccctggtgaccgtcagctccgctagcacca agggcccatccgtcttcccccctggcgccctcctccaagagcacct ctgggggcacagcggccctgggctgcctggtcgatgactacttcc ccgaaccggtgacggtgtcgtggaactcaggcgccctgaccagcg gcgtgcacacctgcccggcttgcctacagtcctcaggactctact ccctcagcagcgtggtgaccgtgccctccagcagcttgggcaccc agacctacatctgcaacgtgaatcacaagcccagcaacaccaagg tggacaagaaagttgagcccaaatctggtgacaaaactcacacat gcccaccgtgcccagcacctgaactcctggggggaccgtcagtct tcctcttccccccaaaacccaaggacaccctcatgatctcccgga cccctgaggtcacatgcgtggtggtggacgtgagccacgaagacc ctgaggtcaagttcaactggtacgtggacggcgtggaggtgcata atgccaagacaaagccgcgggaggagcagtacaacagcacgtacc gtgtggtcagcgtcctcaccgtcctgcaccaggactggctgaatg gcaaggagtacaagtgcaaggtctccaacaaagccctcccagccc ccatcgagaaaaccatctccaaagccaaagggcagccccgagaac cacaggtgtacaccctgcccccatcccgggaggagatgaccaaga accaggtcagcctgacctgcctggtcaaaggcttctatcccagcg acatcgccgtggagtgggagagcaatgggcagccggagaacaact acaagaccacgcctcccgtgctggactccgacggctccttcttcc tctatagccgcctcaccgtggacaagagcaggtggcagcagggga acgtcttctcatgctccgtgatgcatgaggctctgcacaaccact acacgcagaagagcctctccctgtctccgggtaaatga Amino acid sequence of the HC of the humanized
anti-hCD37 Ab1 A1.1

SEQ ID NO: 78

QVQLVQSGAEVKKPGASVKVSCKASGYTFTGYNVNWVRQNNGQRL

EWMGNIDPYYGGTTYNRKFKGRVTITVDTSASTAYMELKSLRSED

TAVYYCARSVGPMDYWGQGTLVTVSSASTKGPSVFPLAPSSKSTS

GGTAALGCLVDDYFPEPVTVSWNSGALTSGVHTCPACLQSSGLYS

LSSVVTVPSSSLGTQTYICNVNHKPSNTKVDKKVEPKSGDKTHTC

PPCPAPELLGGPSVFLFPPKPKDTLMISRTPEVTCVVVDVSHEDP

EVKFNWYVDGVEVHNAKTKPREEQYNSTYRVVSVLTVLHQDWLNG

KEYKCKVSNKALPAPIEKTISKAKGQPREPQVYTLPPSREEMTKN

QVSLTCLVKGFYPSDIAVEWESNGQPENNYKTTPPVLDSDGSFFL

YSRLTVDKSRWQQGNVFSCSVMHEALHNHYTQKSLSLSPGK

Nucleotide sequence encoding the HC of the anti-DNP IgG1 antibody

SEQ ID NO: 79 caggttcaactccaggagtccggccctggcttggttaaacctctg cagacactgtccctgacctgcaccgtgagcggtggctcaataagt agcggcggctactactggtcatggattcgccagcaccccggtaaa ggtctcgaatggattgggtacatctactattctaggagtacttac tacaacccctcacttaaaagcagagtgactatcagtgttgataca tccaaaaaccagtttagcttgaaactgtcatccgtaactgccgcc gacaccgcagtctactattgtgctcggaccggatacagctctgga tggtaccccttttgattactggggacagggtacattggtgactgtc agttcagctagcaccaagggcccatccgtcttcccccctggcgccc tcctccaagagcacctctgggggcacagcggccctgggctgcctg gtcaaggactacttccccgaaccggtgacggtgtcgtggaactca ggcgccctgaccagcggcgtgcacaccttcccggctgtcctacag tcctcaggactctactccctcagcagcgtggtgaccgtgccctcc agcagcttgggcacccagacctacatctgcaacgtgaatcacaag cccagcaacaccaaggtggacaagaaagttgagcccaaatcttgt gacaaaactcacacatgcccaccgtgcccagcacctgaactcctg gggggaccgtcagtcttcctcttccccccaaaacccaaggacacc ctcatgatctcccggacccctgaggtcacatgcgtggtggtggac gtgagccacgaagaccctgaggtcaagttcaactggtacgtggac ggcgtggaggtgcataatgccaagacaaagccgcgggaggagcag tacaacagcacgtaccgtgtggtcagcgtcctcaccgtcctgcac caggactggctgaatggcaaggagtacaagtgcaaggtctccaac -continued aaagccctcccagcccccatcgagaaaaccatctccaaagccaaa
gggcagccccgagaaccacaggtgtacaccctgcccccatcccgg
gaggagatgaccaagaaccaggtcagcctgacctgcctggtcaaa
ggcttctatcccagcgacatcgccgtggagtgggagagcaatggg
cagccggagaacaactacaagaccacgcctcccgtgctggactcc
gacggctccttcttcctctatagcaagctcaccgtggacaagagc
aggtggcagcaggggaacgtcttctcatgctccgtgatgcatgag
gctctgcacaaccactacacgcagaagagcctctccctgtctccg
ggtaaatga Amino acid sequence of the HC of the anti-DNP IgG1 antibody

SEQ ID NO: 80

QVQLQESGPGLVKPLQTLSLTCTVSGGSISSGGYYWSWIRQHPGK
GLEWIGYIYYSRSTYYNPSLKSRVTISVDTSKNQFSLKLSSVTAA
DTAVYYCARTGYSSGWYPFDYWGQGTLVTVSSASTKGPSVFPLAP
SSKSTSGGTAALGCLVKDYFPEPVTVSWNSGALTSGVHTFPAVLQ
SSGLYSLSSVVTVPSSSLGTQTYICNVNHKPSNTKVDKKVEPKSC
DKTHTCPPCPAPELLGGPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSR
EEMTKNQVSLTCLVKGFYPSDIAVEWESNGQPENNYKTTPPVLDS
DGSFFLYSKLTVDKSRWQQGNVFSCSVMHEALHNHYTQKSLSLSP
GK

Nucleotide sequence encoding the LC of the anti-DNP IgG1 antibody

SEQ ID NO: 81 gacatccaaatgaccttgtctccttcaagtctttccgctagtgtt
ggagaccgagttaccataacatgccgggctagtcaaggcattagg
aatgatttgggttggtaccaacaaaaacccggcaaagcacctaag
agacttatatacgccgcctccagtcttcagagcggggtaccttcc
cggttcagtggatctggctcagggactgagtttaccctcacaatc
tctagccttcaacctgaagattttgctacatactactgtctccag
tataattcctctccctggacctttggacagggaaccgaagtggaa
ataaaacgtacggtggctgcaccatctgtcttcatcttcccgcca
tctgatgagcagttgaaatctggaactgcctctgttgtgtgcctg
ctgaataacttctatcccagagaggccaaagtacagtggaaggtg
gataacgccctccaatcgggtaactcccaggagagtgtcacagag
caggacagcaaggacagcacctacagcctcagcagcaccctgacg
ctgagcaaagcagactacgagaaacacaaagtctacgcctgcgaa
gtcacccatcagggcctgagctcgcccgtcacaaagagcttcaac
aggggagagtgttgataa -continued Amino acid sequence of the LC of the anti-DNP IgG1 antibody

SEQ ID NO: 82

DIQMTLSPSSLSASVGDRVTITCRASQGIRNDLGWYQQKPGKAPK
RLIYAASSLQSGVPSRFSGSGSGTEFTLTISSLQPEDFATYYCLQ
YNSSPWTFGQGTEVEIKRTVAAPSVFIFPPSDEQLKSGTASVVCL
LNNFYPREAKVQWKVDNALQSGNSQESVTEQDSKDSTYSLSSTLT
LSKADYEKHKVYACEVTHQGLSSPVTKSFNRGEC

Amino acid sequence of VL CDR1 (by Kabat definition) of the humanized anti-hCLDN18.2 clone 59F9E1

SEQ ID NO: 83

KSSQSLLNAGNQKSYLT

Amino acid sequence of VL CDR2 (by Kabat definition) of the humanized anti-hCLDN18.2 clone 59F9E1

SEQ ID NO: 84

WASTRES

Amino acid sequence of VL CDR3 (by Kabat definition) of the humanized anti-hCLDN18.2 clone 59F9E1

SEQ ID NO: 85

QNDYYYPFT

Amino acid sequence of VH CDR1 (by Kabat definition) of the humanized anti-hCLDN18.2 clone 59F9E1

SEQ ID NO: 86

GYWIE

Amino acid sequence of VH CDR2 (by Kabat definition) of the humanized anti-hCLDN18.2 clone 59F9E1

SEQ ID NO: 87

EILLGSGSIKYNVKFKD

Amino acid sequence of VH CDR3 (by Kabat definition) of the humanized anti-hCLDN18.2 clone 59F9E1

SEQ ID NO: 88

KGLRGNSFDY

SEQ ID NOs: 89 to 106 are in Tables 7-13, herein.

Nucleotide sequence encoding IL15 fused to the C-terminal end of an Fc chain (CDDDGD)

SEQ ID NO: 107 gacaaaacacatacatgccctccttgcccagctccagagcttctt
ggcggaccttctgtattcctcttcccaccaaaaccaaaagacaca
cttatgatttcccgcacacctgaagtcacatgcgtggttgtggac
gtgtcacatgaagaccctgaagtgaagttcaactggtatgttgat
ggggtggaggttcacaatgccaaaaccaagccccgagaggaacaa
tacaatagcacatatcgagtagtgtctgtgctgacagtcctgcat
caagattggctcaatggtaaagagtacaaatgtaaagtttccaat
aaggctttgcctgcccctatcgagaaaaccatatctaaggctaaa
ggccaaccacgcgagcctcaggtttgtactttgcctccctcacgt
gaagagatgaccaagaatcaagtagacctgacttgtcttgtggac ggtttctatcctagtgacatcgccgtggagtgggaatcaaatggg caacccgagaatgactatggcaccacccctcccgtacttgacgat gacgggtcctttttttctgtacagtaagttgactgtggataaatct cgctggcaacaagggaatgtcttctcctgtagtgtcatgcacgaa gccctgcataaccactatacacagaagagcttgtccctttctcct gggaagggcggtggtggctcaggaggtgggggggagcggtggcggt ggatccaattgggtcaatgtcattagcgacctgaagaaaatcgaa gacctcatccaatctatgcacattgacgccacactttatactgaa tccgatgtccacccatcttgtaaggttacagccatgaaatgtttt cttctggagcttcaggtcatttcacttgagtccggtgacgcttca atacacgatactgtagagaatcttatcatttggccaacaactca ttgagtagtaatgggaacgttactgagtccggttgtaaggaatgt gaggaacttgaagaaaaaaacataaaagagtttctccagtccttt gtccacattgtgcaaatgttcataaatacttcctgataa Amino acid sequence encoding IL15 fused to the C-terminal end of an Fc chain (CDDDGD)

SEQ ID NO: 108

DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

EEMTKNQVDLTCLVDGFYPSDIAVEWESNGQPENDYGTTPPVLDD

DGSFFLYSKLTVDKSRWQQGNVFSCSVMHEALHNHYTQKSLSLSP

GKGGGGSGGGGSGGGGSNWVNVISDLKKIEDLIQSMHIDATLYTE

SDVHPSCKVTAMKCFLLELQVISLESGDASIHDTVENLIILANNS

LSSNGNVTESGCKECEELEEKNIKEFLQSFVHIVQMFINTS

Nucleotide sequence encoding IL15Ra Sushi domain fused to the C-terminal end of an Fc chain (CKKPKK)

SEQ ID NO: 109 gacaaaacccatacatgtcctccttgccccgcccccgaattgctt gggggtcctagtgtcttcctttttccaccaaagcccaaagacact ttgatgataagccggactcctgaggttacctgcgtagttgtggat gtatcccacgaagatcctgaagtcaaatttaactggtacgtggac ggagtagaagttcataacgccaagacaaagccccgcgaagaacag tacaacagcacctatcgggtagtatccgtcctgactgtccttcat caagactggttgaatggcaaggaatataaatgtaaggttagtaat aaagctcttcccgctccaattgagaagaccatttctaaggctaaa ggacaaccccgcgagccacaagtctacaccttgcctccatgcagg gaagagatgacaaagaaccaagtgaagctgacatgcttggttaaa ggcttctatcccagtgatatcgccgtggagtgggagtcaaacggt cagcctgaaaatccttacaaaactactccccctgttcttgacaag gacggttcattctttttgtattcaaagttgacagtggataagagc agatggcagcagggtaatgtcttttcttgttccgtgatgcatgag gccctgcataaccattacacacaaaagtccctcagcctctcccca ggaaaagggggtggtggaagcggaggaggcggatccataacatgt cctcctcccatgagcgtcgagcatgcagatatatgggttaagagc tactcactctactccagggaacgatatatatgtaattccggtttc aagcgaaaggcaggtactagctcccttacagaatgcgtactgaac aaggcaaccaatgtagctcattggaccaccccaagtctgaagtgt attcgt Amino acid sequence encoding 11_15Ra Sushi domain fused to the C-terminal end of an Fc chain (CKKPKK)

SEQ ID NO: 110

DKTHTCPPCPAPELLGGPSVFLFPPKPKDTLMISRTPEVTCVWDV

SHEDPEVKFNWYVDGVEVHNAKTKPREEQYNSTYRVVSVLTVLHQ

DWLNGKEYKCKVSNKALPAPIEKTISKAKGQPREPQVYTLPPCRE

EMTKNQVKLTCLVKGFYPSDIAVEWESNGQPENPYKTTPPVLDKD

GSFFLYSKLTVDKSRWQQGNVFSCSVMHEALHNHYTQKSLSLSPG

KGGGGSGGGGSITCPPPMSVEHADIWVKSYSLYSRERYICNSGFK

RKAGTSSLTECVLNKATNVAHWTTPSLKCIR

Nucleotide sequence encoding an Fc chain (CDDDGD)

SEQ ID NO: 111 gagccaaaaagctccgataagacacacacttgccccccctgccca gccccagagctgttgggaggcccttctgtattcctcttcccccca aaacccaaggataccctcatgatcagcagaactcccgaggtgact tgcgtcgtcgtggacgtttctcacgaagaccccgaggtaaaattc aactggtacgtggacggagtggaagtacacaatgctaaaactaaa ccccgagaggagcaatataattctacctaccgcgtagtcagtgtg ctgacagttctccatcaagattggcttaacggcaaagagtataag tgcaaggtctcaaataaggcattgccagctcctatagagaaaact attagtaaagcaaaggggcagcctcgtgaaccccaagtctgtact cttcctccttcaagggaggagatgactaaaaaccaagttgatctc acctgtttggtggacggattttatcctagtgatattgctgtggaa tgggagagtaacgggcagcctgagaacgactacggcaccacccca ccagtccttgacgatgatggctcctttttttcctttattcaaagctc actgtagacaaatctcgttggcagcagggaaacgtgttcagttgt tctgttatgcatgaagctcttcataaccactatacccagaaatca ctgagtctgtcacctggcaaatgataa Amino acid sequence encoding an Fc chain (CDDDGD)

SEQ ID NO: 112

EPKSSDKTHTCPPCPAPELLGGPSVFLFPPKPKDTLMISRTPEVT

CVWDVSHEDPEVKFNWYVDGVEVHNAKTKPREEQYNSTYRVVSVL

TVLHQDWLNGKEYKCKVSNKALPAPIEKTISKAKGQPREPQVCTL

PPSREEMTKNQVDLTCLVDGFYPSDIAVEWESNGQPENDYGTTPP

VLDDDGSFFLYSKLTVDKSRWQQGNVFSCSVMHEALHNHYTQKSL

SLSPGK

-continued

Nucleotide sequence encoding an Fc chain (CKKPKK)

SEQ ID NO: 113 gaaccaaaaagtagtgataaaactcacacttgtccccccctgcccc gcacctgagctccttggaggaccttctgtcttcttgtttcccccct aagcctaaagatacattgatgatttccaggactcccgaagtcact tgtgtggtagttgatgttagccatgaggatcccgaggtaaagttc aactggtatgtcgacggagttgaagtacacaatgccaaaactaaa cccagggaggagcagtacaattctacataccgtgttgtctcagtg ctcaccgtccttcaccaagattggcttaacggaaaagaatacaaa tgtaaagtgagcaacaaagccctcccagcccctatcgagaagaca atatctaaagctaagggtcaaccaagggagcctcaggtctacacc ctcccaccatgtagggaggaaatgacaaagaaccaagttaaactg acatgcctggtcaaaggattctacccctcagatattgctgtggaa -continued tgggaaagcaatggtcaacctgagaatccctacaagaccacccca cccgtactggacaaagacggttcattctttctctacagcaaattg actgtggataaaagcaggtggcaacaagggaacgtgttctcctgt tctgtgatgcacgaagcactccacaaccattatacccagaaaagc ctgagtttgtcccctggcaagtgataa Amino acid sequence encoding an Fc chain (CKKPKK)

SEQ ID NO: 114

EPKSSDKTHTCPPCPAPELLGGPSVFLFPPKPKDTLMISRTPEVT

CVWDVSHEDPEVKFNWYVDGVEVHNAKTKPREEQYNSTYRVVSVL

TVLHQDWLNGKEYKCKVSNKALPAPIEKTISKAKGQPREPQVYTL

PPCREEMTKNQVKLTCLVKGFYPSDIAVEWESNGQPENPYKTTPP

VLDKDGSFFLYSKLTVDKSRWQQGNVFSCSVMHEALHNHYTQKSL

SLSPGK

What is claimed is:

1. A variant-Fc-region comprising a set of amino acid substitutions compared to native human IgG1, IgG2, or IgG4, selected from: a first variant-Fc-region comprising S364D, K370D, N390D, K392G and S400D; or a second variant-Fc-region comprising S364K, N390P and S400K, according to EU numbering.

2. The variant-Fc-region of claim 1, further comprising Y349C in the first variant-Fc-region and S354C in the second variant-Fc-region.

3. The variant-Fc-region of claim 1, wherein said variant-Fc-region is a variant-Fc-region-fusion protein further comprising a partner-ligand recombinantly fused thereto at either the N-terminus or C-terminus.

4. The variant-Fc-region fusion protein of claim 3, wherein the partner-ligand is selected from the group consisting of: extracellular domains of receptors, soluble full-length or domain of cytokines, ligands, enzymes, antibody domains, peptides, anti-CD3 scFv, IL-1, IL-2, IL-3, IL-4, IL-5, IL-6, IL-7, IL-8, IL-10, IL-11, IL-12, IL-13, and IL-18, granulocyte CSF (G-CSF), granulocyte-macrophage CSF (GM-CSF), monocyte macrophage CSF (M-CSF), tumor necrosis factor (TNF) alpha and beta, and interferon-α, β, or γ, or mutein cytokines.

5. A substantially pure heterodimeric-variant-Fc-region fusion protein composition, wherein said composition comprises the first and second variant-Fc-region of claim 1.

6. The substantially pure heterodimeric-variant-Fc-region fusion composition of claim 5, wherein the composition is substantially free of homodimeric proteins, and wherein the amount of homodimeric proteins in said composition is less than 5, 4, 3, 2, 1, 0.5, 0.4, 0.3, 0.2, or 0.1%.

7. The substantially pure heterodimeric-variant-Fc-region fusion composition of claim 6, wherein the amount of homodimeric proteins in said composition is less than 2%.

8. The substantially pure heterodimeric-variant-Fc-region fusion composition of claim 6, wherein the amount of homodimeric proteins in said composition is less than 1%.

9. The substantially pure heterodimeric-variant-Fc-region fusion composition of claim 6, wherein the amount of homodimeric proteins in said composition is less than 0.5%.

10. The substantially pure heterodimeric-variant-Fc-region fusion composition of claim 6, wherein the amount of homodimeric proteins in said composition is less than 0.4%.

11. The substantially pure heterodimeric-variant-Fc-region fusion composition of claim 6, wherein the amount of homodimeric proteins in said composition is less than 0.3%.

12. The substantially pure heterodimeric-variant-Fc-region fusion composition of claim 6, wherein the amount of homodimeric proteins in said composition is less than 0.2%.

13. The substantially pure heterodimeric-variant-Fc-region fusion composition of claim 6, wherein the amount of homodimeric proteins in said composition is less than 0.1%.

14. The substantially pure heterodimeric-variant-Fc-region fusion protein composition of claim 5, wherein:

a. only one of the first and second variant-Fc-regions comprises a partner-ligand attached thereto at either the N-terminus or C-terminus;

b. both the first and second variant-Fc-regions comprise the same partner-ligands attached thereto at either the N-terminus or C-terminus; or C. both the first and second variant-Fc-regions comprise different partner-ligands attached thereto at either the N-terminus or C-terminus.

15. The substantially pure heterodimeric-variant-Fc-region fusion protein composition of claim 14, wherein the partner-ligand is selected from the group consisting of: extracellular domains of receptors, soluble full-length or domain of cytokines, ligands, enzymes, antibody domains, peptides, anti-CD3 scFv, IL-1, IL-2, IL-3, IL-4, IL-5, IL-6, IL-7, IL-8, IL-10, IL-11, IL-12, IL-13, and IL-18, granulocyte CSF (G-CSF), granulocyte-macrophage CSF (GM-CSF), monocyte macrophage CSF (M-CSF), tumor necrosis factor (TNF) alpha and beta, and interferon-α, β, or γ, or mutein cytokines.

16. The substantially pure heterodimeric-variant-Fc-region protein composition of claim 5, wherein said composition is selected from a heterodimeric variant-Fc-region monospecific; or a heterodimeric variant-Fc-region bispecific antibody.

17. A heterodimeric variant-Fc-region-bispecific antibody comprising the first and second variant-Fc region of claim 1, said heterodimeric variant-bispecific antibody further comprising:

a. a first and second Heavy Chain (HC) region, wherein the first and second HC regions differ from each other; and b. a first and second Light Chain (LC) region, wherein the first and second LC regions differ from each other.

18. The heterodimeric bispecific antibody of claim 17, wherein the first HC region comprises substitutions K147D, F170C, V173C in its CH1 domain and C220G in upper hinge region of the HC region; the first LC region comprises substitutions S131K, Q160C, S162C and C214S in its Cκ domain; and the first HC and first LC form a cognate pair, whereas no substitution is introduced in the second HC and the second LC.

19. The heterodimeric bispecific antibody of claim 17, wherein no substitution is introduced in the first HC and the first LC, whereas the second HC region comprises substitutions K147D, F170C, V173C in its CH1 domain and C220G in upper hinge region of the HC region; the second LC region comprises substitutions S131K, Q160C, S162C and C214S in its Cκ domain.

20. The heterodimeric bispecific antibody of claim 17, wherein the heterodimeric bispecific antibody is selected from:

a. anti-hCD20×hCD37 comprising an anti-hCD20 VL CDR1, VL CDR2, VL CDR3 set forth in SEQ ID NO:36, or a complete anti-CD20 VL sequence set forth in SEQ ID NO:36; an anti-hCD20 VH CDR1, VH CDR2, and VH CDR3 set forth in SEQ ID NO:30, or a complete anti-CD20 VH sequence set forth in SEQ ID NO:30; an anti-hCD37 VL CDR1, VL CDR2, VL CDR3 set forth in SEQ ID NO:50, or a complete anti-CD37 VL sequence set forth in SEQ ID NO:50; and an anti-hCD37 VH CDR1, VH CDR2, and VH CDR3 set forth in SEQ ID NO:42, or a complete anti-hCD37 VH sequence set forth in SEQ ID NO:42; and b. anti-hSIRPα×hCLDN18.2 comprising an anti-hSIRPα VL CDR1, VL CDR2, VL CDR3 set forth in SEQ ID NO:74, or a complete anti-hSIRPα VL sequence set forth in SEQ ID NO: 74; an anti-hSIRPα VH CDR1, VH CDR2, and VH CDR3 set forth in SEQ ID NO:70, or a complete anti-hSIRPα VH sequence set forth in SEQ ID NO:70; an anti-hCLDN18.2 VL CDR1, VL CDR2, VL CDR3 set forth in SEQ ID NO:64, or a complete anti-hCLDN18.2 VL sequence set forth in SEQ ID NO:64; and an anti-hCLDN18.2 VH CDR1, VH CDR2, and VH CDR3 set forth in SEQ ID NO:58, or a complete anti-hCLDN18.2 VH sequence set forth in SEQ ID NO:58.

21. The heterodimeric bispecific antibody of claim 17, corresponding to an anti-hCD20×hCD37, selected from the group consisting of:

a. the first HC region corresponding to anti-hCD37 Ab1.A1.2 HC (SEQ ID NO:42); the first LC region corresponding to anti-hCD37 Ab1.A1.1 LC (SEQ ID NO: 50); the second HC region corresponding to anti-hCD20 Ab1.2.5 HC (SEQ ID NO: 30); and the second LC region corresponding to anti-hCD20 Ab1.2 (SEQ ID NO: 36); and b. the first HC region corresponding to anti-hCD37 Ab1.A1.3 HC (SEQ ID NO:44); the first LC region corresponding to anti-hCD37 Ab1.A1.ILC (SEQ ID NO: 50); the second HC region corresponding to anti-hCD20 Ab1.2.6 HC (SEQ ID NO: 32); and the second LC region corresponding to anti-hCD20 Ab1.2 (SEQ ID NO: 36).

22. The heterodimeric bispecific antibody of claim 17, corresponding to an anti-hSIRPα×hCLDN18.2, selected from the group consisting of:

a. the first HC region corresponding to anti-hCLDN18.2 HC1 (SEQ ID NO:58); the first LC region corresponding to anti-hCLDN18.2 LC1 (SEQ ID NO: 64); the second HC region corresponding to anti-hSIRPα HC2 (SEQ ID NO:70); and the second LC region corresponding to anti-hSIRPα LC2 (SEQ ID NO:74).

23. A host cell line that produces the variant-Fc-region, variant-Fc-region fusion protein or heterodimeric-variant-Fc-region antibody of claim 1.

24. The host cell line of claim 23, which is a mammalian cell line.

25. The host cell line of claim 24, which is a CHO cell line.

26. One or more nucleic acid(s) encoding the variant-Fc-region, variant-Fc-region fusion protein or heterodimeric-variant-Fc-region antibody of claim 1.

27. One or more vector(s) containing the nucleic acid(s) of claim 26.

28. The vector(s) of claim 27, each of which is a mammalian expression vector.

29. The vector(s) of claim 27, each of which is a viral vector.

30. The vector(s) of claim 29, each of which is an adenovirus, an adeno-associated virus (AAV), a retrovirus, a vaccinia virus, a modified vaccinia virus Ankara (MVA), a herpes virus, a lentivirus, or a poxvirus vector.

31. A host cell line containing the nucleic acid(s) and/or the vector(s) of claim 26.

32. A substantially pure heterodimeric-variant-Fc-region antibody composition, comprising a set of amino acid substitutions compared to native human IgG1, IgG2, or IgG4, wherein said composition comprises:

a heterodimeric-variant-Fc-region antibody comprising a first variant Fc-region having 4 variant negative charge residues at specified residues on the CH3 region; and comprising a second variant Fc-region having 2 variant and 2 native positive charge residues at the corresponding-specified residues on the CH3 region as in the first Fc-region, wherein an amount of homodimeric antibodies in said composition is less than 5, 4, 3, 2, 1, 0.5, 0.4, 0.3, 0.2, or 0.1%, wherein the first variant Fc-region comprises K392G and has 4 variant negative charge residues comprising S364D, K370D, N390D, and S400D, according to EU numbering.

33. The composition of claim 32, wherein the second variant Fc-region comprises N390P and has 2 variants and 2 native positive charge residues comprising S364K, 370K, 392K, and S400K.

34. The composition of claim 10, further comprising a variant cysteine residue in the CH3 region of the first and second variant Fc-regions.

35. The composition of claim 34, wherein the variant cysteine residue in the CH3 region of the first variant Fc-region corresponds to Y349C.

36. The composition of claim 34, wherein the variant cysteine residue in the CH3 region of the second variant Fc-region corresponds to S354C.

37. The substantially pure heterodimeric-variant-Fc-region antibody composition of claim 32, wherein the amount of homodimeric proteins in said composition is less than 2%.

38. The substantially pure heterodimeric-variant-Fc-region antibody composition of claim 32, wherein the amount of homodimeric proteins in said composition is less than 1%.

39. The substantially heterodimeric-variant-Fc-region antibody composition of claim 32, wherein the amount of homodimeric proteins in said composition is less than 0.5%.

40. The substantially pure heterodimeric-variant-Fc-region antibody composition of claim 32, wherein the amount of homodimeric proteins in said composition is less than 0.4%.

41. The substantially pure heterodimeric-variant-Fc-region antibody composition of claim 32, wherein the amount of homodimeric proteins in said composition is less than 0.3%.

42. The substantially pure heterodimeric-variant-Fc-region antibody composition of claim 32, wherein the amount of homodimeric proteins in said composition is less than 0.2%.

43. The substantially pure heterodimeric-variant-Fc-region antibody composition of claim 32, wherein the amount of homodimeric proteins in said composition is less than 0.1%.

44. A humanized anti-hCLDN18.2 monoclonal antibody, wherein said antibody comprises a variable heavy chain (VH) amino acid sequence corresponding to SEQ ID NO:52; and a variable light chain (VL) amino acid sequence corresponding to SEQ ID NO: 60.

45. The humanized anti-hCLDN18.2 monoclonal antibody of claim 44, further comprising a heavy chain (HC) amino acid sequence selected from SEQ ID NO:54, SEQ ID NO: 56 or SEQ ID NO:58; and a light chain (LC) amino acid sequence corresponding to SEQ ID NO:64.

46. The humanized anti-hCLDN18.2 monoclonal antibody of claim 45, wherein said antibody comprises a heavy chain (HC) amino acid sequence corresponding to SEQ ID NO:58.

* * * * *

SEQUENCE LISTING

```
Sequence total quantity: 114
SEQ ID NO: 1            moltype = DNA  length = 321
FEATURE                 Location/Qualifiers
source                  1..321
                        mol_type = other DNA
                        note = anti-HER2 humAb4D5-8 VL (WT)
                        organism = synthetic construct
SEQUENCE: 1
gatattcaga tgacccagag cccgagcagc ctgagcgcga gcgtgggcga tcgcgtgacc  60
attacctgcc gcgcgagcca ggatgtgaac accgcggtgg cgtggtatca gcagaaacca  120
ggcaaagcgc cgaaactgct gatttatagc gcgagcttcc tgtatagcgg cgtgccgagc  180
cgcttcagcg gcagccgcag cggcaccgat ttcaccctga ccattagcag cctgcagccg  240
gaagatttcg cgacctatta ttgccagcag cattatacca ccccgccgac cttcggccag  300
ggcaccaaag tggaaattaa a                                            321

SEQ ID NO: 2            moltype = AA  length = 107
FEATURE                 Location/Qualifiers
source                  1..107
                        mol_type = protein
                        note = anti-HER2 humAb4D5-8 VL (WT)
                        organism = synthetic construct
SEQUENCE: 2
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIK                107

SEQ ID NO: 3            moltype = DNA  length = 645
FEATURE                 Location/Qualifiers
source                  1..645
                        mol_type = other DNA
                        note = anti-HER2 humAb4D5-8 LC (WT)
                        organism = synthetic construct
SEQUENCE: 3
gatattcaga tgacccagag cccgagcagc ctgagcgcga gcgtgggcga tcgcgtgacc  60
attacctgcc gcgcgagcca ggatgtgaac accgcggtgg cgtggtatca gcagaaacca  120
ggcaaagcgc cgaaactgct gatttatagc gcgagcttcc tgtatagcgg cgtgccgagc  180
cgcttcagcg gcagccgcag cggcaccgat ttcaccctga ccattagcag cctgcagccg  240
gaagatttcg cgacctatta ttgccagcag cattatacca ccccgccgac cttcggccag  300
ggcaccaaag tggaaattaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 4            moltype = AA  length = 214
FEATURE                 Location/Qualifiers
source                  1..214
                        mol_type = protein
                        note = anti-HER2 humAb4D5-8 LC (WT)
```

```
                         organism = synthetic construct
SEQUENCE: 4
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 5             moltype = DNA  length = 360
FEATURE                  Location/Qualifiers
source                   1..360
                         mol_type = other DNA
                         note = anti-HER2 humAb4D5-8 VH (WT)
                         organism = synthetic construct
SEQUENCE: 5
gaagtccaac tggtagagtc gggaggtggc ttggtacagc ccggtgggtc cttgcgactc  60
agctgcgccg cttcgggatt caacatcaaa gacacttaca ttcactgggt gcggcaggca  120
ccggggaagg ggcttgagtg ggtcgccaga atctacccta cgaatggcta tacgcgctac  180
gcggattcag tgaaagggag gtttaccatt tcggcggaca catcgaagaa tacagcatat  240
ctccagatga acagccttcg ggccgaagat accgcggtgt attactgttc cagatgggga  300
ggagatgggt tctatgcgat ggactactgg ggacagggaa cactggtaac cgtctctagt  360

SEQ ID NO: 6             moltype = AA  length = 120
FEATURE                  Location/Qualifiers
source                   1..120
                         mol_type = protein
                         note = anti-HER2 humAb4D5-8 VH (WT)
                         organism = synthetic construct
SEQUENCE: 6
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120

SEQ ID NO: 7             moltype = DNA  length = 1353
FEATURE                  Location/Qualifiers
source                   1..1353
                         mol_type = other DNA
                         note = anti-HER2 humAb4D5-8 IgG1 HC (WT)
                         organism = synthetic construct
SEQUENCE: 7
gaagtccaac tggtagagtc gggaggtggc ttggtacagc ccggtgggtc cttgcgactc  60
agctgcgccg cttcgggatt caacatcaaa gacacttaca ttcactgggt gcggcaggca  120
ccggggaagg ggcttgagtg ggtcgccaga atctacccta cgaatggcta tacgcgctac  180
gcggattcag tgaaagggag gtttaccatt tcggcggaca catcgaagaa tacagcatat  240
ctccagatga acagccttcg ggccgaagat accgcggtgt attactgttc cagatgggga  300
ggagatgggt tctatgcgat ggactactgg ggacagggaa cactggtaac cgtctctagt  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa tga                              1353

SEQ ID NO: 8             moltype = AA  length = 450
FEATURE                  Location/Qualifiers
source                   1..450
                         mol_type = protein
                         note = anti-HER2 humAb4D5-8 IgG1 HC (WT)
                         organism = synthetic construct
SEQUENCE: 8
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 9             moltype = DNA  length = 321
```

```
FEATURE                 Location/Qualifiers
source                  1..321
                        mol_type = other DNA
                        note = Nucleotide sequence encoding the VL domain of the
                         anti-HER2 humAb2C4 (WT)
                        organism = synthetic construct
SEQUENCE: 9
gacatccaga tgacccagag ccccagcagc ctgtctgcca gcgtgggcga cagagtgacc  60
atcacatgca aggccagcca ggacgtgtcc atcggcgtgg cctggtatca gcagaagccc  120
ggcaaggccc ccaagctgct gatctacagc gccagctacc ggtacaccgg cgtgcccagc  180
agattttctg gcagcggctc cggcaccgac ttcaccctga caatcagctc cctgcagccc  240
gaggacttcg ccacctacta ctgccagcag tactacatct acccctacac cttcggccag  300
ggcaccaagg tggaaatcaa g                                            321

SEQ ID NO: 10           moltype = AA  length = 107
FEATURE                 Location/Qualifiers
source                  1..107
                        mol_type = protein
                        note = Amino acid sequence of the VL domain of the
                         anti-HER2 humAb2C4 (WT)
                        organism = synthetic construct
SEQUENCE: 10
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIK                107

SEQ ID NO: 11           moltype = DNA  length = 645
FEATURE                 Location/Qualifiers
source                  1..645
                        mol_type = other DNA
                        note = Nucleotide sequence encoding the LC of the anti-HER2
                         humAb2C4(WT)
                        organism = synthetic construct
SEQUENCE: 11
gacatccaga tgacccagag ccccagcagc ctgtctgcca gcgtgggcga cagagtgacc  60
atcacatgca aggccagcca ggacgtgtcc atcggcgtgg cctggtatca gcagaagccc  120
ggcaaggccc ccaagctgct gatctacagc gccagctacc ggtacaccgg cgtgcccagc  180
agattttctg gcagcggctc cggcaccgac ttcaccctga caatcagctc cctgcagccc  240
gaggacttcg ccacctacta ctgccagcag tactacatct acccctacac cttcggccag  300
ggcaccaagg tggaaatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttag                  645

SEQ ID NO: 12           moltype = AA  length = 214
FEATURE                 Location/Qualifiers
source                  1..214
                        mol_type = protein
                        note = Amino acid sequence of the LC of the anti-HER2
                         humAb2C4 (WT)
                        organism = synthetic construct
SEQUENCE: 12
DIQMTQSPSS LSASVGDRVT ITCKASQDVS IGVAWYQQKP GKAPKLLIYS ASYRYTGVPS  60
RFSGSGSGTD FTLTISSLQP EDFATYYCQQ YYIYPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 13           moltype = DNA  length = 357
FEATURE                 Location/Qualifiers
source                  1..357
                        mol_type = other DNA
                        note = Nucleotide sequence encoding the VH domain of the
                         anti-HER2 humAb2C4 (WT)
                        organism = synthetic construct
SEQUENCE: 13
gaagtgcagc tggtggaatc tggcggcgga ctggtgcagc ctggcggatc tctgagactg  60
agctgtgccg ccagcggctt caccttcacc gactacacca tggactgggt gcgccaggcc  120
cctggcaagg gcctggaatg ggtggccgac gtgaacccca atagcggcgg cagcatctac  180
aaccagcggt tcaagggccg gttcaccctg agcgtggaca gaagcaagaa caccctgtac  240
ctgcagatga acagcctgcg ggccgaggac accgccgtgt actactgcgc cagaaacctg  300
ggccccagct tctacttcga ctactggggc cagggcaccc tcgtgaccgt gtcatct     357

SEQ ID NO: 14           moltype = AA  length = 119
FEATURE                 Location/Qualifiers
source                  1..119
                        mol_type = protein
                        note = Amino acid sequence of the VH domain of the
                         anti-HER2 humAb2C4 (WT)
```

```
                          organism = synthetic construct
SEQUENCE: 14
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSS   119

SEQ ID NO: 15             moltype = DNA  length = 1350
FEATURE                   Location/Qualifiers
source                    1..1350
                          mol_type = other DNA
                          note = Nucleotide sequence encoding the HC of the anti-HER2
                           humAb2C4 IgG1 (WT)
                          organism = synthetic construct
SEQUENCE: 15
gaagtgcagc tggtggaatc tggcggcgga ctggtgcagc ctggcggatc tctgagactg  60
agctgtgccg ccagcggctt caccttcacc gactacacca tggactgggt gcgccaggcc  120
cctggcaagg gcctggaatg ggtggccgac gtgaacccca atagcggcgg cagcatctac  180
aaccagcggt tcaagggccg gttcaccctg agcgtggaca gaagcaagaa caccctgtac  240
ctgcagatga acagcctgcg ggccgaggac accgccgtgt actactgcgc cagaaacctg  300
ggccccagct tctacttcga ctactggggc cagggcaccc tcgtgaccgt gtcatctgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                  1350

SEQ ID NO: 16             moltype = AA  length = 449
FEATURE                   Location/Qualifiers
source                    1..449
                          mol_type = protein
                          note = Amino acid sequence of the HC of the anti-HER2
                           humAb2C4 IgG1 (WT)
                          organism = synthetic construct
SEQUENCE: 16
EVQLVESGGG LVQPGGSLRL SCAASGFTFT DYTMDWVRQA PGKGLEWVAD VNPNSGGSIY  60
NQRFKGRFTL SVDRSKNTLY LQMNSLRAED TAVYYCARNL GPSFYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 17             moltype = DNA  length = 1353
FEATURE                   Location/Qualifiers
source                    1..1353
                          mol_type = other DNA
                          note = DNA sequence encoding anti-HER2 humAb4D5-8 IgG1 HC
                           (CDDDGD)
                          organism = synthetic construct
SEQUENCE: 17
gaagtccaac tggtagagtc gggaggtggc ttggtacagc ccggtgggtc cttgcgactc  60
agctgcgccg cttcgggatt caacatcaaa gacacttaca ttcactgggt gcggcaggca  120
ccggggaagg ggcttgagtg ggtcgccaga atctacccta cgaatggcta tacgcgctac  180
gcggattcag tgaaagggag gtttaccatt tcggcggaca catcgaagaa tacagcatat  240
ctccagatga acagccttcg ggccgaagat accgcggtgt attactgttc cagatgggga  300
ggagatgggt tctatgcgat ggactactgg ggacagggaa cactggtaac cgtctctagt  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
```

```
aaagccaaag ggcagccccg agaaccacag gtgtgcaccc tgcccccatc ccgggaggag  1080
atgaccaaga accaggtcga cctgacctgc ctggtcgacg gcttctatcc cagcgacatc  1140
gccgtggagt gggagagcaa tgggcagccg gagaacgact acggcaccac gcctcccgtg  1200
ctggacgacg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa tga                               1353

SEQ ID NO: 18          moltype = AA  length = 450
FEATURE                Location/Qualifiers
source                 1..450
                       mol_type = protein
                       note = Amino acid sequence of anti-HER2 humAb4D5-8 IgG1 HC
                        (CDDDGD)
                       organism = synthetic construct
SEQUENCE: 18
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VCTLPPSREE  360
MTKNQVDLTC LVDGFYPSDI AVEWESNGQP ENDYGTTPPV LDDDGSFFLY SKLTVDKSRW  420
QQGNVFSCSV MHEALHNHYT QKSLSLSPGK                                  450

SEQ ID NO: 19          moltype = DNA  length = 1353
FEATURE                Location/Qualifiers
source                 1..1353
                       mol_type = other DNA
                       note = Nucleotide sequence encoding the anti-HER2
                        humAb4D5-8 IgG1 HC (CKKPKK)
                       organism = synthetic construct
SEQUENCE: 19
gaagtccaac tggtagagtc gggaggtggc ttggtacagc ccggtgggtc cttgcgactc  60
agctgcgccg cttcgggatt caacatcaaa gacacttaca ttcactgggt gcggcaggca  120
ccggggaagg ggcttgagtg ggtcgccaga atctacccta cgaatggcta tacgcgctac  180
gcggattcag tgaaagggag gtttaccatt tcggcggaca catcgaagaa tacagcatat  240
ctccagatga acagccttcg ggccgaagat accgcggtgt attactgttc cagatgggga  300
ggagatgggt tctatgcgat ggactactgg ggacagggaa cactggtaac cgtctctagt  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtgtacaccc tgcccccatg ccgggaggag  1080
atgaccaaga accaggtcaa gctgacctgc ctggtcaagg gcttctatcc cagcgacatc  1140
gccgtggagt gggagagcaa tgggcagccg gagaacccct acaagaccac gcctcccgtg  1200
ctggacaagg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa tga                               1353

SEQ ID NO: 20          moltype = AA  length = 450
FEATURE                Location/Qualifiers
source                 1..450
                       mol_type = protein
                       note = anti-HER2 humAb4D5-8 IgG1 HC (CKKPKK)
                       organism = synthetic construct
SEQUENCE: 20
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPCREE  360
MTKNQVKLTC LVKGFYPSDI AVEWESNGQP ENPYKTTPPV LDKDGSFFLY SKLTVDKSRW  420
QQGNVFSCSV MHEALHNHYT QKSLSLSPGK                                  450

SEQ ID NO: 21          moltype = DNA  length = 699
FEATURE                Location/Qualifiers
source                 1..699
                       mol_type = other DNA
                       note = Dummy Fc (C220G and CDDDGD)
                       organism = synthetic construct
SEQUENCE: 21
```

-continued

```
gagcccaaat ctggtgacaa aactcacaca tgcccaccgt gcccagcacc tgaactcctg  60
gggggaccgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt gcaccctgcc cccatcccgg  420
gaggagatga ccaagaacca ggtcgacctg acctgcctgg tcgatggctt ctatcccagc  480
gacatcgccg tggagtggga gagcaatggg cagccggaga acgactacgg gaccacgcct  540
cccgtgctgg acgacgacgg ctccttcttc ctctatagca agctcaccgt ggacaagagc  600
aggtggcagc aggggaacgt cttctcatgc tccgtgatgc atgaggctct gcacaaccac  660
tacacgcaga agagcctctc cctgtctccg ggtaaatga                         699

SEQ ID NO: 22          moltype = AA  length = 232
FEATURE                Location/Qualifiers
source                 1..232
                       mol_type = protein
                       note = Dummy Fc (C220G and CDDDGD)
                       organism = synthetic construct
SEQUENCE: 22
EPKSGDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR EEMTKNQVDL TCLVDGFYPS DIAVEWESNG QPENDYGTTP  180
PVLDDDGSFF LYSKLTVDKS RWQQGNVFSC SVMHEALHNH YTQKSLSLSP GK          232

SEQ ID NO: 23          moltype = DNA  length = 699
FEATURE                Location/Qualifiers
source                 1..699
                       mol_type = other DNA
                       note = Dummy Fc (C220G and CKKPKK)
                       organism = synthetic construct
SEQUENCE: 23
gagcccaaat ctggtgacaa aactcacaca tgcccaccgt gcccagcacc tgaactcctg  60
gggggaccgt cagtcttcct cttcccccca aaacccaagg acaccctcat gatctcccgg  120
acccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatgccgg  420
gaggagatga ccaagaacca ggtcaagctg acctgcctgg tcaagggctt ctatcccagc  480
gacatcgccg tggagtggga gagcaatggg cagccggaga acccctacaa gaccacgcct  540
cccgtgctgg acaaggacgg ctccttcttc ctctatagca agctcaccgt ggacaagagc  600
aggtggcagc aggggaacgt cttctcatgc tccgtgatgc atgaggctct gcacaaccac  660
tacacgcaga agagcctctc cctgtctccg ggtaaatga                         699

SEQ ID NO: 24          moltype = AA  length = 232
FEATURE                Location/Qualifiers
source                 1..232
                       mol_type = protein
                       note = Dummy Fc (C220G and CKKPKK)
                       organism = synthetic construct
SEQUENCE: 24
EPKSGDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPCR EEMTKNQVKL TCLVKGFYPS DIAVEWESNG QPENPYKTTP  180
PVLDKDGSFF LYSKLTVDKS RWQQGNVFSC SVMHEALHNH YTQKSLSLSP GK          232

SEQ ID NO: 25          moltype = DNA  length = 366
FEATURE                Location/Qualifiers
source                 1..366
                       mol_type = other DNA
                       note = Nucleotide sequence encoding the VH of anti-hCD20
                        antibodies Ab1.2, Ab1.2.2.1, Ab1.2.5, Ab1.2.6
                       organism = synthetic construct
SEQUENCE: 25
caggtgcagc tggtgcagtc tggcgccgag gtgaagaaac ctggctcttc agtgaaggtg  60
tcctgcaagg cttccggcta cacattcacc agctacaaca tgcactgggt ccggcaggcc  120
cctggacaag gattagaatg gatgggcgct atctaccccg gcaacggcga cacctcttac  180
aaccagaaat tccagggcag agtgaccctg accgtggaca agtcctcttc caccgcctac  240
atggaactga gctccctgag atccgaggat accgccgtgt acttctgtgc cagagtggtg  300
tactactcca actcctactg gtacttcgac gtgtggggca ccggcactat ggtcacagtt  360
tcctct                                                             366

SEQ ID NO: 26          moltype = AA  length = 122
FEATURE                Location/Qualifiers
source                 1..122
                       mol_type = protein
                       note = Amino acid sequence of the VH of anti-hCD20
                        antibodies Ab1.2, Ab1.2.2.1, Ab1.2.5, Ab1.2.6
```

```
                         organism = synthetic construct
SEQUENCE: 26
QVQLVQSGAE VKKPGSSVKV SCKASGYTFT SYNMHWVRQA PGQGLEWMGA IYPGNGDTSY  60
NQKFQGRVTL TVDKSSSTAY MELSSLRSED TAVYFCARVV YYSNSYWYFD VWGTGTMVTV  120
SS                                                                 122

SEQ ID NO: 27            moltype = DNA  length = 1350
FEATURE                  Location/Qualifiers
source                   1..1350
                         mol_type = other DNA
                         note = Nucleotide sequence encoding the HC of anti-hCD20
                          Ab1.2 IgG (WT), having CH1 domain and upper hinge from
                          IgG4, and hinge, CH2, CH3 from IgG1
                         organism = synthetic construct
SEQUENCE: 27
caggtgcagc tggtgcagtc tggcgccgaa gtgaagaaac ccggctcctc cgtgaaggtg  60
tcctgcaagg cctccggcta cacctttacc agctacaaca tgcactgggt gcgacaggcc  120
cctggacagg gcctggaatg gatgggcgct atctaccctg gcaacggcga cacctcctac  180
aaccagaaat tccagggcag agtgaccctg accgtggaca agtcctcctc caccgcctac  240
atggaactgt cctccctgcg gagcgaggat accgccgtgt acttctgtgc ccgggtggtg  300
tactactcca actcctactg gtacttcgac gtgtggggca ccggcacaat ggtcaccgtg  360
tcctccgcta gcaccaaggg gccatccgtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggcccccc atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                   1350

SEQ ID NO: 28            moltype = AA  length = 449
FEATURE                  Location/Qualifiers
source                   1..449
                         mol_type = protein
                         note = Amino acid sequence of the HC of anti-hCD20 Ab1.2
                          IgG (WT), having CH1 domain and upper hinge from IgG4, and
                          hinge, CH2, CH3 from IgG1
                         organism = synthetic construct
SEQUENCE: 28
QVQLVQSGAE VKKPGSSVKV SCKASGYTFT SYNMHWVRQA PGQGLEWMGA IYPGNGDTSY  60
NQKFQGRVTL TVDKSSSTAY MELSSLRSED TAVYFCARVV YYSNSYWYFD VWGTGTMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 29            moltype = DNA  length = 1350
FEATURE                  Location/Qualifiers
source                   1..1350
                         mol_type = other DNA
                         note = Nucleotide sequence encoding the HC of anti-hCD20
                          Ab1.2.5 IgG (CDDDGD), having CH1 domain and upper hinge
                          from IgG4, and substitutions CDDDGD in IgG1 CH3 for
                          heterodimer formation
                         organism = synthetic construct
SEQUENCE: 29
caggtgcagc tggtgcagtc tggcgccgag gtgaagaaac ctggctcttc agtgaaggtg  60
tcctgcaagg cttccggcta cacattcacc agctacaaca tgcactgggt ccggcaggcc  120
cctggacaag gattagaatg gatgggcgct atctaccccg gcaacggcga cacctcttac  180
aaccagaaat tccagggcag agtgaccctg accgtggaca agtcctcttc caccgcctac  240
atggaactga gctccctgag atccgaggat accgccgtgt acttctgtgc cagagtggtg  300
tactactcca actcctactg gtacttcgac gtgtggggca ccggcactat ggtcacagtt  360
tcctctgcca gcaccaaggg acccagcgtt ttccctctgg ctccttgctc cagatccacc  420
tctgagtcca cagctgctct gggctgcctg gtcaaggact actttccaga gccagtgacc  480
gtgtcctgga actctggcgc tctgacatct ggcgtgcaca cattccctgc tgtgctgcag  540
tcatctggcc tgtactctct gtcctctgtc gtgaccgtgc ctagctcctc cctgggcacc  600
aagacctaca cctgtaatgt ggaccacaag ccttccaaca ccaaggtgga caagcgcgtg  660
gaatctaagt acggcccacc atgcccaccg tgcccagcac ctgaactcct gggcggaccg  720
```

```
tcagtcttcc tcttccctcc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tgcaccctgc ccccatcccg ggaggagatg  1080
accaagaacc aggtggacct gacctgcctg gtggacggct tctatcccag cgacatcgcc  1140
gtggagtggg agagcaatgg gcagccggag aacgactacg gcaccacgcc tcccgtgctg  1200
gacgacgacg gctccttctt cctctatagc aagctcaccg tggacaagag caggtggcag  1260
caggggaacg tcttctcatg ctccgtgatg catgaggctc tgcacaacca ctacacgcag  1320
aaaagcctct ccctgtctcc gggtaaataa                                   1350

SEQ ID NO: 30          moltype = AA  length = 449
FEATURE                Location/Qualifiers
source                 1..449
                       mol_type = protein
                       note = Amino acid sequence of the HC of anti-hCD20 Ab1.2.5
                        IgG (CDDDGD), having CH1 domain and upper hinge from IgG4,
                        and substitutions CDDDGD in IgG1 CH3 for heterodimer
                        formation
                       organism = synthetic construct
SEQUENCE: 30
QVQLVQSGAE VKKPGSSVKV SCKASGYTFT SYNMHWVRQA PGQGLEWMGA IYPGNGDTSY  60
NQKFQGRVTL TVDKSSSTAY MELSSLRSED TAVYFCARVV YYSNSYWYFD VWGTGTMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV CTLPPSREEM  360
TKNQVDLTCL VDGFYPSDIA VEWESNGQPE NDYGTTPPVL DDDGSFFLYS KLTVDKSRWQ  420
QGNVFSCSVM HEALHNHYTQ KSLSLSPGK                                    449

SEQ ID NO: 31          moltype = DNA  length = 1350
FEATURE                Location/Qualifiers
source                 1..1350
                       mol_type = other DNA
                       note = Nucleotide sequence encoding the HC of anti-hCD20
                        Ab1.2.6 IgG (CKKPKK), having CH1 domain and upper hinge
                        from IgG4, and substitutions CKKPKK in IgG1 CH3 for
                        heterodimer formation
                       organism = synthetic construct
SEQUENCE: 31
caggtgcagc tggtgcagtc tggcgccgag gtgaagaaac ctggctcttc agtgaaggtg  60
tcctgcaagg cttccggcta cacattcacc agctacaaca tgcactgggt ccggcaggcc  120
cctggacaag gattagaatg gatgggcgct atctaccccg gcaacggcga cacctcttac  180
aaccagaaat tccagggcag agtgaccctg accgtggaca agtcctcttc caccgcctac  240
atggaactga gctccctgag atccgaggat accgccgtgt acttctgtgc cagagtggtg  300
tactactcca actcctactg gtacttcgac gtgtggggca ccggcactat ggtcacagtt  360
tcctctgcca gcaccaaggg acccagcgtt ttccctctgg ctccttgctc cagatccacc  420
tctgagtcca cagctgctct gggctgcctg gtcaaggact actttccaga gccagtgacc  480
gtgtcctgga actctggcgc tctgacatct ggcgtgcaca cattccctgc tgtgctgcag  540
tcatctggcc tgtactctct gtcctctgtc gtgaccgtgc ctagctcctc cctgggcacc  600
aagacctaca cctgtaatgt ggaccacaag ccttccaaca ccaaggtgga caagcgcgtg  660
gaatctaagt acggcccacc atgtcctcca tgtcctgctc cagaactgct cggcggacct  720
tccgtgttcc tgtttcctcc aaagcctaag gacaccctga tgatctctcg gacccctgaa  780
gtgacctgcg tggtggtgga tgtgtctcac gaggatcccg aagtgaagtt caattggtac  840
gtggacggcg tggaagtgca caacgccaag accaagccta gagaggaaca gtacaactcc  900
acctacagag tggtgtccgt gctgaccgtg ctgcaccagg attggctgaa cggcaaagag  960
tacaagtgca aggtgtccaa caaggccctg cctgctccta tcgaaaagac catcagcaag  1020
gccaagggcc agcccaggga accccaggtt tacaccctgc ctccatgccg ggaagagatg  1080
accaagaatc aagtgaagct gacctgtctc gtgaagggct tctacccctc cgacatcgcc  1140
gtggaatggg agtctaatgg ccagcctgag aatccctaca agacaacccc tcctgtgctg  1200
gacaaggacg gctcattctt cctgtactcc aagctgacag tggacaagtc cagatggcag  1260
cagggcaacg tgttctcctg ctccgtgatg cacgaggccc tgcacaatca ctacacccag  1320
aagtccctgt ctctgtcccc tggcaaataa                                   1350

SEQ ID NO: 32          moltype = AA  length = 449
FEATURE                Location/Qualifiers
source                 1..449
                       mol_type = protein
                       note = Amino acid sequence of the HC of anti-hCD20 Ab1.2.6
                        IgG (CKKPKK), having CH1 domain from IgG4, upper hinge
                        from IgG4, and substitutions CKKPKK for heterodimer
                        formation
                       organism = synthetic construct
SEQUENCE: 32
QVQLVQSGAE VKKPGSSVKV SCKASGYTFT SYNMHWVRQA PGQGLEWMGA IYPGNGDTSY  60
NQKFQGRVTL TVDKSSSTAY MELSSLRSED TAVYFCARVV YYSNSYWYFD VWGTGTMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPELLGGP  240
```

-continued

```
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPCREEM  360
TKNQVKLTCL VKGFYPSDIA VEWESNGQPE NPYKTTPPVL DKDGSFFLYS KLTVDKSRWQ  420
QGNVFSCSVM HEALHNHYTQ KSLSLSPGK                                   449

SEQ ID NO: 33           moltype = DNA  length = 318
FEATURE                 Location/Qualifiers
source                  1..318
                        mol_type = other DNA
                        note = Nucleotide sequence encoding the VL of the humanized
                         anti-hCD20 antibodies Ab1.2, Ab1.2.2.1, Ab1.2.5, Ab1.2.6
                        organism = synthetic construct
SEQUENCE: 33
gagatcgtgc tgacccagtc ccccgacttc cagtccgtga cccccaaaga aaaagtgaca  60
attacctgcc gggcctcctc ctccgtgtcc tacatgcact ggtatcagca gaagcccgac  120
cagtccccta agcccctgat ctacgcccct tccaacctgg cctctggcgt gccctctaga  180
ttctccggct ctggctctgg caccgactac accctgacca tcaactccct ggaagccgag  240
gacgccgcca cctactactg ccagcagtgg tccttcaacc cccccacctt tggcgctggc  300
accaagctgg aaatcaag                                               318

SEQ ID NO: 34           moltype = AA  length = 106
FEATURE                 Location/Qualifiers
source                  1..106
                        mol_type = protein
                        note = Amino acid sequence of the VL of the humanized
                         anti-hCD20 antibodies Ab1.2, Ab1.2.2.1, Ab1.2.5, Ab1.2.6
                        organism = synthetic construct
SEQUENCE: 34
EIVLTQSPDF QSVTPKEKVT ITCRASSSVS YMHWYQQKPD QSPKPLIYAP SNLASGVPSR  60
FSGSGSGTDY TLTINSLEAE DAATYYCQQW SFNPPTFGAG TKLEIK                106

SEQ ID NO: 35           moltype = DNA  length = 642
FEATURE                 Location/Qualifiers
source                  1..642
                        mol_type = other DNA
                        note = Nucleotide sequence encoding the LC of the humanized
                         anti-hCD20 antibodies Ab1.2, Ab1.2.2.1, Ab1.2.5, Ab1.2.6
                        organism = synthetic construct
SEQUENCE: 35
gagatcgtgc tgacccagtc ccccgacttc cagtccgtga cccccaaaga aaaagtgaca  60
attacctgcc gggcctcctc ctccgtgtcc tacatgcact ggtatcagca gaagcccgac  120
cagtccccta agcccctgat ctacgcccct tccaacctgg cctctggcgt gccctctaga  180
ttctccggct ctggctctgg caccgactac accctgacca tcaactccct ggaagccgag  240
gacgccgcca cctactactg ccagcagtgg tccttcaacc cccccacctt tggcgctggc  300
accaagctgg aaatcaagcg gaccgtggcc gctccctccg tgttcatctt cccaccttcc  360
gacgagcagc tgaagtccgg caccgcttct gtcgtgtgcc tgctgaacaa cttctacccc  420
cgcgaggcca aggtgcagtg gaaggtggac aacgccctgc agtccggcaa ctcccaggaa  480
tccgtgaccg agcaggactc caaggacagc acctactccc tgtcctctac cctgaccctg  540
tccaaggccg actacgagaa gcacaaggtg tacgcctgcg aagtgaccca ccagggcctg  600
tctagccccg tgaccaagtc tttcaaccgg ggcgagtgct ga                    642

SEQ ID NO: 36           moltype = AA  length = 213
FEATURE                 Location/Qualifiers
source                  1..213
                        mol_type = protein
                        note = Amino acid sequence of the LC of the humanized
                         anti-hCD20 antibodies Ab1.2, Ab1.2.2.1, Ab1.2.5, Ab1.2.6
                        organism = synthetic construct
SEQUENCE: 36
EIVLTQSPDF QSVTPKEKVT ITCRASSSVS YMHWYQQKPD QSPKPLIYAP SNLASGVPSR  60
FSGSGSGTDY TLTINSLEAE DAATYYCQQW SFNPPTFGAG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 37           moltype = DNA  length = 348
FEATURE                 Location/Qualifiers
source                  1..348
                        mol_type = other DNA
                        note = Nucleotide sequence encoding the VH of anti-hCD37
                         antibodies Ab1.A1, Ab1.A1.1, Ab1.A1.2 and Ab1.A1.3
                        organism = synthetic construct
SEQUENCE: 37
caggtgcagc tggttcagtc tggcgccgaa gtgaagaaac ctggcgcctc tgtgaaggtg  60
tcctgcaagg cttctggcta cacctttacc ggctacaacg tgaactgggt ccgacagaac  120
aacggccagc ggctggaatg gatgggcaac atcgatcctt actacggcgg caccacctac  180
aaccggaagt tcaagggcag agtgaccatc accgtggaca cctctgcctc caccgcctac  240
atggaactga agtccctgag atccgaggac accgccgtgt actactgcgc taggtctgtg  300
ggccctatgg actattgggg ccagggaaca ctggtcaccg tgtcctct              348
```

-continued

```
SEQ ID NO: 38          moltype = AA  length = 116
FEATURE                Location/Qualifiers
source                 1..116
                       mol_type = protein
                       note = Amino acid sequence of the VH of anti-hCD37
                        antibodies Ab1.A1, Ab1.A1.1, Ab1.A1.2 and Ab1.A1.3
                       organism = synthetic construct
SEQUENCE: 38
QVQLVQSGAE VKKPGASVKV SCKASGYTFT GYNVNWVRQN NGQRLEWMGN IDPYYGGTTY  60
NRKFKGRVTI TVDTSASTAY MELKSLRSED TAVYYCARSV GPMDYWGQGT LVTVSS      116

SEQ ID NO: 39          moltype = DNA  length = 1341
FEATURE                Location/Qualifiers
source                 1..1341
                       mol_type = other DNA
                       note = Nucleotide sequence encoding the HC of anti-hCD37
                        Ab1.A1 IgG1 (WT)
                       organism = synthetic construct
SEQUENCE: 39
caagtgcagc tcgtccagtc cggggcagag gttaagaagc ccggcgctag tgtgaaggtg  60
agctgcaagg cctctggcta tactttcaca gggtacaacg tgaactgggt gcgccagaac  120
aacggccaac ggttggagtg gatgggtaac atcgatccct actacggggg tactacctac  180
aacaggaaat tcaaaggacg ggtgactatc accgtggaca catctgcttc taccgcctac  240
atggagctga agtctttgcg gtctgaggac accgccgtct attactgtgc cagatccgtg  300
ggccctatgg attattgggg tcaagggacc ctggtgaccg tcagctccgc tagcaccaag  360
ggcccatccg tcttccccct ggcgccctcc tccaagagca cctctggggg cacagcggcc  420
ctgggctgcc tggtcaagga ctacttcccc gaaccggtga cggtgtcgtg gaactcaggc  480
gccctgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagaaag ttgagcccaa atcttgtgac  660
aaaactcaca catgcccacc gtgcccagca cctgaactcc tggggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaatg a                                           1341

SEQ ID NO: 40          moltype = AA  length = 446
FEATURE                Location/Qualifiers
source                 1..446
                       mol_type = protein
                       note = Amino acid sequence of the HC of anti-hCD37 Ab1.A1
                        IgG1 (WT)
                       organism = synthetic construct
SEQUENCE: 40
QVQLVQSGAE VKKPGASVKV SCKASGYTFT GYNVNWVRQN NGQRLEWMGN IDPYYGGTTY  60
NRKFKGRVTI TVDTSASTAY MELKSLRSED TAVYYCARSV GPMDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 41          moltype = DNA  length = 1341
FEATURE                Location/Qualifiers
source                 1..1341
                       mol_type = other DNA
                       note = Nucleotide sequence encoding the HC of anti-hCD37
                        Ab1.A1.2 IgG1 (DCCG + CKKPKK), having DCCG mutations in
                        CH1 domain for cognate LC/HC pairings and substitutions
                        CKKPKK in CH3 domain for heterodimeric Fc formation
                       organism = synthetic construct
SEQUENCE: 41
caggtgcagc tggttcagtc tggcgccgaa gtgaagaaac ctggcgcctc tgtgaaggtg  60
tcctgcaagg cttctggcta cacctttacc ggctacaacg tgaactgggt ccgacagaac  120
aacggccagc ggctggaatg gatgggcaac atcgatcctt actacggcgg caccacctac  180
aaccggaagt tcaagggcag agtgaccatc accgtggaca cctctgcctc caccgcctac  240
atggaactga agtccctgag atccgaggac accgccgtgt actactgcgc taggtctgtg  300
ggccctatgg actattgggg ccagggaaca ctggtcaccg tgtcctctgc tagcaccaag  360
ggcccatccg tcttccccct ggcgccctcc tccaagagca cctctggggg cacagcggcc  420
ctgggctgcc tggtcgatga ctacttcccc gaaccggtga cggtgtcgtg gaactcaggc  480
gccctgacca gcggcgtgca cacatgcccc gcctgcctac agtcctcagg actctactcc  540
```

-continued

```
ctcagcagcg tggtgaccgt gccctccagc agcttgggca cccagaccta catctgcaac  600
gtgaatcaca agcccagcaa caccaaggtg gacaagaaag ttgagcccaa atctggtgac  660
aaaactcaca catgtcctcc atgtcctgct ccagaactgc tcggcggacc ttccgtgttc  720
ctgtttcctc caaagcctaa ggacaccctg atgatctctc ggacccctga agtgacctgc  780
gtggtggtgg atgtgtctca cgaggatccc gaagtgaagt tcaattggta cgtggacggc  840
gtggaagtgc acaacgccaa gaccaagcct agagaggaac agtacaactc cacctacaga  900
gtggtgtccg tgctgaccgt gctgcaccag gattggctga acggcaaaga gtacaagtgc  960
aaggtgtcca acaaggccct gcctgctcct atcgaaaaga ccatcagcaa ggccaagggc  1020
cagcccaggg aaccccaggt ttacaccctg cctccatgcc gggaagagat gaccaagaat  1080
caagtgaagc tgacctgtct cgtgaagggc ttctacccct ccgacatcgc cgtggaatgg  1140
gagtctaatg gccagcctga gaatccctac aagacaaccc ctcctgtgct ggacaaggac  1200
ggctcattct tcctgtactc caagctgaca gtggacaagt ccagatggca gcagggcaac  1260
gtgttctcct gctccgtgat gcacgaggcc ctgcacaatc actacaccca gaagtccctg  1320
tctctgtccc ctggcaaata a                                            1341
```

```
SEQ ID NO: 42          moltype = AA  length = 446
FEATURE                Location/Qualifiers
source                 1..446
                       mol_type = protein
                       note = Amino acid sequence encoding the HC of anti-hCD37
                        Ab1.A1.2 IgG1 (DCCG + CKKPKK), having DCCG mutations in
                        CH1 domain for cognate LC/HC pairings and substitutions
                        CKKPKK in CH3 domain for heterodimer formation
                       organism = synthetic construct
SEQUENCE: 42
QVQLVQSGAE VKKPGASVKV SCKASGYTFT GYNVNWVRQN NGQRLEWMGN IDPYYGGTTY  60
NRKFKGRVTI TVDTSASTAY MELKSLRSED TAVYYCARSV GPMDYWGQGT LVTVSSASTK  120
GPSVFPLAPS SKSTSGGTAA LGCLVDDYFP EPVTVSWNSG ALTSGVHTCP ACLQSSGLYS  180
LSSVVTVPSS SLGTQTYICN VNHKPSNTKV DKKVEPKSGD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPCREEMTKN  360
QVKLTCLVKG FYPSDIAVEW ESNGQPENPY KTTPPVLDKD GSFFLYSKLT VDKSRWQQGN  420
VFSCSVMHEA LHNHYTQKSL SLSPGK                                       446
```

```
SEQ ID NO: 43          moltype = DNA  length = 1341
FEATURE                Location/Qualifiers
source                 1..1341
                       mol_type = other DNA
                       note = Nucleotide sequence encoding the HC of anti-hCD37
                        Ab1.A1.3 IgG1 (DCCG + CDDDGD), having DCCG mutations in
                        CH1 domain for cognate LC/HC pairings and substitutions
                        CDDDGD in CH3 domain for heterodimeric Fc formation
                       organism = synthetic construct
SEQUENCE: 43
caggtgcagc tggttcagtc tggcgccgaa gtgaagaaac ctggcgcctc tgtgaaggtg  60
tcctgcaagg cttctggcta cacctttacc ggctacaacg tgaactgggt ccgacagaac  120
aacggccagc ggctggaatg gatgggcaac atcgatcctt actacggcgg caccacctac  180
aaccggaagt tcaagggcag agtgaccatc accgtggaca cctctgcctc caccgcctac  240
atggaactga agtccctgag atccgaggac accgccgtgt actactgcgc taggtctgtg  300
ggccctatgg actattgggg ccagggaaca ctggtcaccg tgtcctctgc tagcaccaag  360
ggcccatccg tcttccccct ggcgccctcc tccaagagca cctctggggg cacagcggcc  420
ctgggctgcc tggtcgatga ctacttcccc gaaccggtga cggtgtcgtg gaactcaggc  480
gccctgacca gcggcgtgca cacatgcccc gcctgcctac agtcctcagg actctactcc  540
ctcagcagcg tggtgaccgt gccctccagc agcttgggca cccagaccta catctgcaac  600
gtgaatcaca agcccagcaa caccaaggtg gacaagaaag ttgagcccaa atctggtgac  660
aaaactcaca catgcccacc gtgcccagca cctgaactcc tgggcggacc gtcagtcttc  720
ctcttccctc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagccccc atcgagaaaa ccatctccaa agccaaaggg  1020
cagccccgag aaccacaggt gtgcaccctg cccccatccc gggaggagat gaccaagaac  1080
caggtggacc tgacctgcct ggtggacggc ttctatccca gcgacatcgc cgtggagtgg  1140
gagagcaatg ggcagccgga gaacgactac ggcaccacgc ctcccgtgct ggacgacgac  1200
ggctccttct tcctctatag caagctcacc gtggacaaga gcaggtggca gcaggggaac  1260
gtcttctcat gctccgtgat gcatgaggct ctgcacaacc actacacgca gaaaagcctc  1320
tccctgtctc cgggtaaata a                                            1341
```

```
SEQ ID NO: 44          moltype = AA  length = 446
FEATURE                Location/Qualifiers
source                 1..446
                       mol_type = protein
                       note = Amino acid sequence of the HC of anti-hCD37 Ab1.A1.3
                        IgG1 (DCCG + CDDDGD), having DCCG mutations in CH1 domain
                        for cognate LC/HC pairings and substitutions CDDDGD in CH3
                        domain for heterodimeric Fc formation
                       organism = synthetic construct
SEQUENCE: 44
QVQLVQSGAE VKKPGASVKV SCKASGYTFT GYNVNWVRQN NGQRLEWMGN IDPYYGGTTY  60
```

```
NRKFKGRVTI TVDTSASTAY MELKSLRSED TAVYYCARSV GPMDYWGQGT LVTVSSASTK  120
GPSVFPLAPS SKSTSGGTAA LGCLVDDYFP EPVTVSWNSG ALTSGVHTCP ACLQSSGLYS  180
LSSVVTVPSS SLGTQTYICN VNHKPSNTKV DKKVEPKSGD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVCTL PPSREEMTKN  360
QVDLTCLVDG FYPSDIAVEW ESNGQPENDY GTTPPVLDDD GSFFLYSKLT VDKSRWQQGN  420
VFSCSVMHEA LHNHYTQKSL SLSPGK                                       446

SEQ ID NO: 45          moltype = DNA  length = 321
FEATURE                Location/Qualifiers
source                 1..321
                       mol_type = other DNA
                       note = Nucleotide sequence encoding the VL of the humanized
                        anti-hCD37 antibodies Ab1.A1, Ab1.A1.1, Ab1.A1.2, Ab1.A1.3
                       organism = synthetic construct
SEQUENCE: 45
gacatccaga tgacccagtc cccgtcctct ctgagcgcca gtgtcgggga ccgcgtcacc  60
attacctgtc gtaccagtga gaacgtctac aactatctgg cctggtatca gcagaaacca  120
ggcaaggccc ctaagctgtt gatctatttt gcaaagaccc tggctgaagg cgtcccctcc  180
cggtttagcg ggagtggctc cggtacacag tttaccttga caattagcag cctgcagccg  240
gaagactccg cctcctatta ctgtcagcat cacagcgata acccctggac atttggtggg  300
ggcaccgagc tggagatcaa g                                            321

SEQ ID NO: 46          moltype = AA  length = 107
FEATURE                Location/Qualifiers
source                 1..107
                       mol_type = protein
                       note = Amino acid sequence ofthe VL of the humanized
                        anti-hCD37 antibodies Ab1.A1, Ab1.A1.1, Ab1.A1.2, Ab1.A1.3
                       organism = synthetic construct
SEQUENCE: 46
DIQMTQSPSS LSASVGDRVT ITCRTSENVY NYLAWYQQKP GKAPKLLIYF AKTLAEGVPS  60
RFSGSGSGTQ FTLTISSLQP EDSASYYCQH HSDNPWTFGG GTELEIK                107

SEQ ID NO: 47          moltype = DNA  length = 645
FEATURE                Location/Qualifiers
source                 1..645
                       mol_type = other DNA
                       note = Nucleotide sequence encoding the LC of thehumanized
                        anti-hCD37 Ab1.A1 (WT)
                       organism = synthetic construct
SEQUENCE: 47
gacatccaga tgacccagtc cccgtcctct ctgagcgcca gtgtcgggga ccgcgtcacc  60
attacctgtc gtaccagtga gaacgtctac aactatctgg cctggtatca gcagaaacca  120
ggcaaggccc ctaagctgtt gatctatttt gcaaagaccc tggctgaagg cgtcccctcc  180
cggtttagcg ggagtggctc cggtacacag tttaccttga caattagcag cctgcagccg  240
gaagactccg cctcctatta ctgtcagcat cacagcgata acccctggac atttggtggg  300
ggcaccgagc tggagatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttga                  645

SEQ ID NO: 48          moltype = AA  length = 214
FEATURE                Location/Qualifiers
source                 1..214
                       mol_type = protein
                       note = Amino acid sequence of the LC of the humanized
                        anti-hCD37 Ab1.A1 (WT)
                       organism = synthetic construct
SEQUENCE: 48
DIQMTQSPSS LSASVGDRVT ITCRTSENVY NYLAWYQQKP GKAPKLLIYF AKTLAEGVPS  60
RFSGSGSGTQ FTLTISSLQP EDSASYYCQH HSDNPWTFGG GTELEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 49          moltype = DNA  length = 645
FEATURE                Location/Qualifiers
source                 1..645
                       mol_type = other DNA
                       note = Nucleotide sequence encoding the LC of the humanized
                        anti-hCD37 Ab1.A1.1, Ab1.A1.2, Ab1.A1.3 (KCCS)
                       organism = synthetic construct
SEQUENCE: 49
gacatccaga tgacccagtc cccgtcctct ctgagcgcca gtgtcgggga ccgcgtcacc  60
attacctgtc gtaccagtga gaacgtctac aactatctgg cctggtatca gcagaaacca  120
ggcaaggccc ctaagctgtt gatctatttt gcaaagaccc tggctgaagg cgtcccctcc  180
cggtttagcg ggagtggctc cggtacacag tttaccttga caattagcag cctgcagccg  240
```

```
gaagactccg cctcctatta ctgtcagcat cacagcgata acccctggac atttggtggg  300
ggcaccgagc tggagatcaa gcgtacggtg gctgcaccat ctgtcttcat cttcccgcca  360
tctgatgagc agttgaaatc tggaactgcc aaggttgtgt gcctgctgaa taacttctat  420
cccagagagg ccaaagtaca gtggaaggtg gataacgccc tccaatcggg taactcctgc  480
gagtgtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagaga gctga                   645

SEQ ID NO: 50          moltype = AA  length = 214
FEATURE                Location/Qualifiers
source                 1..214
                       mol_type = protein
                       note = Amino acid sequence of the LC of the humanized
                        anti-hCD37 Ab1.A1.1, Ab1.A1.2, Ab1.A1.3 (KCCS)
                       organism = synthetic construct
SEQUENCE: 50
DIQMTQSPSS LSASVGDRVT ITCRTSENVY NYLAWYQQKP GKAPKLLIYF AKTLAEGVPS  60
RFSGSGSGTQ FTLTISSLQP EDSASYYCQH HSDNPWTFGG GTELEIKRTV AAPSVFIFPP  120
SDEQLKSGTA KVVCLLNNFY PREAKVQWKV DNALQSGNSC ECVTEQDSKD STYSLSSTLT  180
LSKADYEKHK VYACEVTHQG LSSPVTKSFN RGES                               214

SEQ ID NO: 51          moltype = DNA  length = 357
FEATURE                Location/Qualifiers
source                 1..357
                       mol_type = other DNA
                       note = Nucleotide sequence encoding the VH of
                        anti-hCLDN18.2 59F9E1
                       organism = synthetic construct
SEQUENCE: 51
caggttcagc tggttcagtc tggcgccgaa gtgaagaaac ctggctcctc cgtgaaggtg  60
tcctgcaagg cttctggcta taccctgacc ggctactgga tcgagtggct gagacagagg  120
cctggacagg gacttgagtg gatgggagag atcctgctcg gctccggctc catcaagtac  180
aacgtgaagt tcaaggaccg cgtgaccatc accgccgacg agtctacctc taccgcctac  240
atggaactgt ccagcctgag atctgaggac accgccgtgt actactgcgc cagaaagggc  300
ctgagaggca actccttcga ttactggggc cagggcacac tggtcaccgt gtcctct     357

SEQ ID NO: 52          moltype = AA  length = 119
FEATURE                Location/Qualifiers
source                 1..119
                       mol_type = protein
                       note = Amino acid sequence of the VH of anti-hCLDN18.2
                        clone 59F9E1
                       organism = synthetic construct
SEQUENCE: 52
QVQLVQSGAE VKKPGSSVKV SCKASGYTLT GYWIEWLRQR PGQGLEWMGE ILLGSGSIKY  60
NVKFKDRVTI TADESTSTAY MELSSLRSED TAVYYCARKG LRGNSFDYWG QGTLVTVSS   119

SEQ ID NO: 53          moltype = DNA  length = 1353
FEATURE                Location/Qualifiers
source                 1..1353
                       mol_type = other DNA
                       note = Nucleotide sequence encoding the HC of humanized
                        anti-hCLDN18.2 clone 59F9E1 IgG1 (WT)
                       organism = synthetic construct
SEQUENCE: 53
caggttcagc tggttcagtc tggcgccgaa gtgaagaaac ctggctcctc cgtgaaggtg  60
tcctgcaagg cttctggcta taccctgacc ggctactgga tcgagtggct gagacagagg  120
cctggacagg gacttgagtg gatgggagag atcctgctcg gctccggctc catcaagtac  180
aacgtgaagt tcaaggaccg cgtgaccatc accgccgacg agtctacctc taccgcctac  240
atggaactgt ccagcctgag atctgaggac accgccgtgt actactgcgc cagaaagggc  300
ctgagaggca actccttcga ttactggggc cagggcacac tggtcaccgt gtcctctgct  360
agcaccaagg gacccagcgt gttccctctg gctccttcca gcaagtctac atccggcgga  420
acagctgctc tgggctgcct ggtcaaggac tactttcctg agcctgtgac cgtgtcttgg  480
aactctggcg ctctgacaag cggcgtgcac acctttccag ctgtgctgca atcctccggc  540
ctgtactctc tgtcctccgt cgtgaccgtg ccttctagct ctctgggcac ccagacctac  600
atctgcaatg tgaaccacaa gccttccaac accaaggtgg acaagaaggt ggaacccaag  660
tcctgcgaca agacccacac ctgtcctcca tgtcctgctc cagaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga tag                                1353
```

-continued

```
SEQ ID NO: 54          moltype = AA  length = 449
FEATURE                Location/Qualifiers
source                 1..449
                       mol_type = protein
                       note = Amino acid sequence of the HC of humanized
                        anti-hCLDN18.2 clone 59F9E1 IgG1 (WT)
                       organism = synthetic construct
SEQUENCE: 54
QVQLVQSGAE VKKPGSSVKV SCKASGYTLT GYWIEWLRQR PGQGLEWMGE ILLGSGSIKY  60
NVKFKDRVTI TADESTSTAY MELSSLRSED TAVYYCARKG LRGNSFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 55          moltype = DNA  length = 1353
FEATURE                Location/Qualifiers
source                 1..1353
                       mol_type = other DNA
                       note = Nucleotide sequence encoding the HC of
                        anti-hCLDN18.2 59F9E1 IgG1 with substitutions 147D, F170C,
                        V173C in CH1 region and C220G in upper hinge region for
                        cognate HC/LC pairing (DCCG)
                       organism = synthetic construct
SEQUENCE: 55
caggttcagc tggttcagtc tggcgccgaa gtgaagaaac ctggctcctc cgtgaaggtg  60
tcctgcaagg cttctggcta taccctgacc ggctactgga tcgagtggct gagacagagg  120
cctggacagg gacttgagtg gatgggagag atcctgctcg gctccggctc catcaagtac  180
aacgtgaagt tcaaggaccg cgtgaccatc accgccgacg agtctacctc taccgcctac  240
atggaactgt ccagcctgag atctgaggac accgccgtgt actactgcgc cagaaagggc  300
ctgagaggca actccttcga ttactggggc cagggcacac tggtcaccgt gtcctctgct  360
agcaccaagg gacccagcgt gttccctctg gctccttcca gcaagtctac atccggcgga  420
acagctgctc tgggctgcct ggtcgacgac tactttcctg agcctgtgac cgtgtcttgg  480
aactctggcg ctctgacaag cggcgtgcac acctgcccag cttgcctgca atcctccggc  540
ctgtactctc tgtcctccgt cgtgaccgtg ccttctagct ctctgggcac ccagacctac  600
atctgcaatg tgaaccacaa gccttccaac accaaggtgg acaagaaggt ggaacccaag  660
tccggcgaca agacccacac ctgtcctcca tgtcctgctc cagaactcct gggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga tag                             1353

SEQ ID NO: 56          moltype = AA  length = 449
FEATURE                Location/Qualifiers
source                 1..449
                       mol_type = protein
                       note = Amino acid sequence of the HC of anti-hCLDN18.2
                        59F9E1 IgG1 with substitutions 147D, F170C, V173C in CH1
                        region and C220G in upper hinge region for cognate HC/LC
                        pairing (DCCG)
                       organism = synthetic construct
SEQUENCE: 56
QVQLVQSGAE VKKPGSSVKV SCKASGYTLT GYWIEWLRQR PGQGLEWMGE ILLGSGSIKY  60
NVKFKDRVTI TADESTSTAY MELSSLRSED TAVYYCARKG LRGNSFDYWG QGTLVTVSSA  120
STKGPSVFPL APSSKSTSGG TAALGCLVDD YFPEPVTVSW NSGALTSGVH TCPACLQSSG  180
LYSLSSVVTV PSSSLGTQTY ICNVNHKPSN TKVDKKVEPK SGDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 57          moltype = DNA  length = 1353
FEATURE                Location/Qualifiers
source                 1..1353
                       mol_type = other DNA
                       note = Nucleotide sequence encoding the HC of
                        anti-hCLDN18.2 59F9E1 IgG1 with substitutions 147D, F170C,
                        V173C, C220G for cognate LC/HC pairing and substitutions
                        Y349C, S364D, K370D, N390D, K392G,S400D to force
                        heterodimer formation (DCCG + CDDDGD)
```

organism = synthetic construct
SEQUENCE: 57
caggttcagc tggttcagtc tggcgccgaa gtgaagaaac ctggctcctc cgtgaaggtg 60
tcctgcaagg cttctggcta taccctgacc ggctactgga tcgagtggct gagacagagg 120
cctggacagg gacttgagtg gatgggagag atcctgctcg gctccggctc catcaagtac 180
aacgtgaagt tcaaggaccg cgtgaccatc accgccgacg agtctacctc taccgcctac 240
atggaactgt ccagcctgag atctgaggac accgccgtgt actactgcgc cagaaagggc 300
ctgagaggca actccttcga ttactggggc cagggcacac tggtcaccgt gtcctctgct 360
agcaccaagg gacccagcgt gttccctctg gctccttcca gcaagtctac atccggcgga 420
acagctgctc tgggctgcct ggtcgacgac tactttcctg agcctgtgac cgtgtcttgg 480
aactctggcg ctctgacaag cggcgtgcac acctgcccag cttgcctgca atcctccggc 540
ctgtactctc tgtcctccgt cgtgaccgtg ccttctagct ctctgggcac ccagacctac 600
atctgcaatg tgaaccacaa gccttccaac accaaggtgg acaagaaggt ggaacccaag 660
tccggcgaca agacccacac ctgtcctcca tgtcctgctc cagaactgct cggcggaccc 720
agcgtgttcc tgtttcctcc aaagcctaag gacaccctga tgatctctcg gacccctgaa 780
gtgacctgcg tggtggtgga tgtgtctcac gaggacccag aagtgaagtt taattggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tgcaccctgc ccccatcccg ggaggagatg 1080
accaagaacc aggtcgacct gacctgcctg gtcgacggct tctatcccag cgacatcgcc 1140
gtggagtggg agagcaatgg gcagccggag aacgactacg gcaccacgcc tcccgtgctg 1200
gacgacgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggcaaatga taa 1353

SEQ ID NO: 58 moltype = AA length = 449
FEATURE Location/Qualifiers
source 1..449
mol_type = protein
note = Amino acid sequence of the HC of anti-hCLDN18.2 59F9E1 IgG1 with substitutions 147D, F170C, V173C, C220G for cognate LC/HC pairing and substitutions Y349C, S364D, K370D, N390D, K392G, S400D to force heterodimeric Fc formation (DCCG + CDDDGD)
organism = synthetic construct
SEQUENCE: 58
QVQLVQSGAE VKKPGSSVKV SCKASGYTLT GYWIEWLRQR PGQGLEWMGE ILLGSGSIKY 60
NVKFKDRVTI TADESTSTAY MELSSLRSED TAVYYCARKG LRGNSFDYWG QGTLVTVSSA 120
STKGPSVFPL APSSKSTSGG TAALGCLVDD YFPEPVTVSW NSGALTSGVH TCPACLQSSG 180
LYSLSSVVTV PSSSLGTQTY ICNVNHKPSN TKVDKKVEPK SGDKTHTCPP CPAPELLGGP 240
SVFLFPPKPK DTLMISRTPE VTCVVVDVSH EDPEVKFNWY VDGVEVHNAK TKPREEQYNS 300
TYRVVSVLTV LHQDWLNGKE YKCKVSNKAL PAPIEKTISK AKGQPREPQV CTLPPSREEM 360
TKNQVDLTCL VDGFYPSDIA VEWESNGQPE NDYGTTPPVL DDDGSFFLYS KLTVDKSRWQ 420
QGNVFSCSVM HEALHNHYTQ KSLSLSPGK 449

SEQ ID NO: 59 moltype = DNA length = 339
FEATURE Location/Qualifiers
source 1..339
mol_type = other DNA
note = Nucleotide sequence encoding the VL of the humanized anti-hCLDN18.2 59F9E1
organism = synthetic construct
SEQUENCE: 59
gatatcgtaa tgacacaatc accttcatca ctgaccgtga gtctcgggga aaaagctact 60
atatcctgta aatcctccca atcacttctt aacgctggga accaaaagtc ttatcttact 120
tggtaccagc aaaagcccgg tcaaccacct aagcggctca tttattgggc ttccaccaga 180
gagtctgggg taccagaccg cttctctgga agcggcagtg ggactgactt tactttgacc 240
atttcatctc tgcaagcaga agacttggca gtttattatt gtcaaaacga ttactattac 300
ccatttacat tcggtcaagg aactaaagtg gaaataaaa 339

SEQ ID NO: 60 moltype = AA length = 113
FEATURE Location/Qualifiers
source 1..113
mol_type = protein
note = Amino acid sequence of the VL of the humanized anti-hCLDN18.2 59F9E1
organism = synthetic construct
SEQUENCE: 60
DIVMTQSPSS LTVSLGEKAT ISCKSSQSLL NAGNQKSYLT WYQQKPGQPP KRLIYWASTR 60
ESGVPDRFSG SGSGTDFTLT ISSLQAEDLA VYYCQNDYYY PFTFGQGTKV EIK 113

SEQ ID NO: 61 moltype = DNA length = 666
FEATURE Location/Qualifiers
source 1..666
mol_type = other DNA
note = Nucleotide sequence encoding the LC of the humanized anti-hCLDN18.2 clone 59F9E1 (WT)
organism = synthetic construct

```
SEQUENCE: 61
gatatcgtaa tgacacaatc accttcatca ctgaccgtga gtctcgggga aaaagctact  60
atatcctgta aatcctccca atcacttctt aactctggga accaaaagtc ttatcttact  120
tggtaccagc aaaagcccgg tcaaccacct aagcggctca tttattgggc ttccaccaga  180
gagtctgggg taccagaccg cttctctgga agcggcagtg ggactgactt tactttgacc  240
atttcatctc tgcaagcaga agacttggca gtttattatt gtcaaaacga ttactattac  300
ccatttacat tcggtcaagg aactaaagtg gaaataaaac gtacggtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tgatag                                                            666

SEQ ID NO: 62          moltype = AA  length = 220
FEATURE                Location/Qualifiers
source                 1..220
                       mol_type = protein
                       note = Amino acid sequence of the LC of the humanized
                        anti-hCLDN18.2 clone 59F9E1 (WT)
                       organism = synthetic construct
SEQUENCE: 62
DIVMTQSPSS LTVSLGEKAT ISCKSSQSLL NSGNQKSYLT WYQQKPGQPP KRLIYWASTR  60
ESGVPDRFSG SGSGTDFTLT ISSLQAEDLA VYYCQNDYYY PFTFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 63          moltype = DNA  length = 666
FEATURE                Location/Qualifiers
source                 1..666
                       mol_type = other DNA
                       note = Nucleotide sequence encoding the LC of the humanized
                        anti-hCLDN18.2 clone 59F9E1 with mutations S131K, Q160C,
                        S162C, and C214S (KCCS)
                       organism = synthetic construct
SEQUENCE: 63
gatatcgtaa tgacacaatc accttcatca ctgaccgtga gtctcgggga aaaagctact  60
atatcctgta aatcctccca atcacttctt aacgctggga accaaaagtc ttatcttact  120
tggtaccagc aaaagcccgg tcaaccacct aagcggctca tttattgggc ttccaccaga  180
gagtctgggg taccagaccg cttctctgga agcggcagtg ggactgactt tactttgacc  240
atttcatctc tgcaagcaga agacttggca gtttattatt gtcaaaacga ttactattac  300
ccatttacat tcggtcaagg aactaaagtg gaaataaaac gtacggtggc tgcaccatct  360
gtcttcatct tcccgccatc tgatgagcag ttgaaatctg gaactgccaa ggttgtgtgc  420
ctgctgaata acttctatcc cagagaggcc aaagtacagt ggaaggtgga taacgccctc  480
caatcgggta actcctgcga gtgtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagagc  660
taatga                                                            666

SEQ ID NO: 64          moltype = AA  length = 220
FEATURE                Location/Qualifiers
source                 1..220
                       mol_type = protein
                       note = Amino acid sequence of the LC of the humanized
                        anti-hCLDN18.2 clone 59F9E1 with mutations S131K, Q160C,
                        S162C, and C214S (KCCS)
                       organism = synthetic construct
SEQUENCE: 64
DIVMTQSPSS LTVSLGEKAT ISCKSSQSLL NAGNQKSYLT WYQQKPGQPP KRLIYWASTR  60
ESGVPDRFSG SGSGTDFTLT ISSLQAEDLA VYYCQNDYYY PFTFGQGTKV EIKRTVAAPS  120
VFIFPPSDEQ LKSGTAKVVC LLNNFYPREA KVQWKVDNAL QSGNSCECVT EQDSKDSTYS  180
LSSTLTLSKA DYEKHKVYAC EVTHQGLSSP VTKSFNRGES                       220

SEQ ID NO: 65          moltype = DNA  length = 354
FEATURE                Location/Qualifiers
source                 1..354
                       mol_type = other DNA
                       note = Nucleotide sequence encoding the VH of
                        anti-hSIRP-alpha clone #24
                       organism = synthetic construct
SEQUENCE: 65
gaggtgcagc tggtggaatc tggcggagga cttgtgaagc ctggcggctc tctgagactg  60
tcttgtgccg cttccggctt caccttctcc agctacgtga tgtcctgggt ccgacagacc  120
cctggcaaag gactggaatg ggtcgccaca atctcctccg gcggcaccta cacctactat  180
cccgactctg tgaagggcag attcaccctg tccagagaca acgccaagaa ctccctgtac  240
ctgcagatga acagcctgag agccgaggac accgccgtgt actactgtgc ttctcagctg  300
accggctccg agttcgatta ttggggccag ggcaccaccg tgaccgtgtc ctct        354

SEQ ID NO: 66          moltype = AA  length = 118
```

```
FEATURE                Location/Qualifiers
source                 1..118
                       mol_type = protein
                       note = Amino acid sequence of the VH of anti-hSIRP-alpha
                        clone #24
                       organism = synthetic construct
SEQUENCE: 66
EVQLVESGGG LVKPGGSLRL SCAASGFTFS SYVMSWVRQT PGKGLEWVAT ISSGGTYTYY  60
PDSVKGRFTL SRDNAKNSLY LQMNSLRAED TAVYYCASQL TGSEFDYWGQ GTTVTVSS    118

SEQ ID NO: 67          moltype = DNA  length = 1404
FEATURE                Location/Qualifiers
source                 1..1404
                       mol_type = other DNA
                       note = Nucleotide sequence encoding the HC of
                        anti-hSIRP-alpha clone #24 IgG (WT)
                       organism = synthetic construct
SEQUENCE: 67
atggacatga gagtgcccgc tcagctgctg ggactgctgc tgttgtggtt gagaggcgct  60
agatgcgagg tgcagctggt ggaatctggc ggaggacttg tgaagcctgg cggctctctg  120
agactgtctt gtgccgcttc cggcttcacc ttctccagct acgtgatgtc ctgggtccga  180
cagacccctg gcaaaggact ggaatgggtc gccacaatct cctccggcgg cacctacacc  240
tactatcccg actctgtgaa gggcagattc accctgtcca gagacaacgc caagaactcc  300
ctgtacctgc agatgaacag cctgagagcc gaggacaccg ccgtgtacta ctgtgcttct  360
cagctgaccg gctccgagtt cgattattgg ggccagggca ccaccgtgac cgtgtcctct  420
gcttctacca agggacccag cgtgttccct ctggctcctt gctccagatc cacctccgag  480
tctacagctg ctctgggctg cctggtcaag gactactttc ctgagcctgt gacagtgtcc  540
tggaactctg gcgctctgac atccggcgtg cacacatttc cagctgtgct gcagtcctcc  600
ggcctgtact ctctgtcctc tgtcgtgaca gtgccctcct ctagcctggg caccaagacc  660
tatacctgca atgtggacca caagccttcc aacaccaagg tggacaagcg cgtggaatct  720
aagtacggcc ctccttgtcc tccatgtcct gctcctccag tggctggccc ttccgtgttt  780
ctgttccctc caaagcctaa ggacaccctg atgatctctc ggacccctga agtgacctgc  840
gtggtggtgg atgtgtctca cgaggatcct gaggtgcagt tcaattggta cgtggacggc  900
gtggaagtgc acaatgccaa gaccaagcct agagaggaac agttcaactc caccttcaga  960
gtggtgtccg tgctgaccgt ggtgcatcag gattggctga acggcaaaga gtacaagtgc  1020
aaggtgtcca acaaaggcct ggccgctcct atcgaaaaga ccatctctaa gaccaagggg  1080
cagccccggg aacctcaggt ttacacactg cctccaagcc gggaagagat gaccaagaac  1140
caggtgtccc tgacctgcct cgtgaagggc ttctaccctt ccgatatcgc cgtggaatgg  1200
gagtccaatg gccagccaga gaacaactac aagaccacac ctcctatgct ggactccgac  1260
ggctcattct tcctgtactc caagctgaca gtggacaagt ccagatggca gcagggcaac  1320
gtgttctcct gcagcgtgat gcacgaggcc ctgcacaatc actacaccca gaagtccctg  1380
tctctgagcc ctggcaagta atga                                        1404

SEQ ID NO: 68          moltype = AA  length = 444
FEATURE                Location/Qualifiers
source                 1..444
                       mol_type = protein
                       note = Amino acid sequence of the HC of anti-hSIRP-alpha
                        clone #24 IgG (WT)
                       organism = synthetic construct
SEQUENCE: 68
EVQLVESGGG LVKPGGSLRL SCAASGFTFS SYVMSWVRQT PGKGLEWVAT ISSGGTYTYY  60
PDSVKGRFTL SRDNAKNSLY LQMNSLRAED TAVYYCASQL TGSEFDYWGQ GTTVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP PVAGPSVFLF  240
PPKPKDTLMI SRTPEVTCVV VDVSHEDPEV QFNWYVDGVE VHNAKTKPRE EQFNSTFRVV  300
SVLTVVHQDW LNGKEYKCKV SNKGLAAPIE KTISKTKGQP REPQVYTLPP SREEMTKNQV  360
SLTCLVKGFY PSDIAVEWES NGQPENNYKT TPPMLDSDGS FFLYSKLTVD KSRWQQGNVF  420
SCSVMHEALH NHYTQKSLSL SPGK                                        444

SEQ ID NO: 69          moltype = DNA  length = 1350
FEATURE                Location/Qualifiers
source                 1..1350
                       mol_type = other DNA
                       note = Nucleotide sequence encoding the HC of
                        anti-hSIRP-alpha clone #24 IgG with S354C, S364K, N390P
                        and S400K in CH3 region for heterodimeric Fc formation
                        (CKKPKK)
                       organism = synthetic construct
SEQUENCE: 69
gaggtgcagc tggtggaatc tggcggagga cttgtgaagc ctggcggctc tctgagactg  60
tcttgtgccg cttccggctt caccttctcc agctacgtga tgtcctgggt ccgacagacc  120
cctggcaaag gactggaatg ggtcgccaca atctcctccg gcggcaccta cacctactat  180
cccgactctg tgaagggcag attcaccctg tccagagaca acgccaagaa ctccctgtac  240
ctgcagatga acagcctgag agccgaggac accgccgtgt actactgtgc ttctcagctg  300
accggctccg agttcgatta ttggggccag ggcaccaccg tgaccgtgtc ctctgctagc  360
accaagggcc catccgtctt cccccctggcg ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
```

```
tactccctca gcagcgtggt gaccgtgccc tccagcagct tgggcaccca gacctacatc  600
tgcaacgtga atcacaagcc cagcaacacc aaggtggaca agaaagttga gcccaaatct  660
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc  1020
aaagggcagc cccgagaacc acaggtgtac accctgcccc catgccggga ggagatgacc  1080
aagaaccagg tcaagctgac ctgcctggtc aaaggcttct atcccagcga catcgccgtg  1140
gagtgggaga gcaatgggca gccggagaac ccttacaaga ccacgcctcc cgtgctggac  1200
aaggacggct ccttcttcct ctatagcaag ctcaccgtgg acaagagcag gtggcagcag  1260
gggaacgtct tctcatgctc cgtgatgcat gaggctctgc acaaccacta cacgcagaag  1320
agcctctccc tgtctccggg caaatgataa                                  1350

SEQ ID NO: 70          moltype = AA  length = 448
FEATURE                Location/Qualifiers
source                 1..448
                       mol_type = protein
                       note = Amino acid sequence of the HC of anti-hSIRP-alpha
                        clone #24 IgG with S354C, S364K, N390P and S400K for
                        heterodimeric Fc formation (CKKPKK)
                       organism = synthetic construct
SEQUENCE: 70
EVQLVESGGG LVKPGGSLRL SCAASGFTFS SYVMSWVRQT PGKGLEWVAT ISSGGTYTYY  60
PDSVKGRFTL SRDNAKNSLY LQMNSLRAED TAVYYCASQL TGSEFDYWGQ GTTVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPCREEMT  360
KNQVKLTCLV KGFYPSDIAV EWESNGQPEN PYKTTPPVLD KDGSFFLYSK LTVDKSRWQQ  420
GNVFSCSVMH EALHNHYTQK SLSLSPGK                                    448

SEQ ID NO: 71          moltype = DNA  length = 336
FEATURE                Location/Qualifiers
source                 1..336
                       mol_type = other DNA
                       note = Nucleotide sequence encoding the VL of the humanized
                        anti-hSIRP-alpha clone #24
                       organism = synthetic construct
SEQUENCE: 71
gacattgtct tgacccaatc acctgcaagc ctcgccgtat ctctcgggga gcgggccaca  60
atttcttgcc gggcatcaga aagtgtagac ttgtatggca cttcctttat gcattggtat  120
caacaaaaac ccggccaacc tcctaaactc ttgatttatc gggcctccaa cctcgaatcc  180
ggtgtgcctg atcgtttttc aggttcagga agcagaacag acttcacact caccataaac  240
cccctccagg ctgaagacgt cgccacttac tattgtcacc agtcttcaga cgagctgcct  300
tggacatttg gaggtggaac taaggttgag atcaaa                            336

SEQ ID NO: 72          moltype = AA  length = 112
FEATURE                Location/Qualifiers
source                 1..112
                       mol_type = protein
                       note = Amino acid sequence of the VL of the humanized
                        anti-hSIRP-alpha clone #24
                       organism = synthetic construct
SEQUENCE: 72
DIVLTQSPAS LAVSLGERAT ISCRASESVD LYGTSFMHWY QQKPGQPPKL LIYRASNLES  60
GVPDRFSGSG SRTDFTLTIN PLQAEDVATY YCHQSSDELP WTFGGGTKVE IK          112

SEQ ID NO: 73          moltype = DNA  length = 663
FEATURE                Location/Qualifiers
source                 1..663
                       mol_type = other DNA
                       note = Nucleotide sequence encoding the LC of the humanized
                        anti-hSIRP-alpha clone #24 (WT)
                       organism = synthetic construct
SEQUENCE: 73
gacattgtct tgacccaatc acctgcaagc ctcgccgtat ctctcgggga gcgggccaca  60
atttcttgcc gggcatcaga aagtgtagac ttgtatggca cttcctttat gcattggtat  120
caacaaaaac ccggccaacc tcctaaactc ttgatttatc gggcctccaa cctcgaatcc  180
ggtgtgcctg atcgtttttc aggttcagga agcagaacag acttcacact caccataaac  240
cccctccagg ctgaagacgt cgccacttac tattgtcacc agtcttcaga cgagctgcct  300
tggacatttg gaggtggaac taaggttgag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttga  660
taa                                                                663
```

```
SEQ ID NO: 74          moltype = AA  length = 219
FEATURE                Location/Qualifiers
source                 1..219
                       mol_type = protein
                       note = Amino acid sequence of the LC of the humanized
                        anti-hSIRP-alpha clone #24 (WT)
                       organism = synthetic construct
SEQUENCE: 74
DIVLTQSPAS LAVSLGERAT ISCRASESVD LYGTSFMHWY QQKPGQPPKL LIYRASNLES  60
GVPDRFSGSG SRTDFTLTIN PLQAEDVATY YCHQSSDELP WTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 75          moltype = DNA  length = 1350
FEATURE                Location/Qualifiers
source                 1..1350
                       mol_type = other DNA
                       note = Nucleotide sequence encoding the HC of the humanized
                        anti-hCD20 Ab1.2.2.1
                       organism = synthetic construct
SEQUENCE: 75
caggtgcagc tggtgcagtc tggcgccgaa gtgaagaaac ccggctcctc cgtgaaggtg  60
tcctgcaagg cctccggcta cacctttacc agctacaaca tgcactgggt gcgacaggcc  120
cctggacagg gcctggaatg gatgggcgct atctaccctg gcaacggcga cacctcctac  180
aaccagaaat tccagggcag agtgaccctg accgtggaca agtcctcctc caccgcctac  240
atggaactgt cctccctgcg gagcgaggat accgccgtgt acttctgtgc ccgggtggtg  300
tactactcca actcctactg gtacttcgac gtgtggggca ccggcacaat ggtcaccgtg  360
tcctccgcta gcaccaaggg gccatccgtc ttccccctgg cgccctgctc caggagcacc  420
tccgagagca cagccgccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacg  600
aagacctaca cctgcaacgt agatcacaag cccagcaaca ccaaggtgga caagagagtt  660
gagtccaaat atggcccccc atgcccaccg tgcccagcac ctgaactcct ggggggaccg  720
gacgtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacgcc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
cgctccgacg gctccttctt cctctatagc gagctcaccg tggacaagag caggtggcag  1260
caggggaacg tcttctcatg ctccgtgatg catgaggctc tgcacaacca ctacacgcag  1320
aagagcctct ccctgtctcc gggtaaatga                                   1350

SEQ ID NO: 76          moltype = AA  length = 449
FEATURE                Location/Qualifiers
source                 1..449
                       mol_type = protein
                       note = Amino acid sequence of the HC of the humanized
                        anti-hCD20 Ab1.2.2.1
                       organism = synthetic construct
SEQUENCE: 76
QVQLVQSGAE VKKPGSSVKV SCKASGYTFT SYNMHWVRQA PGQGLEWMGA IYPGNGDTSY  60
NQKFQGRVTL TVDKSSSTAY MELSSLRSED TAVYFCARVV YYSNSYWYFD VWGTGTMVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPELLGGP  240
DVFLFPPKPK DTLMISRTPE VTCVVVDVSH EDPEVKFNWY VDGVEVHNAK TKPREEQYNA  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL RSDGSFFLYS ELTVDKSRWQ  420
QGNVFSCSVM HEALHNHYTQ KSLSLSPGK                                    449

SEQ ID NO: 77          moltype = DNA  length = 1341
FEATURE                Location/Qualifiers
source                 1..1341
                       mol_type = other DNA
                       note = Nucleotide sequence encoding the HC of the humanized
                        anti-hCD37 Ab1.A1.1
                       organism = synthetic construct
SEQUENCE: 77
caagtgcagc tcgtccagtc cggggcagag gttaagaagc ccggcgctag tgtgaaggtg  60
agctgcaagg cctctggcta tactttcaca gggtacaacg tgaactgggt gcgccagaac  120
aacggccaac ggttggagtg gatgggtaac atcgatccct actacggggg tactacctac  180
aacaggaaat tcaaaggacg ggtgactatc accgtggaca catctgcttc taccgcctac  240
atggagctga agtctttgcg gtctgaggac accgccgtct attactgtgc cagatccgtg  300
ggccctatgg attattgggg tcaagggacc ctggtgaccg tcagctccgc tagcaccaag  360
ggcccatccg tcttcccct ggcgccctcc tccaagagca cctctggggg cacagcggcc  420
ctgggctgcc tggtcgatga ctacttcccc gaaccggtga cggtgtcgtg gaactcaggc  480
```

```
gccctgacca gcggcgtgca cacctgcccg gcttgcctac agtcctcagg actctactcc  540
ctcagcagcg tggtgaccgt gccctccagc agcttgggca cccagaccta catctgcaac  600
gtgaatcaca agcccagcaa caccaaggtg gacaagaaag ttgagcccaa atctggtgac  660
aaaactcaca catgcccacc gtgcccagca cctgaactcc tggggggacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
aaggtctcca acaaagccct cccagccccc atcgagaaaa ccatctccaa agccaaaggg  1020
cagccccgag aaccacaggt gtacaccctg cccccatccc gggaggagat gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag ccgcctcacc gtggacaaga gcaggtggca gcaggggaac  1260
gtcttctcat gctccgtgat gcatgaggct ctgcacaacc actacacgca gaagagcctc  1320
tccctgtctc cgggtaaatg a                                            1341

SEQ ID NO: 78           moltype = AA  length = 446
FEATURE                 Location/Qualifiers
source                  1..446
                        mol_type = protein
                        note = Amino acid sequence of the HC of the humanized
                         anti-hCD37 Ab1.A1.1
                        organism = synthetic construct
SEQUENCE: 78
QVQLVQSGAE VKKPGASVKV SCKASGYTFT GYNVNWVRQN NGQRLEWMGN IDPYYGGTTY  60
NRKFKGRVTI TVDTSASTAY MELKSLRSED TAVYYCARSV GPMDYWGQGT LVTVSSASTK  120
GPSVFPLAPS SKSTSGGTAA LGCLVDDYFP EPVTVSWNSG ALTSGVHTCP ACLQSSGLYS  180
LSSVVTVPSS SLGTQTYICN VNHKPSNTKV DKKVEPKSGD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSREEMTKN  360
QVSLTCLVKG FYPSDIAVEW ESNGQPENNY KTTPPVLDSD GSFFLYSRLT VDKSRWQQGN  420
VFSCSVMHEA LHNHYTQKSL SLSPGK                                      446

SEQ ID NO: 79           moltype = DNA  length = 1359
FEATURE                 Location/Qualifiers
source                  1..1359
                        mol_type = other DNA
                        note = Nucleotide sequence encoding the HC of the anti-DNP
                         IgG1 antibody
                        organism = synthetic construct
SEQUENCE: 79
caggttcaac tccaggagtc cggccctggc ttggttaaac ctctgcagac actgtccctg  60
acctgcaccg tgagcggtgg ctcaataagt agcggcggct actactggtc atggattcgc  120
cagcaccccg gtaaaggtct cgaatggatt gggtacatct actattctag gagtacttac  180
tacaacccct cacttaaaag cagagtgact atcagtgttg atacatccaa aaaccagttt  240
agcttgaaac tgtcatccgt aactgccgcc gacaccgcag tctactattg tgctcggacc  300
ggatacagct ctggatggta cccctttgat tactggggac agggtacatt ggtgactgtc  360
agttcagcta gcaccaaggg cccatccgtc ttccccctgg cgccctcctc caagagcacc  420
tctgggggca cagcggccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacc  600
cagacctaca tctgcaacgt gaatcacaag cccagcaaca ccaaggtgga caagaaagtt  660
gagcccaaat cttgtgacaa aactcacaca tgcccaccgt gcccagcacc tgaactcctg  720
gggggaccgt cagtcttcct cttcccccca aaacccaagg acaccctcat gatctcccgg  780
acccctgagg tcacatgcgt ggtggtggac gtgagccacg aagaccctga ggtcaagttc  840
aactggtacg tggacggcgt ggaggtgcat aatgccaaga caaagccgcg ggaggagcag  900
tacaacagca cgtaccgtgt ggtcagcgtc ctcaccgtcc tgcaccagga ctggctgaat  960
ggcaaggagt acaagtgcaa ggtctccaac aaagccctcc cagcccccat cgagaaaacc  1020
atctccaaag ccaaagggca gccccgagaa ccacaggtgt acaccctgcc cccatcccgg  1080
gaggagatga ccaagaacca ggtcagcctg acctgcctgg tcaaaggctt ctatcccagc  1140
gacatcgccg tggagtggga gagcaatggg cagccggaga acaactacaa gaccacgcct  1200
cccgtgctgg actccgacgg ctccttcttc ctctatagca agctcaccgt ggacaagagc  1260
aggtggcagc aggggaacgt cttctcatgc tccgtgatgc atgaggctct gcacaaccac  1320
tacacgcaga agagcctctc cctgtctccg ggtaaatga                        1359

SEQ ID NO: 80           moltype = AA  length = 452
FEATURE                 Location/Qualifiers
source                  1..452
                        mol_type = protein
                        note = Amino acid sequence of the HC of the anti-DNP IgG1
                         antibody
                        organism = synthetic construct
SEQUENCE: 80
QVQLQESGPG LVKPLQTLSL TCTVSGGSIS SGGYYWSWIR QHPGKGLEWI GYIYYSRSTY  60
YNPSLKSRVT ISVDTSKNQF SLKLSSVTAA DTAVYYCART GYSSGWYPFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
```

```
EEMTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                               452

SEQ ID NO: 81          moltype = DNA  length = 648
FEATURE                Location/Qualifiers
source                 1..648
                       mol_type = other DNA
                       note = Nucleotide sequence encoding the LC of the anti-DNP
                        IgG1 antibody
                       organism = synthetic construct
SEQUENCE: 81
gacatccaaa tgaccttgtc tccttcaagt ctttccgcta gtgttggaga ccgagttacc  60
ataacatgcc gggctagtca aggcattagg aatgatttgg gttggtacca acaaaaaccc  120
ggcaaagcac ctaagagact tatatacgcc gcctccagtc ttcagagcgg ggtaccttcc  180
cggttcagtg gatctggctc agggactgag tttaccctca caatctctag ccttcaacct  240
gaagattttg ctacatacta ctgtctccag tataattcct ctccctggac ctttggacag  300
ggaaccgaag tggaaataaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gttgataa              648

SEQ ID NO: 82          moltype = AA  length = 214
FEATURE                Location/Qualifiers
source                 1..214
                       mol_type = protein
                       note = Amino acid sequence of the LC of the anti-DNP IgG1
                        antibody
                       organism = synthetic construct
SEQUENCE: 82
DIQMTLSPSS LSASVGDRVT ITCRASQGIR NDLGWYQQKP GKAPKRLIYA ASSLQSGVPS  60
RFSGSGSGTE FTLTISSLQP EDFATYYCLQ YNSSPWTFGQ GTEVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 83          moltype = AA  length = 17
FEATURE                Location/Qualifiers
source                 1..17
                       mol_type = protein
                       note = Amino acid sequence of VL CDR1 (by Kabat definition)
                        of the humanized anti-hCLDN18.2 clone 59F9E1
                       organism = synthetic construct
SEQUENCE: 83
KSSQSLLNAG NQKSYLT                                                17

SEQ ID NO: 84          moltype = AA  length = 7
FEATURE                Location/Qualifiers
source                 1..7
                       mol_type = protein
                       note = Amino acid sequence of VL CDR2 (by Kabat definition)
                        of the humanized anti-hCLDN18.2 clone 59F9E1
                       organism = synthetic construct
SEQUENCE: 84
WASTRES                                                           7

SEQ ID NO: 85          moltype = AA  length = 9
FEATURE                Location/Qualifiers
source                 1..9
                       mol_type = protein
                       note = Amino acid sequence of VL CDR3 (by Kabat definition)
                        of the humanized anti-hCLDN18.2 clone 59F9E1
                       organism = synthetic construct
SEQUENCE: 85
QNDYYYPFT                                                         9

SEQ ID NO: 86          moltype = AA  length = 5
FEATURE                Location/Qualifiers
source                 1..5
                       mol_type = protein
                       note = Amino acid sequence of VH CDR1 (by Kabat definition)
                        of the humanized anti-hCLDN18.2 clone 59F9E1
                       organism = synthetic construct
SEQUENCE: 86
GYWIE                                                             5

SEQ ID NO: 87          moltype = AA  length = 17
FEATURE                Location/Qualifiers
source                 1..17
```

```
                         mol_type = protein
                         note = Amino acid sequence of VH CDR2 (by Kabat definition)
                          of the humanized anti-hCLDN18.2 clone 59F9E1
                         organism = synthetic construct
SEQUENCE: 87
EILLGSGSIK YNVKFKD                                                    17

SEQ ID NO: 88            moltype = AA  length = 10
FEATURE                  Location/Qualifiers
source                   1..10
                         mol_type = protein
                         note = Amino acid sequence of VH CDR3 (by Kabat definition)
                          of the humanized anti-hCLDN18.2 clone 59F9E1
                         organism = synthetic construct
SEQUENCE: 88
KGLRGNSFDY                                                            10

SEQ ID NO: 89            moltype =   length =
SEQUENCE: 89
000

SEQ ID NO: 90            moltype = AA  length = 98
FEATURE                  Location/Qualifiers
MOD_RES                  1..5
                         note = Any amino acid ordinarily found in living organisms
MOD_RES                  7..9
                         note = Any amino acid ordinarily found in living organisms
MOD_RES                  11..15
                         note = Any amino acid ordinarily found in living organisms
MOD_RES                  16
                         note = arginine or lysine
MOD_RES                  17..26
                         note = Any amino acid ordinarily found in living organisms
MOD_RES                  29
                         note = Any amino acid ordinarily found in living organisms
MOD_RES                  31..33
                         note = Any amino acid ordinarily found in living organisms
MOD_RES                  35..40
                         note = Any amino acid ordinarily found in living organisms
MOD_RES                  42..50
                         note = Any amino acid ordinarily found in living organisms
MOD_RES                  52
                         note = Any amino acid ordinarily found in living organisms
MOD_RES                  54..55
                         note = Any amino acid ordinarily found in living organisms
MOD_RES                  57..63
                         note = Any amino acid ordinarily found in living organisms
MOD_RES                  65
                         note = Any amino acid ordinarily found in living organisms
MOD_RES                  68..82
                         note = Any amino acid ordinarily found in living organisms
MOD_RES                  84..98
                         note = Any amino acid ordinarily found in living organisms
source                   1..98
                         mol_type = protein
                         note = Consensus amino acid sequence for a CH1 domain
                         organism = synthetic construct
SEQUENCE: 90
XXXXXPXXXP XXXXXXXXXX XXXXXXCLXK XXXPXXXXXX WXXXXXXXXX HXFXXVXXXX  60
XXXTXSSXXX XXXXXXXXXX XXCXXXXXXX XXXXXXXX                          98

SEQ ID NO: 91            moltype = AA  length = 98
FEATURE                  Location/Qualifiers
source                   1..98
                         mol_type = protein
                         organism = Homo sapiens
SEQUENCE: 91
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKV                          98

SEQ ID NO: 92            moltype = AA  length = 98
FEATURE                  Location/Qualifiers
source                   1..98
                         mol_type = protein
                         organism = Homo sapiens
SEQUENCE: 92
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTV                          98
```

```
SEQ ID NO: 93           moltype = AA  length = 98
FEATURE                 Location/Qualifiers
source                  1..98
                        mol_type = protein
                        organism = Homo sapiens
SEQUENCE: 93
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRV                          98

SEQ ID NO: 94           moltype = AA  length = 98
FEATURE                 Location/Qualifiers
source                  1..98
                        mol_type = protein
                        organism = Homo sapiens
SEQUENCE: 94
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRV                          98

SEQ ID NO: 95           moltype = AA  length = 232
FEATURE                 Location/Qualifiers
source                  1..232
                        mol_type = protein
                        organism = Homo sapiens
SEQUENCE: 95
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 96           moltype = AA  length = 228
FEATURE                 Location/Qualifiers
source                  1..228
                        mol_type = protein
                        organism = Homo sapiens
SEQUENCE: 96
ERKCCVECPP CPAPPVAGPS VFLFPPKPKD TLMISRTPEV TCVVVDVSHE DPEVQFNWYV  60
DGMEVHNAKT KPREEQFNST FRVVSVLTVV HQDWLNGKEY KCKVSNKGLP APIEKTISKT  120
KGQPREPQVY TLPPSREEMT KNQVSLTCLV KGFYPSDIAV EWESNGQPEN NYKTTPPMLD  180
SDGSFFLYSK LTVDKSRWQQ GNVFSCSVMH EALHNHYTQK SLSLSPGK              228

SEQ ID NO: 97           moltype = AA  length = 279
FEATURE                 Location/Qualifiers
source                  1..279
                        mol_type = protein
                        organism = Homo sapiens
SEQUENCE: 97
ELKTPLGDTT HTCPRCPEPK SCDTPPPCPR CPEPKSCDTP PPCPRCPEPK SCDTPPPCPR  60
CPAPELLGGP SVFLFPPKPK DTLMISRTPE VTCVVVDVSH EDPEVQFKWY VDGVEVHNAK  120
TKPREEQYNS TFRVVSVLTV LHQDWLNGKE YKCKVSNKAL PAPIEKTISK TKGQPREPQV  180
YTLPPSREEM TKNQVSLTCL VKGFYPSDIA VEWESSGQPE NNYNTTPPML DSDGSFFLYS  240
KLTVDKSRWQ QGNIFSCSVM HEALHNRFTQ KSLSLSPGK                         279

SEQ ID NO: 98           moltype = AA  length = 229
FEATURE                 Location/Qualifiers
source                  1..229
                        mol_type = protein
                        organism = Homo sapiens
SEQUENCE: 98
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 99           moltype =   length =
SEQUENCE: 99
000

SEQ ID NO: 100          moltype = AA  length = 107
FEATURE                 Location/Qualifiers
MOD_RES                 1..5
                        note = Any amino acid ordinarily found in living organisms
MOD_RES                 7..11
                        note = Any amino acid ordinarily found in living organisms
MOD_RES                 14..23
                        note = Any amino acid ordinarily found in living organisms
MOD_RES                 25
                        note = Any amino acid ordinarily found in living organisms
MOD_RES                 28..33
                        note = Any amino acid ordinarily found in living organisms
```

```
MOD_RES                 35..38
                        note = Any amino acid ordinarily found in living organisms
MOD_RES                 40
                        note = Any amino acid ordinarily found in living organisms
MOD_RES                 42..52
                        note = Any amino acid ordinarily found in living organisms
MOD_RES                 54
                        note = Any amino acid ordinarily found in living organisms
MOD_RES                 56
                        note = Any amino acid ordinarily found in living organisms
MOD_RES                 58..66
                        note = Any amino acid ordinarily found in living organisms
MOD_RES                 68
                        note = Any amino acid ordinarily found in living organisms
MOD_RES                 75..86
                        note = Any amino acid ordinarily found in living organisms
MOD_RES                 88..90
                        note = Any amino acid ordinarily found in living organisms
MOD_RES                 92..106
                        note = Any amino acid ordinarily found in living organisms
source                  1..107
                        mol_type = protein
                        note = Consensus amino acid sequence for a CL kappa domain
                        organism = synthetic construct
SEQUENCE: 100
XXXXXPXXXX XPPXXXXXXX XXXSXVCXXX XXXPXXXXVX WXXXXXXXXX XXQXSXTXXX  60
XXXXXXSXSS TLTLXXXXXX XXXXXXCXXX HXXXXXXXXX XXXXXXC                107

SEQ ID NO: 101          moltype = AA  length = 107
FEATURE                 Location/Qualifiers
MOD_RES                 1..5
                        note = Any amino acid ordinarily found in living organisms
MOD_RES                 7..11
                        note = Any amino acid ordinarily found in living organisms
MOD_RES                 14..23
                        note = Any amino acid ordinarily found in living organisms
MOD_RES                 25
                        note = Any amino acid ordinarily found in living organisms
MOD_RES                 28..33
                        note = Any amino acid ordinarily found in living organisms
MOD_RES                 35..38
                        note = Any amino acid ordinarily found in living organisms
MOD_RES                 40
                        note = Any amino acid ordinarily found in living organisms
MOD_RES                 42..52
                        note = Any amino acid ordinarily found in living organisms
MOD_RES                 54
                        note = Any amino acid ordinarily found in living organisms
MOD_RES                 56
                        note = Any amino acid ordinarily found in living organisms
MOD_RES                 58..66
                        note = Any amino acid ordinarily found in living organisms
MOD_RES                 67
                        note = alanine or methionine
MOD_RES                 68
                        note = Any amino acid ordinarily found in living organisms
MOD_RES                 75..86
                        note = Any amino acid ordinarily found in living organisms
MOD_RES                 88..90
                        note = Any amino acid ordinarily found in living organisms
MOD_RES                 92..106
                        note = Any amino acid ordinarily found in living organisms
source                  1..107
                        mol_type = protein
                        note = Consensus amino acid sequence for a CL lambda domain
                        organism = synthetic construct
SEQUENCE: 101
XXXXXPXXXX XPPXXXXXXX XXXAXVCXXX XXXPXXXXVX WXXXXXXXXX XXEXTXPXXX  60
XXXXXXXXSS YLSLXXXXXX XXXXXXCXXX HXXXXXXXXX XXXXXXC                107

SEQ ID NO: 102          moltype = AA  length = 107
FEATURE                 Location/Qualifiers
source                  1..107
                        mol_type = protein
                        organism = Homo sapiens
SEQUENCE: 102
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107
```

```
SEQ ID NO: 103         moltype = AA  length = 107
FEATURE                Location/Qualifiers
source                 1..107
                       mol_type = protein
                       organism = Homo sapiens
SEQUENCE: 103
RTVAAPSVFI FPPSDEQLKS GTASVVCLLN NFYPREAKVQ WKVDNALQSG NSQESVTEQE  60
SKDSTYSLSS TLTLSKADYE KHKVYAGEVT HQGLSSPVTK SFNRGEC                107

SEQ ID NO: 104         moltype = AA  length = 107
FEATURE                Location/Qualifiers
source                 1..107
                       mol_type = protein
                       organism = Homo sapiens
SEQUENCE: 104
RTVAAPSVFI FPPSDEQLKS GTASVVCLLN NFYPREAKVQ RKVDNALQSG NSQESVTEQE  60
SKDSTYSLSS TLTLSKADYE KHKVYACEVT HQGLSSPVTK SFNRGEC                107

SEQ ID NO: 105         moltype = AA  length = 107
FEATURE                Location/Qualifiers
source                 1..107
                       mol_type = protein
                       organism = Homo sapiens
SEQUENCE: 105
RTVAAPSVFI FPPSDEQLKS GTASVVCLLN NFYPREAKVQ WKVDNALQSG NSQESVTEQD  60
SKDSTYSLSS TLTLSKADYE KHKLYACEVT HQGLSSPVTK SFNRGEC                107

SEQ ID NO: 106         moltype = AA  length = 107
FEATURE                Location/Qualifiers
source                 1..107
                       mol_type = protein
                       organism = Homo sapiens
SEQUENCE: 106
RTVAAPSVFI FPPSDEQLKS GTASVVCLLN NFYPREAKVQ WKVDNALQSG NSQESVTEQD  60
SKDSTYSLSN TLTLSKADYE KHKVYACEVT HQGLSSPVTK SFNRGEC                107

SEQ ID NO: 107         moltype = DNA  length = 1074
FEATURE                Location/Qualifiers
source                 1..1074
                       mol_type = other DNA
                       note = Nucleotide sequence encoding IL15 fused to the
                        C-terminal end of an Fc chain (CDDDGD)
                       organism = synthetic construct
SEQUENCE: 107
gacaaaacac atacatgccc tccttgccca gctccagagc ttcttggcgg accttctgta  60
ttcctcttcc caccaaaacc aaaagacaca cttatgattt cccgcacacc tgaagtcaca  120
tgcgtggttg tggacgtgtc acatgaagac cctgaagtga agttcaactg gtatgttgat  180
ggggtggagg ttcacaatgc caaaaccaag ccccgagagg aacaatacaa tagcacatat  240
cgagtagtgt ctgtgctgac agtcctgcat caagattggc tcaatggtaa agagtacaaa  300
tgtaaagttt ccaataaggc tttgcctgcc cctatcgaga aaaccatatc taaggctaaa  360
ggccaaccac gcgagcctca ggtttgtact ttgcctccct cacgtgaaga gatgaccaag  420
aatcaagtag acctgacttg tcttgtggac ggtttctatc ctagtgacat cgccgtggag  480
tgggaatcaa atgggcaacc cgagaatgac tatggcacca cccctcccgt acttgacgat  540
gacgggtcct tttttctgta cagtaagttg actgtggata aatctcgctg gcaacaaggg  600
aatgtcttct cctgtagtgt catgcacgaa gccctgcata accactatac acagaagagc  660
ttgtcccttt ctcctgggaa gggcggtggt ggctcaggag gtggggggag cggtggcggt  720
ggatccaatt gggtcaatgt cattagcgac ctgaagaaaa tcgaagacct catccaatct  780
atgcacattg acgccacact ttatactgaa tccgatgtcc acccatcttg taaggttaca  840
gccatgaaat gttttcttct ggagcttcag gtcatttcac ttgagtccgg tgacgcttca  900
atacacgata ctgtagagaa tcttatcatt ttggccaaca actcattgag tagtaatggg  960
aacgttactg agtccggttg taaggaatgt gaggaacttg aagaaaaaaa cataaaagag  1020
tttctccagt cctttgtcca cattgtgcaa atgttcataa atacttcctg ataa        1074

SEQ ID NO: 108         moltype = AA  length = 356
FEATURE                Location/Qualifiers
source                 1..356
                       mol_type = protein
                       note = Amino acid sequence encoding IL15 fused to the
                        C-terminal end of an Fc chain (CDDDGD)
                       organism = synthetic construct
SEQUENCE: 108
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSREEMTK NQVDLTCLVD GFYPSDIAVE WESNGQPEND YGTTPPVLDD  180
DGSFFLYSKL TVDKSRWQQG NVFSCSVMHE ALHNHYTQKS LSLSPGKGGG GSGGGGSGGG  240
GSNWVNVISD LKKIEDLIQS MHIDATLYTE SDVHPSCKVT AMKCFLLELQ VISLESGDAS  300
IHDTVENLII LANNSLSSNG NVTESGCKEC EELEEKNIKE FLQSFVHIVQ MFINTS      356

SEQ ID NO: 109         moltype = DNA  length = 906
```

```
FEATURE                Location/Qualifiers
source                 1..906
                       mol_type = other DNA
                       note = Nucleotide sequence encoding IL15Ra Sushi domain
                        fused to the C-terminal end of an Fc chain (CKKPKK)
                       organism = synthetic construct
SEQUENCE: 109
gacaaaaccc atacatgtcc tccttgcccc gcccccgaat tgcttggggg tcctagtgtc  60
ttccttttc caccaaagcc caaagacact ttgatgataa gccggactcc tgaggttacc  120
tgcgtagttg tggatgtatc ccacgaagat cctgaagtca aatttaactg gtacgtggac  180
ggagtagaag ttcataacgc caagacaaag ccccgcgaag aacagtacaa cagcacctat  240
cgggtagtat ccgtcctgac tgtccttcat caagactggt tgaatggcaa ggaatataaa  300
tgtaaggtta gtaataaagc tcttcccgct ccaattgaga agaccatttc taaggctaaa  360
ggacaacccc gcgagccaca agtctacacc ttgcctccat gcagggaaga gatgacaaag  420
aaccaagtga agctgacatg cttggttaaa ggcttctatc ccagtgatat cgccgtggag  480
tgggagtcaa acggtcagcc tgaaaatcct tacaaaacta ctccccctgt tcttgacaag  540
gacggttcat tctttttgta ttcaaagttg acagtggata agagcagatg gcagcagggt  600
aatgtctttt cttgttccgt gatgcatgag gccctgcata accattacac acaaaagtcc  660
ctcagcctct ccccaggaaa agggggtggt ggaagcggag gaggcggatc cataacatgt  720
cctcctccca tgagcgtcga gcatgcagat atatgggtta agagctactc actctactcc  780
agggaacgat atatatgtaa ttccggtttc aagcgaaagg caggtactag ctcccttaca  840
gaatgcgtac tgaacaaggc aaccaatgta gctcattgga ccaccccaag tctgaagtgt  900
attcgt                                                             906

SEQ ID NO: 110         moltype = AA  length = 302
FEATURE                Location/Qualifiers
source                 1..302
                       mol_type = protein
                       note = Amino acid sequence encoding IL15Ra Sushi domain
                        fused to the C-terminal end of an Fc chain (CKKPKK)
                       organism = synthetic construct
SEQUENCE: 110
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCREEMTK NQVKLTCLVK GFYPSDIAVE WESNGQPENP YKTTPPVLDK  180
DGSFFLYSKL TVDKSRWQQG NVFSCSVMHE ALHNHYTQKS LSLSPGKGGG GSGGGGSITC  240
PPPMSVEHAD IWVKSYSLYS RERYICNSGF KRKAGTSSLT ECVLNKATNV AHWTTPSLKC  300
IR                                                                 302

SEQ ID NO: 111         moltype = DNA  length = 702
FEATURE                Location/Qualifiers
source                 1..702
                       mol_type = other DNA
                       note = Nucleotide sequence encoding an Fc chain (CDDDGD)
                       organism = synthetic construct
SEQUENCE: 111
gagccaaaaa gctccgataa gacacacact tgcccccct gcccagcccc agagctgttg  60
ggaggccctt ctgtattcct cttcccccca aaacccaagg ataccctcat gatcagcaga  120
actcccgagg tgacttgcgt cgtcgtggac gtttctcacg aagaccccga ggtaaaattc  180
aactggtacg tggacggagt ggaagtacac aatgctaaaa ctaaaccccg agaggagcaa  240
tataattcta cctaccgcgt agtcagtgtg ctgacagttc tccatcaaga ttggcttaac  300
ggcaaagagt ataagtgcaa ggtctcaaat aaggcattgc cagctcctat agagaaaact  360
attagtaaag caaaggggca gcctcgtgaa ccccaagtct gtactcttcc tccttcaagg  420
gaggagatga ctaaaaacca agttgatctc acctgtttgg tggacggatt ttatcctagt  480
gatattgctg tggaatggga gagtaacggg cagcctgaga acgactacgg caccacccca  540
ccagtccttg acgatgatgg ctccttttc ctttattcaa agctcactgt agacaaatct  600
cgttggcagc agggaaacgt gttcagttgt tctgttatgc atgaagctct tcataaccac  660
tatacccaga aatcactgag tctgtcacct ggcaaatgat aa                     702

SEQ ID NO: 112         moltype = AA  length = 232
FEATURE                Location/Qualifiers
source                 1..232
                       mol_type = protein
                       note = Amino acid sequence encoding an Fc chain (CDDDGD)
                       organism = synthetic construct
SEQUENCE: 112
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR EEMTKNQVDL TCLVDGFYPS DIAVEWESNG QPENDYGTTP  180
PVLDDDGSFF LYSKLTVDKS RWQQGNVFSC SVMHEALHNH YTQKSLSLSP GK          232

SEQ ID NO: 113         moltype = DNA  length = 702
FEATURE                Location/Qualifiers
source                 1..702
                       mol_type = other DNA
                       note = Nucleotide sequence encoding an Fc chain (CKKPKK)
                       organism = synthetic construct
SEQUENCE: 113
gaaccaaaaa gtagtgataa aactcacact tgtcccccct gccccgcacc tgagctcctt  60
```

-continued

```
ggaggacctt ctgtcttctt gtttccccct aagcctaaag atacattgat gatttccagg  120
actcccgaag tcacttgtgt ggtagttgat gttagccatg aggatcccga ggtaaagttc  180
aactggtatg tcgacggagt tgaagtacac aatgccaaaa ctaaacccag ggaggagcag  240
tacaattcta cataccgtgt tgtctcagtg ctcaccgtcc ttcaccaaga ttggcttaac  300
ggaaaagaat acaaatgtaa agtgagcaac aaagccctcc cagcccctat cgagaagaca  360
atatctaaag ctaagggtca accaagggag cctcaggtct acaccctccc accatgtagg  420
gaggaaatga caaagaacca agttaaactg acatgcctgg tcaaaggatt ctacccctca  480
gatattgctg tggaatggga aagcaatggt caacctgaga atccctacaa gaccacccca  540
cccgtactgg acaaagacgg ttcattcttt ctctacagca aattgactgt ggataaaagc  600
aggtggcaac aagggaacgt gttctcctgt tctgtgatgc acgaagcact ccacaaccat  660
tatacccaga aaagcctgag tttgtcccct ggcaagtgat aa                     702

SEQ ID NO: 114          moltype = AA  length = 232
FEATURE                 Location/Qualifiers
source                  1..232
                        mol_type = protein
                        note = Amino acid sequence encoding an Fc chain (CKKPKK)
                        organism = synthetic construct
SEQUENCE: 114
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPCR EEMTKNQVKL TCLVKGFYPS DIAVEWESNG QPENPYKTTP  180
PVLDKDGSFF LYSKLTVDKS RWQQGNVFSC SVMHEALHNH YTQKSLSLSP GK          232
```